US006528253B1

(12) United States Patent
Mitcham et al.

(10) Patent No.: US 6,528,253 B1
(45) Date of Patent: Mar. 4, 2003

(54) COMPOSITIONS AND METHODS FOR DIAGNOSIS OF OVARIAN CANCER

(75) Inventors: Jennifer L. Mitcham, Redmond, WA (US); Tony N. Frudakis, Sarasota, FL (US); Gordon E. King, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/215,681

(22) Filed: Dec. 17, 1998

(51) Int. Cl.[7] .......................... C12Q 1/68; G01N 33/48; C07H 21/04

(52) U.S. Cl. ............................ 435/6; 436/64; 536/24.3; 536/24.31

(58) Field of Search ............................ 435/6; 536/23.1, 536/24.31, 24.3; 436/64

(56) References Cited

PUBLICATIONS

Gencore Version 4.5, Compugen, AA075578, AA291512, AA411046, AA434329, AA404609 1998.*

Lathe, R., "Synthetic Oligonucleotide Probes Deduced from Amino Acid Sequence Data", J. Mol. Biol., vol. 183, pp. 1–12 1985.*

Accession Number T21429 Aug. 1996.*

Accession Number H53701 Sep. 1995.*

Heller et al., "Discovery and analysis of inflammatory disease–related genes using cDNA microarrays,"*Proc. Natl. Acad. Sci USA* 94:2150–2155, Mar. 1997.

Jin et al., "Human T cell leukemia virus type 1 oncoprotein tax targets the human mitotic checkpoint protein MAD1," *Cell* 93:81–91, Apr. 3, 1998.

Schena et al., "Parallel human genome analysis: microarray–based expression monitoring of 1000 genes, " *Proc. Natl. Acad. Sci. USA* 93:10614–10619, Oct. 1996.

* cited by examiner

*Primary Examiner*—Anthony C. Caputa
*Assistant Examiner*—Karen A. Canella
(74) *Attorney, Agent, or Firm*—Seed Intellectual Property Law Group PLLC

(57) ABSTRACT

Compositions and methods for the diagnosis of cancer, such as ovarian cancer, are disclosed. Compositions may comprise one or more ovarian carcinoma proteins, immunogenic portions thereof or polynucleotides that encode such portions. Such compositions may be used, for example, for the detecting and monitoring diseases such as ovarian cancer.

12 Claims, 91 Drawing Sheets

11729.1 contg

TTAGAGAGGCACAGAAGGAAGAAGAGTTAAAAGCAGCAAAGCCGGGTTTTTTTGTTTTGT
TTTGTTTTGTTTTGTTTTGAGATGGAGTCTCACTCTGTTGCCCAAGCTGGAGTACAACGGCA
TGATCTCAGCTCGCTGCAACCTCCGCCTCCCACGTTCAAGTGATTCTCCTGCCTCAGCCTCC
CAAGTAGCTGGGATTACAGGCGCCCGCCACCACGCTCAGCTAATTTTTTTTGTATTTTTAGT
AGAGACAGGGTTTCACCAGGTTGGCCAGGCTGCTCTTGAACTCCTGACCTCAGGTGATCCA
CCCGCCTCGGCCTCCCAAAGTGCTGGGATTACAGGCGTGAGCCACCACGCCCGGCCCCCAA
AGCTGTTTCTTTTGTCTTTAGCGTAAAGCTCTCCTGCCATGCAGTATCTACATAACTGACGT
GACTGCCAGCAAGCTCAGTCACTCCGTGGTC

11729-45.21.21.cons1

TAGGATGTGTTGGACCCTCTGTGTCAAAAAAAACCTCACAAAGAATCCCCTGCTCATTACA
GAAGAAGATGCATTTAAAATATGGGTTATTTTCAACTTTTTATCTGAGGACAAGTATCCAT
TAATTATTGTGTCAGAAGAGATTGAATACCTGCTTAAGAAGCTTACAGAAGCTATGGGAG
GAGGTTGGCAGCAAGAACAATTTGAACATTATAAAATCAACTTTGATGACAGTAAAAATG
GCCTTTCTGCATGGGAACTTATTGAGCTTATTGGAAATGGACAGTTTAGCAAAGGCATGGA
CCGGCAGACTGTGTCTATGGCAATTAATGAAGTCTTTAATGAACTTATATTAGATGTGTTA
AAGCAGGGTTACATGATGAAAAAGGGCCACAGACGGAAAAACTGGACTGAAAGATGGTT
TGTACTAAAACCCAACATAATTTCTTACTATGTGAGTGAGGATCTGAAGGATAAGAAAGG
AGACATTCTCTTGGATGAAAATTGCTGTGTAGAGTCCTTGCCTGACAAAGATGGAAA

11729-45.21.21.cons2

TTAGAGAGGCACAGAAGGAAGAAGAGTTAAAAGCAGCAAAGCCGGGTTTTTTTGTTTTGT
TTTGTTTTGTTTTGTTTTGAGATGGAGTCTCACTCTGTTGCCCAAGCTGGAGTACAACGGCA
TGATCTCAGCTCGCTGCAACCTCCGCCTCCCACGTTCAAGTGATTCTCCTGCCTCAGCCTCC
CAAGTAGCTGGGATTACAGGCGCCCGCCACCACGCTCAGCTAATTTTTTTTGTATTTTTAGT
AGAGACAGGGTTTCACCAGGTTGGCCAGGCTGCTCTTGAACTCCTGACCTCAGGTGATCCA
CCCGCCTCGGCCTCCCAAAGTGCTGGGATTACAGGCGTGAGCCACCACGCCCGGCCCCCAA
AGCTGTTTCTTTTGTCTTTAGCGTAAAGCTCTCCTGCCATGCAGTATCTACATAACTGACGT
GACTGCCAGCAAGCTCAGTCACTCCGTGGTC

11731.1contig

TCTTTTTCTTTCGATTTCCTTCAATTTGTCACGTTTGATTTTATGAAGTTGTTCAAGGGCTAA
CTGCTGTGTATTATAGCTTTCTCTGAGTTCCTTCAGCTGATTGTTAAATGAATCCATTTCTG
AGAGCTTAGATGCAGTTTCTTTTTCAAGAGCATCTAATTGTTCTTTAAGTCTTTGGCATAAT
TCTTCCTTTTCTGATGACTTTTTATGAAGTAAACTGATCCCTGAATCAGGTGTGTTACTGAG
CTGCATGTTTTTAATTCTTTCGTTTAATAGCTGCTTCTCAGGGACCAGATAGATAAGCTTAT
TTTGATATTCCTTAAGCTCTTGTTGAAGTTGTTTGATTTCCATAATTTCCAGGTCACACTGT
TTATCCAAAACTTCTAGCTCAGTCTTTTGTGTTTGCTTTCTGATTTGGACATCTTGTAGTCTG
CCTGAGATCTGCTGATGXTTTCCATTCACTGCTTCCAGTTCCAGGTGGAGACTTTXCTTTCT
GGAGCTCAGCCTGACAATGCCTTCTTGXTCCCT

*FIG. 1A*

11731.2contig

AGCCAGATGGCTGAGAGCTGCAAGAAGAAGTCAGGATCATGATGGCTCAGTTTCCCACAG
CGATGAATGGAGGGCCAAATATGTGGGCTATTACATCTGAAGAACGTACTAAGCATGATA
AACAGTTTGATAACCTCAAACCTTCAGGAGGTTACATAACAGGTGATCAAGCCCGTACTTT
TTTCCTACAGTCAGGTCTGCCGGCCCCGGTTTTAGCTGAAATATGGGCCTTATCAGATCTG
AACAAGGATGGGAAGATGGACCAGCAAGAGTTCTCTATAGCTATGAAACTCATCAAGTTA
AAGTTGCAGGGCCAACAGCTGCCTGTAGTCCTCCCTCCTATCATGAAACAACCCCCTATGT
TCTCTCCACTAATCTCTGCTCGTTTTGGGATGGGAAGCATGCCCAATCTGTCCATTCATCAG
CCATTGCCTCCAGTTGCACCTATAGCAACACCCTTGTCTTCTGCTACTTCAGGGACCAGTAT
TCCTCCCCTAATGATGCCTGCTCCCCTAGTGCCTTCTGTTAGTA

11734.1contig

AATAGATTTAATGCAGAGTGTCAACTTCAATTGATTGATAGTGGCTGCCTAGAGTGCTGTG
TTGAGTAGGTTTCTGAGGATGCACCCTGGCTTGAAGAGAAAGACTGGCAGGATTAACAAT
ATCTAAAATCTCACTTGTAGGAGAAACCACAGGCACCAGAGCTGCCACTGGTGCTGGCAC
CAGCTCCACCAAGGCCAGCGAAGAGCCCAAATGTGAGAGTGGCGGTCAGGCTGGCACCAG
CACTGAAGCCACCACTGGTGCTGGCACTGGCACTGGCACTGTTATTGGTACTGGTACTGGC
ACCAGTGCTGGCACTGCCACTCTCTTGGGCTTTGGCTTTAGCTTCTGCTCCCGCCTGGATCC
GGGCTTTGGCCCAGGGTCCGATATCAGCTTCGTCCCAGTTGCAGGGCCCGGCAGCATTCTC
CGAGCCGAGCCCAATGCCCATTCGAGCTCTAATCTCGGCCCTAGCCTTGGCTTCAGCTGCA
GCCTCAGCTGCAGCCTTCAAATCCGCTTCCATCGCCTCTCGGTAC

11734.2contig

GCCAAGAAAGCCCGAAAGGTGAAGCATCTGGATGGGGAAGAGGATGGCAGCAGTGATCA
GAGTCAGGCTTCTGGAACCACAGGTGGCCGAAGGGTCTCAAAGGCCCTAATGGCCTCAAT
GGCCCGCAGGGCTTCAAGGGGTCCCATAGCCTTTTGGGCCCGCAGGGCATCAAGGACTCG
GTTGGCTGCTTGGGCCCGGAGAGCCTTGCTCTCCCTGAGATCACCTAAAGCCCGTAGGGGC
AAGGCTCGCCGTAGAGCTGCCAAGCTCCAGTCATCCCAAGAGCCTGAAGCACCACCACCT
CGGGATGTGGCCCTTTTGCAAGGGAGGGCAAATGATTTGGTGAAGTACCTTTTGGCTAAAG
ACCAGACGAAGATTCCCATCAAGCGCTCGGACATGCTGAAGGACATCATCAAAGAATACA
CTGATGTGTACCCCGAAATCATTGAACGAGCAGGCTATTCCTTGGAGAAGGTATTTGGGAT
TCAATTGAAGGAAATTGATAAGAATGACCACTTGTACATTCTTCTCAGC

11736.1contg

GAGGTCTCACTATGTTGCCCAGGCTGTTCTTGAACTCCTGGGATCAAGCAATCCACCCATG
TTGGTCTCCAAAAGTGCTGGGATCATAGGCGTGAGCCACCTCACCCAGCCACCAATTTTCA
ATCAGGAAGACTTTTTCCTTCTTCAAGAAGTGAAGGGTTTCCAGAGTATAGCTACACTATT
GCTTGCCTGAGGGTGACTACAAAATTGCTTGCTAAAAGGTTAGGATGGGTAAAGAATTAG
ATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCT
TGGAGTAAACTCCATTACTCATCCCAAGAAACCATATTATAAGTATCACTGATAATAAGAA
CAACAGGACCTTGTCATAAATTCTGGATAAGAGAAATAGTCTCTGGGTGTTTGXTCTTAAT
TGATAAAATTTACTTGTCCATCTTTTAGTTCAGAATCACAAAA

*FIG. 1B*

11736.2contig

AAGCGGAAATGAGAAAGGAGGGAAAATCATGTGGTATTGAGCGGAAAACTGCTGGATGA
CAGGGCTCAGTCCTGTTGGAGAACTCTGGGTGGTGCTGTAGAACAGGGCCACTCACAGTG
GGGTGCACAGACCAGCACGGCTCTGTGACCTGTTTGTTACAGGTCCATGATGAGGTAAAC
AATACACTGAGTATAAGGGTTGGTTTAGAAACTCTTACAGCAATTTGACAAAGTAATCTTC
TGTGCAGTGAATCTAAGAAAAAAATTGGGGCTGTATTTGTATGTTCCTTTTTTTCATTTCAT
GTTCTGAGTTACCTATTTTTATTGCATTTTACAAAAGCATCCTTCCATGAAGGACCGGAAGT
TAAAAACAAAGCAGGTCCTTTATCACAGCACTGTCGTAGAACACAGTTCAGAGTTATCCAC
CCAAGGAGCCAGGGAGCTGGGCTAAACCAAAGAATTTTGCTTTTGGTTAATCATCAGGTA
CTTGAGTTGGAATTGTTTTAATCCCATCATTACCAGGCTGGAXGTG

11739-1&2

CCGCGGCTCCTGTCCAGACCCTGACCCTCCCTCCCAAGGCTCAACCGTCCCCCAACAACCG
CCAGCCTTGTACTGATGTCGGCTGCGAGAGCCTGTGCTTAAGTAAGAATCAGGCCTTATTG
GAGACATTCAAGCAAAGGTTGGACAACTACTTTTCCAGAACAGAAAGGAAACTCATGCAT
CAGAAAAGGTGACTAATAAAGGTACCAGAAGAATATGGCTGCACAAATACCAGAATCTGA
TCAGATAAAACAGTTTAAGGAATTTCTGGGGACCTACAATAAACTTACAGAGACCTGCTTT
TTGGACTGTGTTAGAGACTTCACAACAAGAGAAGTAAAACCTGAAGAGACCACCTGTTCA
GAACATTGCTTACAGAAATATTTAAAAATGACACAAAGAATATCCATGAGATTTCAGGAA
TATCATATTCAGCAGAATGAAGCCCTGGCAGCCAAAGCAGGACTCCTTGGCCAACCACGA
TAGAGAAGTCCTGATGGATGAACTTTTGATGAAAGATTGCCAACAGCTGCTTTATTGGAAA
TGAGGACTCATCTGATAGAATCCCCTGAAAGCAGTAGCCACCATGTTCAACCATCTGTCAT
GACTGTTTGGCAAATGGAAACCGCTGGAGAAACAAAATTGCTATTTACCAGGAATAATCA
CAATAGAAGGTCTTATTGTTCAGTGAAATAATAAGATGCAACATTTGTTGAGGCCTTATGA
TTCAGCAGCTTGGTCACTTGATTAGAAAAATAAACCATTGTTTCTTCAATTGTGACTGTTA
ATTTTAAAGCAACTTATGTGTTCGATCATGTATGAGATAGAAAAATTTTTATTACTCAAAG
TAAAATAAATGGA

11740.1.contig

GAAAAAAAATATAAAACACACTTTTGCGAAAACGGTGGCCCTAAAAGAGGAAAAGAATTT
CACCAATATAAATCCAATTTTATGAAAACTGACAATTTAATCCAAGAATCACTTTTGTAAA
TGAAGCTAGCAAGTGATGATATGATAAAATAAACGTGGAGGAAATAAAAACACAAGACTT
GGCATAAGATATATCCACTTTTGATATTAAACTTGTGAAGCATATTCTTCGACAAATTGTG
AAAGCGTTCCTGATCTTGCTTGTTCTCCATTTCAAATAAGGAGGCATATCACATCCCAAGA
GTAACAGAAAAAGAAAAAAGACATTTTTGCATTTTGAGATGAACCAAAGACACAAAACAA
AACGAACAAAGTGTCATGTCTAATTCTAGCCTCTGAAATAAACCTTGAACATCTCCTACAA
GGCACCGTGATTTTTGTAATTCTAACCTGAAGAAATGTGATGACTTTTGTGGACATGAAAA
TCAGATGAGAAAACTGTGGTCTTTCCAAAGCCTGAACTCCCCTGAAAACCTTTGCA

*FIG. 1C*

11766.1.contig

CTGGGATCATTTCTCTTGATGTCATAAAAGACTCTTCTTCTTCCTCTTCATCCTCTTCTTCAT
CCTCTTCTGTACAGTGCTGCCGGGTACAACGGCTATCTTTGTCTTTATCCTGAGATGAAGAT
GATGCTTCTGTTTCTCCTACCATAACTGAAGAAATTTCGCTGGAAGTCGTTTGACTGGCTGT
TTCTCTGACTTCACCTTCTTTGTCAAACCTGAGTCTTTTTACCTCATGCCCCTCAGCTTCCAC
AGCATCTTCATCTGGATGTTTATTTTTCAAAGGGCTCACTGAGGAAACTTCTGATTCAGAG
GTCGAAGAGTCACTGTGATTTTTCTCCTCATTTTGCTGCAAATTTGCCTCTTTGCTGTCTGT
GCTCTCAGGCAACCCATTTGTTGTCATGGGGGCTGACAAAGAAACCTTTGGTCGATTAAGT
GGCCTGGGTGTCCCAGGCCCATTTATATTAGACCTCTCAGTATAGCTTGGTGAATTTCCAG
GAAACATAACACCATTCATTCGATTTAAACTATTGGAATTGGTTTT

11766.2.contig

GAGGGTTGGTGGTAGCGGCTTGGGGAGGTGCTCGCTCTGTCGGTCTTGCTCTCTCGCACGC
TTCCCCCGGCTCCCTTCGTTTCCCCCCCCCGGTCGCCTGCGTGCCGGAGTGTGTGCGAGGG
AGGGGGAGGGCGTCGGGGGGGTGGGGGGAGGCGTTCCGGTCCCCAAGAGACCCGCGGAG
GGAGGCGGAGGCTGTGAGGGACTCCGGGAAGCCATGGACGTCGAGAGGCTCCAGGAGGC
GCTGAAAGATTTTGAGAAGAGGGGGAAAAAGGAAGTTTGTCCTGTCCTGGATCAGTTTCT
TTGTCATGTAGCCAAGACTGGAGAAACAATGATTCAGTGGTCCCAATTTAAAGGCTATTTT
ATTTTCAAACTGGAGAAAGTGATGGATGATTTCAGAACTTCAGCTCCTGAGCCAAGAGGTC
CTCCCAACCCTAATGTCGA

11773.2.contig

AAGCAGGCGGCTCCCGCGCTCGCAGGGCCGTGCCACCTGCCCGCCCGCCCGCTCGCTCGCT
CGCCCGCCGCGCCGCGCTGCCGACCGCCAGCATGCTGCCGAGAGTGGGCTGCCCCGCGCT
GCCGXTGCCG

11775-1&2

ATCTCTTGTATGCCAAATATTTAATATAAATCTTTGAAACAAGTTCAGATGAAATAAAAAT
CAAAGTTTGCAAAAACGTGAAGATTAACTTAATTGTCAAATATTCCTCATTGCCCCAAATC
AGTATTTTTTTTATTTCTATGCAAAAGTATGCCTTCAAACTGCTTAAATGATATATGATATG
ATACACAAACCAGTTTTCAAATAGTAAAGCCAGTCATCTTGCAATTGTAAGAAATAGGTA
AAAGATTATAAGACACCTTACACACACACACACACACACACACGTGTGCACGCCAATGAC
AAAAAACAATTTGGCCTCTCCTAAAATAAGAACATGAAGACCCTTAATTGCTGCCAGGAG
GGAACACTGTGTCACCCCTCCCTACAATCCAGGTAGTTTCCTTTAATCCAATAGCAAATCT
GGGCATATTTGAGAGGAGTGATTCTGACAGCCACGTTGAAATCCTGTGGGGAACCATTCAT
GTCCACCCACTGGTGCCCTGAAAAAATGCCAATAATTTTTCGCTCCCACTTCTGCTGCTGtC
TCTTCCACATCCTCACATAGACCCCAGACCCGCTGGCCCCTGGCTGGGCATCGCATTGCTG
GTAGAGCAAGTCATAGGTCTCGTCTTTGACGTCACAGAAGCGATACACCAAATTGCCTGGT
CGGTCATTGTCATAACCAGAGA

*FIG. 1D*

11777.1&2.cons

CAGACGGGGTTTCACTATGTTGGCTAGGCTGGTCTTGAACTCCTGACTTCAGGTGATCTGC
CTGCCTTGGCCTCCCAAAGTGCTGGGATTACAGGCATAAGCCACTGCGCCCGGCTGATCTG
ATGGTTTCATAAGGCTTTTCCCCCTTTTGCTCAGCACTTCTCCTTCCTGCCGCCATGTGAAG
AAGGACATGTTTGCTTCCCCTTCCACCACGATTGTAAGTTGTTTCCTGAGGCCTCCCCGGCC
ATGCTGAACTGTGAGTCAATTAAACCTCTTTCCTTTATAAATTATCCAGTTTTGGGTATGTC
TTTATTAGTAGAATGAGAACAGACTAATACAACCCTTAAAGGAGACTGACGGAGAGGATT
CTTCCTGGATCCCAGCACTTCCTCTGAATGCTACTGACATTCTTCTTGAGGACTTTAAACTG
GGAGATAGAAAACAGATTCCATGGCTCAGCAGCCTGAGAGCAGGGAGGGAGCCAAGCTA
TAGATGACATGGGCAGCCTCCCCTGAGGCCAGGTGTGGCCGAACCTGGGCAGTGCTGCcAC
CCACCCCACCAGGGCCAAGTCCTGTCCTTGGAGAGCCAAGCCTCAATCACTGCTAGCCTCA
AGTGTCCCCAAGCCACAGTGGCTAGGGGGACTCAGGGAACAGTTCCCAGTCTGCCCTACTT
CTCTTACCTTTACCCCTCATACCTCCAAAGTAGACCATGTTCATGAGGTCCAAAGG 11779.2.contig AAGCGAGGAAGCCACTGCGGCTCCTGGCTGAAAAGCGGCGCCAGGCTCGGGAACAGAGG
GAACGCGAAGAACAGGAGCGGAAGCTGCAGGCTGAAAGGGACAAGCGAATGCGAGAGG
AGCAGCTGGCCCGGGAGGCTGAAGCCCGGGCTGAACGTGAGGCCGAGGCGCGGAGACGG
GAGGAGCAGGAGGCTCGAGAGAAGGCGCAGGCTGAGCAGGAGGAGCAGGAGCGACTGCA
GAAGCAGAAAGAGGAAGCCGAAGCCCGGTCCCGGGAAGAAGCTGAGCGCCAGCGCCAGG
AGCGGGAAAAGCACTTTCAGAAGGAGGAACAGGAGAGACAAGAGCGAAGAAAGCGGCTG
GAGGAGATAATGAAGAGGACTCGGAAATCAGAAGCCGCCGAAACCAAGAAGCAGGATGC
AAAGGAGACCGCAGCTAACAATTCCGGCCCAGACCCTTGTGAAAGCTGTAGAGACTCGGC
CCTCTGGGCTTCCAGAAAGGATTCTATTGCAGAAAGGAAGGAGCTXGGCCCCCCAXGGA 11781 & 37.cons CTCTGTGGAAAACTGATGAGGAATGAATTTACCATTACCCATGTTCTCATCCCCAAGCAAA
GTGCTGGGTCTGATTACTGCAACACAGAGAACGAAGAAGAACTTTTCCTCATACAGGATC
AGCAGGGCCTCATCACACTGGGCTGGATTCATACTCACCCCACACAGACCGCGTTTCTCTC
CAGTGTCGACCTACACACTCACTGCTCTTACCAGATGATGTTGCCAGAGTCAGTAGCCATT
GTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTG
TAGCTGCAGCCACGTGACTGTTGTGGACAGAGCAGTGACCATCACAGACCTTCGATGAGC
GTTTGAGTCCAACACCTTCCAAGAACAACAAAACCATATCAGTGTACTGTAGCCCCTTAAT
TTAAGCTTTCTAGAAAGCTTTGGAAGTTTTTGTAGATAGTAGAAAGGGGGGCATCACXTGA
GAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGA
AATTAAGTAGCTCAGAAATTAAGAAAGAATGGTATAATGAACCCCCATATACCCTTCCTTC
TGGATTCACCAATTGTTAACATTTTTTTCCTCTCAGCTATCCTTCTAATTTCTCTCTAATTTC
AATTTGTTTATATTTACCTCTGGGCTCAATAAGGGCATCTGTGCAGAAATTTGGAAGCCAT
TTAGAAAATCTTTTGGATTTTCCTGTGGTTTATGGCAATATGAATGGAGCTTATTACTGGG
GTGAGGGACAGCTTACTCCATTTGACCAGATTGTTTGGCTAACACATCCCGAAGAATGATT
TTGTCAGGAATTATTGTTATTTAATAAATATTTCAGGATATTTTTCCTCTACAATAAAGTAA
CAAT

CTCTGTGGAAAACTGATGAGGAATGAATTTACCATTACCCATGTTCTCATCCCCAAGCAAA
GTGCTGGGTCTGATTACTGCAACACAGAGAACGAAGAAGAACTTTTCCTCATACAGGATC
AGCAGGGCCTCATCACACTGGGCTGGATTCATACTCACCCCACACAGACCGCGTTTCTCTC
CAGTGTCGACCTACACACTCACTGCTCTTACCAGATGATGTTGCCAGAGTCAGTAGCCATT
GTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTG
TAGCTGCAGCCACGTGACTGTTGTGGACAGAGCAGTGACCATCACAGACCTTCGATGAGC
GTTTGAGTCCAACACCTTCCAAGAACAACAAAACCATATCAGTGTACTGTAGCCCCTTAAT
TTAAGCTTTCTAGAAAGCTTTGGAAGTTTTTGTAGATAGTAGAAAGGGGGGCATCACCTGA
GAAAGAGCTGATTTTGTATTTCAGGTTTGAAAAGAAATAACTGAACATATTTTTAGGCAA
GTCAGAAAGAGAACATGGTCACCCAAAAGCAACTGTAACTCAGAAATTAAGTTACTCAGA
AATTAAGTAGCTCAGAAATTAAGAAAGAATGGTATAATGAACCCCCATATACCCTTCCTTC
TGGATTCACCAATTGTTAACATTTTTTCCTCTCAGCTATCCTTCTAATTTCTCTCTAATTTC
AATTTGTTTATATTTACCTCTGGGCTCAATAAGGGCATCTGTGCAGAAATTTGGAAGCCAT
TTAGAAAATCTTTTGGATTTTCCTGTGGTTTATGGCAATATGAATGGAGCTTATTACTGGG
GTGAGGGACAGCTTACTCCATTTGACCAGATTGTTTGGCTAACACATCCCGAAGAATGATT
TTGTCAGGAATTATTGTTATTTAATAAATATTTCAGGATATTTTTCCTCTACAATAAAGTAA
CAATTA

11784-1 & 2

GGACGACAAGGCCATGGCGATATCGGATCCGAATTCAAGCCTTTGGAATTAAATAAACCT
GGAACAGGGAAGGTGAAAGTTGGAGTGAGATGTCTTCCATATCTATACCTTTGTGCACAGT
TGAATGGGAACTGTTTGGGTTTAGGGCATCTTAGAGTTGATTGATGGAAAAAGCAGACAG
GAACTGGTGGGAGGTCAAGTGGGGAAGTTGGTGAATGTGGAATAACTTACCTTTGTGCTC
CACTTAAACCAGATGTGTTGCAGCTTTCCTGACATGCAAGGATCTACTTTAATTCCACACT
CTCATTAATAAATTGAATAAAAGGGAATGTTTTGGCACCTGATATAATCTGCCAGGCTATG
TGACAGTAGGAAGGAATGGTTTCCCCTAACAAGCCCAATGCACTGGTCTGACTTTATAAAT
TATTTAATAAAATGAACTATTATC

11785.2.contig

GGCAGTGACATTCACCATCATGGGAACCACCTTCCCTTTTCTTCAGGATTCTCTGTAGTGG
AAGAGAGCACCCAGTGTTGGGCTGAAAACATCTGAAAGTAGGGAGAAGAACCTAAAATA
ATCAGTATCTCAGAGGGCTCTAAGGTGCCAAGAAGTCTCACTGGACATTTAAGTGCCAAC
AAAGGCATACTTTCGGAATCGCCAAGTCAAAACTTTCTAACTTCTGTCTCTCTCAGAGACA
AGTGAGACTCAAGAGTCTACTGCTTTAGTGGCAACTACAGAAAACTGGTGTTACCCAGAA
AAACAGGAGCAATTAGAAATGGTTCCAATATTTCAAAGCTCCGCAAACAGGATGTGCTTT
CCTTTGCCCATTTAGGGTTTCTTCTCTTTCCTTTCTCTTTATTAACCACT

*FIG. 1F*

11718-1&2 cons

TGCGCTGAAAACAACGGCCTCCTTTACTGTTAAAATGCAGCCACAGGTGCTTAGCCGTGGG
CATCTCAACCACCAGCCTCTGTGGGGGGCAGGTGGGCGTCCCTGTGGGCCTCTGGGCCCAC
GTCCAGCCTCTGTCCTCTGCCTTCCGTTCTTCGACAGTGTTCCCGGCATCCCTGGTCACTTG
GTACTTGGCGTGGGCCTCCTGTGCTGCTCCAGCAGCTCCTCCAGGXGGTCGGCCCGCTTCA
CCGCAGCCTCATGTTGTGTCCGGAGGCTGCTCACGGCCTCCTCCTTCCTCGCGAGGGCTGT
CTTCACCCTCCGGXGCACCTCCTCCAGCTCCAGCTGCTGGCGGGCCTGCAGCGTGGCCAGC
TCGGCCTTGGCCTGCCGCGTCTCCTCCTCARAGGCTGCCAGCCGGTCCTCGAACTCCTGGC
GGATCACCTGGGCCAGGTTGCTGCGCTCGCTAGAAAGCTGCTCGTTCACCGCCTGCGCATC
CTCCAGCGCCCGCTCCTTCTGCCGCACAAGGCCCTGCAGACGCAGATTCTCGCCCTCGGCcT
CCCCAAGCTGGCCCTTCAGCTCCGAGCACCGCTCCTGAAGCTTCCGCTCCGACTGCTCCAG
CTCGGAGAGCTCGGCCTCGTACTTGTCCCGTAAGCGCTTGATGCGGCTCTCGGCAGCCTTC
TCACTCTCCTCCTTGGCCAGCGCCATGTCGGCCTCCAGCCGGTGAATGACCAGCTCAATCT
CCTTGTCCCGGCCTTTCCGGATTTCTTCCCTCAGCTCCTGTTCCCGGTTCAGCAGCCACGCC
TCCTCCTTCCTGGTGCGGCCGGCCTCCCACGCCTGCCTCTCCAGCTCCAGCTGCTGCTTCAG
GGTATTCAGCTCCATCTGGCGGGCCTGCAGCGTGGCCA

13690.4

CAACTTATTACTTGAAATTATAATATAGCCTGTCCGTTTGCTGTTTCCAGGCTGTGATATAT
TTTCCTAGTGGTTTGACTTTAAAAATAAATAAGGTTTAATTTTCTCCCC

13693.1

TGCAAGTCACGGGAGTTTATTTATTTAATTTTTTTCCCCAGATGGAGACTCTGTCGCCCAGG
CTGGAGTGCAATGGTGTGATCTTGGCTCACTGCAACCTCCACCTCCTGGGTTCAAGCGATT
CTCCTGCCACAGCCTCCCGAGTAGCTGGGATTACAGGTGCCCGCCACCACACCCAGCTAAT
TTTTATATTTTTAGTAAAGACAGGGTTTCCCCATGTTGGCCAGGCTGGTCTTGAACTTCTGA
CCTCAGGTGATCCACCTGCCTCGGCCTCCCAAAGTGTTGGGATTACAGGCGTGAGCTACCC
GTGCCTGGCCAGCCACTGGAGTTTAAAGGACAGTCATGTTGGCTCCAGCCTAAGGCGGCA
TTTTCCCCCATCAGAAAGCCCGCGGCTCCTGTACCTCAAAATAGGGCACCTGTAAAGTCAG
TCAGTGAAGTCTCTGCTCTAACTGGCCACCCGGGGCCATTGGCNTCTGACACAGCCTTGCC
AGGANGCCTGCATCTGCAAAAGAAAAGTTCACTTCCTTTCCG

13694.1

CAGAGAATCTKAGAAAGATGTCGCGTTTTCTTTTAATGAATGAGAGAAGCCCATTTGTATC
CCTGAATCATTGAGAAAAGGCGGCGGTGGCGACAGCGGCGACCTAGGGATCGATCTGGAG
GGACTTGGGGAGCGTGCAGAGACCTCTAGCTCGAGCGCGAGGGACCTCCCGCCGGGATGC
CTGGGGAGCAGATGGACCCTACTGGAAGTCAGTTGGATTCAGATTTCTCTCAGCAAGATAC
TCCTTGCCTGATAATTGAAGATTCTCAGCCTGAAAGCCAGGTTCTAGAGGATGATTCTGGT
TCTCACTTCAGTATGCTATCTCGACACCTTCCTAATCTCCAGACGCACAAAGAAAATCCTG
TGTTGGATGTTGNGTCCAATCCTTGAACAAACAGCTGGAGAAGAACGAGGAGACCGGTAA
TAGTGGGTTCAATGAACATTTGAAAGAAAACCAGGTTGCAGACCCTG

GACTGTCCTGAACAAGGGACCTCTGACCAGAGAGCTGCAGGAGATGCAGAGTGGTGGCAG
GAGTGGAAGCCAAAGAACACCCACCTTCCTCCCTTGAAGGAGTAGAGCAACCATCAGAAG
ATACTGTTTTATTGCTCTGGTCAAACAAGTCTTCCTGAGTTGACAAAACCTCAGGCTCTGGT
GACTTCTGAATCTGCAGTCCACTTTCCATAAGTTCTTGTGCAGACAACTGTTCTTTTGCTTC
CATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGC
TGGACTGTTCTGCTATGGGGATATCTTCGTTGGACTGTTCTTCATGCTTAATTGCAGTATTA
GCATCCACATCAGACAGCCTGGTATAACCAGAGTTGGTGGTTACTGATTGTAGCTGCTCTT
TGTCCACTTCATATGGCACAAGTATTTTCCTCAACATCCTGGCTCTGGGAAG 13695.1

GAAATGTATATTTAATCATTCTCTTGAACGATCAGAACTCTRAAATCAGTTTTCTATAACAR
CATGTAATACAGTCACCGTGGCTCCAAGGTCCAGGAAGGCAGTGGTTAACACATGAAGAG
TGTGGGAAGGGGGCTGGAAACAAAGTATTCTTTTCCTTCAAAGCTTCATTCCTCAAGGCCT
CAATTCAAGCAGTCATTGTCCTTGCTTTCAAAAGTCTGTGTGTGCTTCATGGAAGGTATAT
GTTTGTTGCCTTAATTTGAATTGTGGCCAGGAAGGGTCTGGAGATCTAAATTCAGAGTAAG
AAAACCTGAGCTAGAACTCAGGCATTTCTCTTACAGAACTTGGCTTGCAGGGTAGAATGA
ANGGAAAGAAACTTAGAAGCTCAACAAGCTGAAGATAATCCCATCAGGCATTTCCCATAG
GCCTTGCAACTCTGTTCACTGAGAGATGTTATCCTG 13695.2

AGTCTGGAGTGAGCAAACAAGAGCAAGAAACAARRAGAAGCCAAAAGCAGAAGGCTCCA
ATATGAACAAGATAAATCTATCTTCAAAGACATATTAGAAGTTGGGAAAATAATTCATGT
GAACTAGACAAGTGTGTTAAGAGTGATAAGTAAAATGCACGTGGAGACAAGTGCATCCCC
AGATCTCAGGGACCTCCCCCTGCCTGTCACCTGGGGAGTGAGAGGACAGGATAGTGCATG
TTCTTTGTCTCTGAATTTTTAGTTATATGTGCTGTAATGTTGCTCTGAGGAAGCCCCTGGAA
AGTCTATCCCAACATATCCACATCTTATATTCCACAAATTAAGCTGTAGTATGTACCCTAA
GACGCTGCTAATTGACTGCCACTTCGCAACTCAGGGGCGGCTGCATTTTAGTAATGGGTCA
AATGATTCACTTTTTATGATGCTTCCCAAGGTGCCTTGGCTTCTCTTCCCAACTGACAAATG
CCCAAGTTGAGAAAAATGATCATAATTTTAGCATAAACCGAGCAATCGGCGACCCC 13697.1

TAGCTGTCTTCCTCACTCTTATGGCAATGACCCCATATCTTAATGGATTAAGATAATGAAA
GTGTATTTCTTACACTCTGTATCTATCACCAGAAGCTGAGGTGATAGCCCGCTTGTCATTGT
CATCCATATTCTGGGACTCAGGCGGGAACTTTCTGGAATATTGCCAGGGAGCATGGCAGA
GGGGCACAGTGCATTCTGGGGGAATGCACATTGGCTCAGCCTGGGTAATGAGTGATATAC
ATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGA
ATTGTAAGCTCCCATAATTCCCATGTGTTGTGGGAGGGACCTGGTG

ATCATGAGGATGTTACCAAAGGGATGGTACTAAACCATTTGTATTCGTCTGTTTTCACACT
GCTTTGAAGATACTACCTGAGACTGGGTAATTTATAAACAAAAGAGATTTAATTGACTCAC
AGTTCTGCATGGCTGAAGAGGCCTCAGGAAACTTACAGTCATGGTGGAAGGCAAAGGAGG
AGCAAGGCATGTCTTACATGTCAGTAGGAGAGAGAGCGAGAGCAGGAGAACCTGCCACTT
ATAAACCATTCAGATCTCATAACTCCCTATCATGAGAAAAACATGGAGGAAACCACCCTC
ATGATCCAATCACCTCCCGCCAGGTCCCTCCCTCGACACGTGGGGATTATAATTCAGGATT
AGAGGGACACAGAGACAAACCATATCATCATTCATGAGAAATCCACCCTCATAGTCCAAT
CAGCTCCTACCAGGCCCCACCTCCAACACTGGGGATTGCAATTCAACATGAGATTTGGATG
GGGACACAGATTCAAACCATATCATAC

13699.1&2

CATGGCCTTTCTCCTTAGAGGCCAGAGGTGCTGCCCTGGCTGGGAGTGAAGCTCCAGGCAC
TACCAGCTTTCCTGATTTTCCCGTTTGGTCCATGTGAAGAGCTACCACGAGCCCCAGCCTCA
CAGTGTCCACTCAAGGGCAGCTTGGTCCTCTTGTCCTGCAGAGGCAGGCTGGTGTGACCCT
GGGAACTTGACCCGGGAACAACAGGTGGCCCAGAGTGAGTGTGGCCTGGCCCCTCAACCT
AGTGTCCGTCCTCCTCTCTCCTGGAGCCAGTCTTGAGTTTAAAGGCATTAAGTGTTAGATA
CAAGCTCCTTGTGGCTGGAAAAACACCCCTCTGCTGATAAAGCTCAGGGGGCACTGAGGA
AGCAGAGGCCCCTTGGGGGTGCCCTCCTGAAGAGAGCGTCAGGCCATCAGCTCTGTCCCTC
TGGTGCTCCCACGTCTGTTCCTCACCCTCCATCTCTGGGAGCAGCTGCACCTGACTGGCCAC
GCGGGGGCAGTGGAGGCACAGGCTCAGGGTGGCCGGGCTACCTGGCACCCTATGGCTTAC
AAAGTAGAGTTGGCCCAGTTTCCTTCCACCTGAGGGGAGCACTCTGACTCCTAACAGTCTT
CCTTGCCCTGCCATCATCTGGGGTGGCTGGCTGTCAAGAAAGGCCGGGCATGCTTTCTAAA
CACAGCCACAGGAGGCTTGTAGGGCATCTTCCAGGTGGGGAAACAGTCTTAGATAAGTAA
GGTGACTTGCCTAAGGCCTCCCAGCACCCTTGATCTTGGAGTCTCACAGCAGACTGCATGT
SAACAACTGGAACCGAAAACATGCCTCAGTATAAAA

13703.3

CCAGAACCTCCTTCTCTTTGGAGAATGGGGAGGCCTCTTGGAGACACAGAGGGTTTCACCT
TGGATGACCTCTAGAGAAATTGCCCAAGAAGCCCACCTTCTGGTCCCAACCTGCAGACCCC
ACAGCAGTCAGTTGGTCAGGCCCTGCTGTAGAAGGTCACTTGGCTCCATTGCCTGCTTCCA
ACCAATGGGCAGGAGAGAAGGCCTTTATTTCTCGCCCACCCATTCTCCTGTACCAGCACCT
CCGTTTTCAGTCAGYGTTGTCCAGCAACGGTACCGTTTACACAGTCA

13705.1

TGCATGTAGTTTTATTTATGTGTTTTSGTCTGGAAAACCAAGTGTCCCAGCAGCATGACTGA
ACATCACTCACTTCCCCTACTTGATCTACAAGGCCAACGCCGAGAGCCCAGACCAGGATTC
CAAACACACTGCACGAGAATATTGTGGATCCGCTGTCAGGTAAGTGTCCGTCACTGACCCA
RACGCTGTTACGTGGCACATGACTGTACAGTGCCACGTAACAGCACTGTACTTTTCTCCCA
TGAACAGTTACCTGCCATGTATCTACATGATTCAGAACATTTTGAACAGTTAATTCTGACA
CTTGAATAATCCCATCAAAAACCGTAAAATCACTTTGATGTTTGTAACGACAACATAGCAT
CACTTTACGACAGAATCATCTGGAAAAACAGAACAACGAATACATACATCTTAAAAAATG
CTGGGGTGGGCCAGGCACAGCTTCACGCCTGTAATCCCAGCACTTTGGGAGGCTTAAGCG
GGTG

*FIG. 1I*

TGGGGCGGAAAGAAGCCAAGGCCAAGGAGCTGGTGCGGCAGCTGCAGCTGGAGGCCGAG
GAGCAGAGGAAGCAGAAGAAGCGGCAGAGTGTGTCGGGCCTGCACAGATACCTTCACTTG
CTGGATGGAAATGAAAATTACCCGTGTCTTGTGGATGCAGACGGTGATGTGATTTCCTTCC
CACCAATAACCAACAGTGAGAAGACAAAGGTTAAGAAAACGACTTCTGATTTGTTTTTGG
AAGTAACAAGTGCCACCAGTCTGCAGATTTGCAAGGATGTCATGGATGCCCTCATTCTGAA
AATGGCAAGAAATGAAAAAGTACACTTTAGAAAATAAAGAGGAAGGATCACTCTCAGAT
ACTGAAGCCGATGCAGTCTCTGGACAACTTCCAGATCCCACAACGAATCCCAGTGCTGGA
AAGGACGGGCCCTTCCTTCTGGTGGTGGAACANGTCCCGGTGGTGGATCTTGGAANGGAA
CCTGAANGTGGTGTACCCCGTCCAAGGCCGACCTTGGCCAC 13707.4

TCCCGCGCTCGCAGGGCNCGTGCCACCTGCCYGTCCGCCCGCTCGCTCGCTCGCCCGCCGC
GCCGCGCTGCCGACCGYCAGCATGCTGCCGAGAGTGGGCTGCCCCGCGCTGCCGCTGCCG
CCGCCGCCGCTGCTGCCGCTGCTGCCGCTGCTGCTGCTGC 13708.1&2

GGCGGGTAGGCATGGAACTGAGAAGAACGAAGAAGCTTTCAGACTACGTGGGGAAGAAT
GAAAAAACCAAAATTATCGCCAAGATTCAGCAAAGGGGACAGGGAGCTCCAGCCCGAGA
GCCTATTATTAGCAGTGAGGAGCAGAAGCAGCTGATGCTGTACTATCACAGAAGACAAGA
GGAGCTCAAGAGATTGGAAGAAAATGATGATGATGCCTATTTAAACTCACCATGGGCGGA
TAACACTGCTTTGAAAAGACATTTTCATGGAGTGAAAGACATAAAGTGGAGACCAAGATG
AAGTTCACCAGCTGATGACACTTCCAAAGAGATTAGCTCACCT 13709.1

TCTGAAGGTTAAATGTTTCATCTAAATAGGGATAATGRTAAACACCTATAGCATAGAGTTG
TTTGAGATTAAATGAGATAATACATGTAAAATTATGTGCCTGGCATACAGCAAGATTGTTG
TTGTTGTTGATGATGATGATGATGATGATAATATTTTTCTATCCCCAGTGCACAACTGCTTG
AACCTATTAGATAATCAATACATGTTTCTTGAACTGAGATCAATTTCCCCATGTTGTCTGAC
TGATGAAGCCCTACATTTTCTTCTAGAGGAGATGACATTTGAGCAAGATCTTAAAGAAAAT
CAGATGCCTTCACCTGACCACTGCTTGGTGATCCCATGGCACTTTGTACATCTCTCCATTAG
CTCTCATCTCACCAGCCCATCATTATTGTATGTGCTGCCTTCTGAAGCTTGCAGCTGGCTAC
CATCMGGTAGAATAAAAATCATCCTTTCATAAAATAGTGACCCTCCTTTTTTATTTGCATTT
CCCAAAGCCAAGCACCGTGGGANGGTAG 13709.2

TATGAAGAAGGGAAAAGAAGATAATTTGTGAAAGAAATGGGTCCAGTTACTAGTCTTTGA
AAAGGGTCAGTCTGTAGCTCTTCTTAATGAGAATAGGCAGCTTTCAGTTGCTCAGGGTCAG
ATTTCCTTAGTGGTGTATCTAATCACAGGAAACATCTGTGGTTCCCTCCAGTCTCTTTCTGG
GGGACTTGGGCCCACTTCTCATTTCATTTAATTAGAGGAAATAGAACTCAAAGTACAATTT
ACTGTTGTTTAACAATGCCACAAAGACATGGTTGGGAGCTATTTCTTGATTTGTGTAAAAT
GCTGTTTTTGTGTGCTCATAATGGTTCCAAAAATTGGGTGCTGGCCAAAGAGAGATACTGT
TACAGAAGCCAGCAAGAAGACCTCTGTTCATTCACACCCCCGGGGATATCAGGAATTGAC
TCCAGTGTGTGCAAATCCAGTTTGGCCTATCTTCT 13712.1&2

TGAGGGACTGATTGGTTTGCTCTCTGCTATTCAATTCCCCAAGCCCACTTGTTCCTGCAGCG
TCCTCCTTCTCATTCCCTTTAGTTGTACCCTCTCTTTCATCTGAGACCTTTCCTTCTTGATGT
CGCCTTTTCTTCTTCTTGCTTTTTCTGATGTTCTGCTCAGCATGTTCTGGGTGCTTCTCATCT
GCATCATTCCTTTCAGATGCTGTAGCTTCTTCCTCCTCTTTCTGCCTCCTTTTCTTTTTCTTTT
TTTTGGGGGGCTTGCTCTCTGACTGCAGTTGAGGGGCCCCAGGGTCCTGGCCTTTGAGACG
AGCCAGGAAGGCCTGCTCCTGGGCCTCTAGGCGAGCAAGCTTGGCCTTCATTGTGATCCCA
AGACGGGCAGCCTTGTGTGCTGTTCGCCCCTCACAGGCTTGGAGCAGCATCTCATCAGTCA
GAATCTTTGGGGACTTGGACCCCTGGTTGTCGTCATCACTGCAGCTCTCCAAGTCTTTGTTT
GGCTTCTCTCCACCTGAAGTCAATGTAGCCATCTTCACAAACTTCTGATACAGCAAGTTGG
GCTTGGGATGATTATAACGGGTGGTCTCCTTAGAAAGGCTCCTTATCTGTACTCCATCCTG
CCCAGTTTCCACTACCAAGTTGGCCGCAGTCTTGTTGAAGAGCTCATTCCACCAGTGGTTT
GTGAACTCCTTGGCAGGGTCATGTCCTACCCCATGAGTGTCTTGCTTCAGYGTCACCCTGA
GAGCCTGAGTGATACCATTCTCCTTCCG 13714.1&2

GACAACATGAAATAAATCCTAGAGGACAAAATTAAACTCAATAGAGTGTAGTCTAGTTAA
AAACTCGAAAAATGAGCAAGTCTGGTGGGAGTGGAGGAAGGGCTATACTATAAATCCAAG
TGGGCCTCCTGATCTTAACAAGCCATGCTCATTATACACATCTCTGAACTGGACATACCAC
CTTTACGCAGGAAACAGGGCTTGGAACTTCTAAGGGAAATTAACATGCACCACCCACATC
TAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATAT
CTATACCTTTGTGCACAGTTGAATGGGAACTGTTTGGGTTTAGGGCATCTTAGAGTTGATT
GATGGAAAAAGCAGACAGGAACTGGTGGGAGGTCAAGTGGGGAAGTTGGTGAATGTGGA
ATAACTTACCTTTGTGCTCCACTTAAACCAGATGTGTTGCAGCTTTCCTGACATGCAAGGA
TCTACTTTAATTCCACACTCTCATTAATAAATTGAATAAAAGGGAATGTTTTGGCACCTGA
TATAATCTGCCAGGCTATGTGACAGTAGGAAGGAATGGTTTCCCCTAACAAGCCCAATGC
ACTGGTCTGACTTTATAAATTATTTAATAAAATGAACTATTATC

AAACTGGACCTGCAACAGGGACATGAATTTACTGCARGGTCTGAGCAAGCTCAGCCCCTCT
ACCTCAGGGCCCCACAGCCATGACTACCTCCCCCAGGAGCGGGAGGGTGAAGGGGGCCTG
TCTCTGCAAGTGGAGCCAGAGTGGAGGAATGAGCTCTGAAGACACAGCACCCAGCCTTCT
CGCACCAGCCAAGCCTTAACTGCCTGCCTGACCCTGAACCAGAACCCAGCTGAACTGCCCC
TCCAAGGGACAGGAAGGCTGGGGGAGGGAGTTTACAACCCAAGCCATTCCACCCCCTCCC
CTGCTGGGGAGAATGACACATCAAGCTGCTAACAATTGGGGGAAGGGGAAGGAAGAAAA
CTCTGAAAACAAAATCTTGT 13722.3

CATGCGTTTCACCACTGTTGGCCAGGCTGGTCTCGAACTCCTGGCCTCAAGCAATCCACCC
GCCTCAGCCTCCAAAAGTGCTGGGATTACAGATGTGAGCCATGGCACCATGCCAAAAGGC
TATATTCCTGGCTCTGTGTTTCCGAGACTGCTTTTAATCCCAACTTCTCTACATTTAGATTA
AAAAATATTTTATTCATGGTCAATCTGGAACATAATTACTGCATCTTAAGTTTCCACTGAT
GTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCT
GATAGGTTCTTTATTTTTTCAAAATATATTTGCCATGGGATGCTAATTTGCAATAAGGCGC
ATAATGAGAATACCCCAAACTGGA 13722.4

GTTGGACCCCCAGGGACTGGAAAGACACTTCTTGCCCGAGCTGTGGCGGGAGAAGCTGAT
GTTCCTTTTTATTATGCTTCTGGATCCGAATTTGATGAGATGTTTGTGGGTGTGGGAGCCAG
CCGTATCAGAAATCTTTTTAGGGAAGCAAAGGCGAATGCTCCTTGTGTTATATTTATTGAT
GAATTAGATTCTGTTGGTGGGAAGAGAATTGAATCTCCAATGCATCCATATTCAAGGCAGA
CCATAAATCAACTTCTTGCTGAAATGGATGGTTTTAAACCCAATGAAGGAGTTATCATAAT
AGGAGCCACAAACTTCCCAGAGGCATTAGATAATGCCTTAATACCGTCCTGGTCGTTTTGA
CATGCAAGTTACAGTTCCAAGGCCAGATGTAAAAGGTCGAACAGAAATTTTGAAATGGTA
TCTCAATAAAATAAAGTTTGATCAATCCCGTTGATCCAGAAATTATAGCCTCGAGGTACTG
GTGGCTTTTCCGGAAGCAGAGTTGGGAGAATCTT 13724-13698-13748

GCCTACAACATCCAGAAAGAGTCTACCCTGCACCTGGTGCTSCGTCTCAGAGGTGGGATGC
AGATCTTCGTGAAGACCCTGACTGGTAAGACCATCACTCTCGAAGTGGAGCCGAGTGACA
CCATYGAGAACGTCAAAGCAAAGATCCARGACAAGGAAGGCRTYCCTCCTGACCAGCAGA
GGTTGATCTTTGCCGGAAAGCAGCTGGAAGATGGDCGCACCCTGTCTGACTACAACATCC
AGAAAGAGTCYACCCTGCACCTGGTGCTCCGTCTCAGAGGTGGGATGCARATCTTCGTGA
AGACCCTGACTGGTAAGACCATCACCCTCGAGGTGGAGCCCAGTGACACCATCGAGAATG
TCAAGGCAAAGATCCAAGATAAGGAAGGCATCCCTCCTGATCAGCAGAGGTTGATCTTTG
CTGGGAAACAGCTGGAAGATGGACGCACCCTGTCTGACTACAACATCCAGAAAGAGTCCA
CTCTGCACTTGGTCCTGCGCTTGAGGGGGGGTGTCTAAGTTTCCCCTTTTAAGGTTTCMAC
AAATTTCATTGCACTTTCCTTTCAATAAAGTTGTTGCATTCCC

GAACTGGGCCCTGAGCCCAAGTCATGCCTTGTGTCCGCATCTGCCGTGTCACCTCTGTKCC
TGCCCCTCACCCCTCCCTCCTGGTCTTCTGAGCCAGCACCATCTCCAAATAGCCTATTCCTT
CCTGCAAATCACACACACATGCGGGCCACACATACCTGCTGCCCTGGAGATGGGGAAGTA
GGAGAGATGAATAGAGGCCCATACATTGTACAGAAGGAGGGGCAGGTGCAGATAAAAGC
AGCAGACCCAGCGGCAGCTGAGGTGCATGGAGCACGGTTGGGGCCGGCATTGGGCTGAGC
ACCTGATGGGCCTCATCTCGTGAATCCTCGAGGCAGCGCCACAGCAGAGGAGTTAAGTGG
CACCTGGGCCGAGCAGAGCAGGAGACTGAGGGTCAGAGTGGAGGCTAAGCTGCCCTGGA
ACTCCTCAATCTTGCCTGCCCCCTAGTATGAAGCCCCCTTCCTGCCCCTACAATTCCTGA 13732.1

ATGGATCTTACTTTGCCACCCAGGTTGGAGTGCAGTGCTGCAATCTTGGCTCACTGCAGCC
TTAACCTCCCAGGCTCAAGCTATCCTCCTGCCAAAGCCTTCCACATAGCTGGGACTACAGG
TACACNGCCACCACACCCAGCTAAAATTTTTGTATTTTTTGTAGAGACGGGATCTCGCCAC
GTTGCCCAGGCTGGTCCCATCCTGACCTCAAGCAGATCTGCCCACCTCAGCCCCCCAACGT
GCTAGGATTACAGGCGTGAGCCACCGCACCCAGCCTTTGTTTTGCTTTTAATGGAATCACC
AGTTCCCCTCCGTGTCTCAGCAGCAGCTGTGAGAAATGCTTTGCATCTGTGACCTTTATGA
AGGGGAACTTCCATGCTGAATGAGGGTAGGATTACATGCTCCTGTTTCCCGGGGGTCAAG
AAAGCCTCAGACTCCAGCATGATAAGCAGGGTGAG 13732.2

ATAGGGGCTTTAAGGAGGGAATTCAGGTTCAATGAGGTCGTAAGGCCAGGGCTCTTATCC
AGTAAGACTGGGGTCCTTAGATGAGAAAGAGACACCCGAGGTCCTTCTCTCTGCCGTGTG
AGGATGCATCAAGAAGGCGGCCGTCTGCAAGCGAAGGAGAGGCCGCACCAGAAACCGAC
ACCTTCATCTTGGACTTGCAGCCTCTAGAACTGAGAAAATAACTGTCTGTTGGTTAAGCCA
CCCAGTTTGTAGTATTCTCTTATGGCTTCCTAAGCAGACTAACAAACAAACACCCAAAATT
AACTGATGGCTTCGCTGTCTTCTGTAAAAATTGCTATGAGAGAACTTTTCACTCACTGTTTT
GCAGTTTCTCCCTCAGTCCCTGGTTCTTTCTTCTCACATAATCCCAATTTCAATTTATAGTTC
ATGGCCCAGGCAGAGTCATTCATCACGGCATCTCCTGAGCTAAACCAGCACCTGCTCTGCT
CACTTCTTGACTGGCTGCTCATCATCAGCCCTCTTGCAGAGATTTCATTTCCTCCCGTGCCA
GGTACTTCACGCACCAAGCTCA

GGATAATGAAGTTGTTTTATTTAGCTTGGACAAAAAGGCATATTCCTCTATTTTCTTATACA
ACAAATATCCCCAAAATAAAGCAAGCATATATATCTTGAATGTGTAATAATCCAGTGATA
AACAAGAGCAGTACTTTAAAAGAAAAAAAAATATGTATTTCTGTCAGGTTAAAATGAGAA
TCAAAACCATTTACTCTGCTAACTCATTATTTTTTGCTTTCTTTTTGGTTAAGAGAGGCAAT
GCAATACACTGAAAAAGGTTTTTATCTTATCTGGCATTGGAATTAGACATATTCAAACCCC
AGCCCCCATTTCCAAACTTTAAGACCACAAACAAGTAATTTACTTTTCTGAACATTGGTTTT
TTCTGGAAAATGGGAATTATAAAATAGACTTTGCAGACTCTTATGAGATTAAATAAGATA
ATGTATGAAATTCTTTCTTCTTTTTTACTTCTTTTTCCTTTTTGAGATGGAGTCTCACCCCGT
CACCCAGGCTGGAGTACAGTG 13735.2

CCACTGCACTCCAGCCTGGGTGACGGAGTGAGACTCTGTCTCAAAAAAACAAACAAACAA
ACAAACAAAAAACTGAAAAGGAAATAGAGTTCCTCTTTCCTCATATATGAATATATTATTT
CAACAGATTGTTGATCACCTACCATATGCTTGGTATTGTTCTAATTGCTGGGGATACAGCA
AGAGGTTCTGCAGAACTTCATGGAGCATGAAAGTAAATAAACAAAGTTAATTTCAAGGCC
AGGCATGGTTGCTCACACCTTTAGTCCCAGCACTTTGGGAGGCTGAGGCAGGTGGATCACT
TGGGCCCAGGAGTTCAAGGCTGCAGTGAGCCAAGATTGTGCCACTACTCTCCAGGCTGGG
CAACAGAGCAAGACCCTGTCTCAGGGGGAACAAAAAGTTAATTTCAGATTTTGTTAAGTG
CTGTAAAGGAAGTAAATAGGTTGATATTCAAGAGAGCACCTGAAGGCCAGGCGTGGTGGC
TCACGCCTGTGGTCTAACGCTTTGGGAAGCCCGAGCGGGCGGATCACAAGGTCAGGAGAA
TTTTGGCCAGGCATGGTG 13736.1

AGAATCCATTTATTGGGTTTTAAACTAGTTACACAACTGAAATCAGTTTGGCACTACTTTA
TACAGGGATTACGCCTGTGTATGCCGACACTTAAATACTGTACCAGGACCACTGCTGTGCT
TAGGTCTGTATTCAGTCATTCAGCATGTAGATACTAAAAATATACTGTAGTGTTCCTTTAA
GGAAGACTGTACAGGGTGTGTTGCAAGATGACATTCACCAATTTGTGAATTATTTCAACCC
AGAAGATACCTTTCACTCTATAAACTTGTCATAGGCAAACATGTGGTGTTAGCATTGAGAG
ATGCACACAAAATGTTACATAAAAGTTCAGACATTCTAATGATAAGTGAACTGAAAAAA
AAAAAAACCCCACATCTCAATTTTTGTAACAAGATAAAGAAAATAATTTAAAAACACAAA
AAATGGCATTCAGTGGGTACAAAGCC 13737.1&2

CAAATATTTAATATAAATCTTTGAAACAAGTTCAGAKGAAATAAAAATCAAAGTTTGCAA
AAACGTGAAGATTAACTTAATTGTCAAATATTCCTCATTGCCCCAAATCAGTATTTTTTTA
TTTCTATGCAAAAGTATGCCTTCAAACTGCTTAAATGATATATGATATGATACACAAACCA
GTTTTCAAATAGTAAAGCCAGTCATCTTGCAATTGTAAGAAATAGGTAAAAGATTATAAG
ACACCTTACACACACACACACACACACACACACGTGTGCACcGCCAATGACAAAAAAC
AATTTGGCCTCTCCTAAAATAAGAACATGAAGACCCTTAATTGCTGCCAGGAGGGAACAC
TGTGTCACCCCTCCCTACAATCCAGGTAGTTTCCTTTAATCCAATAGCAAATCTGGGCATAT
TTGAGAGGAGTGATTCTGACAGCCACSGTTGAAATCCTGTGGGGAACCATTCATGTCCACC
CACTGGTGCCCTGAAAAAATGCCAATAATTTTTCGCTCCCACTTCTGCTGCTGTCTCTTCCA
CATCCTCACATAGACCCCAGACCCGCTGGCCCCTGGCTGGGCATCGCATTGCTGGTAGAGC
AAGTCATAGGTCTCGTCTTTGACGTCACAGAAGCGATACACCAAATTGCCTGGTCGGTCAT
TGTCATAACCAG

TTTGACTTTAGTAGGGGTCTGAACTATTTATTTTACTTTGCCMGTAATATTTARACCYTATA
TATCTTTCATTATGCCATCTTATCTTCTAATGBCAAGGGAACAGWTGCTAAMCTGGCTTCT
GCATTWATCACATTAAAAATGGCTTTCTTGGAAAATCTTCTTGATATGAATAAAGGATCTT
TTAVAGCCATCATTTAAAGCMGGNTTCTCTCCAACACGAGTCTGCTSASGGGGGGKGAGCT
GTGAACTCTGGCTGAAGGCTTTCCCATACACACTGCAATGACMTGGTTTCTGACCAGBGTG
AGTTA 13738.2

AGAGAAGCCCCATAAATGCAATCAGTGTGGGAAGGCCTTCAGTCAGAGCTCAAGCCTTTT
CCTCCATCATCGGGTTCATACTGGAGAGAAACCCTATGTATGTAATGAATGCGGCAGAGCC
TTTGGTTTTAACTCTCATCTTACTGAACACGTAAGGATTCACACAGGAGAAAAACCCTATG
TTTGTAATGAGTGCGGCAAAGCCTTTCGTCGGAGTTCCACTCTTGTTCAGCATCGAAGAGT
TCACACTGGGGAGAAGCCCTACCAGTGCGTTGAATGTGGGAAAGCTTTCAGCCAGAGCTC
CCAGCTCACCCTACATCAGCCGAGTTCACACTGGAGAGAAGCCCTATGACTGTGGTGACTG
TGGGAAGGCCTTCAGCCGGAGGTCAACCCTCATTCAGCATCAGAAAGTTCACAGCGGAGA
GACTCGTAAGTGCAGAAAACATGGTCCAGCCTTTGTTCATGGCTCCAGCCTCACAGCAGAT
GGACAGATTCCCACTGGAGAGAAGCACGGCAGAACCTTTAACCATGGTGCAAATCTCATT
CTGCGCTGGACAGTTC 13739.1&2

GAGACAGGGTCTCACTTTGTCACCCAGGCTGGAATGCAGTGGTGCGATCTTACGTAGCTCA
CTGCAGCCCTGACCTCCTGGACTCAAACAATTCTCCTGCCTCAGCCCTGCAAGTAGCTGGG
ACTGTGGGTGCATGCCACCATGCCTGGCTAACTTTTGTAGTTTTTGTAAAGATGGGGTTTT
GCCATGTTGCACATGCTGGTCTTGAACTCCTGAGCTCAAACGATCTGCCCACCTCGGCCTC
CCAGAATGTTGGGATTACAGGGGTAAACCACCACGCCTGGCCCCATTAGGGTATTCTTAGC
ATCCACTTGCTCACTGAGATTAATCATAAGAGATGATAAGCACTGGAAGAAAAAATTTTT
ACTAGGCTTTGGATATTTTTTTCCTTTTTCAGCTTTATACAGAGGATTGGATCTTTAGTTTTC
CTTTAACTGATAATAAAACATTGAAAGGAAATAAGTTTACCTGAGATTCACAGAGATAAC
CGGCATCACTCCCTTGCTCAATTCCAGTCTTTACCACATCAATTATTTTCAGAGGTGCAGGA
TAAAGGCCTTTAGTCTGCTTTCGCACTTTTTCTTCCACTTTTTTGTAAACCTGTTGCCTGACA
AATGGAATTGACAGCGTATGCCATGACTATTCCATTTGTCAGGCATACGCTGTCAATTTTT
CCACCAATCCCTTGTCTCTCTTTGGAGAGATCTTCTTATCAGCTAGTCCTTTGGCAAAAGTA
ATTGCAACTTCTTCTAGGTATTCTATTGTCCGTTCCACTGGTGGAACCCCTGGGACCAGGA
CTAAAACCTCCAG 13741.1

ATCTCATATATATATTTCTTCCTGACTTTATTTGCTTGCTTCTGNCACGCATTTAAAATATC
ACAGAGACCAAAATAGAGCGGCTTTCTGGTGGAACGCATGGCAGTCACAGGACAAAATAC
AAAACTAGGGGGCTCTGTCTTCTCATACATCATACAATTTTCAAGTATTTTTTTTATGTACA
AAGAGCTACTCTATCTGAAAAAAAATTAAAAAATAAATGAGACAAGATAGTTTATGCATC
CTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACA
GGGCAAGTGCCAGGGTAGGTGGGGACCAGTGGAGACAGGAACCAGCAACATACTTTGGC
CTGGAAGATAAGGAGAAAGTCTCAGAAACACACTGGTGGGAAGCAATCCCACNGGCCGT
GCCCCANGAGCTTCCCACCTGCTGCTGGCTCCCTGGGTGGCTTTGGGAACAGCTTGGGCAG
GCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAA
AATTATGATTTATAGCCTTCTCAAATACCTGCCATACTTGATATCTCAACCAGAGCTAATTT
TACCTCTTTACAAATTAAATAAGCAAGTAACTGGATCCACAATTTATAATACCTGTCAATT
TTTTCTGTATTAAACCTCTATCATAGTTTAAGCCTATTAGGGTACTTAATCCTTACAAATAA
ACAGGTTTAAAATCACCTCAATAGGCAACTGCCCTTCTGGTTTTCTTCTTTGACTAAACAAT
CTGAATGCTTAAGATTTTCCACTTTGGGTGCTAGCAGTACACAGTGTTACACTCTGTATTCC
AGACTTCTTAAATTATAGAAAAAGGAATGTACACTTTTTGTATTCTTTCTGAGCAGGGCCG
GGAGGCAACATCATCTACCATGGTAGGGACTTGTATGCATGGACTACTTTA 14351.1

ACTCTGTCGCCCAGGCTGGAGCCCABTGGMGCGATCTCGACTCCCTGCAAGCTMCGCCTC
ACAGGWTCATGCCATTCTCCTGCCTCAGCATCTGGAGTAGCTGGGACTACAGGCGCCAGC
CACCATGCCCAGCTAATTTTT 14351.2

ACCTTAAAGACATAGGAGAATTTATACTGGGAGAGAAAGCTTACAAATGTAAGGTTTCTG
ACAAGACTTGGGAGTGATTCACACCTGGAACAACATACTGGACTTCACACTGGABAGAAA
CCTTACAAGTGTAATGAGTGTGGCAAAGCCTTTGGCAAGCAGTCAACACTTATTCACCATC
AGGCAATTCA 14354.2

AGTCAGGATCATGATGGCTCAGTTTCCCACAGCGATGAATGGAGGGCCAAATATGTGGGC
TATTACATCTGAAGAACGTACTAAGCATGATAAACAGTTTGATAACCTCAAACCTTCAGGA
GGTTACATAACAGGTGATCAAGCCCGTACTTTTTTCCTACAGTCAGGTCTGCCGGCCCCGG
TTTTAGCTGAAATATGGGCCTTATCAGATCTGAACAAGGATGGGAAGATGGACCAGCAAG
AGTTCTCTATAGCTATGAAACTCATCAAGTTAAAGTTGCAGGGCCAACAGCTGCCTGTAGT
CCTCCCTCCTATCATGAAACAACCCCCTATGTTCTCTCCACTAATCTCTGCTCGTTTTGGGA
TGGGAAGCATGCCCAATCTGTCCATTCATCAGCCATTGCCTCCAGTTGCACCTATAGCAAC
ACCCTTGTCTTCTGCTACTTCAGGGACCAGTATTCCTCCCTAATGATGCCTGCT 14354.1

CTTTCGATTTCCTTCAATTTGTCACGTTTGATTTTATGAAGTTGTTCAAGGGCTAACTGCTG
TGTATTATAGCTTTCTCTGAGTTCCTTCAGCTGATTGTTAAATGAATCCATTTCTGAGAGCT
TAGATGCAGTTTCTTTTTCAAGAGCATCTAATTGTTCTTTAAGTCTTTGGCATAATTCTTCC
TTTTCTGATGACTTTCTATGAAGTAAACTGATCCCTGAATCAGGTGTGTTACTGAGCTGCAT
GTTTTTAATTCTTTCGTTTAATAGCTGCTTCTCAGGGACCAGATAGATAAGCTTATTTTGAT
ATTCCTTAAGCTCTTGGTGAAGTTGTTCGATTTCCATAATTTCCAGGTCACACTGGTTATCC
CAAACTTCT

GTGGAGGTGAAACGGAGGCAAGAAAGGGGGCTACCTCAGGAGCGAGGGACAAAGGGGGC
GTGAGGCACCTAGGCCGCGGCACCCCGGCGACAGGAAGCCGTCCTGAACCGGGCTACCGG
GTAGGGGAAGGGCCCGCGTAGTCCTCGCAGGGCCCCAGAGCTGGAGTCGGCTCCACAGCC
CCGGGCCGTCGGCTTCTCACTTCCTGGACCTCCCCGGCGCCCGGGCCTGAGGACTGGCTCG
GCGGAGGGAGAAGAGGAAACAGACTTGAGCAGCTCCCCGTTGTCTCGCAACTCCACTGCC
GAGGAACTCTCATTTCTTCCCTCGCTCCTTCACCCCCCACCTCATGTAGAAAGGTGCTGAA
GCGTCCGGAGGGAAGAAGAACCTGGGCTACCGTCCTGGCCTTCCCMCCCCCTTCCCGGGG
CGCTTTGGTGGGCGTGGAGTTGGGGTTGGGGGGGTGGGTGGGGGTTCTTTTTTGGAGTGCT
GGGGAACTTTTTTCCCTTCTTCAGGTCAGGGGAAAGGGAATGCCCAATTCAGAGAGACAT
GGGGGCAAGAAGGACGGGAGTGGAGGAGCTTCTGGAACTTTGCAGCCGTCATCGGGAGG
CGGCAGCTCTAACAGCAGAGAGCGTCACCGCTTGGTATCGAAGCACAAGCGGCATAAGTC
CAAACACTCCAAAGACATGGGGTTGGTGACCCCCGAAGCAGCATCCCTGGGCACAGTTAT
CAAACCTTTGGTGGAGTATGATGATATCAGCTCTGATTCCGACACCTTCTCCGATGACATG
GCCTTCAAACTAGACCGAAGGGAGAACGACGAACGTCGTGGATCAGATCGGAGCGACCGC
CTGCACAAACATCGTCACCACCAGCACAGGCGTTCCCGGGACTTACTAAAAGCTAAACAG
ACCG 16432-1

GACATGTTTGCCTGCAGGGGACCAGAGACAATGGGATTAGCCAGTGCTCACTGTTCTTTAT
GCTTCCAGAGAGGATGGGGACAGCTCTCAGGTCAGAATCCAGGCTGAGAAGGCCATGCTG
GTTGGGGGCCCCCGGAAGCACGGTCCGGATCCTCCCTGGCATCAGCGTAGACCCGCTGCTC
AGGCTTGGGGTACCAAACTCATGCTCTGTACTGTTTTGGCCCCATGCGGTGAGAGGAAAAC
CTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGG
CCTCTGGAGGCTCGTGGCCTAAGGCAGGGCTCCGTAAGGCTGATCGGCTGAACTGGGTGG
GGTGAGGGTTTCTGACCCTTCGCTTCCCATCCCATAACCGCTGTCAATGAGCTCACACTGT
GGTCA 16432-2

GATGGCATGGTCGTTGCTAATGTGCCTGCTGGGATGGAGCACTTCCTCCTGTGAGCCCAGG
GGACCCGCCTGTCCCTGGAGCTTGGGGCAAGGAGGGAAGAGTGATACCAGGAAGGTGGG
GCTGCAGCCAGGGGCCAGAGTCAGTTCAGGGAGTGGTCCTCGGCCCTCAAAGCTCCTCCG
GGGACTGCTCAGGAGTGATGGTGCCCTGGAGTTTGCCCCAACTTCCCTGGCCACCCTGGAA
GGTGCCTGGCTGCTCCAGGCCTCTAGGCTGGGCTGATGGGTTTCTCCAGGACACAAGTATC
ATTAAAGCCACCCTCTCCTCAGCTTGTCAGGCCGCACATGTGGGACAGGCTGTGCTCACAA
CCCCCTCGCCTGCCCTGCCCTCCATCAGGAGGAGCCAGTGGAACCTTCGGAAAGCTCCCAG
CATCTCAGCAGCCCTCAAAAGTCGTCCTGGGGCAAGCTCTGGTTCTCCTGACTGGAGGTCA
TCTGGGCTTGGCCTGCTCTCTCTCGC 17184.3

TAAAAAAGTGTAACAAAGGTTTATTTAGACTTTCTTCATGCCCCCAGATCCAGGATGTCTA
TGTAAACCGTTATCTTACAAAGAAAGCACAATATTTGGTATAAACTAAGTCAGTGACTTGC
TTAACTGAAATAGCGTCCATCCAAAAGTGGGTTTAAGGTAAAACTACCTGACGATATTGGC
GGGGATCCTGCAGTTTGGACTGCTTGCCGGGTTTGTCCAGGGTTCCGGGTCTGTTCTTGGC
ACTCATGGGGACAGGCATCCTGCTCGTCTGTGGGGCCCCGCTGGAGCCCTTACGTGAAGCT
GAAGGTATCGACCSTAGGGGGCTCTAGGGCAGTGGGACCTTCATCCGGAACTAACAAGGG
TCGGGGAGAGGCCTCTTGGGCTATGTGGG

CAAGCGTTCCTTTATGGATGTAAATTCAAACAGTCATGCTGAGCCATCCCGGGCTGACAGT
CACGTTWAAGACACTAGGTCGGGCGCCACAGTGCCACCCAAGGAGAAGAAGAATTTGGA
ATTTTTCCATGAAGATGTACGGAAATCTGATGTTGAATATGAAAATGGCCCCCAAATGGAA
TTCCAAAAGGTTACCACAGGGGCTGTAAGACCTAGTGACCCTCCTAAGTGGGAAAGAGGA
ATGGAGAATAGTATTTCTGATGCATCAAGAACATCAGAATATAAAACTGAGATCATAATG
AAGGAAAATTCCATATCCAATATGAGTTTACTCAGAGACAGTAGAAACTATTCCCAGG

17185.1

TAGGAATAACAAATGTTTATTCAGAAATGGATAAGTAATACATAATCACCCTTCATCTCTT
AATGCCCCTTCCTCTCCTTCTGCACAGGAGACACAGATGGGTAACATAGAGGCATGGGAA
GTGGAGGAGGACACAGGACTAGCCCACCACCTTCTCTTCCCGGTCTCCCAAGATGACTGCT
TATAGAGTGGAGGAGGCAAACAGGTCCCCTCAATGTACCAGATGGTCACCTATAGCACCA
GCTCCAGATGGCCACGTGGTTGCAGCTGGACTCAATGAAACTCTGTGACAACCAGAAGAT
ACCTGCTTTGGGATGAGAGGGAGGATAAAGCCATGCAGGGAGGATATTTACCATCCCTAC
CCTAAGCACAGTGCAAGCAGTGAGCCCCCGGCTCCCAGTACCTGAAAAACCAAGGCCTAC
TGNCTTTTGGATGCTCTCTTGGGCCACG

17188.2

AAGCCTCCTGCCCTGGAAATCTGGAGCCCCTTGGAGCTGAGCTGGACGGGGCAGGGAGGG
GCTGAGAGGCAAGACCGTCTCCCTCCTGCTGCAGCTGCTTCCCCAGCAGCCACTGCTGGGC
ACAGCAGAAACGCCAGCAGAGAAAATGGGAGCCGAGAGTCCTTAGCCCTGGAGCTGAGG
CTGCCTCTGGGCTGACCCGCTGGCTGTACGTGGCCAGAACTGGGGTTGGCATCTGGCATCC
ATTTGAGGCCAGGGTGGAGGAAAGGGAGGCCAACAGAGGAAAACCTATTCCTGCTGTGAC
AACACAGCCCTTGTCCCACGCAGCCTAAGTGCAGGGAGCGTGATGAAGTCAGGCAGCCAG
TCGGGGAGGACGAGGTAACTCAGCAGCAATGTCACCTTGTAGCCTATGCGCTCAATGGCC
CGGAGGGGCAGCAACCCCCCGCACACGTCAGCCAACAGCAGTGCCTCTGCAGGCACCAAG
AGAGCGATGATGGACTTGAGCGCCGTGTTC

17190.1

GTTTGGCAGAAGACATGTTTAATAACATTTTCATATTTAAAAAATACAGCAACAATTCTCT
ATCTGTCCACCATCTTGCCTTGCCCTTCCTGGGGCTGAGGCAGACAAAGGAAAGGTAATGA
GGTTAGGGCCCCCAGGCGGGCTAAGTGCTATTGGCCTGCTCCTGCTCAAAGAGAGCCATA
GCCAGCTGGGCACGGCCCCCTAGCCCCTCCAGGTTGCTGAGGCGGCAGCGGTGGTAGAGT
TCTTCACTGAGCCGTGGGCTGCAGTCTCGCAGGGAGAACTTCTGCACCAGCCCTGGCTCTA
CGGCCCGAAAGAGGTGGAGCCCTGAGAACCGGAGGAAAACATCCATCACCTCCAGCCCCT
CCAGGGCTTCCTCCTCTTCCTGGCCTGCCAGTTCACCTGCCAGCCGGGCTCGGGCCGCCAG
GTAGTCAGCGTTGTAGAAGCAGCCCTCCGCAGAAGCCTGCCGGTCAAATCTCCCCGCTATA
GGAGCCCCCCGGGAGGGGTCAGCACC

CAAGTTGAACGTCAGGCTTGGCAGAGGTGGAGTGTAGATGAAAACAAAGGTGTGATTATG
AAGAGGATGTGAGTCCTTTGGGTGTAGGAGAGAAAGGCTGTTGAGCTTCTATTTCAAGAT
ACTTTTACCTGTGCAAAAAGCACATTTTCCACCTCCTTCTCATGGCATTTGTGTAAGGTGAG
TATGATTCCTATTCCATCTGCATTTTAGAGGTGAAGAATAACGTACAAGGGATTCAGTGAT
TAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCAT
TCCCTCCAACCCAGGCTCAGATCCGGAACCTGACCGTGCTGACCCCCGAAGGGGAGGCAG
GGCTGAGCTGGCCCGTTGGGCTCCCTGCTCCTTTCACACCACACTCTCGCTTTGAGGTGCTG
GGCTGGGACTACTTCACAGAGCAGC

17191.2&89.2

TGGCCTGGGCAGGATTGGGAGAGAGGTAGCTACCCGGATGCAGTCCTTTGGGATGAAGAC
TATAGGGTATGACCCCATCATTTCCCCAGAGGTCTCGGCCTCCTTTGGTGTTCAGCAGCTG
CCCCTGGAGGAGATCTGGCCTCTCTGTGATTTCATCACTGTGCACACTCCTCTCCTGCCCTC
CACGACAGGCTTGCTGAATGACAACACCTTTGCCCAGTGCAAGAAGGGGGTGCGTGTGGT
GAACTGTGCCCGTGGAGGGATCGTGGACGAAGGCGCCCTGCTCCGGGCCCTGCAGTCTGG
CCAGTGTGCCGGGGCTGCACTGGACGTGTTTACGGAAGAGCCGCCACGGGACCGGGCCTT
GGTGGACCATGAGAATGTCATCAGCTGTCCCCACCTGGGTGCCAGCACCAAGGAGGCTCA
GAGCCGCTGTGGGGAGGAAATTGCTGTTCAGTTCGTGGACATGGTGAAGGGGAAATCTCT
CACGGGGGTTGTGAATGCCCAGGCCCTT

*FIG. 1S*

AGCCAGATGGCTGAGAGCTGCAAGAAGAAGTCAGGATCATGATGGCTCAGTTTCCCACAG
CGATGAATGGAGGGCCAAATATGTGGGCTATTACATCTGAAGAACGTACTAAGCATGATA
AACAGTTTGATAACCTCAAACCTTCAGGAGGTTACATAACAGGTGATCAAGCCCGTACTTT
TTTCCTACAGTCAGGTCTGCCGGCCCCGGTTTTAGCTGAAATATGGGCCTTATCAGATCTG
AACAAGGATGGGAAGATGGACCAGCAAGAGTTCTCTATAGCTATGAAACTCATCAAGTTA
AAGTTGCAGGGCCAACAGCTGCCTGTAGTCCTCCCTCCTATCATGAAACAACCCCCTATGT
TCTCTCCACTAATCTCTGCTCGTTTTGGGATGGGAAGCATGCCCAATCTGTCCATTCATCAG
CCATTGCCTCCAGTTGCACCTATAGCAACACCCTTGTCTTCTGCTACTTCAGGGACCAGTAT
TCCTCCCCTAATGATGCCTGCTCCCCTAGTGCCTTCTGTTAGTACATCCTCATTACCAAATG
GAACTGCCAGTCTCATTCAGCCTTTATCCATTCCTTATTCTTCTTCAACATTGCCTCATGCA
TCATCTTACAGCCTGATGATGGGAGGATTTGGTGGTGCTAGTATCCAGAAGGCCCAGTCTC
TGATTGATTTAGGATCTAGTAGCTCAACTTCCTCAACTGCTTCCCTCTCAGGGAACTCACCT
AAGACAGGGACCTCAGAGTGGGCAGTTCCTCAGCCTTCAAGATTAAAGTATCGGCAAAAA
TTTAATAGTCTAGACAAAGGCATGAGCGGATACCTCTCAGGTTTTCAAGCTAGAAATGCCC
TTCTTCAGTCAAATCTCTCTCAAACTCAGCTAGCTACTATTTGGACTCTGGCTGACATCGAT
GGTGACGGACAGTTGAAAGCTGAAGAATTTATTCTGGCGATGCACCTCACTGACATGGCC
AAAGCTGGACAGCCACTACCACTGACGTTGCCTCCCGAGCTTGTCCCTCCATCTTTCAGAG
GGGGAAAGCAAGTTGATTCTGTTAATGGAACTCTGCCTTCATATCAGAAAACACAAGAAG
AAGAGCCTCAGAAGAAACTGCCAGTTACTTTTGAGGACAAACGGAAAGCCAACTATGAAC
GAGGAAACATGGAGCTGGAGAAGCGACGCCAAGTGTTGATGGAGCAGCAGCAGAGGGAG
GCTGAACGCAAAGCCCAGAAAGAGAAGGAAGAGTGGGAGCGGAAACAGAGAGAACTGC
AAGAGCAAGAATGGAAGAAGCAGCTGGAGTTGGAGAAACGCTTGGAGAAACAGAGAGAG
CTGGAGAGACAGCGGGAGGAAGAGAGGAGAAAGGAGATAGAAAGACGAGAGGCAGCAA
AACAGGAGCTTGAGAGACAACGCCGTTTAGAATGGGAAAGACTCCGTCGGCAGGAGCTGC
TCAGTCAGAAGACCAGGGAACAAGAAGACATTGTCAGGCTGAGCTCCAGAAAGAAAAGT
CTCCACCTGGAACTGGAAGCAGTGAATGGAAAACATCAGCAGATCTCAGGCAGACTACAA
GATGTCCAAATCAGAAAGCAAACACAAAAGACTGAGCTAGAAGTTTTGGATAAACAGTGT
GACCTGGAAATTATGGAAATCAAACAACTTCAACAAGAGCTTAAGGAATATCAAAATAAG
CTTATCTATCTGGTCCCTGAGAAGCAGCTATTAAACGAAAGAATTAAAAACATGCAGCTCA
GTAACACACCTGATTCAGGGATCAGTTTACTTCATAAAAAGTCATCAGAAAAGGAAGAAT
TATGCCAAAGACTTAAAGAACAATTAGATGCTCTTGAAAAAGAAACTGCATCTAAGCTCT
CAGAAATGGATTCATTTAACAATCAGCTGAAGGAACTCAGAGAAAGCTATAATACACAGC
AGTTAGCCCTTGAACAACTTCATAAAATCAAACGTGACAAATTGAAGGAAATCGAAAGAA
AAAGATTAGAGCAAAAAAAAAAAAA

*FIG. 2A*

ATGGCAGTGACATTCACCATCATGGGAACCACCTTCCCTTTTCTTCAGGATTCTCTGTAGTG
GAAGAGAGCACCCAGTGTTGGGCTGAAAACATCTGAAAGTAGGGAGAAGAACCTAAAAT
AATCAGTATCTCAGAGGGCTCTAAGGTGCCAAGAAGTCTCACTGGACATTTAAGTGCCAA
CAAAGGCATACTTTCGGAATCGCCAAGTCAAAACTTTCTAACTTCTGTCTCTCTCAGAGAC
AAGTGAGACTCAAGAGTCTACTGCTTTAGTGGCAACTACAGAAAACTGGTGTTACCCAGA
AAAACAGGAGCAATTAGAAATGGTTCCAATATTTCAAAGCTCCGCAAACAGGATGTGCTT
TCCTTTGCCCATTTAGGGTTTCTTCTCTTTCCTTTCTCTTTATTAACCACTA

*FIG. 2B*

ATATCTAGAAGTCTGGAGTGAGCAAACAAGAGCAAGAAACAAAAAGAAGCCAAAAGCAG
AAGGCTCCAATATGAACAAGATAAATCTATCTTCAAAGACATATTAGAAGTTGGGAAAAT
AATTCATGTGAACTAGACAAGTGTGTTAAGAGTGATAAGTAAAATGCACGTGGAGACAAG
TGCATCCCCAGATCTCAGGGACCTCCCCCTGCCTGTCACCTGGGGAGTGAGAGGACAGGAT
AGTGCATGTTCTTTGTCTCTGAATTTTTAGTTATATGTGCTGTAATGTTGCTCTGAGGAAGC
CCCTGGAAAGTCTATCCCAACATATCCACATCTTATATTCCACAAATTAAGCTGTAGTATG
TACCCTAAGACGCTGCTAATTGACTGCCACTTCGCAACTCAGGGGCGGCTGCATTTTAGTA
ATGGGTCAAATGATTCACTTTTTATGATGCTTCCAAAGGTGCCTTGGCTTCTCTTCCCAACT
GACAAATGCCAAAGTTGAGAAAAATGATCATAATTTTAGCATAAACAGAGCAGTCGGCGA
CACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATT
ATGTCATCACAAGCTCTGAGGCTTCTCCTTTCCATCCTGCGTGGACAGCTAAGACCTCAGT
TTTCAATAGCATCTAGAGCAGTGGGACTCAGCTGGGGTGATTTCGCCCCCCATCTCCGGGG
GAATGTCTGAAGACAATTTTGTTACCTCAATGAGGGAGTGGAGGAGGATACAGTGCTACT
ACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTG
AGTAGAAAAGGGCCTGGAAAGAGGGGAGCCAACAAATCTGTCTGCTTCCTCACATTAGTC
ATTGGCAAATAAGCATTCTGTCTCTTTGGCTGCTGCCTCAGCACAGAGAGCCAGAACTCTA
TCGGGCACCAGGATAACATCTCTCAGTGAACAGAGTTGACAAGGCCTATGGGAAATGCCT
GATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATC
TCCAGACCCTTCCTGGCCACAATTCAAATTAAGGCAACAAACATATACCTTCCATGAAGCA
CACACAGACTTTTGAAAGCAAGGACAATGACTGCTTGAATTGAGGCCTTGAGGAATGAAG
CTTTGAAGGAAAAGAATACTTTGTTTCCAGCCCCCTTCCCACACTCTTCATGTGTTAACCAC
TGCCTTCCTGGACCTTGGAGCCACGGTGACTGTATTACATGTTGTTATAGAAAACTGATTTT
AGAGTTCTGATCGTTCAAGAGAATGATTAAATATACATTTCCTA

*FIG. 2C*

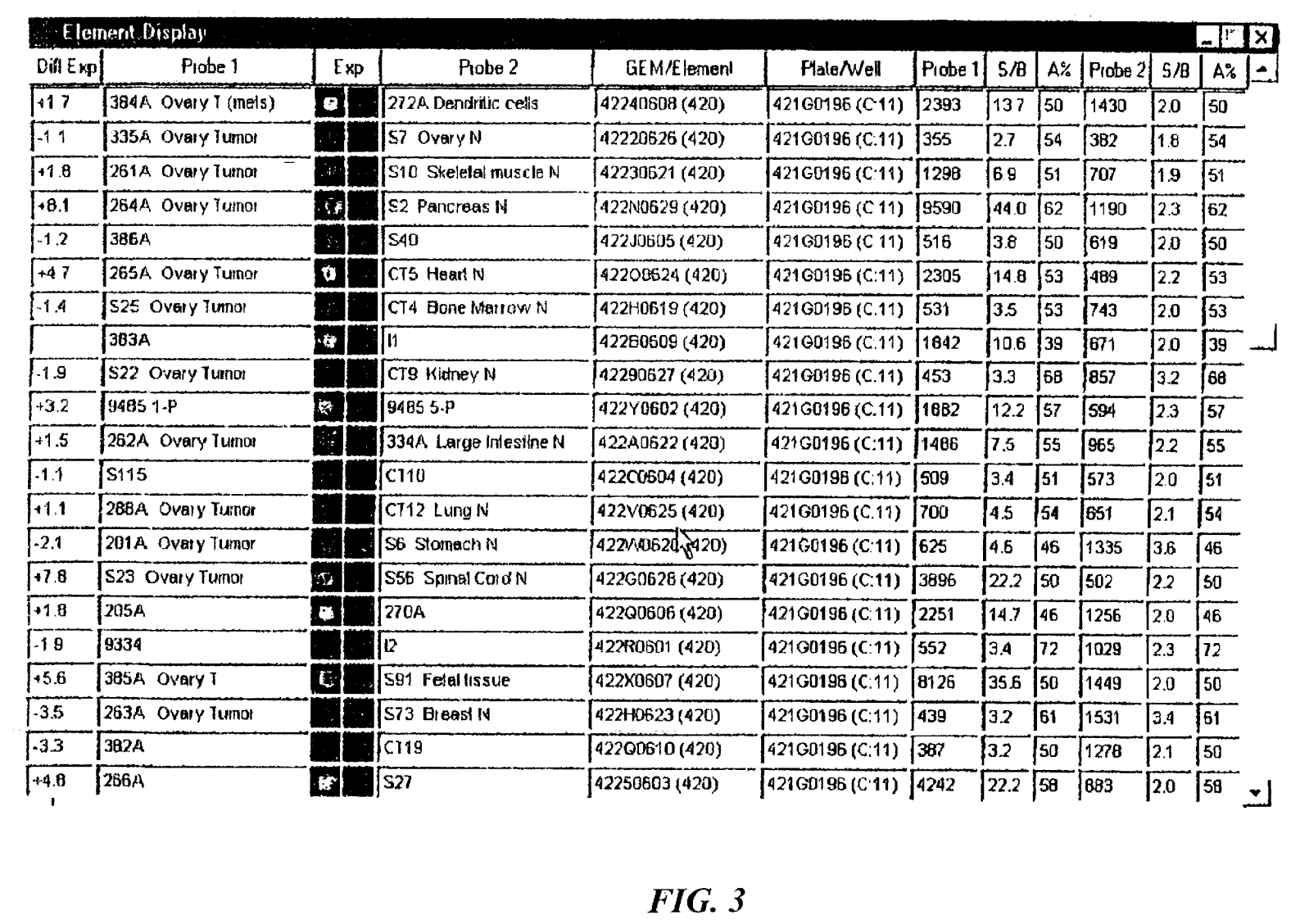

Element Display

| Diff Exp | Probe 1 | Exp | Probe 2 | GEM/Element | Plate/Well | Probe 1 | S/B | A% | Probe 2 | S/B | A% |
|---|---|---|---|---|---|---|---|---|---|---|---|
| +1.7 | 384A Ovary T (mets) | | 272A Dendritic cells | 42240608 (420) | 421G0196 (C:11) | 2393 | 13.7 | 50 | 1430 | 2.0 | 50 |
| -1.1 | 335A Ovary Tumor | | S7 Ovary N | 42220626 (420) | 421G0196 (C:11) | 355 | 2.7 | 54 | 382 | 1.8 | 54 |
| +1.8 | 261A Ovary Tumor | | S10 Skeletal muscle N | 42230621 (420) | 421G0196 (C:11) | 1298 | 6.9 | 51 | 707 | 1.9 | 51 |
| +8.1 | 264A Ovary Tumor | | S2 Pancreas N | 422N0629 (420) | 421G0196 (C:11) | 9590 | 44.0 | 62 | 1190 | 2.3 | 62 |
| -1.2 | 386A | | S40 | 422J0605 (420) | 421G0196 (C:11) | 516 | 3.8 | 50 | 619 | 2.0 | 50 |
| +4.7 | 265A Ovary Tumor | | CT5 Heart N | 422O0624 (420) | 421G0196 (C:11) | 2305 | 14.8 | 53 | 489 | 2.2 | 53 |
| -1.4 | S25 Ovary Tumor | | CT4 Bone Marrow N | 422H0619 (420) | 421G0196 (C:11) | 531 | 3.5 | 53 | 743 | 2.0 | 53 |
| | 383A | | I1 | 422B0609 (420) | 421G0196 (C:11) | 1642 | 10.6 | 39 | 671 | 2.0 | 39 |
| -1.9 | S22 Ovary Tumor | | CT9 Kidney N | 42290627 (420) | 421G0196 (C:11) | 453 | 3.3 | 68 | 857 | 3.2 | 68 |
| +3.2 | 9485 1-P | | 9485 5-P | 422Y0602 (420) | 421G0196 (C:11) | 1682 | 12.2 | 57 | 594 | 2.3 | 57 |
| +1.5 | 262A Ovary Tumor | | 334A Large Intestine N | 422A0622 (420) | 421G0196 (C:11) | 1486 | 7.5 | 55 | 965 | 2.2 | 55 |
| -1.1 | S115 | | CT10 | 422C0604 (420) | 421G0196 (C:11) | 509 | 3.4 | 51 | 573 | 2.0 | 51 |
| +1.1 | 288A Ovary Tumor | | CT12 Lung N | 422V0625 (420) | 421G0196 (C:11) | 700 | 4.5 | 54 | 651 | 2.1 | 54 |
| -2.1 | 201A Ovary Tumor | | S6 Stomach N | 422W0620 (420) | 421G0196 (C:11) | 625 | 4.6 | 46 | 1335 | 3.6 | 46 |
| +7.8 | S23 Ovary Tumor | | S56 Spinal Cord N | 422G0628 (420) | 421G0196 (C:11) | 3896 | 22.2 | 50 | 502 | 2.2 | 50 |
| +1.8 | 205A | | 270A | 422Q0606 (420) | 421G0196 (C:11) | 2251 | 14.7 | 46 | 1256 | 2.0 | 46 |
| -1.9 | 9334 | | I2 | 422R0601 (420) | 421G0196 (C:11) | 552 | 3.4 | 72 | 1029 | 2.3 | 72 |
| +5.6 | 385A Ovary T | | S91 Fetal tissue | 422X0607 (420) | 421G0196 (C:11) | 8126 | 35.6 | 50 | 1449 | 2.0 | 50 |
| -3.5 | 263A Ovary Tumor | | S73 Breast N | 422H0623 (420) | 421G0196 (C:11) | 439 | 3.2 | 61 | 1531 | 3.4 | 61 |
| -3.3 | 382A | | CT19 | 422Q0610 (420) | 421G0196 (C:11) | 387 | 3.2 | 50 | 1278 | 2.1 | 50 |
| +4.8 | 266A | | S27 | 42250603 (420) | 421G0196 (C:11) | 4242 | 22.2 | 58 | 883 | 2.0 | 58 |

FIG. 3

TCGAGCGGCCGCCCGGGCAGGTCCTTCAGACTTGGACTGTGTCACACTGCCAGGCTTCCAG
GGCTCCAACTTGCAGACGGCCTGTTGTGGGACAGTCTCTGTAATCGCGAAAGCAACCATG
GAAGACCTGGGGGAAAACACCATGGTTTTATCCACCCTGAGATCTTTGAACAACTTCATCT
CTCAGCGTGCGGAGGGAGGCTCTGGACTGGATATTTCTACCTCGGCCGCGACCACGCT

*FIG. 4*

TAGCGYGGTCGCGGCCGAGGYCTGCTTYTCTGTCCAGCCCAGGGCCTGTGGGGTCAGGGC
GGTGGGTGCAGATGGCATCCACTCCGGTGGCTTCCCCATCTTTCTCTGGCCTGAGCAAGGT
CAGCCTGCAGCCAGAGTACAGAGGGCCAACACTGGTGTTCTTGAACAAGGGCCTTAGCAG
GCCCTGAAGGRCCCTCTCTGTAGTGTTGAACTTCCTGGAGCCAGGCCACATGTTCTCCTCAT
ACCGCAGGYTAGYGATGGTGAAGTTGAGGGTGAAATAGTATTMANGRAGATGGCTGGCA
RACCTGCCCGGGCGGCCGCTCSAAATCC

*FIG. 5*

AGCGTGGTCGCGGCCGAGGTGTCCTTCAGGGTCTGCTTATGCCCTTGTTCAAGAACACCAG
TGTCAGCTCTCTGTACTCTGGTTGCAGACTGACCTTGCTCAGGCCTGAGAAGGATGGGGCA
GCCACCAGAGTGGATGCTGTCTGCACCCATCGTCCTGACCCCAAAAGCCCTGGACTGGACA
GAGAGCGGCTGTACTGGAAGCTGAGCCAGCTGACCCACGGCATCACTGAGCTGGGCCCCT
ACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

TTGGGGNTTTMGAGCGGCCGCCCGGGCAGGTACCGGGGTGGTCAGCGAGGAGCCATTCAC
ACTGAACTTCACCATCAACAACCTGCGGTATGAGGAGAACATGCAGCACCCTGGCTCCAG
GAAGTTCAACACCACGGAGAGGGTCCTTCAGGGCCTGCTCAGGTCCCTGTTCAAGAGCAC
CAGTGTTGGCCCTCTGTACTCTGGCTGCAGACTGACTTTGCTCAGACTTGAGAAACATGGG
GCAGCCACTGGAGTGGACGCCATCTGCACCCTCCGCCTTGATCCCACTGGTCCTGGACTGG
ACAGAGAGCGGCTATACTGGGAGCTGAGCCAGTCCTCTGGCGGNGACNCCNCTT

*B*

AGCGTGGTCGCGGCCGAGGTCCAGTCGCAGCATGCTCTTTCTCCTGCCCACTGGCACAGTG
AGGAAGATCTCTGCTGTCAGTGAGAAGGCTGTCATCCACTGAGATGGCAGTCAAAAGTGC
ATTTAATACACCTAACGTATCGAACATCATAGCTTGGCCCAGGTTATCTCATATGTGCTCA
GAACACTTACAATAGCCTGCAGACCTGCCCGGGCGGCCGCTCGA

*FIG. 7A and 7B*

TGTGGTGTTGAACTTCCTGGAGNCAGGGTGACCCATGTCCTCCCCATACTGCAGGTTGGTG
ATGGTGAAGTTGAGGGTGAATGGTACCAGGAGAGGGCCAGCAGCCATAATTGTSGRGCKG
SMGMSSGAGGMWGGWGTYYCWGAGGTTCYRARRTCCACTGTGGAGGTCCCAGGAGTGCT
GGTGGTGGGCACAGAGSTCYGATGGGTGAAACCATTGACATAGAGACTGTTCCTGTCCAG
GGTGTAGGGGCCCAGCTCTTYRATGYCATTGGYCAGTTKGCTYAGCTCCCAGTACAGCCRC
TCTCKGYYGMGWCCAGSGCTTTTGGGGTCAAGATGATGGATGCAGATGGCATCCACTCCA
GTGGCTGCTCCATCCTTCTCGGACCTGAGAGAGGTCAGTCTGCAGCCAGAGTACAGAGGG
CCAACACTGGTGTTCTTTGAATA

*FIG. 8*

TCGAGCGGCCGCCCGGGCAGGTCAGGAAGCACATTGGTCTTAGAGCCACTGCCTCCTGGA
TTCCACCTGTGCTGCGGACATCTCCAGGGAGTGCAGAAGGGAAGCAGGTCAAACTGCTCA
GATCAGTCAGACTGGCTGTTCTCAGTTCTCACCTGAGCAAGGTCAGTCTGCAGCCAGAGTA
CAGAGGGCCAACACTGGTGTTCTTGAACAAGGGCTTGAGCAGACCCTGCAGAACCCTCTTC
CGTGGTGTTGAACTTCCTGGAAACCAGGGTGTTGCATGTTTTTCCTCATAATGCAAGGTTG
GTGATGG

*FIG. 9*

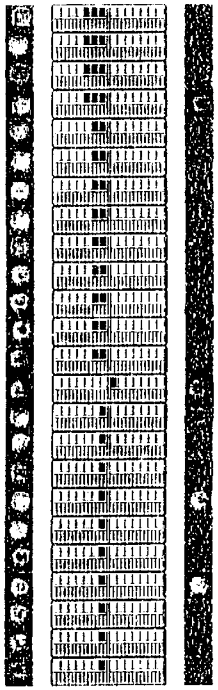

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 42100188 {D3} | +7.0 | 205A Ovary T | | | | 270A Liver N | 422Q0606 | 8620 | 1240 | 57.7 | 65 | 2.2 | 65 |
| 42100188 {D3} | +5.9 | S23 Ovary Tumor | | | | S56 Spinal Cord N | 422G0628 | 5894 | 1002 | 35.3 | 89 | 3.9 | 89 |
| 42100188 {D3} | +5.7 | 385A Ovary T | | | | S91 Fetal tissue | 422X0607 | 12151 | 2121 | 54.3 | 73 | 2.8 | 73 |
| 42100188 {D3} | +5.1 | 426A Ovary T (met | | | | 415A Aorta N | 422X0611 | 7487 | 1480 | 53.0 | 73 | 9.7 | 73 |
| 42100188 {D3} | +3.5 | 263A Ovary Tumor | | | | S73 Breast N | 422H0623 | 7302 | 2116 | 39.2 | 84 | 4.5 | 84 |
| 42100188 {D3} | +3.3 | 383A Ovary T (met | | | | 11 Colon N | 422B0609 | 3714 | 1113 | 20.4 | 83 | 2.6 | 83 |
| 42100188 {D3} | +3.0 | 9334 Ovary T (SCH | | | | 12 Skin N | 422R0601 | 2435 | 814 | 12.1 | 75 | 2.1 | 75 |
| 42100188 {D3} | +2.6 | 384A Ovary T (met | | | | 272A Dendritic cells | 42240608 | 4578 | 1754 | 25.0 | 69 | 2.3 | 69 |
| 42100188 {D3} | +2.2 | 264A Ovary Tumor | | | | S2 Pancreas N | 422N0629 | 7904 | 3596 | 38.5 | 81 | 5.6 | 81 |
| 42100188 {D3} | +2.0 | 386A Ovary T | | | | S40 PBMC (activat | 422J0605 | 2191 | 1081 | 14.0 | 90 | 2.9 | 90 |
| 42100188 {D3} | +2.0 | S115 Ovary T (met | | | | CT10 Small intestin | 422C0604 | 1979 | 971 | 10.4 | 80 | 2.7 | 80 |
| 42100188 {D3} | +2.0 | 265A Ovary Tumor | | | | CT5 Heart N | 422O0624 | 1911 | 964 | 13.9 | 93 | 3.4 | 93 |
| 42100188 {D3} | +2.0 | 335A Ovary Tumor | | | | S7 Ovary N | 42220626 | 1666 | 817 | 9.8 | 100 | 3.0 | 100 |
| 42100188 {D3} | -1.9 | 428A Ovary T (met | | | | 243A Esophagus N | 42240612 | 1827 | 3480 | 13.4 | 97 | 9.5 | 97 |
| 42100188 {D3} | +1.6 | 261A Ovary Tumor | | | | S10 Skeletal muscle | 42230621 | 5914 | 3653 | 30.4 | 86 | 6.0 | 86 |
| 42100188 {D3} | +1.6 | 266A Ovary T | | | | S27 Ovary N | 42250603 | 2039 | 1274 | 11.9 | 50 | 2.6 | 50 |
| 42100188 {D3} | +1.6 | S22 Ovary Tumor | | | | CT9 Kidney N | 42290627 | 1736 | 1072 | 11.0 | 92 | 4.0 | 92 |
| 42100188 {D3} | +1.4 | 9485 1-P Ovary T (S | | | | 9485 5-P Ovary T (S | 422Y0602 | 4204 | 3074 | 23.0 | 93 | 7.7 | 93 |
| 42100188 {D3} | +1.4 | 262A Ovary Tumor | | | | 334A Large Intestin | 422A0622 | 3002 | 2101 | 16.6 | 89 | 4.0 | 89 |
| 42100188 {D3} | +1.3 | S25 Ovary Tumor | | | | CT4 Bone Marrow | 422H0619 | 1643 | 1297 | 9.6 | 90 | 3.1 | 90 |
| 42100188 {D3} | +1.2 | 429A Ovary T (met | | | | 364A Ovary N | 422I0614 | 2521 | 2084 | 22.0 | 65 | 23.9 | 65 |
| 42100188 {D3} | +1.2 | 382A Ovary T | | | | CT19 Brain N | 422Q0610 | 2072 | 1663 | 10.9 | 88 | 2.3 | 88 |
| 42100188 {D3} | +1.2 | 288A Ovary Tumor | | | | CT12 Lung N | 422V0625 | 1840 | 1473 | 10.7 | 87 | 3.8 | 87 |
| 42100188 {D3} | +1.1 | 201A Ovary Tumor | | | | S6 Stomach N | 422W0620 | 1329 | 1204 | 9.1 | 90 | 3.5 | 90 |

FIG. 10

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 421B0181 {C3} | +18.8 | 385A Ovary T | 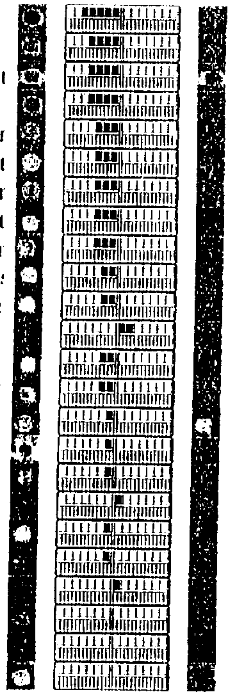 | | | S91 Fetal tissue | 422X0607 | 26711 | 1424 | 103.3 | 54 | 2.0 | 54 |
| 421B0181 {C3} | +11.5 | S23 Ovary Tumor | | | | S56 Spinal Cord N | 422G0628 | 13559 | 1179 | 65.3 | 68 | 3.9 | 68 |
| 421B0181 {C3} | +11.1 | 426A Ovary T (met | | | | 415A Aorta N | 422X0611 | 14125 | 1273 | 67.3 | 61 | 5.6 | 61 |
| 421B0181 {C3} | +10.8 | 205A Ovary T | | | | 270A Liver N | 422Q0606 | 16121 | 1488 | 93.1 | 43 | 2.3 | 43 |
| 421B0181 {C3} | +5.1 | 263A Ovary Tumor | | | | S73 Breast N | 422H0623 | 11326 | 2235 | 58.2 | 68 | 4.4 | 68 |
| 421B0181 {C3} | +4.6 | 384A Ovary T (met | | | | 272A Dendritic cells | 42240608 | 6583 | 1424 | 24.5 | 40 | 2.1 | 40 |
| 421B0181 {C3} | +4.4 | 264A Ovary Tumor | | | | S2 Pancreas N | 422N0629 | 9865 | 2245 | 40.9 | 64 | 3.6 | 64 |
| 421B0181 {C3} | +4.4 | 429A Ovary T (met | | | | 364A Ovary N | 422I0614 | 2803 | 638 | 22.6 | 60 | 7.4 | 60 |
| 421B0181 {C3} | +4.2 | 261A Ovary Tumor | | | | S10 Skeletal muscle | 42230621 | 8271 | 1949 | 39.5 | 68 | 3.6 | 68 |
| 421B0181 {C3} | +3.8 | S115 Ovary T (mets | | | | CT10 Small intestine | 422C0604 | 2281 | 607 | 11.6 | 60 | 2.1 | 60 |
| 421B0181 {C3} | +2.5 | 265A Ovary Tumor | | | | CT5 Heart N | 422O0624 | 3192 | 1293 | 19.2 | 68 | 4.0 | 68 |
| 421B0181 {C3} | -2.3 | S22 Ovary Tumor | | | | CT9 Kidney N | 42290627 | 565 | 1276 | 3.6 | 70 | 3.9 | 70 |
| 421B0181 {C3} | +2.2 | 266A Ovary T | | | | S27 Ovary N | 42250603 | 2774 | 1260 | 14.3 | 46 | 2.7 | 46 |
| 421B0181 {C3} | +2.1 | 9334 Ovary T (SCII | | | | 12 Skin N | 422R0601 | 1774 | 837 | 8.4 | 56 | 2.1 | 56 |
| 421B0181 {C3} | +1.9 | 9485 1-P Ovary T (S | | | | 9485 5-P Ovary T (S | 422Y0602 | 6967 | 3726 | 41.5 | 70 | 9.2 | 70 |
| 421B0181 {C3} | +1.6 | 382A Ovary T | | | | CT19 Brain N | 422Q0610 | 2313 | 1471 | 6.2 | 50 | 1.9 | 50 |
| 421B0181 {C3} | +1.6 | 288A Ovary Tumor | | | | CT12 Lung N | 422V0625 | 1657 | 1054 | 9.7 | 69 | 2.9 | 69 |
| 421B0181 {C3} | -1.5 | S25 Ovary Tumor | | | | CT4 Bone Marrow | 422H0619 | 848 | 1243 | 4.5 | 65 | 2.7 | 65 |
| 421B0181 {C3} | +1.4 | 262A Ovary Tumor | | | | 334A Large Intestine | 422A0622 | 3171 | 2214 | 16.8 | 69 | 3.8 | 69 |
| 421B0181 {C3} | +1.2 | 386A Ovary T | | | | S40 PBMC (activat | 422J0605 | 630 | 544 | 4.2 | 53 | 1.9 | 53 |
| 421B0181 {C3} | -1.2 | 335A Ovary Tumor | | | | S7 Ovary N | 42220626 | 592 | 730 | 3.7 | 75 | 2.6 | 75 |
| 421B0181 {C3} | -1.0 | 201A Ovary Tumor | | | | S6 Stomach N | 422W0620 | 1197 | 1237 | 7.8 | 65 | 3.5 | 65 |
| 421B0181 {C3} | -1.0 | 428A Ovary T (met | | | | 243A Esophagus N | 42240612 | 783 | 797 | 4.5 | 95 | 2.4 | 95 |
| 421B0181 {C3} | | 383A Ovary T (mets | | | | 11 Colon N | 422B0609 | 3470 | 862 | 8.9 | 24 | 1.7 | 24 |

*FIG. 11*

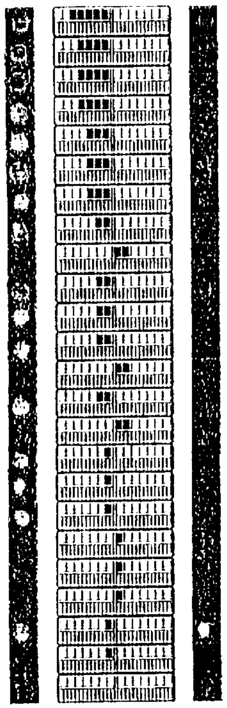

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 42110182 {117} | +16.7 | 426A Ovary T (met | | | | 415A Aorta N | 422X0611 | 7706 | 462 | 46.3 | 75 | 3.5 | 75 |
| 42110182 {117} | +10.7 | 205A Ovary T | | | | 270A Liver N | 422Q0606 | 10171 | 950 | 61.2 | 41 | 1.8 | 41 |
| 42110182 {117} | +9.9 | 385A Ovary T | | | | S91 Fetal tissue | 422X0607 | 14415 | 1459 | 62.1 | 48 | 2.2 | 48 |
| 42110182 {117} | +8.8 | S23 Ovary Tumor | | | | S56 Spinal Cord N | 422G0628 | 7781 | 880 | 47.3 | 73 | 3.4 | 73 |
| 42110182 {117} | +6.4 | 383A Ovary T (mets | | | | 11 Colon N | 422B0609 | 4807 | 748 | 27.6 | 47 | 2.2 | 47 |
| 42110182 {117} | +5.1 | 263A Ovary Tumor | | | | S73 Breast N | 422H0623 | 9815 | 1909 | 57.1 | 74 | 4.2 | 74 |
| 42110182 {117} | +4.9 | 429A Ovary T (met | | | | 364A Ovary N | 422I0614 | 2661 | 543 | 20.3 | 61 | 6.7 | 61 |
| 42110182 {117} | +3.5 | 264A Ovary Tumor | | | | S2 Pancreas N | 422N0629 | 7934 | 2274 | 38.8 | 71 | 3.9 | 71 |
| 42110182 {117} | -2.9 | S25 Ovary Tumor | | | | CT4 Bone Marrow | 422H0619 | 480 | 1375 | 3.5 | 80 | 3.0 | 80 |
| 42110182 {117} | +2.8 | 261A Ovary Tumor | | | | S10 Skeletal musch | 42230621 | 8993 | 3245 | 34.6 | 69 | 5.1 | 69 |
| 42110182 {117} | +2.5 | S115 Ovary T (met: | | | | CT10 Small intestin | 422C0604 | 1864 | 738 | 8.1 | 67 | 2.2 | 67 |
| 42110182 {117} | +2.3 | 9334 Ovary T (SCH | | | | 12 Skin N | 422R0601 | 2552 | 1113 | 12.7 | 41 | 2.6 | 41 |
| 42110182 {117} | -2.3 | S22 Ovary Tumor | | | | CT9 Kidney N | 42290627 | 386 | 889 | 3.2 | 69 | 3.4 | 69 |
| 42110182 {117} | +2.2 | 384A Ovary T (met | | | | 272A Dendritic cell: | 42240608 | 3516 | 1567 | 18.7 | 55 | 2.2 | 55 |
| 42110182 {117} | -2.2 | 382A Ovary T | | | | CT19 Brain N | 422Q0610 | 608 | 1320 | 4.2 | 60 | 2.3 | 60 |
| 42110182 {117} | +1.9 | 265A Ovary Tumor | | | | CT5 Heart N | 422O0624 | 2063 | 1080 | 13.6 | 87 | 3.5 | 87 |
| 42110182 {117} | +1.8 | 266A Ovary T | | | | S27 Ovary N | 42250603 | 1550 | 847 | 7.0 | 58 | 2.1 | 58 |
| 42110182 {117} | +1.5 | 262A Ovary Tumor | | | | 334A Large Intestir | 422A0622 | 2559 | 1651 | 13.2 | 73 | 3.2 | 73 |
| 42110182 {117} | -1.4 | 386A Ovary T | | | | S40 PBMC (activat | 422J0605 | 534 | 738 | 3.9 | 62 | 2.2 | 62 |
| 42110182 {117} | -1.3 | 288A Ovary Tumor | | | | CT12 Lung N | 422V0625 | 893 | 1120 | 5.3 | 66 | 3.1 | 66 |
| 42110182 {117} | -1.3 | 335A Ovary Tumor | | | | S7 Ovary N | 42220626 | 440 | 567 | 3.3 | 60 | 2.2 | 60 |
| 42110182 {117} | +1.2 | 9485 1-P Ovary T (S | | | | 9485 5-P Ovary T (S | 422Y0602 | 4188 | 3529 | 21.6 | 66 | 9.5 | 66 |
| 42110182 {117} | +1.1 | 428A Ovary T (met | | | | 243A Esophagus N | 42240612 | 725 | 689 | 6.2 | 65 | 2.8 | 65 |
| 42110182 {117} | -1.0 | 201A Ovary Tumor | | | | S6 Stomach N | 422W0620 | 1008 | 1018 | 7.4 | 62 | 3.2 | 62 |

FIG. 12

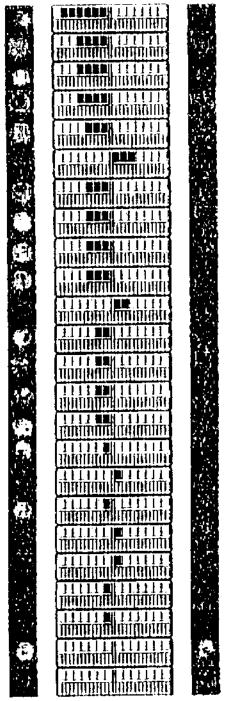

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 {D1} | +33.2 | 426A Ovary T (met | | | 415A Aorta N | 422X0611 | 8072 | 243 | 55.2 | 67 | 2.4 | 67 |
| 421V0189 {D1} | +13.7 | S23 Ovary Tumor | | | S56 Spinal Cord N | 422G0628 | 7367 | 537 | 42.6 | 69 | 2.5 | 69 |
| 421V0189 {D1} | +12.6 | 429A Ovary T (met | | | 364A Ovary N | 422I0614 | 2850 | 227 | 21.7 | 64 | 3.5 | 64 |
| 421V0189 {D1} | +8.0 | 385A Ovary T | | | S91 Fetal tissue | 422X0607 | 11711 | 1469 | 54.0 | 58 | 2.2 | 58 |
| 421V0189 {D1} | +7.3 | 263A Ovary Tumor | | | S73 Breast N | 422H0623 | 6949 | 952 | 37.8 | 69 | 2.6 | 69 |
| 421V0189 {D1} | -5.8 | S25 Ovary Tumor | | | CT4 Bone Marrow | 422H0619 | 208 | 1210 | 2.1 | 44 | 2.9 | 44 |
| 421V0189 {D1} | +5.0 | 205A Ovary T | | | 270A Liver N | 422Q0606 | 8676 | 1737 | 52.3 | 57 | 2.6 | 57 |
| 421V0189 {D1} | +4.5 | 383A Ovary T (mets | | | 11 Colon N | 422B0609 | 3149 | 707 | 17.4 | 57 | 2.0 | 57 |
| 421V0189 {D1} | +4.4 | 261A Ovary Tumor | | | S10 Skeletal muscle | 42230621 | 6332 | 1443 | 29.1 | 77 | 2.9 | 77 |
| 421V0189 {D1} | +4.2 | 264A Ovary Tumor | | | S2 Pancreas N | 422N0629 | 7612 | 1809 | 38.1 | 79 | 3.3 | 79 |
| 421V0189 {D1} | -3.2 | 382A Ovary T | | | CT19 Brain N | 422Q0610 | 468 | 1508 | 3.4 | 60 | 2.3 | 60 |
| 421V0189 {D1} | +2.9 | 9334 Ovary T (SCII | | | 12 Skin N | 422R0601 | 2500 | 860 | 12.3 | 51 | 2.1 | 51 |
| 421V0189 {D1} | +2.5 | S115 Ovary T (met: | | | CT10 Small intestin | 422C0604 | 1424 | 569 | 6.7 | 61 | 2.1 | 61 |
| 421V0189 {D1} | +2.4 | 265A Ovary Tumor | | | CT5 Heart N | 422O0624 | 1742 | 723 | 11.8 | 70 | 2.8 | 70 |
| 421V0189 {D1} | +2.3 | 384A Ovary T (met | | | 272A Dendritic cells | 42240608 | 3083 | 1342 | 17.0 | 62 | 2.0 | 62 |
| 421V0189 {D1} | +1.9 | 266A Ovary T | | | S27 Ovary N | 42250603 | 1370 | 732 | 8.0 | 47 | 2.0 | 47 |
| 421V0189 {D1} | -1.9 | 386A Ovary T | | | S40 PBMC (activat | 422J0605 | 307 | 580 | 2.6 | 41 | 2.0 | 41 |
| 421V0189 {D1} | +1.7 | 262A Ovary Tumor | | | 334A Large Intestir | 422A0622 | 2097 | 1202 | 11.2 | 86 | 2.7 | 86 |
| 421V0189 {D1} | -1.3 | 335A Ovary Tumor | | | S7 Ovary N | 42220626 | 373 | 470 | 2.9 | 47 | 2.0 | 47 |
| 421V0189 {D1} | -1.1 | 288A Ovary Tumor | | | CT12 Lung N | 422V0625 | 969 | 1094 | 5.6 | 72 | 2.9 | 72 |
| 421V0189 {D1} | +1.1 | 201A Ovary Tumor | | | S6 Stomach N | 422W0620 | 750 | 672 | 5.6 | 62 | 2.4 | 62 |
| 421V0189 {D1} | +1.1 | 428A Ovary T (met | | | 243A Esophagus N | 42240612 | 498 | 446 | 4.2 | 73 | 2.1 | 73 |
| 421V0189 {D1} | -1.0 | 9485 1-P Ovary T (S | | | 9485 5-P Ovary T (S | 422Y0602 | 3117 | 3174 | 16.7 | 91 | 8.2 | 91 |
| 421V0189 {D1} | | S22 Ovary Tumor | | | CT9 Kidney N | 42290627 | 224 | 409 | 2.3 | 48 | 2.3 | 48 |

FIG. 13

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 421H0187 {E11} | +20.2 | 426A Ovary T (met | 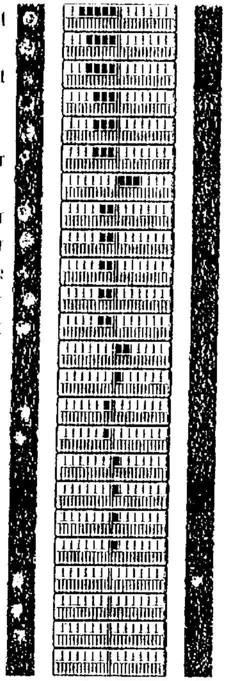 | | | 415A Aorta N | 422X0611 | 5441 | 270 | 36.3 | 50 | 2.3 | 50 |
| 421H0187 {E11} | +10.0 | S23 Ovary Tumor | | | | S56 Spinal Cord N | 422G0628 | 5318 | 533 | 27.1 | 56 | 2.3 | 56 |
| 421H0187 {E11} | +8.3 | 429A Ovary T (met | | | | 364A Ovary N | 422I0614 | 1252 | 150 | 10.1 | 58 | 2.5 | 58 |
| 421H0187 {E11} | +5.7 | 385A Ovary T | | | | S91 Fetal tissue | 422X0607 | 9507 | 1668 | 35.8 | 45 | 2.1 | 45 |
| 421H0187 {E11} | +4.4 | 205A Ovary T | | | | 270A Liver N | 422Q0606 | 5456 | 1235 | 31.1 | 50 | 2.0 | 50 |
| 421H0187 {E11} | +4.2 | 265A Ovary Tumor | | | | CT5 Heart N | 422O0624 | 1834 | 438 | 11.9 | 48 | 2.0 | 48 |
| 421H0187 {E11} | -4.1 | 382A Ovary T | | | | CT19 Brain N | 422Q0610 | 309 | 1259 | 2.6 | 48 | 2.0 | 48 |
| 421H0187 {E11} | +3.6 | 261A Ovary Tumor | | | | S10 Skeletal muscle | 4223O621 | 3733 | 1036 | 17.7 | 55 | 2.3 | 55 |
| 421H0187 {E11} | +3.4 | 263A Ovary Tumor | | | | S73 Breast N | 422H0623 | 4163 | 1239 | 23.0 | 62 | 3.0 | 62 |
| 421H0187 {E11} | +2.5 | S115 Ovary T (met: | | | | CT10 Small intestin | 422C0604 | 1565 | 627 | 8.8 | 47 | 2.1 | 47 |
| 421H0187 {E11} | +2.1 | 264A Ovary Tumor | | | | S2 Pancreas N | 422N0629 | 3455 | 1630 | 14.9 | 60 | 3.0 | 60 |
| 421H0187 {E11} | +2.1 | 384A Ovary T (met | | | | 272A Dendritic cells | 42240608 | 2667 | 1270 | 13.4 | 44 | 1.9 | 44 |
| 421H0187 {E11} | -2.1 | S22 Ovary Tumor | | | | CT9 Kidney N | 42290627 | 291 | 605 | 2.4 | 51 | 2.5 | 51 |
| 421H0187 {E11} | -1.7 | 386A Ovary T | | | | S40 PBMC (activat | 422J0605 | 410 | 687 | 3.2 | 47 | 2.0 | 47 |
| 421H0187 {E11} | +1.6 | 9334 Ovary T (SCII | | | | 12 Skin N | 422R0601 | 1622 | 984 | 7.9 | 44 | 2.2 | 44 |
| 421H0187 {E11} | +1.5 | 262A Ovary Tumor | | | | 334A Large Intestin | 422A0622 | 1892 | 1245 | 10.1 | 50 | 2.6 | 50 |
| 421H0187 {E11} | -1.5 | 288A Ovary Tumor | | | | CT12 Lung N | 422V0625 | 604 | 908 | 4.1 | 62 | 2.6 | 62 |
| 421H0187 {E11} | -1.4 | 428A Ovary T (met | | | | 243A Esophagus N | 42240612 | 236 | 325 | 2.7 | 78 | 1.9 | 78 |
| 421H0187 {E11} | -1.3 | 335A Ovary Tumor | | | | S7 Ovary N | 42220626 | 382 | 501 | 2.9 | 58 | 2.0 | 58 |
| 421H0187 {E11} | -1.2 | 201A Ovary Tumor | | | | S6 Stomach N | 422W0620 | 558 | 677 | 4.2 | 58 | 2.3 | 58 |
| 421H0187 {E11} | +1.0 | 9485 1-P Ovary T (S | | | | 9485 5-P Ovary T (S | 422Y0602 | 2582 | 2493 | 15.1 | 57 | 6.3 | 57 |
| 421H0187 {E11} | | 383A Ovary T (mets | | | | 11 Colon N | 422B0609 | 2261 | 562 | 12.5 | 38 | 1.7 | 38 |
| 421H0187 {E11} | | 266A Ovary T | | | | S27 Ovary N | 42250603 | 1739 | 965 | 9.7 | 36 | 2.2 | 36 |
| 421H0187 {E11} | | S25 Ovary Tumor | | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTA
CAAATGGAATTTCATCTTGTTTCCATGCTGAGTAGTGAAACAGTGACAAAGCTAATCATAA
TAACCTACATCAAAAGAGAACTAAGCTAACACTGCTCACTTTCTTTTTAACAGGCAAAATA
TAAATATATGCACTCTAXAATGCACAATGGTTTAGTCACTAAAAAATTCAAATGGGATCTT
GAAGAATGTATGCAAATCCAGGGTGCAGTGAAGATGAGCTGAGATGCTGTGCAACTGTTT
AAGGGTTCCTGGCACTGCATCTCTTGGCCACTAGCTGAATCTTGACATGGAAGGTTTTAGC
TAATGCCAAGTGGAGATGCAGAAAATGCTAAGTTGACTTAGGGGCTGTGCACAGGAACTA
AAAGGCAGGAAAGTACTAAATATTGCTGAGAGCATCCACCCCAGGAAGGACTTTACCTTC
CAGGAGCTCCAAACTGGCACCACCCCCAGTGCTCACATGGCTGACTTTATCCTCCGTGTTC
CATTTGGCACAGCAAGTGGCAGTG

11721-2

AAGGCTGGTGGGTTTTTGATCCTGCTGGAGAACCTCCGCTTTCATGTGGAGGAAGAAGGG
AAGGGAAAAGATGCTTCTGGGAACAAGGTTAAAGCCGAGCCAGCCAAAATAGAAGCTTTC
CGAGCTTCACTTTCCAAGCTAGGGGATGTCTATGTCAATGATGCTTTTGGCACTGCTCACA
GAGCCCACAGCTCCATGGTAGGAGTCAATCTGCCACAGAAGGCTGGTGGGTTTTTGATGA
AGAAGGAGCTGAACTACTTTGCAAAGGCCTTGGAGAGCCCAGAGCGACCCTTCCTGGCCA
TCCTGGGCGGAGCTAAAGTTGCAGACAAGATCCAGCTCATCAATAATATGCTGGACAAAG
TCAATGAGATGATTATTGGTGGTGGAATGGCTTTTACCTTCCTTAAGGTGCTCAACAACAT
GGAGATTGGCACTTCTCTGTTTGATGAAGAGGGAGCCAAGATTGTCAAAGACCTAATGTCC
AAAGCTGAGAAGAATGGTGTGAAGATTACCTTGCCTGTTGACTTTGTCACTGCTGACAAGT
TTGATGA

11724-1

TTTGTTCCTTACATTTTTCTAAAGAGTTACTTAAATCAGTCAACTGGTCTTTGAGACTCTTA
AGTTCTGATTCCAACTTAGCTAATTCATTCTGAGAACTGTGGTATAGGTGGCGTGTCTCTTC
TAGCTGGGACAAAAGTTCTTTGTTTTCCCCCTGTAGAGTATCACAGACCTTCTGCTGAAGC
TGGACCTCTGTCTGGGCCTTGGACTCCCAAATCTGCTTGTCATGTTCAAGCCTGGAAATGTT
AATCTTTAATTCTTCCATATGGATGGACATCTGTCTAAGTTGATCCTTTAGAACACTGCAAT
TATCTTCTTTGAGTCTAATTTCTTCTTCTTTGCTTTGAATCGCATCACTAAACTTCCTCTCCC
ATTTCTTAGCTTCATCTATCACCCTGTCACGATCATCCTGGAGGGAAGACATGCTCTTAGTA
AAGGCTGCAAGCTGGGTCACAGTACTGTCCAAGTTTTCCTGAAGTTGCTGAACTTCCTTGT
CTTTCTTGTTCAAAGTAACCTGAATCTCTCCAATTGTCTCTTCCAAGTGGACTTTTTCTCTGC
GCAAAGCATCCAG

11724-2

TCATTGCCTGTGATGGCATCTGGAATGTGATGAGCAGCCAGGAAGTTGTAGATTTCATTCA
ATCAAAGGATTCAGCATGTGGTGGAAGCTGTGAGGCAAGAGAAACAAGAACTGTATGGCA
AGTTAAGAAGCACAGAGGCAAACAAGAAGGAGACAGAAAAGCAGTTGCAGGAAGCTGAG
CAAGAAATGGAGGAAATGAAAGAAAAGATGAGAAAGTTTGCTAAATCTAAACAGCAGAA
AATCCTAGAGCTGGAAGAAGAGAATGACCGGCTTAGGGCAGAGGTGCACCCTGCAGGAG
ATACAGCTAAAGAGTGTATGGAAACACTTCTTTCTTCCAATGCCAGCATGAAGGAAGAAC
TTGAAAGGGTCAAAATGGAGTATGAAACCCTTTCTAAGAAGTTTCAGTCTTTAATGTCTGA
GAAAGACTCTCTAAGTGAAGAGGTTCAAGATTTAAAGCATCAGATAGAAGGTAATGTATC
TAAACAAGCTAACCTAGAGGCCACCGAGAAACATGATAACCAAACGAATGTCACTGAAGA
GGGAACACAGTCTATACCAGGT

AAGCCAATAATCACCATTTATTACTTAATATATGCCAACCACTGTACTTGGCAGTTCACAA
ATTCTCACCGTTACAACAACCCCATGAGGTATTTATTCCCATTCTATAGATAGGGAAACCA
CAGCTCAAGTAAGTTAGGAAACTGAGCCAAGTATACACAGAATACGAAGTGGCAAAACTA
GAAGGAAAGACTGACACTGCTATCTGCTGGCCTCCAGTGTCCTGGCTCTTTTCACACGGGtT
CAATGTCTCCAGCGCTGCTGCTGCTGCTGCATTACCATGCCCTCATTGTTTTTCTTCCTCTG
GTGTTCAACTGCATCCTTCAAAGAATCTAACTCATTCCAGAGACCACTTATTTCTTTCTCTC
TTTCTGAAATTACTTTTAATAATTCTTCATGAGGGGGAAAAGAAGATGCCTGTTGGTAGTT
TTGTTGTTTAAGCTGCTCAATTTGGGACTTAAACAATTTGTTTTCATCTTGTACATCCTGTA
ACAGCTGTGTTTTGCTAGAAAGATCACTCTCCCTCTCTTTTAGCATGGCTTCTAACCTCTTC
AATTCATTTTCCTTTTCTTTCAACACAATCTCAAGTTCTTCAAACTGTGATGCAGAAGAGGC
CTCTTTCAAGTTATGTTGTGCTACTTCCTGAACATGTGCTTTTAAAGATTCATTTTCTTCTTG
AAGATCCTGTAACCACTTCCCTGTATTGGCTAGGTCTTTCTCTTTCTCTTCCAAAACAGCCT
TCATGGTATTCATCTGTTCCTCTTTTCCTTTTAATAAGTTCAGGAGCTTCAGAAC 11726-1&2

CAAGCTTTTTTTTTTTTTTAAAAAGTGTTAGCATTAATGTTTTATTGTCACGCAGATGGCA
ACTGGGTTTATGTCTTCATATTTTATATTTTTGTAAATTAAAAAAATTACAAGTTTTAAATA
GCCAATGGCTGGTTATATTTTCAGAAAACATGATTAGACTAATTCATTAATGGTGGCTTCA
AGCTTTTCCTTATTGGCTCCAGAAAATTCACCCACCTTTTGTCCCTTCTTAAAAAACTGGAA
TGTTGGCATGCATTTGACTTCACACTCTGAAGCAACATCCTGACAGTCATCCACATCTACTT
CAAGGAATATCACGTTGGAATACTTTTCAGAGAGGGAATGAAAGAAAGGCTTGATCATTT
TGCAAGGCCCACACCACGTGGCTGAGAAGTCAACTACTACAAGTTTATCACCTGCAGCGTC
CAAGGCTTCCTGAAAAGCAGTCTTGCTCTCGATCTGCTTCACCATCTTGGCTGCTGGAGTCT
GACGAGCGGCTGTAAGGACCGATGGAAATGGATCCAAAGCACCAAACAGAGCTTCAAGA
CTCGCTGCTTGGCTTGAATTCGGATCCGATATCGCCATGGCCT 11727-1&2

AAGTGTTAGCATTAATGTTTTATTGTCACGCAGATGGCAACTGGGTTTATGTCTTCATATTT
TATATTTTTGTAAATTAAAAAAATTMCAAGTTTTAAATAGCCAATGGCTGGTTATATTTTC
AGAAAACATGATTAGACTAATTCATTAATGGTGGCTTCAAGCTTTTCCTTATTGGCTCCAG
AAAATTCACCCACCTTTTGTCCCTTCTTAAAAAACTGGAATGTTGGCATGCATTTGACTTCA
CACTCTGAAGCAACATCCTGACAGTCATCCACATCTACTTCAAGGAATATCACGTTGGAAT
ACTTTTCAGAGAGGGAATGAAAGAAAGGCTTGATCATTTTGCAAGGCCCACACCACGTGG
CTGAGAAGTCAACTACTACAAGTTTATCACCTGCAGCGTCCAAGGCTTCCTGAAAAGCAGT
CTTGCTCTCGATCTGCTTCACCATCTTGGCTGCTGGAGTCTGACGAGCGGCTGTAAGGACC
GATGGAAATGGATCCAAAGCACCAAACAGAGCTTCAAGACTCGCTGCTTGGCATGAATTC
GGATCCGA

TACAAACTTTATTGAAACGCACACGCGCACACACACAAACACCCCTGTGGATAGGGAAAA
GCACCTGGCCACAGGGTCCACTGAAACGGGGAGGGGATGGCAGCTTGTAATGTGGCTTTT
GCCACAACCCCCTTCTGACAGGGAAGGCCTTAGATTGAGGCCCCACCTCCCATGGTGATGG
GGAGCTCAGAATGGGGTCCAGGGAGAATTTGGTTAGGGGGAGGTGCTAGGGAGGCATGA
GCAGAGGGCACCCTCCGAGTGGGGTCCCGAGGGCTGCAGAGTCTTCAGTACTGTCCCTCAC
AGCAGCTGTCTCAAGGCTGGGTCCCTCAAAGGGGCGTCCCAGCGCGGGGCCTCCCTGCGC
AAACACTTGGTACCCCTGGCTGCGCAGCGGAAGCCAGCAGGACAGCAGTGGCGCCGATCA
GCACAACAGACGCCCTGGCGGTAGGGACAGCAGGCCCAGCCCTGTCGGTTGTCTCGGCAG
CAGGTCTGGTTATCATGGCAGAAGTGTCCTTCCCACACTTCACGTCCTTCACACCCACGTG
AXGGCTACXGGCCAGGAAG

11728.2.40.19.19

CCCGTGGGTGCCATCCACGGAGTTGTTACCTGATCTTTGGAAGCAGGATCGCCCGTCTGCA
CTGCAGTGGAAGCCCCGTGGGCAGCAGTGATGGCCATCCCCGCATGCCACGGCCTCTGGG
AAGGGGCAGCAACTGGAAGTCCCTGAGACGGTAAAGATGCAGGAGTGGCCGGCAGAGCA
GTGGGCATCAACCTGGCAGGGGCCACCCAGATGCCTGCTCAGTGTTGTGGGCCATTTGTCC
AGAAGGGGACGGCAGCAGCTGTAGCTGGCTCCTCCGGGGTCCAGGCAGCAGGCCACAGGG
CAGAACTGACCATCTGGGCACCGCGTTCCAGCCACCAGCCCTGCTGTTAAGGCCACCCAGC
TCACCAGGGTCCACATGGTCTGCCTGCGTCCGACTCCGCGGTCCTTGGGCCCTGATGGTTC
TACCTGCTGTGAGCTGCCCAGTGGGAAGTATGGCTGCTGCCAATGCCCAACGCCACCTGCT
GCTCCGATCACCTGCACTGCTGCCCCAAGACACTGTGTGTGACCTGATCCAGAGTAAGTGC
CTCTCCAAGGAGAACG

11730-1

GAATCACCTTTCTGGTTTAGCTAGTACTTTGTACAGAACAATGAGGTTTCCCACAGCGGAG
TCTCCCTGGGCTCTGTTTGGCTCTCGGTAAGGCAGGCCTACACCTTTTCCTCTCCTCTATGG
AGAGGGGAATATGCATTAAGGTGAAAAGTCACCTTCCAAAAGTGAGAAAGGGATTCGATT
GCTGCTTCAGGACTGTGGAATTATTTGGAATGTTTTACAAATGGTTGCTACAAAACAACAA
AAAAGGTAATTACAAAATGTGTACATCACAACATGCTTTTTAAAGACATTATGCATTGTGC
TCACATTCCCTTAAATGTTGTTTCCAAAGGTGCTCAGCCTCTAGCCCAGCTGGATTCTCCGG
GAAGAGGCAGAGACAGTTTGGCGAAAAAGACACAGGGAAGGAGGGGGTGGTGAAAGGA
GAAAGCAGCCTTCCAGTTAAAGATCAGCCCTCAGTTAAAGGTCAGCTTCCCGCAXGCTGGC
CTCAXGCGGAGTCTGGGTCAGAGGGAGGAGCAGCAGCAGGGTGGGACTGGGGCGT

11730-2

AACCGGAGCGCGAGCAGTAGCTGGGTGGGCACCATGGCTGGGATCACCACCATCGAGGCG
GTGAAGCGCAAGATCCAGGTTCTGCAGCAGCAGGCAGATGATGCAGAGGAGCGAGCTGA
GCGCCTCCAGCGAGAAGTTGAGGGAGAAAGGCGGGCCCGGGAACAGGCTGAGGCTGAGG
TGGCCTCCTTGAACCGTAGGATCCAGCTGGTTGAAGAAGAGCTGGACCGTGCTCAGGAGC
GCCTGGCCACTGCCCTGCAAAAGCTGGAAGAAGCTGAAAAAGCTGCTGATGAGAGTGAGA
GAGGTATGAAGGTTATTGAAAACCGGGCCTTAAAAGATGAAGAAAAGATGGAACTCCAG
GAAATCCAACTCAAAGAAGCTAAGCACATTGCAGAAGAGGCAGATAGGAAGTATGAAGA
GGTGGCTCGTAAGTTGGTGATCATTGAAGGAGACTTGGAACGCACAGAGGAACGAGCTGA
GCTGGCAGAGTCCCGTTGCCGAGAGATGGATGAGCAGATTAGACTGATGGACCAGAACCT
GAAGTGTCTGAGTGC

*FIG. 15C*

11732.1contig

GAGAACTTGGCCTTTATTGTGGGCCCAGGAGGGCACAAAGGTCAGGAGGCCCAAGGGAGG
GATCTGGTTTTCTGGATAGCCAGGTCATAGCATGGGTATCAGTAGGAATCCGCTGTAGCTG
CACAGGCCTCACTTGCTGCAGTTCCGGGGAGAACACCTGCACTGCATGGCGTTGATGACCT
CGTGGTACACGACAGAGCCATTGGTGCAGTGCAAGGGCACGCGCATGGGCTCCGTCCTCG
AGGGCAGGCAGCAGGAGCATTGCTCCTGCACATCCTCGATGTCAATGGAGTACACAGCTT
TGCTGGCACACTTTCCCTGGCAGTAATGAATGTCCACTTCCTCTTGGGACTTACAATCTCCC
ACTTTGATGTACTGCACCTTGGCTGTGATGTCTTTGCAATCAGGCTCCTCACATGTGTCACA
GCAGGTGCCTGGAATTTTCACGATTTTGCCTCCTTCAGCCAGACACTTGTGTTCATCAAATG
GTGGGCAGCCCGTGACCCTCTTCTCCCAGATGTACTCTCCTCT

11732.2contig

GCCTGGACCTTGCCGGATCAGTGCCACACAGTGACTTGCTTGGCAAATGGCCAGACCTTGC
TGCAGAGTCATCGTGTCAATTGTGACCATGGACCCCGGCCTTCATGTGCCAACAGCCAGTC
TCCTGTTCGGGTGGAGGAGACGTGTGGCTGCCGCTGGACCTGCCCTTGTGTGTGCACGGGC
AGTTCCACTCGGCACATCGTCACCTTCGATGGGCAGAATTTCAAGCTTACTGGTAGCTGCT
CCTATGTCATCTTTCAAAACAAGGAGCAGGACCTGGAAGTGCTCCTCCACAATGGGGCCTG
CAGCCCCGGGGCAAAACAAGCCTGCATGAAGTCCATTGAGATTAAGCATGCTGGCGTCTC
TGCTGAGCTGCACAGTAACATGGAGATGGCAGTGGATGGGAGACTGGTCCTTGCCCCGTA
CGTTGGTGAAAACATGGAAGTCAGCATCTACGGCGCTATCATGTATGAAGTCAGGTTTACC
CATCTTGGCCACATCCTCACATACACCGCCXCAAAACAACGAGTT

11735-1-2

AGATCAACCTCTGCTGGTCAGGAGGAATGCCTTCCTTGTCTTGGATCTTTGCTTTGACGTTC
TCGATAGTRWCAaCTKKRYTSRAMSKMAAGKGYRATGRWMTTKSYWGWRASYKTMWWM
RSGRARAYTTaGaCAYCCCMCCTCWgAGaCGSAGKACCARGTGCAgAgGTGGACTCTTTCTG
GATGTTGTAGTCAGACAGGGTGCGTCCATCTTCCAGCTGTTTCCCAGCAAAGATCAACCTC
TGCTGATCAGGAGGGATGCCTTCCTTATCTTGGATCTTTGCCTTGACATTCTCGATGGTGTC
ACTGGGCTCCACCTCGAGGGTGATGGTCTTACCAGTCAGGGTCTTCACGAAGATYTGCATC
CCACCTCTGAGACGGAGCACCAGGTGCAGGGTRGACTCTTTCTGGATGTTGTAGTCAGACA
GGGTGCGYCCATCTTCCAGCTGcTTTCCSaGCAAAGATCAACCTCTGCTGGTCAGGAGGRAT
GCCTTCCTTGTCYTGGATCTTTGCYTTGACRTTCTCRATGGTGTCACTCGGCTCCACTTCGA
GAGTGATGGTCTTACCAGTCAGGGTCTTCACGAAGATCTGCATCCCACCTCTAA

11740.2.contig

AAGTCACAAACAGACAAAGATTATTACCAGCTGCAAGCTATATTAGAAGCTGAACGAAGA
GACAGAGGTCATGATTCTGAGATGATTGGAGACCTTCAAGCTCGAATTACATCTTTACAAG
AGGAGGTGAAGCATCTCAAACATAATCTCGAAAAAGTGGAAGGAGAAAGAAAAGAGGCT
CAAGACATGCTTAATCACTCAGAAAAGGAAAAGAATAATTTAGAGATAGATTTAAACTAC
AAACTTAAATCATTACAACAACGGTTAGAACAAGAGGTAAATGAACACAAAGTAACCAAA
GCTCGTTTAACTGACAAACATCAATCTATTGAAGAGGCAAAGTCTGTGGCAATGTGTGAG
ATGGAAAAAAAGCTGAAAGAAGAAAGAGAAGCTCGAGAGAAGGCTGAAAATCGGGTTGT
TCAGATTGAGAAACAGTGTTCCATGCTAGACGTTGATCTGAAGCAATCTCAGCAGAAACT
AGAACATTTGACTGGAAATAAAGAAAGGATGGAGGATGAAGTTAAGAATCTA

*FIG. 15D*

11765.2&64.2.contig

CGCCTCCACCATGTCCATCAGGGTGACCCAGAAGTCCTACAAGGTGTCCACCTCTGGCCCC
CGGGCCTTCAGCAGCCGCTCCTACACGAGTGGGCCCGGTTCCCGCATCAGCTCCTCGAGCT
TCTCCCGAGTGGGCAGCAGCAACTTTCGCGGTGGCCTGGGCGGCGGCTATGGTGGGGCCA
GCGGCATGGGAGGCATCACCGCAGTTACGGTCAACCAGAGCCTGCTGAGCCCCCTTGTCCT
GGAGGTGGACCCCAACATCCAGGCCGTGCGCACCCAGGAGAAGGAGCAGATCAAGACCCT
CAACAACAAGTTTGCCTCCTTCATAGACAAGGTACGGTTCCTGGAGCAGCAGAACAAGAT
GCTGGAGACCAAGTGGAGCCTCCTGCAGCAGCAGAAGACGGCTCGAAGCAACATGGACA
ACATGTTCGAGAGCTACATCAACARCCTTAGGCGGCAGCTGGAGACTCTGGGCCAGGAGA
AGCTGAAGCTGGAGGCGGAGCTTGGCAACATGCAGGGGCTGGTGGAGGACTTCAAGAAC
AAGTATGAGGATGAGATCAATAAGCGTACAGAGATGGAGAACGAATTTGTCCTCATCAAG
AAGGATGTGGATGAAGCTTACATGAACAAGGTAGAGCTGGAGTCTCGCCTGGAAGGGCTG
ACCGACGAGATCAACTTCCTCAGGCAGCTGTATGAAGAGGAGATCCGGGAGCTGCAGTCC
CAGATCTCGGACACATCTGTGGTGCTGTCCATGGACAACAGCCGCTCCCTGGACATGGACA
GCATCATTGCTGAGGTCAAGGCACAGTACGAGGATATTGCCAACCGCAGCCGGGCTGAGG
CTGAGAGCATGTACCAGGTCAAGTATGAGGAGCTGCAGAGCCTGGCTGGGAAGCACGGGG
ATGACCTGCGGCGCACAAAGACTGAGATCTCTGAGATGAACCCGGAACATCAGCCCGGCT
XCAGGCTGAGATTGAGGGCCTCAAAGGCCAGAXGGCTTXCCTGGAXGXCCGCCAT

11767.2.contig

CCCGGAGCCAGCCAACGAGCGGAAAATGGCAGACAATTTTTCGCTCCATGATGCGTTATCT
GGGTCTGGAAACCCAAACCCTCAAGGATGGCCTGGCGCATGGGGGAACCAGCCTGCTGGG
GCAGGGGGCTACCCAGGGGCTTCCTATCCTGGGGCCTACCCCGGGCAGGCACCCCCAGGG
GCTTATCCTGGACAGGCACCTCCAGGCGCCTACCCTGGAGCACCTGGAGCTTATCCCGGAG
CACCTGCACCTGGAGTCTACCCAGGGCCACCCAGCGGCCCTGGGGCCTACCCATCTTCTGG
ACAGCCAAGTGCCACCGGAGCCTACCCTGCCACTGGCCCCTATGGCGCCCCTGCTGGGCCA
CTGATTGTGCCTTATAACCTGCCTTTGCCTGGGGGAGTGGTGCCTCGCATGCTGATAACAA
TTCTGGGCACGGTGAAGCCCAATGCAAACAGAATTGCTTTAGATTTCCAAAGAGGGAATG
ATGTTGCCTTCCACTTTAACCCACGCTTCAATGAGAACAACAGGAGAGTCATTGGTTGCAA
TACAAAGCTGGATAA

11768-1&2

GGGAATGCAACAACTTTATTGAAAGGAAAGTGCAATGAAATTTGTTGAAACCTTAAAAGG
GGAAACTTAGACACCCCCCCTCRAgCGMAGKACCARGTGCARAgGTGGACTCTTTCTGGAT
GTTGTAGTCAGACAGGGTRCGWCCATCTTCCAGCTGTTTYCCRGCAAAGATCAACCTCTGC
TGATCAGGAGGRATGCCTTCCTTATCTTGGATCTTTGCCTTGACATTCTCGATGGTGTCACT
GGGCTCCACCTCGAGGGTGATGGTCTTACCAGTCAGGGTCTTCACGAAGATYTGCATCCCA
CCTCTGAGACGGAGCACCAGGTGCAGGGTRGACTCTTTCTGGATGTTGTAGTCAGACAGG
GTGCGYCCATCTTCCAGCTGcTTTCCSaGCAAAGATCAACCTCTGCTGGTCAGGAGGRATGC
CTTCCTTGTCYTGGATCTTTGCYTTGACRTTCTCAATGGTGTCACTCGGCTCCACTTCGAGA
GTGATGGTCTTACCAGTCAGGGTCTTCACGAAGATCTGCATCCCACCTCTAAGACGGAGCA
CCAGGTGCAGGGTGGACTCTTTCTGGATGgTTGTAGTCAGACAGGGTGCGTCCATCTTCCA
GCTGTTTCCCAGCAAAGATCAACCT

AGGTTGATCTTTGCTGGGAAACAGCTGGAAGATGGACGCACCCTGTCTGACTACAAcCATC
CAGAAAGAGTCCACCCTGCACCTGGTGCTCCGTCTTAGAGGTGGGATGCAGATCTTCGTGA
AGACCCTGACTGGTAAGACCATCACTCTCGAAGTGGAGCCGAGTGACACCATTGAGAAYG
TCAARGCAAAGATCCARGACAAGGAAGGCATYCCTCCTGACCAGCAGAGGTTGATCTTTG
CtSGGAAAgCAGCTGGAAGATGGRCGCACCCTGTCTGACTACAACATCCAGAAAGAGTCYA
CCCTGCACCTGGTGCTCCGTCTCAGAGGTGGGATGCARATCTTCGTGAAGACCCTGACTGG
TAAGACCATCACCCTCGAGGTGGAGCCCAGTGACACCATCGAGAATGTCAAGGCAAAGAT
CCAAGATAAGGAAGGCATCCCTCCTGATCAGCAGAGGTTGATCTTTGCTGGGAAACAGCT
GGAAGATGGACGCACCCTGTCTGACTACAACATCCAGAAAGAGTCCACcTYTGCACYTGGT
MCTBCGtCTYaGAGGKGGGRTGcaaaTCTWMGTKWagaCaCtCaCTKKYAAGRYYaTCAMCMWt
gAKKTCgAKYSCASTKWCaCTWTCRAKAAMGTYRWWGCAWagaTCCMAGACAAGGAAGGC
ATTCCTCCTGACCAGCAGAGGTTGATCT

11769.1.contig

ATGGAGTCTCACTCTGTCGACCAGGCTGGAGCGCTGTGGTGCGATATCGGCTCACTGCAGT
CTCCACTTCCTGGGTTCAAGCGATCCTCCTGCCTCAGCCTCCCGAGTAGCTGGGACTACAG
GCAGGCGTCACCATAATTTTTGTATTTTTAGTAGAGACATGGTTTCGCCATGTTGGCTGGG
CTGGTCTCGAACTCCTGACCTCAAGTGATCTGTCCTGGCCTCCCAAAGTGTTGGGATTACA
GGCGAAAGCCAACGCTCCCGGCCAGGGAACAACTTTAGAATGAAGGAAATATGCAAAAG
AACATCACATCAAGGATCAATTAATTACCATCTATTAATTACTATATGTGGGTAATTATGA
CTATTTCCCAAGCATTCTACGTTGACTGCTTGAGAAGATGTTTGTCCTGCATGGTGGAGAG
TGGAGAAGGGCCAGGATTCTTAGGTT

11769.2.contig

AGCGCGGTCTTCCGGCGCGAGAAAGCTGAAGGTGATGTGGCCGCCCTCAACCGACGCATC
CAGCTCGTTGAGGAGGAGTTGGACAGGGCTCAGGAACGACTGGCCACGGCCCTGCAGAAG
CTGGAGGAGGCAGAAAAAGCTGCAGATGAGAGTGAGAGAGGAATGAAGGTGATAGAAAA
CCGGGCCATGAAGGATGAGGAGAAGATGGAGATTCAGGAGATGCAGCTCAAAGAGGCCA
AGCACATTGCGGAAGAGGCTGACCGCAAATACGAGGAGGTAGCTCGTAAGCTGGTCATCC
TGGAGGGTGAGCTGGAGAGGGCAGAGGAGCGTGCGGAGGTGTCTGAACTAAAATGTGGT
GACCTGGAAGAAGAACTCAAGAATGTTACTAACAATCTGAAATCTCTGGAGGCTGCATCT
GAAAAGTATTCTGAAAAGGAGGACAAATATGAAGAAGAAATTAAACTTCTGTCTGACAAA
CTGAAAGAGGCTGAGACCCGTGCTGAATTTGCAGAGAGAACGGTTGCAAAACTGGAAAAG
ACAATTGATGACCTGGAAGAGAAACTTGCCCAGC

11770.1.contig

GTGCACAGGTCCCATTTATTGTAGAAAATAATAATAATTACAGTGATGAATAGCTCTTCTT
AAATTACAAAACAGAAACCACAAAGAAGGAAGAGGAAAAACCCCAGGACTTCCAAGGGT
GAAGCTGTCCCCTCCTCCCTGCCACCCTCCCAGGCTCATTAGTGTCCTTGGAAGGGGCAGA
GGACTCAGAGGGGATCAGTCTCCAGGGGCCCTGGGCTGAAGCGGGTGAGGCAGAGAGTCC
TGAGGCCACAGAGCTGGGCAACCTGAGCCGCCTCTCTGGCCCCCTCCCCCACCACTGCCCA
AACCTGTTTACAGCACCTTCGCCCCTCCCCTCTAAACCCGTCCATCCACTCTGCACTTCCCA
GGCAGGTGGGTGGGCCAGGCCTCAGCCATACTCCTGGGCGCGGGTTTCGGTGAGCAAGGC
ACAGTCCCAGAGGTGATATCAAGGCCT

*FIG. 15F*

11770.2.contig

GCAAGGAACTGGTCTGCTCACACTTGCTGGCTTGCGCATCAGGACTGGCTTTATCTCCTGA
CTCACGGTGCAAAGGTGCACTCTGCGAACGTTAAGTCCGTCCCCAGCGCTTGGAATCCTAC
GGCCCCCACAGCCGGATCCCCTCAGCCTTCCAGGTCCTCAACTCCCGTGGACGCTGAACAA
TGGCCTCCATGGGGCTACAGGTAATGGGCATCGCGCTGGCCGTCCTGGGCTGGCTGGCCGT
CATGCTGTGCTGCGCGCTGCCCATGTGGCGCGTGACGGCCTTCATCGGCAGCAACATTGTC
ACCTCGCAGACCATCTGGGAGGGCCTATGGATGAACTGCGTGGTGCAGAGCACCGGCCAG
ATGCAGTGCAAGGTGTACGACTCGCTGCTGGCACTGCCGCAGGACCTGCAGGCGGCCCGC
GCCCTCGTCATCATCA

11773.1.contig

TGCAAAAGGGACACAGGGGTTCAAAAATAAAAATTTCTCTTCCCCCTCCCCAAACCTGTAC
CCCAGCTCCCCGACCACAACCCCCTTCCTCCCCCGGGGAAAGCAAGAAGGAGCAGGTGTG
GCATCTGCAGCTGGGAAGAGAGAGGCCGGGGAGGTGCCGAGCTCGGTGCTGGTCTCTTTC
CAAATATAAATACXTGTGTCAGAACTGGAAAATCCTCCAGCACCCACCACCCAAGCACTCT
CCGTTTTCTGCCGGTGTTTGGAGAGGGGCGGGGGGCAGGGGCGCCAGGCACCGGCTGGCT
GCGGTCTACTGCATCCGCTGGGTGTGCACCCCGCGAGCCTCCTGCTGCTCATTGTAGAAGA
GATGACACTCGGGGTCCCCCCGGATGGTGGGGGCTCCCTGGATCAGCTTCCCGGTGTTGGG
GTTCACACACCAGCACTCCCCACGCTGCCCGTTCAGAGACATCTTGCACTGTTTGAGGTTG
TACAGGCCATGCTTGTCACAGTTG

11778.1.contig

GGGTTGGAGGGACTGGTTCTTTATTTCAAAAAGACACTTGTCAATATTCAGTATCAAAACA
GTTGCACTATTGATTTCTCTTTCTCCCAATCGGCCCCAAAGAGACCACATAAAAGGAGAGT
ACATTTTAAGCCAATAAGCTGCAGGATGTACACCTAACAGACCTCCTAGAAACCTTACCAG
AAAATGGGGACTGGGTAGGGAAGGAAACTTAAAAGATCAACAAACTGCCAGCCCACGGA
CTGCAGAGGCTGTCACAGCCAGATGGGGTGGCCAGGGTGCCACAAACCCAAAGCAAAGTT
TCAAAATAATATAAAATTTAAAAAGTTTTGTACATAAGCTATTCAAGATTTCTCCAGCACT
GACTGATACAAAGCACAATTGAGATGGCACTTCTAGAGACAGCAGCTTCAAACCCAGAAA
AGGGTGATGAGATGAGTTTCACATGGCTAAATCAGTGGCAAAAACACAGTCTTCTTTCTTT
CTTTCTTTCAAGGAGGCAGGAAAGCAATTAAGTGGTCACCTCAACATAAGGGGGACATGA
TCCATTCTGTAAGCAGTTGTGAAGGGG

11778-2&30-2

CAGGAACCGGAGCGCGAGCAGTAGCTGGGTGGGCACCATGGCTGGGATCACCACCATCGA
GGCGGTGAAGCGCAAGATCCAGGTTCTGCAGCAGCAGGCAGATGATGCAGAGGAGCGAG
CTGAGCGCCTCCAGCGAGAAGTTGAGGGAGAAAGGCGGGCCCGGGAACAGGCTGAGGCT
GAGGTGGCCTCCTTGAACCGTAGGATCCAGCTGGTTGAAGAAGAGCTGGACCGTGCTCAG
GAGCGCCTGGCCACTGCCCTGCAAAAGCTGGAAGAAGCTGAAAAAGCTGCTGATGAGAGT
GAGAGAGGTATGAAGGTTATTGAAAACCGGGCCTTAAAAGATGAAGAAAAGATGGAACT
CCAGGAAATCCAACTCAAAGAAGCTAAGCACATTGCAGAAGAGGCAGATAGGAAGTATG
AAGAGGTGGCTCGTAAGTTGGTGATCATTGAAGGAGACTTGGAACGCACAGAGGAACGAG
CTGAGCTGGCAGAGTCCCGTTGCCGAGAGATGGATGAGCAGATTAGACTGATGGACCAGA
ACCTGAAGTGTCTGAGTGC

*FIG. 15G*

11782.1.contig

ATCTACGTCATCAATCAGGCTGGAGACACCATGTTCAATCGAGCTAAGCTGCTCAATATTG
GCTTTCAAGAGGCCTTGAAGGACTATGATTACAACTGCTTTGTGTTCAGTGATGTGGACCT
CATTCCGATGGACGACCGTAATGCCTACAGGTGTTTTTCGCAGCCACGGCACATTTCTGTT
GCAATGGACAAGTTCGGGTTTAGCCTGCCATATGTTCAGTATTTTGGAGGTGTCTCTGCTCT
CAGTAAACAACAGTTTCTTGCCATCAATGGATTCCCTAATAATTATTGGGGTTGGGGAGGA
GAAGATGACGACATTTTTAACAGATTAGTTCATAAAGGCATGTCTATATCACGTCCAAATG
CTGTAGTAGGGAGGTGTCGAATGATCCGGCATTCAAGAGACAAGAAAAATGAGCCCAATC
CTCAGAGGTTTGACCGGATCGCACATACAAAGGAAACGATGCGCTTCGATGGTTTGAACT
CACTTACCTACAAGGTGTTGGATGTCAGAGATACCCGTTATATACCCAAATCAC

11782.2.contig

CTAGACCTCTAATTAAAAGGCACAATCATGCTGGAGAATGAACAGTCTGACCCCGAGGGC
CACAGCGAATTTTAGGGAAGGAGGCAAAGAGGTGAGAAGGGAAAGGAAAGAAGGAAGG
AAGGAGAACAATAAGAACTGGAGACGTTGGGTGGGTCAGGGAGTGTGGTGGAGGCTCGG
AGAGATGGTAAACAAACCTGACTGCTATGAGTTTTCAACCCCATAGTCTAGGGCCATGAG
GGCGTCAGTTCTTGGTGGCTGAGGGTCCTTCCACCCAGCCCACCTGGGGGAGTGGAGTGG
GGAGTTCTGCCAGGTAAGCAGATGTTGTCTCCCAAGTTCCTGACCCAGATGTCTGGCAGGA
TAACGCTGACCTGTTCCCTCAACAAGGGACCTGAAAGTAATTTTGCTCTTTAC

11783-1 & 2

CCGAATTCAAGCGTCAACGATCCYTCCCTTACCATCAAATCAATTGGCCACCAATGGTACT
GAACCTACGAGTACACCGACTACgGGCGGACTAATCTTCAACTCCTACATACTTCCCCCAT
TATTCCTAGAACCAGGCGACCTGCGACTCCTTGACGTTGACAATCGAGTAGTACTCCCGAT
TGAAGCCCCCATTCGTATAATAATTACATCACAAGACGTCTTGCACTCATGAGCTGTCCCC
ACATTAGGCTTAAAAACAGATGCAATTCCCGGACGTCTAAGCCAAACCACTTTCACCGCTA
CACGACCGGGGGTATACTACGGTCAATGCTCTGAAATCTGTGGAGCAAACCACAGTTTCAT
GCCCATCGTCCTAGAATTAATTCCCCTAAAAATCTTTGAAATAGGGCCCGTATTTACCCTA
TAGCACCCCCTCTACCCCCTCTAG

11786.1.contig

GCTCTTCACACTTTTATTGTTAATTCTCTTCACATGGCAGATACAGAGCTGTCGTCTTGAAG
ACCACCACTGACCAGGAAATGCCACTTTTACAAAATCATCCCCCCTTTTCATGATTGGAAC
AGTTTTCCTGACCGTCTGGGAGCGTTGAAGGGTGACCAGCACATTTGCACATGCAAAAAA
GGAGTGACCCCAAGGCCTCAACCACACTTCCCAGAGCTCACCATGGGCTGCAGGTGACTT
GCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGAT
AAGGAACAGCCACAGCACTTCATGCTTGTGAGGGTTAGCTGTAGGAGCGGGTGAAAGGAT
TCCAGTTTATGAAAATTTAAAGCAAACAACGGTTTTTAGCTGGGTGGGAAACAGGAAAAC
TGTGATGTCGGCCAATGACCACCATTTTTCTGCCCATGTGAAGGTCCCCATGAAACC

*FIG. 15H*

11786.2.contig

CAAGCGCTTGGCGTTTGGACCCAGTTCAGTGAGGTTCTTGGGTTTTGTGCCTTTGGGGATTT
TGGTTTGACCCAGGGGTCAGCCTTAGGAAGGTCTTCAGGAGGAGGCCGAGTTCCCCTTCAG
TACCACCCCTCTCTCCCCACTTTCCCTCTCCCGGCAACATCTCTGGGAATCAACAGCATATT
GACACGTTGGAGCCGAGCCTGAACATGCCCCTCGGCCCCAGCACATGGAAAACCCCCTTC
CTTGCCTAAGGTGTCTGAGTTTCTGGCTCTTGAGGCATTTCCAGACTTGAAATTCTCATCAG
TCCATTGCTCTTGAGTCTTTGCAGAGAACCTCAGATCAGGTGCACCTGGGAGAAAGACTTT
GTCCCCACTTACAGATCTATCTCCTCCCTTGGGAAGGGCAGGGAATGGGGACGGTGTATGG
AGGGGAAGGGATCTCCTGCGCCCTTCATTGCCACACTTGGTGGGACCATGAACATCTTTAG
TGTCTGAGCTTCTCAAATTACTGCAATAGGA

13691.1&2

AGCGTCAAATCAGAATGGAAAAGACTCAAAACCATCATCAACACCAAGATCAAAAGGAC
AAGRATCCTTCAAGAAACAGGAAAAAACTCCTAAAACACCAAAAGGACCTAGTTCTGTAG
AAGACATTAAAGCAAAAATGCAAGCAAGTATAGAAAAAGGTGGTTCTCTTCCCAAAGTGG
AAGCCAAATTCATCAATTATGTGAAGAATTGCTTCCGGATGACTGACCAAGAGGCTATTCA
AGATCTCTGGCAGTGGAGGAAGTCTCTTTAAGAAAATAGTTTAAACAATTTGTTAAAAAAT
TTTCCGTCTTATTTCATTTCTGTAACAGTTGATATCTGGCTGTCCTTTTTATAATGCAGAGT
GAGAACTTTCCCTACCGTGTTTGATAAATGTTGTCCAGGTTCTATTGCCAAGAATGTGTTGT
CCAAAATGCCTGTTTAGTTTTTAAAGATGGAACTCCACCCTTTGCTTGGTTTTAAGTATGTA
TGGAATGTTATGATAGGACATAGTAGTAGCGGTGGTCAGACATGGAAATGGTGGGSMGAC
AAAAATATACATGTGAAATAA

13692.1&2

TCCGAATTCCAAGCGAATTATGGACAAACGATTCCTTTTAGAGGATTACTTTTTTCAATTTC
GGTTTTAGTAATCTAGGCTTTGCCTGTAAAGAATACAACGATGGATTTTAAATACTGTTTG
TGGAATGTGTTTAAAGGATTGATTCTAGAACCTTTGTATATTTGATAGTATTTCTAACTTTC
ATTTCTTTACTGTTTGCAGTTAATGTTCATGTTCTGCTATGCAATCGTTTATATGCACGTTTC
TTTAATTTTTTTAGATTTTCCTGGATGTATAGTTTAAACAACAAAAAGTCTATTTAAAACTG
TAGCAGTAGTTTACAGTTCTAGCAAAGAGGAAAGTTGTGGGGTTAAACTTTGTATTTTCTT
TCTTATAGAGGCTTCTAAAAAGGTATTTTTATATGTTCTTTTTAACAAATATTGTGTACAAC
CTTTAAAACATCAATGTTTGGATCAAAACAAGACCCAGCTTATTTTCTGC

13693.2

TGTGGTGGCGCGGGCTGAGGTGGAGGCCCAGGACTCTGACCCTGCCCCTGCCTTCAGCAA
GGCCCCCGGCAGCGCCGGCCACTACGAACTGCCGTGGGTTGAAAAATATAGGCCAGTAAA
GCTGAATGAAATTGTCGGGAATGAAGACACCGTGAGCAGGCTAGAGGTCTTTGCAAGGGA
AGGAAATGTGCCCAACATCATCATTGCGGGCCCTCCAGGAACCGGCAAGACCACAAGCAT
TCTGTGCTTGGCCCGGGCCCTGCTGGGCCCAGCACTCAAAGATGCCATGTTGGAACTCAAT
GCTTCAAATGACAGGGGCATTGACGTTGTGAGGAATAAAATTAAAATGTTTGCTCAACAA
AAAGTCACTCTTCCCAAAGGCCGACATAAGATCATCATTCTGGATGAAGCAGACAGCATG
ACCGACGGAGCCCAGCAAGCCTTGAGGAGAACCATGGAAATCTACTCTAAAACCACTCGT
TCGCCCTTGCTTGTAATGCTTCGGATAAGATCATCGAGCC

CTTTGCAAAGCTTTTATTTCATGTCTGCGGCATGGAATCCACCTGCACATGGCATCTTAGCT
GTGAAGGAGAAAGCAGTGCACGAGAAGGAATGAGTGGGCGGAACCAACGGCCTCCACAA
GCTGCCTTCCAGCAGCCTGCCAAGGCCATGGCAGAGAGAGACTGCAAACAAACACAAGCA
AACAGAGTCTCTTCACAGCTGGAGTCTGAAAGCTCATAGTGGCATGTGTGAATCTGACAA
AATTAAAAGTGTGCATAGTCCATTACATGCATAAAACACTAATAATAATCCTGTTTACACG
TGACTGCAGCAGGCAGGTCCAGCTCCACCACTGCCCTCCTGCCACATCACATCAAGTGCCA
TGGTTTAGAGGGTTTTTCATATGTAATTCTTTTATTCTGTAAAAGGTAACAAAATATACAG
AACAAAACTTTCCCTTTTTAAAACTAATGTTACAAATCTGTATTATCACTTGGATATAAAT
AGTATATAAGCTGATC

13700.1

CAAGGGATATATGTTGAGGGTACRGRGTGACACTGAACAGATCACAAAGCACGAGAAACA
TTAGTTCTCTCCCTCCCCAGCGTCTCCTTCGTCTCCCTGGTTTTCCGATGTCCACAGAGTGA
GATTGTCCCTAAGTAACTGCATGATCAGAGTGCTGKCTTTATAAGACTCTTCATTCAGCGT
ATCCAATTCAGCAATTGCTTCATCAAATGCCGTTTTTGCCAGGCTACAGGCCTTTTCAGGA
GAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTT
CGACACAAGTGGTTTGTTTGTTGCTCCAGATGCCACTTCAGAAAGATACCTAAAATAATCT
CCTTTCATTTTCAAAGTAGAACAC

13700.2

TCCGGAGCCGGGGTAGTCGCCGCCGCCGCCGCCGGTGCAGCCACTGCAGGCACCGCTGCC
GCCGCCTGAGTAGTGGGCTTAGGAAGGAAGAGGTCATCTCGCTCGGAGCTTCGCTCGGAA
GGGTCTTTGTTCCCTGCAGCCCTCCCACGGGAATGACAATGGATAAAAGTGAGCTGGTACA
GAAAGCCAAACTCGCTGAGCAGGCTGAGCGATATGATGATATGGCTGCAGCCATGAAGGC
AGTCACAGAACAGGGGCATGAACTCTCCAACGAAGAGAGAAATCTGCTCTCTGTTGCCTA
CAAGAATGTGGTAAGGCCGCCCGCCGCTCTTCCTGGCGTGTCATCTCCAGCATTGAGCAGA
AAACAGAGAGGAATGAGAAGAAGCAGCAGATGGGCAAAGAGTACCGTGAGAAGATAGA
GGCAGAACTGCAGGACATCTGCAATGATGTTCTGGAGCTTGTTGGACAAATATCTTATTCC
AATGCTACACAACCCAGAAA

13701.1

AAAAAGCAGCARGTTCAACACAAAATAGAAATCTCAAATGTAGGATAGAACAAAACCAA
GTGTGTGAGGGGGGAAGCAACAGCAAAAGGAAGAAATGAGATGTTGCAAAAAAGATGGA
GGAGGGTTCCCCTCTCCTCTGGGGACTGACTCAAACACTGATGTGGCAGTATACACCATTC
CAGAGTCAGGGGTGTTCATTCTTTTTTGGGAGTAAGAAAAGGTGGGGATTAAGAAGACGT
TTCTGGAGGCTTAGGGACCAAGGCTGGTCTCTTTCCCCCCTCCCAACCCCCTTGATCCCTTT
CTCTGATCAGGGGAAAGGAGCTCGAATGAGGGAGGTAGAGTTGGAAAGGGAAAGGATTC
CACTTGACAGAATGGGACAGACTCCTTCCCA

TGGCAATAGCACAGCCATCCAGGAGCTCTTCARGCGCATCTCGGAGCAGTTCACTGCCATG
TTCCGCCGGAAGGCCTTCCTCCACTGGTACACAGGCGAGGGCATGGACGAGATGGAGTTC
ACCGAGGCTGAGAGCAACATGAACGACCTCGTCTCTGAGTATCAAGCAGTACCAGGATGC
CACCGCAGAAGAGGAGGAGGATTTCGGTGAGGAGGCCGAAGAGGAGGCCTAAGGCAGAG
CCCCCATCACCTCAGGCTTCTCAGTTCCCTTAGCCGTCTTACTCAACTGCCCCTTTCCTCTCC
CTCAGAATTTGTGTTTGCTGCCTCTATCTTGTTTTTTGTTTTTTCTTCTGGGGGGGTCTAGAA
CAGTGCCTGGCACATAGTAGGCGCTCAATAAATACTTGGTTGNTGAATGTCTCCT

13702.2

AGCTGGCGCTAGGGCTCGGTTGTGAAATACAGCGTRGTCAGCCCTTGCGCTCAGTGTAGAA
ACCCACGCCTGTAAGGTCGGTCTTCGTCCATCTGCTTTTTTCTGAAATACACTAAGAGCAG
CCACAAAACTGTAACCTCAAGGAAACCATAAAGCTTGGAGTGCCTTAATTTTTAACCAGTT
TCCAATAAAACGGTTTACTACCT

13704.2-13740.2

GGAGATGAAGATGAGGAAGCTGAGTCAGCTACGGGCARGCGGGCAGCTGAAGATGATGA
GGATGACGATGTCGATACCAAGAAGCAGAAGACCGACGAGGATGACTAGACAGCAAAAA
AGGAAAAGTTAAA

13706.1

GATGAAAATTAAATACTTAAATTAATCAAAAGGCACTACGATACCACCTAAAACCTACTG
CCTCAGTGGCAGTAKGCTAAKGAAGATCAAGCTACAGSACATYATCTAATATGAATGTTA
GCAATTACATAKCARGAAGCATGTTTGCTTTCCAGAAGACTATGGNACAATGGTCATTWG
GGCCCAAGAGGATATTTGGCCNGGAAAGGATCAAGATAGATNAANGTAAAG

13706.2

GAGTAGCAACGCAAAGCGCTTGGTATTGAGTCTGTGGGSGACTTCGGTTCCGGTCTCTGCA
GCAGCCGTGATCGCTTAGTGGAGTGCTTAGGGTAGTTGGCCAGGATGCCGAATATCAAAA
TCTTCAGCAGGCAGCTCCCACCAGGACTTATCTCASAAAATTGCTGACCGCCTGGGCCTGG
AGCTAGGCAAGGTGGTGACTAAGAAATTCAGCAACCAGGAGACCTGTGTGGAAATTGGTG
AAAGTGTACCGTGGAGAGGATGTCTACATTGTTCAGAGTGGNTGTGGCGAAATCAATGAC
AATTTAATGGAGCTTTTGATCATGATTAATGCCTGCAAGATTGCTTCAGCCAGCCGGGTTA
CTGCAGTCATCCCATGCTTCCCTTATGCCCCGGCAGGATAAGAAAGATNAGAGCCGGGCC
GCCAATCTCAGCCAAGCTTGGTGCAAATATGCTATCTGTAGCAGTGCAGATCATATTATCA
CCATGGACCTACATGCTTCTCAAATTCANGGCTTTTT

ATGCAAAAGGGGACACAGGGGGTTCAAAAATAAAAATTTCTCTTCCCCCTCCCCAAACCT
GTACCCCAGCTCCCCGACCACAACCCCCTTCCTCCCCCGGGGAAAGCAAGAAGGAGCAGG
TGTGGCATCTGCAGCTGGGAAGAGAGAGGCCGGGGAGGTGCCGAGCTCGGTGCTGGTCTC
TTTCCAAATATAAATACGTGTGTCAGAACTGGAAAATCCTCCAGCACCCACCACCCAAGCA
CTCTCCGTTTTCTGCCGGTGTTTGGAGAGGGGCGGNGGGCAGGGGCGCCAGGCACCGGCT
GGCTGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAA
CAGGCCCAGAGTGGCACTGGACAGACCATGCAGGTGATGCAGCAGATCATCACTAACACA
GGAGAGATCCAGCAGATCCCGGTGCAGCTGAATGCCGGCCAGCTGCAGTATATCCGCTTA
GCCCAGCCTGTATCAGGCACTCAAGTTGTGCAGGGACAGATCCAGACACTTGCCACCAAT
GCTCAACAGATTACACAGACAGAGGTCCAGCAAGGACAGCAGCAGTTCAAGCCAGTTCAC
AAGATGGACAGCAGCTCTACCAGATCCAGCAAGTCACCATGCCTGCGGGCCANGACCTCG
CCAGCCCATGTTCATCCAGTCAAGCCAACCAGCCCTTCNACGGGCAGGCCCCCCAGGTGAC
CGGCGACTGAAGGGCCTGAGCTGGCAAGGCCAANGACACCCAACACAATTTTTGCCATAC
AGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTA
ATGCATTTAAAAAATAAAAGGGAGGTGGGCAGCAAACACACAAAGTCCTAGTTTCCTGGG
TCCCTGGGAGAAAAGAGTGTGGCAATGAATCCACCCACTCTCCACAGGGAATAAATCTGT
CTCTTAAATGCAAAGAATGTTTCCATGGCCTCTGGATGCAAATACACAGAGCTCTGGGGTC
AGAGCAAGGGATGGGGAGAGGACCACGAGTGAAAAAGCAGCTACACACATTCACCTAAT
TCCATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAA
AGAGTTAAGGGAAGGTTTCCTTTCATTCCTGTTCCTTCTCTTTTGCTTTTGAACAGTTTTTA
AATATACTAATAGCTAAGTCATTTGCCAGCCAGGTCCCGGTGAACAGTAGAGAACAAGGA
GCTTGCTAAGAATTAATTTTGCTGTTTTTCACCCCATTCAAACAGAGCTGCCCTGTTCCCTG
ATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCT
ACTTAATAAATATATTTATACTTTGAAATTATGATAACCGATTTTTCCCATGCGGCATCCTA
AGGGCACTTGCCAGCTCTTATCCGGACAGTCAAGCACTGTTGTTGGACAACAGATAAAGG
AAAAGAAAAAGAAGAAAACAACCGCAACTTCTGT

TGAGACGGACCACTGGCCTGGTCCCCCCTCATKTGCTGTCGTAGGACCTGACATGAAACGC
AGATCTAGTGGCAGAGAGGAAGATGATGAGGAACTTCTGAGACGTCGGCAGCTTCAAGAA
GAGCAATTAATGAAGCTTAACTCAGGCCTGGGACAGTTGATCTTGAAAGAAGAGATGGAG
AAAGAGAGCCGGGAAAGGTCATCTCTGTTAGCCAGTCGCTACGATTCTCCCATCAACTCAG
CTTCACATATTCCATCATCTAAAACTGCATCTCTCCCTGGCTATGGAAGAAATGGGCTTCA
CCGGCCTGTTTCTACCGACTTCGCTCAGTATAACAGCTATGGGGATGTCAGCGGGGGAGTG
CGAGATTACCAGACACTTCCAGATGGCCACATGCCTGCAATGAGAATGGACCGAGGAGTG
TCTATGCCCAACATGTTGGAACCAAAGATATTTCCATATGAAATGCTCATGGTGACCAACA
GAGGGCCGAAACCAAATCTCAGAGAGGTGGACAGAA

13713.1&2

TCACTTTATTTTTCTTGTATAAAAACCCTATGTTGTAGCCACAGCTGGAGCCTGAGTCCGCT
GCACGGAGACTCTGGTGTGGGTCTTGACGAGGTGGTCAGTGAACTCCTGATAGGGAGACT
TGGTGAATACAGTCTCCTTCCAGAGGTCGGGGGTCAGGTAGCTGTAGGTCTTAGAAATGGC
ATCAAAGGTGGCCTTGGCGAAGTTGCCCAGGGTGGCAGTGCAGCCCCGGGCTGAGGTGTA
GCAGTCATCGATACCAGCCATCATGAG

13715.4

CTGGAATATAGACCCGTGATCGACAAAACTTTGAACGAGGCTGACTGTGCCACCGTCCCGC
CAGCCATTCGCTCCTACTGATGAGACAAGATGTGGTGATGACAGAATCAGCTTTTGTAATT
ATGTATAATAGCTCATGCATGTGTCCATGTCATAACTGTCTTCATACGCTTCTGCACTCTGG
GGAAGAAGGAGTACATTGAAGGGAGATTGGCACCTAGTGGCTGGGAGCTTGCCAGGAACC
CAGTGGCCAGGGAGCGTGGCACTTACCTTTGTCCCTTGCTTCATTCTTGTGAGATGATAAA
ACTGGGCACAGCTCTTAAATAAAATATAAATGAACA

13717.1&2

TGAATGGGGAGGAGCTGACCCAGGAAATGGAGCTTGNGGAGACCAGGCCTGCAGGGGAT
GGAACCTTCCAGAAGTGGGCATCTGTGGTGGTGCCTCTTGGGAAGGAGCAGAAGTACACA
TGCCATGTGGAACATGAGGGGCTGCCTGAGCCCCTCACCCTGAGATGGGGCAAGGAGGAG
CCTCCTTCATCCACCAAGACTAACACAGTAATCATTGCTGTTCCGGTTGTCCTTGGAGCTGT
GGTCATCCTTGGAGCTGTGATGGCTTTTGTGATGAAGAGGAGGAGAAACACAGGTGGAAA
AGGAGGGGACTATGCTCTGGCTCCAGGCTCCCAGAGCTCTGATATGTCTCTCCCAGATTGT
AAAGTGTGAAGACAGCTGCCTGGTGTGGACTTGGTGACAGACAATGTCTTCACACATCTCC
TGTGACATCCAGAGACCTCAGTTCTCTTTAGTCAAGTGTCTGATGTTCCCTGTGAGTCTGCG
GGCTCAAAGTGAAGAACTGTGGAGCCCAGTCCACCCCTGCACACCAGGACCCTATCCCTG
CACTGCCCTGTGTTCCCTTCCACAGCCAACCTTGCTGCTCCAGCCAAACATTGGTGGACAT
CTGCAGCCTGTCAGCTCCATGCTACCCTGACCTTCAACTCCTCACTTCCACACTGAGAATA
ATAATTTGAATGTGGGTGGCTGGAGAGATGGCTCAGCGCTGACTGCTCTTCCAAAGGTCCT
GAGTTCAAATCCCAGCAACCACATGGTGGCTCACAACCATCTGTAATGGGATCTAATACCC
TCTTCTGCAGTGTCTGAAGACASCTACAGTGTACTTACATATAATAATAAATAAG

GGCCGGGCGCGCGCGCCCCCGCCACACGCACGCCGGGCGTGCCAGTTTATAAAGGGAGAG
AGCAAGCAGCGAGTCTTGAAGCTCTGTTTGGTGCTTTGGATCCATTTCCATCGGTCCTTAC
AGCCGCTCGTCAGACTCCAGCAGCCAAGATGGTGAAGCAGATCGAGAGCAAGACTGCTTT
TCAGGAAGCCTTGGACGCTGCAGGTGATAAACTTGTAGTAGTTGACTTCTCAGCCACGTGG
TGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAA
TGCATGCCAACATTCCAGTTTTTTAAGAAGGGACAAAAGGTGGGTGAATTTTCTGGAGCCA
ATAAGGAAAAGCTTGAAGCCACCATTAATGAATTAGTCTAATCATGTTTTCTGAAAATATA
ACCAGCCATTGGCTATTTAAAACTTGTAATTTTTTTAATTTACAAAAATATAAAATATGAA
GACATAAACCCMGTTGCCATCTGCGTGACAATAAAACATTAATGCTAACACTT 13721.1

TCACATAAGAAATTTAAGCAAGTTACRCTATCTTAAAAAACACAACGAATGCATTTTAATA
GAGAAACCCTTCCCTCCCTCCACCTCCCTCCCCCACCCTCCTCATGAATTAAGAATCTAAG
AGAAGAAGTAACCATAAAACCAAGTTTTGTGGAATCCATCATCCAGAGTGCTTACATGGT
GATTAGGTTAATATTGCCTTCTTACAAAATTTCTATTTTAAAAAAAATTATAACCTTGATTG
CTTATTACAAAAAAATTCAGTACAAAAGTTCAATATATTGAAAAATGCTTTTCCCCTCCCT
CACAGCACCGTTTTATATATAGCAGAGAATAATGAAGAGATTGCTAGTCTAGATGGGGCA
ATCTTCAAATTACACCAAGACGCACAGTGGTTTATTTACCCTCCCCTTCTCATAAG 13721.2

GGAAAGGATTCAAGAATTAGAGGACTTGCTTGCTRRAGAAAAAGACAACTCTCGTCGCAT
GCTGACAGACAAAGAGAGAGAGATGGCGGAAATAAGGGATCAAATGCAGCAACAGCTGA
ATGACTATGAACAGCTTCTTGATGTAAAGTTAGCCCTGGACATGGAAATCAGTGCTTACAG
GAAACTCTTAGAAGGCGAAGAAGAGAGGTTGAAGCTGTCTCCAAGCCCTTCTTCCCGTGT
GACAGTATCCCGAGCATCCTCAAGTCGTAGTGTACCGTACAACTAGAGGAAAGCGGAAGA
GGGTTGATGTGGAAGAATCAGAGGCGAAGTAGTAGTGTTAGCATCTCTCATTCCGCCTCAA
CCACTGGAAATGTTTGCATCGAAGAAATTGATGTTGATGGGAAATTTATCCCGCTTGAAGA
ACACTTCTGAACAGGATCAACCAATGGGAAGGCTTGGGAGATGATCAGAAAAATTGGAGA
CACATCAGTCAGTTATAAATATACCTCAA 13723.1

CATGGGTTTCACCAGGTTGGCCAGGCTGCTCTTGAACTSCTGACCTCAGGTGATCCACCCG
CCTCGGCCTCCCAAAGTGCTGGGATTACAGGCGTGAGCCACCACGCCCGGCCCCCAAAGC
TGTTTCTTTTGTCTTTAGCGTAAAGCTCCTGCCATGCAGTATCTACATAACTGACGTGAC
TGCCAGCAAGCTCAGTCACTCCGTGGTCTTTTTCTCTTTCCAGTTCTTCTCTCTCTCTTCAAG
TTCTGCCTCAGTGAAAGCTGCAGGTCCCCAGTTAAGTGATCAGGTGAGGGTTCTTTGAACC
TGGTTCTATCAGTCGAATTAATCCTTCATGATGG

GATGTGTTGGACCCTCTGTGTCAAAAAAAACCTCACAAAGAATCCCCTGCTCATTACAGAA
GAAGATGCATTTAAAATATGGGTTATTTTCAACTTTTTATCTGAGGACAAGTATCCATTAA
TTATTGTGTCAGAAGAGATTGAATACCTGCTTAAGAAGCTTACAGAAGCTATGGGAGGAG
GTTGGCAGCAAGAACAATTTGAACATTATAAAATCAACTTTGATGACAGTAAAAATGGCC
TTTCTGCATGGGAACTTATTGAGCTTATTGGAAATGGACAGTTTAGCAAAGGCATGGACCG
GCAGACTGTGTCTATGGCAATTAATGAAGTCTTTAATGAACTTATATTAGATGTGTTAAAG
CAGGGTTACATGATGAAAAAGGGCCACAGACGGAAAAACTGGACTGAAAGATGGTTTGTA
CTAAAACCCAACATAATTTCTTACTATGTGAGTGAGGATCTGAAGGATAAGAAAGGAGAC
ATTCTCTTGGATGAAAATTGCTGTGTAGAAGTCCTTGCCTGACAAAAGATGGAAAGAAAT
GCCTTTT 13725.1

GACTGGTTCTTTATTTCAAAAAGACACTTGTCAATATTCAGTRTCAAAACAGTTGCACTATT
GATTTCTCTTTCTCCCAATCGGCCCCAAAGAGACCACATAAAAGGAGAGTACATTTTAAGC
CAATAAGCTGCAGGATGTACACCTAACAGACCTCCTAGAAACCTTACCAGAAAATGGGGA
CTGGGTAGGGAAGGAAACTTAAAAGATCAACAAACTGCCAGCCCACGGACTGCAGAGGCT
GTCACAGCCAGATGGGGTGGCCAGGGTGCCACAAACCCAAAGCAAAGTTTCAAAATAATA
TAAAATTTAAAAAGTTTTGTACATAAGCTATTCAAGATTTCTCCAGCACTGACTGATACAA
AGCACAATTGAGATGGCACTTCTAGAGACAGCAGCTTCAAACCCAGAAAAGGGTGATGAG
ATGAAGTTTCACATGGCTAAATCAGTGGCAAAAACACAGTCTTCTTTCTTTCTTTCTTTCAA
GGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTT
CTGCAGCAGCAGGCAGATGATGCAGAGGAGCGAGCTGAGCGCCTCCAGCGAGAAGTTGA
GGGAGAAAGGCGGGCCCGGGAACAGGCTGAGGCTGAGGTGGCCTCCTTGAACCGTAGGA
TCCAGCTGGTTGAAGAAGAGCTGGACCGTGCTCAGGAGCGCCTGGCCACTGCCCTGCAAA
AGCTGGAAGAAGCTGAAAAAGCTGCTGATGAGAGTGAGAGAGGTATGAAGGTTATTGAA
AACCGGGCCTTAAAAGATGAAGAAAAGATGGAACTCCAGGAAATCCAACTCAAAGAAGC
TAAGCACATTGCAGAAGAGGCAGATAGGAAGTATGAAGAGGTGGCTCGTAAGTTGGTGAT
CATTGAAGGAGACTTGGAACCGCACAGAAGGAACGAGCTTGAGCTTGGCAAAAGTCCCGT
TGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCAC
CTGGAAGCGCCCCGAGAGTGACAGCGTGAGGCTGGGAGGGAGGACTTGGCTTGAGCTTGT
TAAACTCTGCTCTGAGCCTCCTTGTCGCCTGCATTTAGATGGCTCCCGCAAAGAAGGGTGG
CGAGAAGAAAAAGGGCCGTTCTGCCATCAACGAAGTGGTAACCCGAGAATACACCATCAA
CATTCACAAGCGCATCCATGGAGTGGGCTTCAAGAAGCGTGCACCTCGGGCACTCAAAGA
GATTCGGAAATTTGCCATGAAGGAGATGGGAACTCCAGATGTGCGCATTGACACCAGGCT
CAACAAAGCTGTCTGGGCCAAAGGAATAAGGAATGTGCCATACCGAATCCGGTGTGCGGC
TGTCCAGAAAACGTAATGAGGATGAAGATTCACCAAATAAGCTATATACTTTGGTTACCTA
TGTACCTGTTACCACTTTCAAAAATCTACAGACAGTCAATGTGGATGAGAACTAATCGCTG
ATCGTCAGATCAAATAAAGTTATAAAAT

TCGGGAGCCACACTTGGCCCTCTTCCTCTCCAAAGSGCCAGAACCTCCTTCTCTTTGGAGAA
TGGGGAGGCCTCTTGGAGACACAGAGGGTTTCACCTTGGATGACCTCTAGAGAAATTGCC
CAAGAAGCCCACCTTCTGGTCCCAACCTGCAGACCCCACAGCAGTCAGTTGGTCAGGCCCT
GCTGTAGAAGGTCACTTGGCTCCATTGCCTGCTTCCAACCAATGGGCAGGAGAGAAGGCC
TTTATTTCTCGCCCACCCATTCCTCCTGTACCAGCACCTCCGTTTTCAGTCAGTGTTGTCCA
GCAACGGTACCGTTTACACAGTCACCTCAGACACACCATTTCACCTCCCTTGCCAAGCTGT
TAGCCTTAGAGTGATTGCAGTGAACACTGTTTACACACCGTGAATCCATTCCCATCAGTCC
ATTCCAGTTGGCACCAGCCTGAACCATTTGGTACCTGGTGTTAACTGGAGTCCTGTTTACA
AGGTGGAGTCGGGGCTTGCTGACTTCTCTTCATTTGAGGGCAC

13727.2

ACCTAGACAGAAGGTGGGTGAGGGAGGACTGGTAGGAGGCTGAGGCAATTCCTTGGTAGT
TTGTCCTGAAACCCTACTGGAGAAGTCAGCATGAGGCACCTACTGAGAGAAGTGCCCAGA
AACTGCTGACTGCATCTGTTAAGAGTTAACAGTAAAGAGGTAGAAGTGTGTTTCTGAATCA
GAGTGGAAGCGTCTCAAGGGTCCCACAGTGGAGGTCCCTGAGCTACCTCCCTTCCGTGAGT
GGGAAGAGTGAAGCCCATGAAGAACTGAGATGAAGCAAGGATGGGGTTCCTGGGCTCCA
GGCAAGGGCTGTGCTCTCTGCAGCAGGGAGCCCCACGAGTCAGAAGAAAAGAACTAATCA
TTTGTTGCAAGAAACCTTGCCCGGATACTAGCGGAAAACTGGAGGCGGNGGTGGGGGCAC
AGGAAAGTGGAAGTGATTTGATGGAGAGCAGAGAAGCCTATGCACAGTGGCCGAGTCCAC
TTGTAAAGTG

13728.1&2

TTCAAGCAATTGTAACAAGTATATGTAGATTAGAGTGAGCAAAATCATATACAATTTTCAT
TTCCAGTTGCTATTTTCCAAATTGTTCTGTAATGTCGTTAAAATTACTTAAAAATTAACAAA
GCCAAAAATTATATTTATGACAAGAAAGCCATCCCTACATTAATCTTACTTTTCCACTCAC
CGGCCCATCTCCTTCCTCTTTTTCCTAACTATGCCATTAAAACTGTTCTACTGGGCCGGGCG
TGTGGCTCATGCCTGTAATCCCAGCATTTTGGGAGGCCAAGGCAGGCGGATCATGAGGTC
AAGAGATTGAGACCATCCTGGCCAACATGGTGAAACCCCGCCTCGACTAAGAATACAAAA
ATTAGCTGGGCATGGTGGCGCATGCCTGTAGTCTCAGCTACTCGGGAGGCTGAGGCAGAA
GAATCGCTTGAACCCGGGAGGCAGAGGATGCAGTGAGCCCCGATCGCGCCACTGCACTCT
AGCCTGGGCGACAGACTGAGACTCTGCTC

13731.1&2

TGTGCCAGTCTACAGGCCTATCAGCAGCGACTCCTTCAGCAACAGATGGGGTCCCCTGTTC
AGCCCAACCCCATGAGCCCCCAGCAGCATATGCTCCCAAATCAGGCCCAGTCCCCACACCT
ACAAGGCCAGCAGATCCCTAATTCTCTCTCCAATCAAGTGCGCTCTCCCCAGCCTGTCCCTT
CTCCACGGCCACAGTCCCAGCCCCCCCACTCCAGTCCTTCCCCAAGGATGCAGCCTCAGCC
TTCTCCACACCACGTTTCCCCACAGACAAGTTCCCCACATCCTGGACTGGTAGTTGCCCAG
GCCAACCCCATGGAACAAGGGCATTTTGCCAGCC

TGTAAAAACTTGTTTTTAATTTTGTATAAAATAAAGGTGGTCCATGCCCACGGGGGCTGTA
GGAAATCCAAGCAGACCAGCTGGGGTGGGGGGATGTAGCCTACCTCGGGGGACTGTCTGT
CCTCAAAACGGGCTGAGAAGGCCCGTCAGGGGCCCAGGTCCCACAGAGAGGCCTGGGATA
CTCCCCCAACCCGAGGGGCAGACTGGGCAGTGGGGAGCCCCCATCGTGCCCCAGAGGTGG
CCACAGGCTGAAGGAGGGGCCTGAGGCACCGCAGCCTGCAACCCCCAGGGCTGCAGTCCA
CTAACTTTTTACAGAATAAAAGGAACATGGGGATGGGGAAAAAAGCACCAGGTCAGGCA
GGGCCCGAGGGCCCCAGATCCCAGGAGGGCCAGGACTCAGGATGCCAGCACCACCCTAGC
AGCTCCCACAGCTCCTGGCACAGGAGGCCGCCACGGATTGGCACAGGCCGCTGCTGGCCA
TCACGCCACATTTGGAGAACTTGTCCCGACAGAGGTCAGCTCGGAGGAGCTCCTCGTGGGC
ACACACTGTACGAACACAGATCTCCTTGTTAATGACGTACACACGGCGGAGGCTGCGGGG
ACAGGGCACGGGAGGTCTCAGCCCCACTT

13736.2

ATGGCTGCTGGATTTAGGTGGTAATAGGGGCTGTGGGCCATAAATCTGAAGCCTTGAGAA
CCTTGGGTCTGGAGAGCCATGAAGAGGGAAGGAAAAGAGGGCAAGTCCTGAACCTAACC
AATGACCTGATGGATTGCTCGACCAAGACACAGAAGTGAAGTCTGTGTCTGTGCACTTCCC
ACAGACTGGAGTTTTTGGTGCTGAATAGAGCCAGTTGCTAAAAAATTGGGGGTTTGGTGA
AGAAATCTGATTGTTGTGTGTATTCAATGTGTGATTTTAAAAATAAACAGCAACAACAATA
AAAACCCTGACTGGCTGTTTTTTCCCTGTATTCTTTACAACTATTTTTTGACCCTCTGAAAA
TTATTATACTTCACCTAAATGGAAGACTGCTGTGTTTGTGGAAATTTTGTAATTTTTTAATT
TATTTTATTCTCTCTCCTTTTTATTTTGCCTGCAGAATCCGTTGAGAGACTAATAAGGCTTA
ATATTTAATTGATTTGTTTAATATGTATATAAAT

13744.2-13696.2

GGCATGCGAGCGCACTCGGCGGACGCAAGGGCGGCGGGGAGCACACGGAGCACTGCAGG
CGCCGGGTTGGGACAGCGTCTTCGCTGCTGCTGGATAGTCGTGTTTTCGGGGATCGAGGAT
ACTCACCAGAAACCGAAAATGCCGAAACCAATCAATGTCCGAGTTACCACCATGGATGCA
GAGCTGGAGTTTGCAATCCAGCCAAATACAACTGGAAAACAGCTTTTTGATCAGGTGGTA
AAGACTATCGGCCTCCGGGAAGTGTGGTACTTTGGCCTCCACTATGTGGATAATAAAGGAT
TTCCTACCTGGCTGAAGCTGGATAAGAAGGTGTCTGCCCAGGAGGTCAGGAAGGAGAATC
CCCTCCAGTTCAAGTTCCGGGCCAAaGTTCTACCCTGAAGATGTGGCTGAGGAGCTCATCC
AGGACATCACCCAGAAACTTTTCTTCCTTCAAGTGAAGGAAGGAATCCTTAGCGATGAGAT
CTACTGCCCCCCTTGARACTGCCGTGCTCTTGGGGTCCTACGCTTGTGCATGCCAAGTTTGG
GGACTACCACCAAGAAG

13746.1&2-13720.1&2

GAAGGAGTCGGGATACTCAGCATTGATGCACCCCAATTTCAAAGCGGCATTCTTCGGCAG
GTCTCTGGGACAATCTCTAGGGTCACTACCTGGAAACTCGTTAGGGTACAACTGAATGCTG
AAAGGAAAGAACACCTGCAGAACCGGACAGAAATTCACCCCGGCGATCAGCTGATTGATC
TCGGTCGACCAGAAGTCATGGCTAAAGATGACGAGGACGTTGTCAATTCCCTGGGCTTTTC
GAAGTGAGTCCAGCAGCAGTCTGAGGTATTCGGGCCGGTTATGCACCTGGACCACCAGCA
CCAGCTCCCGGGGGGCCCAGGTGCCAGCCTTATCTACATTCCTCAGGGTCTGATCAAAGTT
CAGCTGGTACACCAGGGACCGGTACCGCAGCGTCAGGTTGTCCGCTCGGGCTGGGGGACC
GCCGGGACCAGGGAAGCCGCCGACACGTTGGAGACCCTGCGGATGCCCACAGCCACAGAG
GGGTGGTCCCCACCGCGGCCGCCGGCACCCCGCGCGGGTTCGGCGTCCAGCAACGGTGGG
GCGAGGGCCTCGTTCTTCCTTTGTCGCCCATTGCTGCTCCAGAGGACGAAGCCGCAGGCGG
CCACCACGAGCGTCAGGATTAGCACCTTCCGTTTGTAGATGCGGAACCTCATGGTCTCCAG
GGCCGGGAGCGCAGCTACAGCTCGAGCGTCGGCGCCGCCGCTAGGAGCCGCGGCTCGGCT
TCGTCTCCGTCCTCTCCATTCAGCACCACGGGTCCCGGAAAAAGCTCAGCCSCGGTCCCAA
CCGCACCCTAGCTTCGTTACCTGCGCCTCGCTTG

CAGATTTTTATTTGCAGTCGTCACTGGGGCCGTTTCTTGCTGCTTATTTGTCTGCTAGCCTG
CTCTTCCAGCTGCATGGCCAGGCGCAAGGCCTTGATGACATCTCGCAGGGCTGAGAAATGC
TTGGCTTGCTGGGCCAGAGCAGATTCCGCTTTGTTCACAAAGGTCTCCAGGTCATAGTCTG
GCTGCTCGGTCATCTCAGAGAGCTCAAGCCAGTCTGGTCCTTGCTGTATGATCTCCTTGAG
CTCTTCCATAGCCTTCTCCTCCAGCTCCCTGATCTGAGTCATGGCTTCGTTAAAGCTGGACA
TCTGGGAAGACAGTTCCTCCTCTTCCTTGGATAAATTGCCTGGAATCAGCGCCCCGTTAGA
GCAGGCTTCCATCTCTTCTGTTTCCATTTGAATCAACTGCTCTCCACTGGGCCCACTGTGGG
GGCTCAGCTCCTTGACCCTGCTGCATATCTTAAGGGTGTTTAAAGGATATTCACAGGAGCT
TATGCCTGGT

14347.2

CTCCTCTTGGTACATGAACCCAAGTTGAAAGTGGACTTAACAAAGTATCTGGAGAACCAA
GCATTCTGCTTTGACTTTGCATTTGATGAAACAGCTTCGAATGAAGTTGTCTACAGGTTCAC
AGCAAGGCCACTGGTACAGACAATCTTTGAAGGTGGAAAAGCAACTTGTTTTGCATATGG
CCAGACAGGAAGTGGCAAGACACATACTATGGGCGGAGACCTCTCTGGGAAAGCCCAGAA
TGCATCCAAAGGGATCTATGCCATGGCCTTCCGGGACGTCTTCTTCTGAAGAATCAACCCT
GCTACCGGAAGTTGGGCCTGGAAGTCTATGTGACATTCTTCGAGATCTACAATGGGAAGCT
GTTTGACCTGCTCAACAAGAAGGCCAAGCTTGCGCGTGCTGGAAGACGGCAAGCAACAGG
TGCAAGTGGTGGGGGCTTGCAGGAACATCTGGNTAACTCTGCTTGATGATGGCANTCAAG
ATGATCGACATGGGCAGCGCCTGCAGA

14348.2&14350.1&2

TCCCGAATTCAAGCGACAAATTGGAWAGTGAAATGGAAGATGCCTATCATGAACATCAGG
CAAATCTTTTGCGCCAAGATCTGATGAGACGACAGGAAGAATTAAGACGCATGGAAGAAC
TTCACAATCAAGAAATGCAGAAACGTAAAGAAATGCAATTGAGGCAAGAGGAGGAACGA
CGTAGAAGAGAGGAAGAGATGATGATTCGTCAACGTGAGATGGAAGAACAAATGAGGCG
CCAAAGAGAGGAAAGTTACAGCCGAATGGGCTACATGGATCCACGGGAAAGAGACATGC
GAATGGGTGGCGGAGGAGCAATGAACATGGGAGATCCCTATGGTTCAGGAGGCCAGAAA
TTTCCACCTCTAGGAGGTGGTGGTGGCATAGGTTATGAAGCTAATCCTGGCGTTCCACCAG
CAACCATGAGTGGTTCCATGATGGGAAGTGACATGCGTACTGAGCGCTTTGGGCAGGGAG
GTGCGGGGCCTGTGGGTGGACAGGGTCCTAGAGGAATGGGGCCTGGAACTCCAGCAGGAT
ATGGTAGAGGGAGAGAAGAGTACGAAGGC

14349.1&2

TTCGTGAAGACCCTGACTGGTAAGACCATCACTCTCGAAGTGGAGCCCGAGTGACACCATT
GAGAATGTCAAGGCAAAGATCCAAGACAAGGAAGGCATCCCTCCTGACCAGCAKAGGTTG
ATCTTTGCTGGGAAACAGCTGGAAGATGGACGCACCCTGTCTGACTACAACATCCAGAAA
GAGTCCACCCTGCACCTGGTGCTCCGTCTCAGAGGTGGGATGCAAATCTTCGTGAAGACCC
TGACTGGTAAGACCATCACCCTCGAGGTGGAGCCCAGTGACACCATCGAGAATGTCAAGG
CAAAGATCCAAGATAAGGAAGGCATCCCTCCTGATCAGCAGAGGTTGATCTTTGCTGGGA
AACAGCTGGAAGATGGACGCACCCTGTCTGACTACAACATCCAGAAAGAGTCCACTCTGC
ACTTGGTCCTGCGCTTGAGGGGGGGTGTCTAAGTTTCCCCTTTTAAGGTTTCAACAAATTTC
ATTGCACTTTCCTTTCAATAAAGTTGTTGCATTC

GCGCGGGTGCGTGGGCCACTGGGTGACCGACTTAGCCTGGCCAGACTCTCAGCACCTGGA
AGCGCCCCGAGAGTGACAGCGTGAGGCTGGGAGGGAGGACTTGGCTTGAGCTTGTTAAAC
TCTGCTCTGAGCCTCCTTGTCGCCTGCATTTAGATGGCTCCCGCAAAGAAGGGTGGCGAGA
AGAAAAAGGGCCGTTCTGCCATCAACGAAGTGGTAACCCGAGAATACACCATCAACATTC
ACAAGCGCATCCATGGAGTGGGCTTCAAGAAGCGTGCACCTCGGGCACTCAAAGAGATTC
GGAAATTTGCCATGAAGGAGATGGGAACTCCAGATGTGCGCATTGACACCAGGCTCAACA
AAGCTGTCTGGGCCAAAGGAATAAGGAATGTGCCATACCGAATCCGTGTGCGGCTGTCCA
GAAAACGTAATGAGGATGAAGATTCACCAAATAAGCTATATACTTTGGTTACCTATGTACC
TGTTACCACTTTCAAAAATCTACAGACAGTCAATGTGGATGAGAACTAATCGCTGATCGT

14353.1

AATTCTTTATTTAAATCAACAAACTCATCTTCCTCAAGCCCCAGACCATGGTAGGCAGCCC
TCCCTCTCCATCCCCTCACCCCACCCCTTAGCCACAGTGAAGGGAATGGAAAATGAGAAGC
CACGAGGGCCCCTGCCAGGGAAGGCTGCCCCAGATGTGTGGTGAGCACAGTCAGTGCAGC
TGTGGCTGGGGCAGCAGCTGCCACAGGCTCCTCCCTATAAATTAAGTTCCTGCAGCCACAG
CTGTGGGAGAAGCATACTTGTAGAAGCAAGGCCAGTCCAGCATCAGAAGGCAGAGGCAG
CATCAGTGACTCCCAGCCATGGAATGAACGGAGGACACAGAGCTCAGAGACAGAACAGG
CCAGGGGGAAGAAGGAGAGACAGAATAGGCCAGGGCATGGCGGTGAGGGA

14353.2

TGATGAATCTGGGTGGGCTGGCAGTAGCCCGAGATGATGGGCTCTTCTCTGGGGATCCCAA
CTGGTTCCCTAAGAAATCCAAGGAGAATCCTCGGAACTTCTCGGATAACCAGCTGCAAGA
GGGCAAGAACGTGATCGGGTTACAGATGGGCACCAACCGCGGGGCGTCTCANGCAGGCAT
GACTGGCTACGGGATGCCACGCCAGATCCTCTGATCCCACCCCAGGCCTTGCCCCTGCCCT
CCCACGAATGGTTAATATATATGTAGATATATATTTTAGCAGTGACATTCCCAGAGAGCCC
CAGAGCTCTCAAGCTCCTTTCTGTCAGGGTGGGGGGTTCAAGCCTGTCCTGTCACCTCTGA
AGTGCCTGCTGGCATCCTCTCCCCCATGCTTACTAATACATTCCCTTCCCCATAGCC

17182.1&2

AGCGGAGCTCCCTCCCCTGGTGGCTACAACCCACACACGCCAGGCTCAGGCATCGAGCAG
AACTCCAGCGACTGGGTAACCACTGACATTCAGGTGAAGGTGCGGGACACCTACCTGGAT
ACACAGGTGGTGGGACAGACAGGTGTCATCCGCAGTGTCACGGGGGGCATGTGCTCTGTG
TACCTGAAGGACAGTGAGAAGGTTGTCAGCATTTCCAGTGAGCACCTGGAGCCTATCACC
CCCACCAAGAACAACAAGGTGAAAGTGATCCTGGGCGAGGATCGGGAAGCCACGGGCGT
CCTACTGAGCATTGATGGTGAGGATGGCATTGTCCGTATGGACCTTGATGAGCAGCTCAAG
ATCCTCAACCTCCGCTTCCTGGGGAAGCTCCTGGAAGCCTGAAGCAGGCAGGGCCGGTGG
ACTTCGTCGGATGAAGAGTGATCCTCCTTCCTTCCCTGGCCCTTGGCTGTGACACAAGATC
CTCCTGCAGGGCTAGGCGGATTGTTCTGGATTTCCTTTTGTTTTTCCTTTTAGGTTTCCATCT
TTTCCCTCCCTGGTGCTCATTGGAATCTGAGTAGAGTCTGGGGGAGGGTCCCCACCTTCCT
GTACCTCCTCCCCACAGCTTGCTTTTGTTGTACCGTCTTTCAATAAAAAGAAGCTGTTTGGT
CTA

GGTTCACAGCACTGCTGCTTGTGTGTTGCCGGCCAGGAATTCCAGGCTCACAAGGCTATCT
TAGCAGCTCGTTCTCCGGTTTTTAGTGCCATGTTTGAACATGAAATGGAGGAGAGCAAAAA
GAATCGAGTTGAAATCAATGATGTGGAGCCTGAAGTTTTTAAGGAAATGATGTGCTTCATT
TACACGGGGAAGGCTCCAAACCTCGACAAAATGGCTGATGATTTGCTGGCAGCTGCTGAC
AAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAA
CTCAGGCAGTGGATTTCATCAACTATCATGCTTCGGATGTCTTGGAGACCTCTTGGG

17186.1&2

TCGTAGCCATTTTTCTGCTTCTTTGGAGAATGACGCCACACTGACTGCTCATTGTCGTTGGT
TCCATGCCAATTGGTGAAATAGAACCTCATCCGGTAGTGGAGCCGGAGGGACATCTTGTC
ATCAACGGTGATGGTGCGATTTGGAGCATACCAGAGCTTGGTGTTCTCGCCATACAGGGCA
AAGAGGTTGTGACAAAGAGGAGAGATACGGCATGCCTGTGCAGCCCTGATGCACAGTTCC
TCTGCTGTGTACTCTCCACTGCCCAGCCGGAGGGGCTCCCTGTCCGACAGATAGAAGATCA
CTTCCACCCCTGGCTTG

17187.1&2

TGGCACACTGCTCTTAAGAAACTATGAWGATCTGAGATTTTTTTGTGTATGTTTTTGACTCT
TTTGAGTGGTAATCATATGTGTCTTTATAGATGTACATACCTCCTTGCACAAATGGAGGGG
AATTCATTTTCATCACTGGGAGTGTCCTTAGTGTATAAAAACCATGCTGGTATATGGCTTC
AAGTTGTAAAAATGAAAGTGACTTTAAAAGAAAATAGGGGATGGTCCAGGATCTCCACTG
ATAAGACTGTTTTTAAGTAACTTAAGGACCTTTGGGTCTACAAGTATATGTGAAAAAAATG
AGACTTACTGGGTGAGGAAATTCATTGTTTAAAGATGGTCGTGTGTGTGTGTGTGTGTGTG
TGTGTTGTGTTGTGTTTTGTTTTTTAAGGGAGGGAATTTATTATTTACCGTTGCTTGAAATT
ACTGKGTAAATATATGTYTGATAATGATTTGCTYTTTGVCMACTAAAATTAGGVCTGTATA
AGTWCTARATGCMTCCCTGGGKGTTGATYTTCCMAGATATTGATGATAMCCCTTAAAATT
GTAACCYGCCTTTTTCCCTTTGCTYTCMATTAAAGTCTATTCMAAAG

17191.1&89.1

GGGGGTAGGCTCTTTATTAGACGGTTATTGCTGTACTACAGGGTCAGAGTGCAGTGTAAGC
AGTGTCAGAGGCCCGCGTTCAGCCCAAGAATGTGGATTTTCTCTCCCTATTGATCACAGTG
GGTGGGTTTCTTCAGAAAAGCCCCAGAGGCAGGGACCAGTGAGCTCCAAGGTTAGAAGTG
GAACTGGAAGGCTTCAGTCACATGCTGCTTCCACGCTTCCAGGCTGGGCAGCAAGGAGGA
GATGCCCATGACGTGCCAGGTCTCCCCATCTGACACCAGTGAAGTCTGGTAGGACAGCAG
CCGCACGCCTGCCTCTGCCAGGAGGCCAATCATGGTAGGCAGCATTGCAGGGTCAGAGGT
CTGAGTCCGGAATAGGAGCAGGGGCAGGTCCCTGCGGAGAGGCACTTCTGGCCTGAAGAC
AGCTCCATTGAGCCCCTGCAGTACAGGYGTAGTGCCTTGGACCAAGCCCACAGCCTGGTA
AGGGGCGCCTGCCAGGGCCACGGCCAGGAGGCA

TAATTTCTTAGTCGTTTGGAATCCTTAAGCATGCAAAAGCTTTGAACAGAAGGGTTCACAA
AGGAACCAGGGTTGTCTTATGGCATCCAGTTAAGCCAGAGCTGGGAATGCCTCTGGGTCAT
CCACATCAGGAGCAGAAGCACTTGACTTGTCGGTCCTGCTGCCACGGTTTGGGCGCCCACC
ACGCCCACGTCCACCTCGTCCTCCCCTGCCGCCACGTCCTGGGCGGCCAAGGTCTCCAAAA
TTGATCTCCAGCTGAGACGTTATATCATTTGCTGGCTTCCGGAAATGATGGTCCATAACCG
AATCTTCAGCATGAGCCTCTTCACTCTTTGATTTATGAAGAACAAATCCCTTCTTCCACTGC
CCATCAGCACCTTCATTTGGTTTTCGGATATTAAATTCTACTTTTGCCCGGTCCTTATTTTGA
ATAGCCTTCCACTCATCCAAAGTCATCTCTTTTGGACCCTCCTCTTTTACCTCTTCAACTTCA
TTCTCCTTATTTTCAGTGTCTGCCACTGGATGATGTTCTTCACCTTCAGGTGTTTCCTCAGTC
ACATTTGATTGATCCAAGTCAGTTAATTCGTCTTTGACAGTTCCCCAGTTGTGAGATCCGCT
ACCTCCACGTTTGTCCTCGTGCTTCAGGCCAGATCTATCACTTCCACTATGCCTATCAAATT
CACGTTTGCCACGAGAATCAAATCCATCTCCTCGGCCCATTCCACGTCCACGGCCCCCTCG
ACCTCTTCCAAGACCACCACGACCTCGAATAGGTCGGTCAATAATCGGTCTATCAACTGAA
AATTCGCCTCCTTCACCCTTTTCTTCAAGTGGCTTTTCGAATCTTCGTTCACGAGGTGGTCG
CCTTTCTGGTCTTCTATCAATTATTTTCCCTTCACCCTGAAGTTGTTGATCAGGTCTTCTTCC
AACTCGTGC

17193

AAGCGGATGGACCTGAGTCAGCCGAATCCTAGCCCCTTCCCTTGGGCCTGCTGTGGTGCTC
GACATCAGTGACAGACGGAAGCAGCAGACCATCAAGGCTACGGGAGGCCCGGGGCGCTT
GCGAAGATGAAGTTTGGCTGCCTCTCCTTCCGGCAGCCTTATGCTGGCTTTGTCTTAAATG
GAATCAAGACTGTGGAGACGCGCTGGCGTCCTCTGCTGAGCAGCCAGCGGAACTGTACCA
TCGCCGTCCACATTGCTCACAGGGACTGGGAAGGCGATGCCTGTCGGGAGCTGCTGGTGG
AGAGACTCGGGATGACTCCTGCTCAGATTCAGGCCTTGCTCAGGAAAGGGGAAAAGTTTG
GTCGAGGAGTGATAGCGGGACTCGTTGACATTGGGGAAACTTTGCAATGCCCCGAAGACT
TAACTCCCGATGAGGTTGTGGAACTAGAAAATCAAGCTGCACTGACCAACCTGAAGCAGA
AGTACCTGACTGTGATTTCAAACCCCAGGTGGTTACTGGAGCCCATACCTAGGAAAGGAG
GCAAGGATGTATTCCAGGTAGACATCCCAGAGCACCTGATCCCTTTGGGGCATGAAGTGT
GACAAGTGTGGGCTCCTGAAAGGAATGTTCCRGAGAAACCAGCTAAATCATGGCACCTTC
AATTTGCCATCGTGACGCAGACCTGTATAAATTAGGTTAAAGATGAATTTCCACTGCTTTG
GAGAGTCCCACCCACTAAGCACTGTGCATGTAAACAGGTTCCTTTGCTCAGATGAAGGAA
GTAGGGGGTGGGGCTTTCCTTGTGTGATGCCTCCTTAGGCACACAGGCAATGTCTCAAGTA
CTTTGACCTTAGGGTAGAAGGCAAAGCTGCCAGTAAATGTCTCAGCATTGCTGCTAATTTT
GGTCCTGCTAGTTTCTGGATTGTACAAATAAATGTGTTGTAGATGA

*FIG. 15U*

16443.1.edit

TCGAGCGGCCGCCCGGGCAGGTGTCGGAGTCCAGCACGGGAGGCGTGGTCTTGTAGTTGT
TCTCCGGCTGCCCATTGCTCTCCCACTCCACGGCGATGTCGCTGGGATAGAAGCCTTTGAC
CAGGCAGGTCAGGCTGACCTGGTTCTTGGTCATCTCCTCCCGGGATGGGGGCAGGGTGTAC
ACCTGTGGTTCTCGGGGCTGCCCTTTGGCTTTGGAGATGGTTTTCTCGATGGGGGCTGGGA
GGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTG
GCATTATGCACCTCCACGCCGTCCACGTACCAATTGAACTTGACCTCAGGGTCTTCGTGGC
TCACGTCCACCACCACGCATGTAACCTCAAANCTCGGNCGCGANCACGC

16443.2.edit

AGCGTGGTCGCGGCCGAGGTCTGAGGTTACATGCGTGGTGGTGGACGTGAGCCACGAAGA
CCCTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCTGCA
CCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACAC
CCTGCCCCCATCCCGGGAGGAGATGACCAAGAACCAGGTCAGCCTGACCTGCCTGGTCAA
AGGCTTCTATCCCAGCGACATCGCCCGTGGAGTGGGAGAGCAATGGGCAGCCGGAGAACA
ACTACAAGACCACGCCTCCCGTGCTGGACTCCGACACCTGCCGGGCGGCCGCTCGA

16444.2.edit

AGCGTGGTTNCGGCCGAGGTCCCAACCAAGGCTGCANCCTGGATGCCATCAAAGTCTTCTG
CAACATGGAGACTGGTGAGACCTGCGTGTACCCCACTCAGCCCAGTGTGGCCCAGAAGAA
CTGGTACATCAGCAAGAACCCCAAGGACAAGAGGCATGTCTGGTTCGGCGAGAGCATGAC
CGATGGATTCCAGTTCGAGTATGGCGGCCAGGGCTCCGACCCTGCCGATGTGGACCTGCCC
GGGCGGNCGCTCGA

16445.1.edit

AGCGTGGTCGCGGCCGAGGTCAAGAACCCCGCCCGCACCTGCCGTGACCTCAAGATGTGC
CACTCTGACTGGAAGAGTGGAGAGTACTGGATTGACCCCAACCAAGGCTGCAACCTGGAT
GCCATCAAAGTCTTCTGCAACATGGAGACTGGTGAGACCTGCGTGTACCCCACTCAGCCCA
GTGTGGCCCAGAAGAACTGGTACATCAGCAAGAACCCCAAGGACAAGAGGCATGTCTGGT
TCGGCGAGAGCATGACCGATGGATTCCAGTTCGAGTATGGCGGCCAGGGCTCCGACCCTG
CCGATGTGGACCTGCCCGGGCGGCCGCTCGA

*FIG. 15V*

16445.2.edit

TCGAGCGGTCGCCCGGGCAGGTCCACATCGGCAGGGTCGGAGCCCTGGCCGCCATACTCG
AACTGGAATCCATCGGNCATGCTCTCGCCGAACCAGACATGCCTCTTGNCCTTGGGGTTCT
TGCTGATGTACCAGNTCTTCTGGGCCACACTGGGCTGAGTGGGGTACACGCAGGTCTCACC
ANTCTCCATGTTGCANAAGACTTTGATGGCATCCAGGTTGCAGCCTTGGTTGGGGTCAATC
CAGTACTCTCCACTCTTCCAGACAGAGTGGCACATCTTGAGGTCACGGCAGGTGCGGGCGG
GGTTCTTGACCTCGGTCGCGACCACGCT

16446.1.edit

TCGAGCGGCCGCCCGGGCAGGTCCTCCTCAGAGCGGTAGCTGTTCTTATTGCCCCGGCAGC
CTCCATAGATNAAGTTATTGCANGAGTTCCTCTCCACGTCAAAGTACCAGCGTGGGAAGG
ATGCACGGCAAGGCCCAGTGACTGCGTTGGCGGTGCAGTATTCTTCATAGTTGAACATATC
GCTGGAGTGGACTTCAGAATCCTGCCTTCTGGGAGCACTTGGGACAGAGGAATCCGCTGC
ATTCCTGCTGGTGGACCTCGGCCGCGACCACGCT

16446.2.edit

AGCGTGGTCGCGGCCGAGGTCCACCAGCAGGAATGCAGCGGATTCCTCTGTCCCAAGTGC
TCCCAGAAGGCAGGATTCTGAAGACCACTCCAGCGATATGTTCAACTATGAAGAATACTG
CACCGCCAACGCAGTCACTGGGCCTTGCCGTGCATCCTTCCCACGCTGGTACTTTGACGTG
GAGAGGAACTCCTGCAATAACTTCATCTATGGAGGCTGCCGGGGCAATAAGAACAGCTAC
CGCTCTGAGGAGGACCTGCCCGGGCGGCCGCTCGA

16447.1.edit

TCGAGCGGCCGCCCGGGCAGGTCCACATCGGCAGGGTCGGAGCCCTGGCCGCCATACTCG
AACTGGAATCCATCGGTCATGCTCTCGCCGAACCAGACATGCCTCTTGTCCTTGGGGTTCT
TGCTGATGTACCAGTTCTTCTGGGCCACACTGGGCTGAGTGGGGTACACGCAGGTCTCACC
AGTCTCCATGTTGCAGAAGACTTTGATGGCATCCAGGTTGCAGCCTTGGTTGGGGTCAATC
CAGTACTCTCCACTCTTCCAGCCAGAATGGCACATCTTGAGGTCACGGCANGTGCGGGCGG
GGTTCTTGACCTCGGCCGCGACCACGCT

*FIG. 15W*

16447.2.edit

AGCGTGGTCGCGGCCGAGGTCAAGAAACCCCGCCCGCACCTGCCGTGACCTCAAGATGTG
CCACTCTGGCTGGAAGAGTGGAGAGTACTGGATTGACCCCAACCAAGGCTGCAACCTGGA
TGCCATCAAAGTCTTCTGCAACATGGAGACTGGTGAGACCTGCGTGTACCCCACTCAGCCC
AGTGTGGCCCAGAAGAACTGGTACATCAGCAAGAACCCCAAGGACAAGAGGCATGTCTGG
CTCGGCGAGAGCATGACCGATGGATTCCAGTTCGAGTATGGCGGCCAGGGCTCCGACCCT
GCCGATGTGGACCTGCCCGGGCGGCCGCTCGA

16449.1.edit

AGCGTGGTCGCGGCCGAGGTCCTGTCAGAGTGGCACTGGTAGAAGNTCCAGGAACCCTGA
ACTGTAAGGGTTCTTCATCAGTGCCAACAGGATGACATGAAATGATGTACTCAGAAGTGTC
CTGNAATGGGGCCCATGANATGGTTGNCTGAGAGAGAGCTTCTTGTCCTACATTCGGCGG
GTATGGTCTTGGCCTATGCCTTATGGGGGTGGCCGTTGNGGGCGGTGNGGTCCGCCTAAAA
CCATGTTCCTCAAAGATCATTTGTTGCCCAACACTGGGTTGCTGACCANAAGTGCCAGGAA
GCTGAATACCATTTCCAGTGTCATACCCAGGGTGGGTGACGAAAGGGGTCTTTTGAACTGT
GGAAGGAACATCCAAGATCTCTGNTCCATGAAGATTGGGGTGTGGAAGGGTTACCAGTTG
GGGAAGCTCGCTGTCTTTTTCCTTCCAATCANGGGCTCGCTCTTCTGAATATTCTTCAGGGC
AATGACATAAATTGTATATTCGGTTCCCGGTTCCAGGCCAG

16450.1.edit

TCGAGCGGCCGCCCGGGCAGGTCCACCACACCCAATTCCTTGCTGGTATCATGGCAGCCGC
CACGTGCCAGGATTACCGGCTACATCATCAAGTATGAGAAGCCTGGGTCTCCTCCCAGAGA
AGTGGTCCCTCGGCCCCGCCCTGGTGTCACAGAGGCTACTATTACTGGCCTGGAACCGGGA
ACCGAATATACAATTTATGTCATTGCCCTGAAGAATAATCAGAAGAGCGAGCCCCTGATTG
GAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGG
GTATGACACTGGAAATGGTATTCAGCTTCCTGGCACTTCTGGTCAGCAACCCAGTGTTGGG
CAACAAATGATCTTTGANGAACATGGNTTTAGGCGGACCACACCGGCCACAACGGGCACC
CCCATAAGGCATAGGCCAAGAACATACCCGNCGAATGTAGGACAAGAAGCTCTNTCTCAN
ACAANCATCTCATGGGCCCCATTCCANGACACTTCTGAGTACATCANTTCATGGCATCCTG
GTGGCACTGATAAAAACCCTTACAGTTA

16450.2.edit

AGCGTGGTCGCGGGCGAGGTCCTGTCAGAGTGGCACTGGTAGAAGTTCCAGGAACCCTGA
ACTGTAAGGGTTCTTCATCAGTGCCAACAGGATGACATGAAATGATGTACTCAGAAGTGTC
CTGGAATGGGGCCCATGAGATGGTTGTCTGAGAGAGAGCTTCTTGTCCTACATTCGGCGGG
TATGGTCTTGGCCTATGCCTTATGGGGGTGGCCGTTGTGGGCGGTGTGGTCCGCCTAAAAC
CATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTG
GAAGGAACATCCAAGATCTCTGGTCCATGAAGATTGGGGTGTGGAAGGGTTACCAGTTGG
GGAAGCTCGTCTGTCTTTTTCCTTCCAATCANGGGCTCGCTCTTCTGATTATTCTTCAGGGC
AATGACATAAATTGTATATTCGGNTCCCGGGTNCAGCCAATAATAATAACCCTCTGTGACA
CCANGGCGGGGCCGAAGGANCACT

*FIG. 15X*

16451.1.edit

AGCGTGGTCGCGGCCGAGGTCCTCACCAGAGGTACCACCTACAACATCATAGTGGAGGCA
CTGAAAGACCAGCAGAGGCATAAGGTTCGGGAAGAGGTTGTTACCGTGGGCAACTCTGTC
AACGAAGGCTTGAACCAACCTACGGATGACTCGTGCTTTGACCCCTACACAGTTTCCCATT
ATGCCGTTGGAGATGAGTGGGAACGAATGTCTGAATCAGGCTTTAAACTGTTGTGCCAGTG
CTTANGCTTTGGAAGTGGTCATTTCAGATGTGATTCATCTAGATGGTGCCATGACAATGGT
GTGAACTACAAGATTGGAGAGAAGTGGGACCGTCAGGGAGAAAATGGACCTGCCCGGGC
GGCCGCTCGA

16451.2.edit

TCGAGCGGCCGCCCGGGCAGGTCCATTTTCTCCCTGACGGTCCCACTTCTCTCCAATCTTGT
AGTTCACACCATTGTCATGGCACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGNTGACAGAGTTGCCCACGGTAACAACCTCTTCCCGAACCTTATGCCTCTGCTGGT
CTTTCAGTGCCTCCACTATGATGTTGTAGGTGGTACCTCTGGTGAGGACCTCGGCCGCGAC
CACGCT

16452.1.edit

AGCGTGGCCGCGGCCGAGGTCCATTGGCTGGAACGGCATCAACTTGGAAGCCAGTGATCG
TCTCAGCCTTGGTTCTCCAGCTAATGGTGATGGNGGTCTCAGTAGCATCTGTCACACGAGC
CCTTCTTGGTGGGCTGACATTCTCCAGAGTGGTGACAACACCCTGAGCTGGTCTGCTTGTC
AAAGTGTCCTTAAGAGCATAGACACTCACTTCATATTTGGCGNCCACCATAAGTCCTGATA
CAACCACGGAATGACCTGTCAGGAAC

16452.2.edit

TCGAGCGGCCGCCCGGGCAGGTCCTCAGACCGGGTTCTGAGTACACAGTCAGTGTGGTTGC
CTTGCACGATGATATGGAGAGCCAGCCCCTGATTGGAACCCAGTCCACAGCTATTCCTGCA
CCAACTGACCTGAAGTTCACTCAGGTCACACCCACAAGCCTGAGCGCCCAGTGGACACCA
CCCAATGTTCAGCTCACTGGATATCGAGTGCGGGTGACCCCCAAGGAGAAGACCGGACCA
ATGAAAGAAATCAACCTTGCTCCTGACAGCTCATCCGTGGTTGTATCAGGACTTATGGCGG
CCACCAAATATGAAGTGAGTGTCTATGCTCTTAAGGACACTTTGACAAGCAGACCAGCTCA
GGGTGTTGTCACCACTCTGGAGAATGTCAGCCCACCAAGAAGGGCTCGTGTGACAGATGC
TACTGAGACCACCATCACCATTAGCTGGAGAACCAAGACTGAGACGATCACTGGCTTCCA
AGTTGATGCCGTTCCAGCCAATGGACCTCGGCCGCGACCACGCTT

*FIG. 15Y*

16453.1.edit

AGCGTGGTCGCGGCCGAGGTCTGGCCGAACTGCCAGTGTACAGGGAAGATGTACATGTTA
TAGNTCTTCTCGAAGTCCCGGGCCAGCAGCTCCACGGGGTGGTCTCCTGCCTCCAGGCGCT
TCTCATTCTCATGGATCTTCTTCACCCGCAGCTTCTGCTTCTCAGTCAGAAGGTTGTTGTCC
TCATCCCTCTCATACAGGGTGACCAGGACGTTCTTGAGCCAGTCCCGCATGCGCAGGGGGA
ATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCA
GGAAGAGTCGAAGGTCTTGTTGTCATTGCTGCACACCTTCTCAAACTCGCCAATGGGGGCT
GGGCAGACCTGCCCGGGCGGCCGCTCGA

16453.2.edit

TCGAGCGGCCGCCCGGGCAGGTCTGCCCAGCCCCCATTGGCGAGTTTGAGAAGGNGTGCA
GCAATGACAACAAGACCTTCGACTCTTCCTGCCACTTCTTTGCCACAAAGTGCACCCTGGA
GGGCACCAAGAAGGGCCACAAGCTCCACCTGGACTACATCGGGCCTTGCAAATACATCCC
CCCTTGCCTGGACTCTGAGCTGACCGAATTCCCCCTGCGCATGCGGGACTGGCTCAAGAAC
GTCCTGGTCACCCTGTATGAGAGGGATGAGGACAACAACCTTCTGACTGAGAAGCANAAG
CTGCGGGTGAAGAANATCCATGAGAATGANAAGCGCCTGNAGGCANGAGACCACCCCGT
GGAGCTGCTGGCCCGGGACTTCGAGAAGAACTATAACATGTACATCTTCCCTGTACACTGG
CAGTTCGGCCAGACCTCGGCCGCGACCACGCT

16454.1.edit

AGCGTGGNTGCGGACGACGCCCACAAAGCCATTGTATGTAGTTTTANTTCAGCTGCAAAN
AATACCNCCAGCATCCACCTTACTAACCAGCATATGCAGACA

16454.2.edit

TCGAGCGGTCGCCCGGGCAGGTCTGGGCGGATAGCACCGGGCATATTTTGGAATGGATGA
GGTCTGGCACCCTGAGCAGCCCAGCGAGGACTTGGTCTTAGTTGAGCAATTTGGCTAGGA
GGATAGTATGCAGCACGGTTCTGAGTCTGTGGGATAGCTGCCATGAAGNAACCTGAAGGA
GGCGCTGGCTGGTANGGGTTGATTACAGGGCTGGGAACAGCTCGTACACTTGCCATTCTCT
GCATATACTGGNTAGTGAGGCGAGCCTGGCGCTCTTCTTTGCGCTGAGCTAAAGCTACATA
CAATGGCTTTGNGGACCTCGGCCGCGACCACGCTT

*FIG. 15Z*

16455.1.edit

TCGAGCGGCCGCCCGGGCAGGTCCATTTTCTCCCTGACGGTCCCACTTCTCTCCAATCTTGT
AGTTCACACCATTGTCATGACACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGTTGACAGAAGTTGCCCACGGTAACAACCTCTTCCCGAACCTTATGCCTCTGCTGGT
CTTTCAAGTGCCTCCACTATGATGTTGTAGGTGGCACCTCTGGTGAGGACCTCGGCCGCGA
CCACGCT

16455.2.edit

AGCGTGGTTTGCGGCCGAGGTCCTCACCANAGGTGCCACCTACAACATCATAGTGGAGGC
ACTGAAAGACCAGCAGAGGCATAAGGTTCGGGAAGAGGTTGTTACCGTGGGCAACTCTGT
CAACGAAGGCTTGAACCAACCTACGGATGACTCGTGCTTTGACCCCTACACAGNTTCCCAT
TATGCCGTTGGAGATGAGTGGGAACGAATGTCTGAATCAGGCTTTAAACTGTTGTGCCAGT
GCTTANGCTTTGGAAGTGGTCATTTCAGATGTGATTCATCTANATGGTGTCATGACAATGG
TGNGAACTACAAGATTGGAGAGAAGTGGNACCGTCAGGGGANAAAATGGACCTGCCCGG
GCGGCNCGCTCGA

16456.1.edit

AGCGTGGTCGCGGCCGAGGTCTGGCTTNCTGCTCANGTGATTATCCTGAACCATCCAGGCC
AAATAAGCGCCGGCTATGCCCCTGNATTGGATTGCCACACGGCTCACATTGCATGCAAGTT
TGCTGAGCTGAAGGAAAAGATTGATC

16456.2.edit

TCGAGCGGCCGCCCGGGCAGGTCCAATTGAAACAAACAGTTCTGAGACCGTTCTTCCACCA
CTGATTAAGAGTGGGGNGGCGGGTATTAGGGATAATATTCATTTAGCCTTCTGAGCTTTCT
GGGCAGACTTGGTGACCTTGCCAGCTCCAGCAGCCTTCTGGTCCACTGCTTTGATGACACC
CACCGCAACTGTCTGTCTCATATCACGAACAGCAAAGCGACCCAAAGGTGGATAGTCTGA
GAAGCTCTCAACACACATGGGCTTGCCAGGAACCATATCAACAATGGGCAGCATCACCAG
ACTTCAAGAATTTAAGGGCCATCTTCCAGCTTTTTACCAGAACGGCGATCAATCTTTTCCTT
CAGCTCAGCAAACTTGCATGCAATGTGAGCCG

*FIG. 15AA*

16459.1.edit

TCGAGCGGCCGCCCGGGCAGGTCCAGAGGGCTGTGCTGAAGTTTGCTGCTGCCACTGGAG
CCACTCCAATTGCTGGCCGCTTCACTCCTGGAACCTTCACTAACCAGATCCAGGCAGCCTT
CCGGGAGCCACGGCTTCTTGTGGNTACTGACCCCAGGGCTGACCACCAGCCTCTCACGGAG
GCATCTTATGTTAACCTACCTACCATTGCGCTGTGTAACACAGATTCTCCTCTGCGCTATGT
GGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGN
CATGCCTGATCTGGACTTCTACAGAGATCCTGAAGAGATTGAAAAAGAAGAACAGGCTGN
TTGCTGANAAAGCAAGTGACCAAGGANGAAATTTCANGGGTGAAANGGACTGCTCCCGCT
CCTGAATTCACTGCTACTCAACCTGANGNTGCAGACTGGTCTTGAAGGNGNACANGGGCC
CTCTGGGCCTATTTAAGCANCTTCGGTCGCGAACACGNT 16459.2.edit AGCGTGNGTCGCGGCCGAGGTGCTGAATAGGCACAGAGGGCACCTGTACACCTTCAGACC
AGTCTGCAACCTCAGGCTGAGTAGCAGTGAACTCAGGAGCGGGAGCAGTCCATTCACCCT
GAAATTCCTCCTTGGNCACTGCCTTCTCAGCAGCAGCCTGCTCTTCTTTTTCAATCTCTTCA
GGATCTCTGTAGAAGTACAGATCAGGCATGACCTCCCATGGGTGTTCACGGGAAATGGTG
CCACGCATGCGCAGAACTTCCCGAGCCAGCATCCACCACATCAAACCCACTGAGTGAGCT
CCCTTGTTGTTGCATGGGATGGGCAATGTCCACATAGCGCAGAGGAGAATCTGTGTTACAC
AGCGCAATGGTAGGTAGGTTAACATAAGATGCCTCCGCGAGAAGCTGGTGGTCAGCCCTG
GGGTCAAGTAACCACAAGAAGCCGTGGCTCCCGGAAGGCTGCCTGGATCTGGTTAGTGAA
GGNTCCAGGAGTGAAGCGGCCAACAATTGGAGTGGCTTCAGTGGCAAGCAGCAAACTTCA
GCACAAGCCCTCTGGACCTGCCCGGCGGCCGCTCGA 16460.1.edit TCGAGCGGCCGCCCGGGCAGGTCCATTTTCTCCCTGACGGNCCCACTTCTCTCCAATCTTGT
AGTTCACACCATTGTCATGGCACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGTTGACAGAGTTGCCCACGGTAACAACCTCNTCCCCGAACCTTATGCCTCTGCTGG
GCTTTCAGNGCCTCCACTATGATGNTGTAGGGGGGCACCTCTGGNGANGACCTCGGCCGC
GACCACGCT 16460.2.edit AGCGTGGTCGCGGCCGAGGTCCTCACCAGAGGTGCCACCTACAACATCATAGTGGAGGCA
CTGAAAGACCAGCAGAGGCATAAGGCTCGGGAAGAGGTTGTTACCGTGGGCAACTCTGTC
AACGAAGGCTTGAACCAACCTACGGATGACTCGTGCTTTGACCCCTACACAGTTTCCCATT
ATGCCGTTGGAGATGAGTGGGAACGAATGTCTGAATCAGGCTTTAAACTGTTGTGCCAGTG
CTTANGCTTTGGAAGTGGGTCATTTCAGATGTGATTCATCTAGATGGTGCCATGACAATGG
NGNGAACTACAAGATTGGAGAGAAGTGGNACCGNCAGGGAGAAAATGGACCTGCCCGGG
CGGCCGCTCGA

*FIG. 15BB*

16461.1.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACGCAGGTCTCACCAGT
CTCCATGTTGCAGAAGACTTTGATGGCATCCAGGNTGCAACCTTGGTTGGGGTCAATCCAG
TACTCTCCACTCTTCCAGCCAGAGTGGCACATCTTGAGGTCACGGCAGGTGCGGNCGGGGG
NTTTTGCGGCTGCCCTCTGGNCTTCGGNTGTNCTCNATCTGCTGGCTCA

16461.2.edit

TCGAGCGGCCGCCCGGGCAGGTCTCGCGGTCGCACTGGTGATGCTGGTCCTGTTGGTCCCC
CCGGCCCTCCTGGACCTCCTGGCCCCCCTGGTCCTCCCAGCGCTGGTTTCGACTTCAGCTTC
CTGCCCCAGCCACCTCAAGAGAAGGCTCACGATGGTGGCCGCTACTACCGGGCTGATGAT
GCCAATGTGGTTCGTGACCGTGACCTCGAGGTGGACACCACCCTCAAGAGCCTGAGCCAG
CAGATCGAGAACATCCGGAGCCCAGAGGGCAGNCGCAAGAACCCCGCCCGCACCTGCCGT
GACCTCAAGATGTGCCACTCTGACTGGAAGAGTGGAGAGTACTGGATTGACCCCAACCAA
GCTGCAACCTGGATGCCATCAAAGTCTTCTGCAACATGGAGACTGGTGAGACCTGCGTGTA
CCCCACTCAGCCCAGTGTGGCCCAAAAGAACTGGTACATCAGCAAGAACCCCAAGGACAA
GAAGCATGTCTGGTTCGGCGAGAACATGACCGATGGATTCCAGTTCGAGTATGGCGGGCA
GGGCTCCGACCCTGCCGATGGGGACCTTGGCCGCGAACACGCT

16463.1.edit

AGCGTGGNNGCGGCCGAGGTATAAATATCCAGNCCATATCCTCCCTCCACACGCTGANAG
ATGAAGCTGTNCAAAGATCTCAGGGTGGANAAAACCAT

16463.2.edit

TCGAGCGGCCGCCCGGGCAGGTCCTTCAGACTTGGACTGTGTCACACTGCCAGGCTTCCAG
GGCTCCAACTTGCAGACGGCCTGTTGTGGGACAGTCTCTGTAATCGCGAAAGCAACCATG
GAAGACCTGGGGGAAAACACCATGGTTTTATCCACCCTGAGATCTTTGAACAACTTCATCT
CTCAGCGTGCGGAGGGAGGCTCTGGACTGGATATTTCTACCTCGGCCGCGACCACGCT

*FIG. 15CC*

16464.1.edit

CGAGCGGGCGACCGGGCAGGTNCAGACTCCAATCCANANAACCATCAAGCCAGATGTCAG
AAGCTACACCATCACAGGTTTACAACCAGGCACTGACTACAAGANCTACCTGCACACCTTG
AATGACAATGCTCGGAGCTCCCCTGTGGTCATCGACGCCTCCACTGCCATTGATGCACCAT
CCAACCTGCGTTTCCTGGCCACCACACCCAATTCCTTGCTGGTATCATGGCAGCCGCCACG
TGCCAGGATTACCGGTACATCATCNAGTATGANAAGCCTGGGCCTCCTCCCAGAGAAGNG
GTCCCTCGGCCCCGCCCTGNTGTCCCANAGGNTACTATTACTGNGCCNGCAACCGGCAACC
GATATCNATTTTGNCATTGGCCTTCAACAATAATTA

16464.2.edit

AGCGTGGTTCGCGGCCGANGTCCTGTCAGAGTGGCACTGGTAGAAGTTCCAGGAACCCTG
AACTGTAAGGGTTCTTCATCAGNGCCAACAGGATGACATGAAATGATGTACTCAGAAGTG
TCCTGGAATGGGGCCCATGAGATGGTTGTCTGAGAGAGAGCTTCTTGNCCTGTCTTTTTCC
TTCCAATCAGGGGCTCGCTCTTCTGATTATTCTTCAGGGCAATGACATAAATTGTATATTCG
GGTCCCGGNTCCAGGCCAGTAATAGTANCCTCTGTGACACCAGGGCGGNGCCGAGGGACC
ACTTCTCTGGGAGGAGACCCAGGCTTCTCATACTTGATGATGTAACCGGTAATCCTGGCAC
GTGGCGGCTGCCATGATACCAGCAAGGAATTGGGGTGTGGTGGCCAGGAAACGCAGGTTG
GATGGNGCATCAATGGCAGTGGAGGCCGTCGATGACCACAGGGGGAGCTCCGACATTGTC
ATTCAAGGTG

16465.1.edit

AGCGTGGNCGCGGCCGAGGTGCAGCGCGGGCTGTGCCACCTTCTGCTCTCTGCCCAACGAT
AAGGAGGGTNCCTGCCCCCAGGAGAACATTAACTNTCCCCAGCTCGGCCTCTGCCGG

16465.2.edit

TCGAGCGGCCGCCCGGGCAGGTTTTTTTTGCTGAAAGTGGNTACTTTATTGGNTGGGAAAG
GGAGAAGCTGTGGTCAGCCCAAGAGGGAATACAGAGNCCCGAAAAAGGGGAGGGCAGGT
GGGCTGGAACCAGACGCAGGGCCAGGCAGAAACTTTCTCTCCTCACTGCTCAGCCTGGTG
GTGGCTGGAGCTCANAAATTGGGAGTGACACAGGACACCTTCCCACAGCCATTGCGGCGG
CATTTCATCTGGCCAGGACACTGGCTGTCCACCTGGCACTGGTCCCGACAGAAGCCCGAGC
TGGGGAAAGTTAATGTTCACCTGGGGGCAGGAACCCTCCTTATCATTGNGCAGAGAGCAG
AAGGTGGCACAGCCCGCGCTGCACCTCGGCCGCGACCACGCT

16466.2.edit

TCGAGCGGCCGCCCGGGCAGGTCCACCATAAGTCCTGATACAACCACGGATGAGCTGTCA
GGAGCAAGGTTGATTTCTTTCATTGGTCCGGNCTTCTCCTTGGGGGNCACCCGCACTCGAT
ATCCAGTGAGCTGAACATTGGGTGGCGTCCACTGGGCGCTCAGGCT

16467.2.edit

TCGAGCGGTTCGCCCGGGCAGGTCCACCACACCCAATTCCTTGCTGGTATCATGGCAGCCG
CCACGTGCCAGGATTACCGGCTACATCATCAAGTATGAGAAGCCTGGGTCTCCTCCCAGAG
AAGCGGTCCCTCGGCCCCGCCCTGGTGTCACAGAGGCTACTATTACTGGCCTGGAACCGGG
AACCGAATATACAATTTATGTCATTGNCCTGAAGAATAATCANNAANAGCGANCCCCTGA
TTGGAAGGA

*FIG. 15DD*

01_16469.edit

AGCGTGGTCGCGGCCGAGGTTGTACAAGCTTTTTTTTTTTTTTTTTTTTTTTTTTTTTTTTT
TTTTTTTTTTTTTTTTTTTTTTTTTTT

02_16469.edit

TCGAGCGGNCGCCCGGGCAGGTCTGCCAACACCAAGATTGGCCCCCGCCGCATCCACACA
GTCCGTGTGCGGGGAGGTAACAAGAAATACCGTGCCCTGAGGTTGGACGTGGGGAATTTC
TCCTGGGGCTCAGAGTGTTGTACTCGTAAAACAAGGATCATCGATGTTGTCTACAATGCAT
CTAATAACGAGCTGGTTCGTACCAAGACCCTGGTGAAGAATTGCATCGTGCTCATCGACAG
CACACCGTACCGACAGTGGTACGAGTCCCACTATGCGCTGCCCCTGGGCCGCAAGAAGGG
AGCCAAGCTGACTCCTGAGGAAGAAGAGATTTTAAACAAAAAACGATCTAANAAAAAAA
AAACAAT

03_16470.edit

AGCGTGGTCGCGGCCGAGGTGAAATGGTATTCAGCTTCCTGGCACTTCTGGTCAGCAACCC
AGTGTTGGGCAACAAATGATCTTTGAGGAACATGGTTTTAGGCGGACCACACCGCCCACA
ACGGCCACCCCCATAAGGCATAGGCCAAGACCATACCCGCCGAATGTAGGACAAGAAGCT
CTCTCTCAGACAACCATCTCATGGGCCCCATTCCAGGACACTTCTGAGTACATCATTTCATG
TCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCT
GAACTGTAAGGGTTCTTCATCAGTGCCAACAGGATGACATGAAATGATGTACTCAGAAGT
GTCCTGGAATGGGGCCCATGAGATGGTTGTCTGAGAGAGAGCTTCTTGTCCTACATTCGGC
GGGTATGGTCTTGGCCTATGCCTTATGGGGGTGGCCGTTGTGGGCGGTGTGGTCCGCCTAA
AACCATGTTCCTCAAAGATCATTTGTTGCCCAACACTGGGTTGCTGACCAGAAGTGCCAGG
AAGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGAC
TCGTACCACTGTCGGTACGGTGTGCTGTCGATGAGCACGATGCAATTCTTCACCAGGGTCT
TGGTACGAACCAGCTCGTTATTAGATGCATTGTAGACAACATCGATGATCCTTGTTTTACG
AGTACAACACTCTGAGCCCCAGGAGAAATTCCCCACGTCCAACCTCAGGGCACGGTATTTC
TTGTTACCTCCCCGCACACGGACTGTGTGGATGCGGCGGGGGCCAAGCTGACTCCTGAGGA
AGAAGAGATTTTAAACAAAAAACGATCTAAAAAAAATTCAGAAGAAATATGATGAAAGGA
AAAAGAATGCCAAAATCAGCAGTCTCCTGGAGGAGCAGTTCCAGCAGGGCAAGCTTCTTG
CGTGCATCGCTTCAAGGCCGGGACAGTGTGACCGAGCAGATGGCTATGTGCTAGAGGGCA
AAGAAGTGGAGTTCTATCTTAAGAAAATCAGGGCCCAGAATGGTGNGTCTTCAACTAATC
CAAAGGGGAGTTTCAGACCAGTGCAATCAGCAAAAACATTGATACTGNTGGCCAAATTTA
TTGGTGCAGGGCTTGCACANTANGANNGGCTGGGTCTTGGGGCTTGGATTGGNACAAGCT
TTGGCAGCCTTTTCTTTGGTTTTGCCAAAAACCTTTTGNTGAAGANGANACCTNGGGCGGA
CCCCTTAACCGATTCCACNCCNGGNGGCGTTCTANGGNCCCNCTTG

*FIG. 15EE*

06_16471.edit

AGCGTGGTCGCGGCCGAGGTCTGCTGCTTCAGCGAAGGGTTTCTGGCATAACCAATGATA
AGGCTGCCAAAGACTGTTCCAATACCAGCACCAGAACCAGCCACTCCTACTGTTGCAGCAC
CTGCACCAATAAATTTGGCAGCAGTATCAATGTCTCTGCTGATTGCACTGGTCTGAAACTC
CCTTTGGATTAGCTGAGACACACCATTCTGGGCCCTGATTTTCCTAAGATAGAACTCCAAC
TCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTT
TTTCCTTTCATCATATTTCTTCTGAATTTTTTTAGATCGTTTTTTGTTTAAAATCTCTTCTTCC
TCAGGAGTCAGCTTGGCCCCCGCCGCATCCACACAGTCCGTGTGCGGGGAGGTAACAAGA
AATACCGTGCCCTGAGGTTGGACGTGGGGAATTTCTCCTGGGGCTCAGAGTGGTGTACTCG
TAAAACAAGGATCATCGATGGTGNCTACAATGCATCTAATAACGAGCTGGGTCGGACCCA
AAGAACCTGGNGAANAAATGGATCGNCTCATCGACAGGACACCGTACCCGACAGGGGNA
CGANTCCCACTATGCGCTTGCCCCTGGGCCGCAANAAAGGAAAACTGCCCGGGCGGCCNT
CGAAAGCCCAATTNTGGAAAAAATCCATCACACTGGGNGGCCNGTCGAGCATGCATNTAN
AGGGGCCCATTCCCCCTNANN

07_16472.edit

TCGAGCGGCCGCCCGGGCAGGTCCCCAACCAAGGCTGCAACCTGGATGCCATCAAAGTCT
TCTGCAACATGGAGACTGGTGAGACCTGCGTGTACCCCACTCAGCCCAGTGTGGCCCAGA
AGAACTGGTACATCAGCAAGAACCCCAAGGACAAGAGGCATGTCTGGTTCGGCGAGAGCA
TGACCGATGGATTCCAGTTCGAGTATGGCGGCCAGGGCTCCGACCCTGCCGATGTGGACCT
CGGCCGCGACCACGCT

08_16472.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACGCAGGTCTCACCAGT
CTCCATGTTGCAGAAGACTTTGATGGCATCCAGGTTGCAGCCTTGGTTGGGGACCTGCCCG
GGCGGCCGCTCGA

09_16473.edit

TCGAGCGGCCGCCCGGGCAGGTCCACCACACCCAATTCCTTGCTGGTATCATGGCAGCCGC
CACGTGCCAGGATTACCGGCTACATCATCAAGTATGAGAAGCCTGGGTCTCCTCCCAGAGA
AGTGGTCCCTCGGCCCCGCCCTGGTGTCACAGAGGCTACTATTACTGGCCTGGAACCGGGA
ACCGAATATACAATTTATGTCATTGCCCTGAAGAATAATCAGAAGAGCGAGCCCCTGATTG
GAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGG
GTATGACACTGGAAATGGTATTCAGCTTCCTGGCACTTCTGGTCAGCAACCCAGTGTTGGG
CAACAAATGATCTTTGAGGAACATGGNTTTAGGCGGACCACACCGCCCACAACGGCCACC
CCCATAAGGCATAGGCCAAGACCATACCCGCCGAATGTAGGACAAGAAGCTNTNTNTCAN
ACACCATNTNATGGGCCCCATTCCAGGACACTTCTGAGTACATCATTTATGNCATCTGTGG
CACTTGATGAAAACCCTTACAGTTCAGGGTTCTGGAACTTTTACCAGGCCTNTTACAGGAC
TNGGCCGGACNCCTTAAGCCNATTNCACCCTGGGGCGTTCTANGGTCCCACTCGNNCACTG
GNGAAAATGGCTACTGTN

*FIG. 15FF*

11_16474.edit

AGCGTGGTCGCGGCCGAGGTCCACTAGAGGTCTGTGTGCCATTGCCCAGGCAGAGTCTCTG
CGTTACAAACTCCTAGGAGGGCTTGCTGTGCGGAGGGCCTGCTATGGTGTGCTGCGGTTCA
TCATGGAGAGTGGGGCCAAAGGCTGCGAGGTTGTGGTGTCTGNGAAACTCCNAGGACANG
AGGGCTAAATTCCATGAAGTTTGTGGATGGCCTGATGATCCACAATCGGAGACCCTGTTAA
CTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANA
NTTGGCCTTTAAANAATCCNCCTTGCCTTNNNCACTGTTCANNTNTTTNNTCGTAAACCCT
ATNANTTNNATTANATNNTNNNNNNCTCACCCCCCTCNTCATTNANCCNATANGCTNNNA
ANTCCTTNANNCCTCCCNCCCNNTNCNCTCNTACTNANTNCTTCTNNCCCATTACNNAGCT
CTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCC
NCNTTCCNNCNTTTCGGNTNNTCCCATNCTTTCCANNNCTTCANTCTANCNCNCTNCAACT
TATTTTCCTNTCATCCCTTNTTCTTTACANNCCCCCTNNTCTACTCNNCNNTTNCATTANAT
TTGAAACTNCCACNNCTANTTNCCTCNCTCTACNNTTTTATTTTNCGNTCNCTCTACNTAAT
ANTTTAATNANTTNTCN

12_16474.edit

TCGAGCGGCCGCCCGGGCAGGTCTGCCAAGGAGACCCTGTTATGCTGTGGGGACTGGCTG
GGGCATGGCAGGCGGCTCTGGCTTCCCACCCTTCTGTTCTGAGATGGGGGTGGTGGGCAGT
ATCTCATCTTTGGGTTCCACAATGCTCACGTGGTCAGGCAGGGGCTTCTTAGGGCCAATCT
TACCAGTTGGGTCCCAGGGCAGCATGATCTTCACCTTGATGCCCAGCACACCCTGTCTGAG
CAACACGTGGCGCACAAGCAGTGTCAACGTAGTAAGTTAACAGGGTCTCCGCTGTGGATC
ATCAGGCCATCCACAAACTTCATGGATTTAGCCCTCTGTCCTCGGAGTTTCCCAGACACCA
CAACCTCGCAGCCTTTGGCCCCACTCTCCATGATGAACCGCAGCACACCATAGCAGGCCCT
CCGCACAAGCAAGCCCTCCTAAGAATTTGTAACGCANANACTCTGCTGGCAATGGCACAC
AAACCTCTAGTGGACCTCGGNCGCGACCACGC

13_16475.edit

TCGAGCGGCCGCCCGGGCAGGTCTGGTCCAGGATAGCCTGCGAGTCCTCCTACTGCTACTC
CAGACTTGACATCATATGAATCATACTGGGGAGAATAGTTCTGAGGACCAGTAGGGCATG
ATTCACAGATTCCAGGGGGGCCAGGAGAACCAGGGGACCCTGGTTGTCCTGGAATACCAG
GGTCACCATTTCTCCCAGGAATACCAGGAGGGCCTGGATCTCCCTTGGGGCCTTGAGGTCC
TTGACCATTAGGAGGGCGAGTAGGAGCAGTTGGAGGCTGTGGGCAAACTGCACAACATTC
TCCAAATGGAATTTCTGGGTTGGGGCAGTCTAATTCTTGATCCGTCACATATTATGTCATCG
CAGAGAACGGATCCTGAGTCACAGACACATATTTGGCATGGTTCTGGCTTCCAGACATCTC
TATCCGNCATAGGACTGACCAAGATGGGAACATCCTCCTTCAACAAGCTTNCTGTTGTGCC
AAAAATAATAGTGGGATGAAGCAGACCGAGAAGTANCCAGCTCCCCTTTTTGCACAAAGC
NTCATCATGTCTAAATATCAGACATGAGACTTCTTTGGGCAAAAAAGGAGAAAAAGAAAA
AGCAGTTCAAAGTANCCNCCATCAAGTTGGTTCCTTGCCCNTTCAGCACCCGGGCCCCGTT
ATAAAACACCTNGGGCCGGACCCCCCTT

*FIG. 15GG*

14_16475.edit

AGCGTGGTCGCGGCCGAGGTGTTTTATGACGGGCCCGGTGCTGAAGGGCAGGGAACAACT
TGATGGTGCTACTTTGAACTGCTTTTCTTTTCTCCTTTTTGCACAAAGAGTCTCATGTCTGA
TATTTAGACATGATGAGCTTTGTGCAAAAGGGGAGCTGGCTACTTCTCGCTCTGCTTCATC
CCACTATTATTTTGGCACAACAGGAAGCTGTTGAAGGAGGATGTTCCCATCTTGGTCAGTC
CTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAA
ATTCCATTTGGAGAATGTTGTGCAGTTTGCCCACAGCCTCCAACTGCTCCTACTCGCCCTCC
TAATGGTCAAGGACCTCAAGGCCCCAAGGGAGATCCAGGCCCTCCTGGTATTCCTGGGAG
AAATGGTGACCCTGGTATTCCAGGACAACCAGGGTCCCCTGGTTCTCCTGGCCCCCCTGGA
ATCNGGNGAATCATGCCCTACTGGTCCTCAAACTATTCTCCCANATGATTCATATGATGTC
AAGTCTGGGATAGCNAGTANGGANGGACTCGCAGGCTATTCTGGACCANACCTGCCGGGG
GGGCGTTCGAAAGCCCGAATCTGCANANNTNCNTTCACACTGGCGGCCGTCGAGCTGCTTT
AAAAGGGCCATTCCNCCTTTAGNGNGGGGGANTACAATTACTNGGCGGCGTTTTANANCG
CGNGNCTGGGAAAT

15_16476.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACGCAGGTCTCACCAGT
CTCCATGTTGCAGAAGACTTTGATGGCATCCAGGTTGCAGCCTTGGTTGGGGTCAATCCAG
TACTCTCCACTCTTCCAGTCAGAGTGGCACATCTTGAGGTCACGGCAGGTGCGGGCGGGGT
TCTTGCGGCTGCCCTCTGGGCTCCGGATGTTCTCGATCTGCTGGCTCAGGCTCTTGAGGGTG
GTGTCCACCTCGAGGTCACGGTCACGAACCACATTGGCATCATCAGCCCGGTAGTAGCGGC
CACCATCGTGAGCCTTCTCTTGANGTGGCTGGGGCAGGAACTGAAGTCGAAACCAGCGCT
GGGAGGACCAGGGGGACCAANAGGTCCAGGAAGGGCCCGGGGGGGACCAACAGGACCAG
CATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCC
CCGGCCCTCCTGGACCTCCTGGTCCCCCTGGTCCTCCCAGCGCTGGTTTCGACTTCAGCTTC
CTGCCCCAGCCACCTCAAGAGAAGGCTCACGATGGTGGCCGCTACTACCGGGCTGATGAT
GCCAATGTGGTTCGTGACCGTGACCTCGAGGTGGACACCACCCTCAAGAGCCTGAGCCAG
CAGATCGAGAACATCCGGAGCCCAGAGGGCAGCCGCAAGAACCCCGCCCGCACCTGCCGT
GACCTCAAGATGTGCCACTCTGACTGGAAGAGTGGAGAGTACTGGATTGACCCCAACCAA
GGCTGCAACCTGGATGCCATCAAAGTCTTCTGCAACATGGAGACTGGTGAGACCTGCGTGT
ACCCCACTCAGCCCAGTGTGGCCCAGAAGAACTGGTACATCAGCAAGAACCCCAAGGACA
AGAGGCATGTCTGGTTCGGCGAGAGCATGACCGATGGATTCCAGTTCGAGTATGGCGGCC
AGGGCTCCCACCCTGCCGATGTGGACCTCCGGCCGCGACCACCCTT

*FIG. 15HH*

17_16477.edit

TNGAGCGGCCGCCCGGGCAGGNTGNNAACGCTGGTCCTGCTGGTCCTCCTGGCAAGGCTG
GTGAAGATGGTCACCCTGGAAAACCCGGACGACCTGGTGAGAGAGGAGTTGTTGGACCAC
AGGGTGCTCGTGGTTTCCCTGGAACTCCTGGACTTCCTGGCTTCAAAGGCATTAGGGGACA
CAATGGTCTGGATGGATTGAAGGGACAGCCCGGTGCTCCTGGTGTGAAGGGTGAACCTGG
TGCCCCTGGTGAAAATGGAACTCCAGGTCAAACAGGAGCCCGTGGGCTTCCTGGTGAGAG
AGGACCGTGTTGGTGCCCCTGGCCCANACCTCGGCCGCGACCACGCTAAGCCCGAATTTCC
AGCACACTGGNGGCCGTTACTANTGGATCCGAGCTCGGTACCAAGCTTGGCGTAATCATG
GTCATAGCTGTTTCCTGNGTGAAATTGTTATCCGCTCACAATTTCACACANCATACGAAGC
CGGAAAGCATAAAGTGTAAAGCCTTGGGGTGCTAATGAGTGAGCTAACTCNCATTAAATT
GCGTTGCGCTCACTGCCCGCTTTTCCANNNGGGAAACCNTGGCNTNGCCNGCTTGCNTTAA
NTGAAATCCGCCNACCCCCGGGGAAAAGNCGGTTTGCNGTATTGGGGCNCTTTTTCCCTTT
CCTCGGNTTACTTGANTTANTGGGCTTTGGNCGNTTCGGGTTGNGGCGANCNGGTTCAACN
TCACNCCAAAGGNGGNAANACGGTTTTCCCANAATCCGGGGGNTANCCCAANGNAAAAC
ATNNGNCNAANGGGCT

18_16477.edit

AGCGTGGTTNGCGGCCGAGGTCTGGGCCAGGGGCACCAACACGTCCTCTCTCACCAGGAA
GCCCACGGGCTCCTGTTTGACCTGGAGTTCCATTTTCACCAGGGGCACCAGGTTCACCCTT
CACACCAGGAGCACCGGGCTGTCCCTTCAATCCATNCAGACCATTGTGNCCCCTAATGCCT
TTGAAGCCAGGAAGTCCAGGAGTTCCAGGGAAACCACCGAGCACCCTGTGGTCCAACAAC
TCCTCTCTCACCAGGTCGTCCGGGTTTTCCAGGGTGACCATCTTCACCAGCCTTGCCAGGA
GGACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGT
AGTTCACACCATTGTCATGGCACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTCGGCCGCGACC
ACGCT

22_16479.edit

AGCGTGGTCGCGGCCGAGGTCCTCACCAGAGGTGCCACCTACAACATCATAGTGGAGGCA
CTGAAAGACCAGCAGAGGCATAAGGTTCGGGAAGAGGTTGTTACCGTGGGCAACTCTGTC
AACGAAGGCTTGAACCAACCTACGGATGACTCGTGCTTTGACCCCTACACAGTTTCCCATT
ATGCCGTTGGAGATGAGTGGGAACGAATGTCTGAATCAGGCTTTAAACTGTTGTGCCAGTG
CTTAGGCTTTGGAAGTGGTCATTTCAAGATGTGATTCATCTAGATGGTGCCATGACAATGG
TGTGAACTACAAGATTGGAGAGAAGTGGGACCGTCAGGGAGAAAATGGACCTGCCCGGG
CCGGCCGCTCGA

*FIG. 15II*

24_16480.edit

TCGAGCGNNCGCCCGGGCAGGTCCAGTAGTGCCTTCGGGACTGGGTTCACCCCCAGGTCTG
CGGCAGTTGTCACAGCGCCAGCCCCGCTGGCCTCCAAAGCATGTGCAGGAGCAAATGGCA
CCGAGATATTCCTTCTGCCACTGTTCTCCTACGTGGTATGTCTTCCCATCATCGTAACACGT
TGCCTCATGAGGGTCACACTTGAATTCTCCTTTTCCGTTCCCAAGACATGTGCAGCTCATTT
GGCTGGCTCTATAGTTTGGGGAAAGTTTGTTGAAACTGTGCCACTGACCTTTACTTCCTCCT
TCTCTACTGGAGCTTTCGTACCTTCCACTTCTGCTGTTGGTAAAATGGTGGATCTTCTATCA
ATTTCATTGACAGTACCCACTTCTCCCAAACATCCAGGGAAATAGTGATTTCAGAGCGATT
AGGAGAACCAAATTATGGGGCAGAAATAAGGGGCTTTTCCACAGGTTTTCCTTTGGAGGA
AGATTTCAGTGGTGACTTTAAAAGAATACTCAACAGTGTCTTCATCCCCATAGCAAAAGAA
GAAACNGTAAATGATGGAANGCTTCTGGAGATGCCNNCATTTAAGGGACNCCCAGAACTT
CACCATCTACAGGACCTACTTCAGTTTACANNAAGNCACATANTCTGACTCANAAAGGAC
CCAAGTAGCNCCATGGNCAGCACTTTNAGCCTTTCCCCTGGGGAAAANNTTACNTTCTTAA
ANCCTNGGCCNNGACCCCCTTAAGNCCAAATTNTGGAAAANTTCCNTNCNNCTGGGGGGC
NGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGT
TCTCCGGCTGCCCATTGCTCTCCCACTCCACGGCGATGTCGCTGGGATAGAAGCCTTTGAC
CAGGCAGGTCAGGCTGACCTGGTTCTTGGTCATCTCCTCCCGGGATGGGGGCAGGGTGTAC
ACCTGTGGTTCTCGGGGCTGCCCTTTGGCTTTGGAGATGGTTTTCTCGATGGGGGCTGGGA
GGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTG
GCATTATGCACCTCCACGCCGTCCACGTACCAGTTGAACTTGACCTCAGGGTCTTCGTGGC
TCACGTCCACCACCACGCATGTAACCTCAGACCTCGGCCGCGACCACGCT

26_16481.edit

AGCGTGGTCGCGGCCGAGGTCTGAGGTTACATGCGTGGTGGTGGACGTGAGCCACGAAGA
CCCTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCTGCA
CCAGGACTGGCTGAATGGCAAGGAGTACAAGTGCAAGGTCTCCAACAAAGCCCTCCCAGC
CCCCATCGAGAAAACCATCTCCAAAGCCAAAGGGCAAGCCCCGAGAACCACAGGTGTACA
CCCTGCCCCCATCCCGGGAGGAGATGACCAAGAACCAGGTCAGCCTGACCTGCCTGGTCA
AAGGCTTCTATCCCAGCGACATCGCCGTGGAGTGGGAGAGCAATGGGCAGCCGGAGAACA
ACTACAAGACCACGCCTCCCGTGCTGGACTCCGACACCTGCCCGGGCGGCCGCTCGA

27_16482.edit

TCGAGCGGCCGCCCGGGCAGGTTGAATGGCTCCTCGCTGACCACCCCGGTGCTGGTGGTGG
GTACAGAGCTCCGATGGGTGAAACCATTGACATAGAGACTGTCCCTGTCCAGGGTGTAGG
GGCCCAGCTCAGTGATGCCGTGGGTCAGCTGGCTCAGCTTCCAGTACAGCCGCTCTCTGTC
CAGTCCAGGGCTTTTGGGGTCAGGACGATGGGTGCAGACAGCATCCACTCTGGTGGCTGC
CCCATCCTTCTCAGGCCTGAGCAAGGTCAGTCTGCAACCAGAGTACAGAGAGCTGACACT
GGTGTTCTTGAACAAGGGCATAAGCAGACCCTGAAGGACACCTCGGCCGCGACCACGCT

*FIG. 15JJ*

28_16482.edit

AGCGTGGTCGCGGCCGAGGTGTCCTTCAGGGTCTGCTTATGCCCTTGTTCAAGAACACCAG
TGTCAGCTCTCTGTACTCTGGTTGCAGACTGACCTTGCTCAGGCCTGAGAAGGATGGGGCA
GCCACCAGAGTGGATGCTGTCTGCACCCATCGTCCTGACCCCAAAAGCCCTGGACTGGACA
GAGAGCGGCTGTACTGGAAGCTGAGCCAGCTGACCCACGGCATCACTGAGCTGGGCCCCT
ACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

29_16483.edit

AGCGTGGTCGCGGCCGAGGTCCTGTCAGAGTGGCACTGGTAGAAGTTCCAGGAACCCTGA
ACTGTAAGGGTTCTTCATCAGTGCCAACAGGATGACATGAAATGATGTACTCAGAAGTGTC
CTGGAATGGGGCCCATGAGATGGTTGTCTGAGAGAGAGCTTCTTGTCCTACATTCGGCGGG
TATGGTCTTGGCCTATGCCTTATGGGGGTGGCCGTTGTGGGCGGTGTGGTCCGCCTAAAAC
CATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTG
GAAGGAACATCCAAGATCTCTGGTCCATGAAGATTGGGGTGTGGAAGGGTTACCAGTTGG
GGAAGCTCGTCTGTCTTTTTCCTTCCAATCAGGGGCTCGCTCTTCTGATTATTCTTCAGGGC
AATGACATAAATTGTATATTCGGTCCCGGTTCCAGGCCAGTAATAGTAGCCTCTGTGACAC
CAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNG
GACCTGCCCGGCGGCCGTTCNAAAGCCCAATTCCACACACTTGGNGGCCGTACTATGGATC
CCACTCNGTCCAACTTGGNGGAATATGGCATAACTTTT

31_16484.edit

TCGAGCGGCCGCCCGGGCAGGTCCTTGACCTTTTCAGCAAGTGGGAAGGTGTAATCCGTCT
CCACAGACAAGGCCAGGACTCGTTTGTACCCGTTGATGATAGAATGGGGTACTGATGCAA
CAGTTGGGTAGCCAATCTGCAGACAGACACTGGCAACATTGCGGACACCCTCCAGGAAGC
GAGAATGCAGAGTTTCCTCTGTGATATCAAGCACTTCAGGGTTGTAGATGCTGCCATTGTC
GAACACCTGCTGGATGACCAGCCCAAAGGAGAAGGGGGAGATGTTGAGCATGTTCAGCAG
CGTGGCTTCGCTGGCTCCCACTTTGTCTCCAGTCTTGATCAGACCTCGGCCGCGACCACGCT

37_16487.edit

AGCGTGGTCGCGGCCGAGGTCTGTCCTACAGTCCTCAGGACTCTACTCCCTCAGCAGCGTG
GTGACCGTGCCCTCCAGCAACTTCGGCACCCAGACCTACACCTGCAACGTAGATCACAAGC
CCAGCAACACCAAGGTGGACAAGAGAGTTGAGCCCAAATCTTGTGACAAAACTCACACAT
GCCCACCGTGCCCAGCACCTGAACTCCTGGGGGGACCGTCAGTCTTCCTCTTCCCCCGCAT
CCCCCTTCCAAACCTGCCCGGGCGGCCGCTCG

*FIG. 15KK*

38_16487.edit

CGAGCGGCCGCCCGGGCAGGTTTGGAAGGGGGATGCGGGGGAAGAGGAAGACTGACGGT
CCCCCCAGGAGTTCAGGTGCTGGGCACGGTGGGCATGTGTGAGTTTTGTCACAAGATTTGG
GCTCAACTCTCTTGTCCACCTTGGTGTTGCTGGGCTTGTGATCTACGTTGCAGGTGTAGGTC
TGGGTGCCGAAGTTGCTGGAGGGCACGGTCACCACGCTGCTGAGGGAGTAGAGTCCTGAG
GACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGG
AAGCGCAGATCTGTTTTAAAGTCCTGAGCAATTTCTCGCACCAGACGCTGGAAGGGAAGTT
TGCGAATCAGAAGTTCAGTGGACTTCTGATAACGTCTAATTTCACGGAGCGCCACAGTACC
AGGACCTGCCCGGGCGGCCGCTCGA

42_16489.edit

TCGAGCGGCCGCCCGGGCAGGTCCTGGTACTGNGGCGCTCCGTGAAATTAGACGTTATCA
GAAGTCCACTGAACTTCTGATTCGCAAACTTCCCTTCCAGCGTCTGGTGCGAGAAATTGCT
CAGGACTTTAAAACAGATCTGCGCTTCCAGAGCGCAGCTATCGGTGCTTTGCAGGAGGCA
AGTGAGGACCTCGGCCGCGACCACGCT

45_16491.edit

TCGAGCGGCCGCCCGGGCAGGTCCACATCGGCAGGGTCGGAGCCCTGGCCGCCATACTCG
AACTGGAATCCATCGGTCATGCTCTCGCCGAACCAGACATGCCTCTTGTCCTTGGGGTTCT
TGCTGATGTACCAGTTCTTCTGGGCCACACTGGGCTGAGTGGGGTACACGCAGGTCTCACC
AGTCTCCATGTTGCAGAAGACTTTGATGGCATCCAGGTTGCAGCCTTGGTTGGGGTCAATC
CAGTACTCTCCACTCTTCCAGTCAGAGTGGCACATCTTGAGGTCACGGCAGGTGCGGGCGG
GGTTCTTGACCTCGGCCGCGACCACGCT

*FIG. 15LL*

46_16491.edit

GTGGGNTTGAACCCNTTTNANCTCCGCTTGGTACCGAGCTCGGATCCACTAGTAACGGCCG
CCAGTGTGCTGGAATTCGGCTTAGCGTGGTCGCGGCCGAGGTCAAGAACCCCGCCCGCAC
CTGCCGTGACCTCAAGATGTGCCACTCTGACTGGAAGAGTGGAGAGTACTGGATTGACCC
CAACCAAGGCTGCAACCTGGATGCCATCAAAGTCTTCTGCAACATGGAGACTGGTGAGAC
CTGCGTGTACCCCACTCAGCCCAGTGTGGCCCAGAAGAACTGGTACATCAGCAAGAACCC
CAAGGACAAGAGGCATGTCTGGTTCGGCGAGAGCATGACCGATGGATTCCAGTTCGAGTA
TGGCGGCCAGGGCTCCGACCCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATC
ACTTACGGAGAAACAGGAGGAAATAGCCCTGTCCAGGAGTTCACTGTGCCTGGGAGCAAG
TCTACAGCTACCATCAGCGGCCTTAAACCTGGAGTTGATTATACCATCACTGTGTATGCTG
TCACTGGCCGTGGAGACAGCCCCGCAAGCAGCAAGCCAATTTCCATTAATTACCGAACAG
AAATTGACAAACCATCCCAGATGCAAGTGACCGATGTTCAGGACAACAGCATTAGTGTCA
AGTGGCTGCCTTCAAGTTCCCCTGTTACTGGTTACAGAGTAACCACCACTCCCAAAAATGG
ACCAGGACCAACAAAAACTAAAACTGCAGGTCCAGATCAAACAGAAATGACTATTGAAG
GCTTGCAGCCCACAGTGGAGTATGTGGTTAAGTGTCTATGCTCAGAATCCAAGCGGAGAG
AAGTCAGCCTCTGGTTCAGACTGNAAGTAACCAACATTGATCGCCTAAAGGACTGGCATTC
ACTGATGNGGATGCCGATTCCATCAAAATTGNTTGGGAAAACCCACAGGGGCAAGTTTNC
ANGTCNAGGNGGACCTACTCGAGCCCTGAGGATGGAATCCTTGACTNTTCCTTNNCCTGAT
GGGGAAAAAAAACCTTNAAAACTTGAAGGACCTGCCCGGGCGGCCGTNCAAAACCCAATT
CCACCCCCTTGGGGGCGTTCTATGGGNCCCACTCGGACCAAACTTGGGGTAAN

48_16492.edit

TCGAGCGGCCGCCCGGGCAGGTCCTTGCAGCTCTGCAGTGTCTTCTTCACCATCAGGTGCA
GGGAATAGCTCATGGATTCCATCCTCAGGGCTCGAGTAGGTCACCCTGTACCTGGAAACTT
GCCCCTGTGGGCTTTCCCAAGCAATTTTGATGGAATCGGCATCCACATCAGTGAATGCCAG
TCCTTTAGGGCGATCAATGTTGGTTACTGCAGTCTGAACCAGAGGCTGACTCTCTCCGCTT
GGATTCTGAGCATAGACACTAACCACATACTCCACTGTGGGCTGCAAGCCTTCAATAGTCA
TTTCTGTTTGATCTGGACCTGCAGTTTTAGTTTTTGTTGGTCCTGGTCCATTTTTGGGAGTG
GTGGTTACTCTGTAACCAGTAACAGGGGAACTTGAAGGCAGCCACTTGACACTAATGCTGT
TGTCCTGAACATCGGTCACTTGCATCTGGGATGGTTTGTCAATTTCTGTTCGGTAATTAATG
GAAATTGGCTTGCTGCTTGCGGGGCTTGTCTCCACGGCCAGTGACAGCATACACAGTGATG
GTATAATCAACTCCAGGTTTAAGCCGCTGATGGTAGCTGAAACTTTGCTCCAGGCACAAGT
GAACTCCTGACAGGGCTATTTCCTNCTGTTCTCCGTAAGTGATCCTGTAATATCTCACTGGG
ACAGCAGGANGCATTCCAAAACTTCGGGCGNGACCCCCTAAGCCGAATTNTGCAATATNC
ATCACACTGGCGGGCGCTCGANCATTCATTAAAAGGCCCAATCNCCCCTATAGGGAGTNT
ANTACAATTNG

*FIG. 15MM*

49_16493.edit

TCGAGCGGCCGCCCGGGCAGGTCACTTTTGGTTTTTGGTCATGTTCGGTTGGTCAAAGATA
AAAACTAAGTTTGAGAGATGAATGCAAAGGAAAAAAATATTTTCCAAAGTCCATGTGAAA
TTGTCTCCCATTTTTTTGGCTTTTGAGGGGGTTCAGTTTGGGTTGCTTGTCTGTTTCCGGGTT
GGGGGGAAAGTTGGTTGGGTGGGAGGGAGCCAGGTTGGGATGGAGGGAGTTTACAGGAA
GCAGACAGGGCCAACGTCG

55_16496.edit

AGCGTGGTCGCGGCCGAGGTCCTCACCAGAGGTGCCACCTACAACATCATAGTGGAGGCA
CTGAAAGACCAGCAGAGGCATAAGGTTCGGGAAGAGGTTGTTACCGTGGGCAACTCTGTC
AACGAAGGCTTGAACCAACCTACGGATGACTCGTGCTTTGACCCCTACACAGTTTCCCATT
ATGCCGTTGGAGATGAGTGGGAACGAATGTCTGAATCAGGCTTTAAACTGTTGTGCCAGTG
CTTAGGCTTTGGAAGTGGTCATTTCAGATGTGATTCATCTAGATGGTGCCATGACAATGGT
GTGAACTACAAGATTGGAGAGAAGTGGGACCGTCAGGGAGAAAATGGACCTGCCCGGGC
GGCCGCTCGA

56_16496.edit

TCGAGCGGCCGCCCGGGCAGGTCCATTTTCTCCCTGACGGTCCCACTTCTCTCCAATCTTGT
AGTTCACACCATTGTCATGGCACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTCGGCCGCGACC
ACGCT

59_16498.edit

TCGAGCGGCCGCCCGGGCAGGTCCACCATAAGTCCTGATACAACCACGGATGAGCTGTCA
GGAGCAAGGTTGATTTCTTTCATTGGTCCGGTCTTCTCCTTGGGGGTCACCCGCACTCGATA
TCCAGTGAGCTGAACATTGGGTGGTGTCCACTGGGCGCTCAGGCTTGTGGGTGTGACCTGA
GTGAACTTCAGGTCAGTTGGTGCAGGAATAGTGGTTACTGCAGTCTGAACCAGAGGCTGA
CTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCAT
TTTTGGGAGTGGTGGTTACTCTGTAACCAGTAACAGGGGAACTTGAAGGCAGCCACTTGAC
ACTAATGCTGTTGTCCTGAACATCGGTCACTTGCATCTGGGATGGTTTGNCAATTTCTGTTC
GGTAATTAATGGAAATTGGCTTGCTGCTTGCGGGGCTGTCTCCACGGCCAGTGACAGCATA
CACAGNGATGGNATNATCAACTCCAAGTTTAAGGCCCTGATGGTAACTTTAAACTTGCTCC
CAGCCAGNGAACTTCCGGACAGGGTATTTCTTCTGGTTTTCCGAAAGNGANCCTGGAATNN
TCTCCTTGGANCAGAAGGANCNTCCAAAACTTGGGCCGGAACCCCTT

*FIG. 15NN*

60_16473.edit

AGCGTGGTCGCGGCCGAGGTCCTGTCAGAGTGGCACTGGTAGAAGTTCCAGGAACCCTGA
ACTGTAAGGGTTCTTCATCAGTGCCAACAGGATGACATGAAATGATGTACTCAGAAGTGTC
CTGGAATGGGGCCCATGAGATGGTTGTCTGAGAGAGAGCTTCTTGTCCTACATTCGGCGGG
TATGGTCTTGGCCTATGCCTTATGGGGGTGGCCGTTGTGGGCGGTGTGGTCCGCCTAAAAC
CATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTG
GAAGGAACATCCAAGATCTCTGGTCCATGAAGATTGGGGTGTGGAAGGGTTACCAGTTGG
GGAAGCTCGTCTGTCTTTTTCCTTCCAATCAGGGGCTCGCTCTTCTGATTATTCTTCAGGGC
AATGACATAAATTGTATATTCGGTTCCCGGTTCCAGGCCAGTAATAGTAGCCTCTTGTGAC
ACCAGGCGGGGCCCANGGACCACTTCTCTGGGANGAGACCCAGCTTCTCATACTTGATGAT
GTAACCCGGTAATCCTGCACGTGGCGGCTGNCATGATACCANCAAGGAATTGGGTGNGGN
GGACCTGCCCGGCGGCCCTCNA

60_16498.edit

AGCGTGGTCGCGGCCGAGGTCTGGGATGCTCCTGCTGTCACAGTGAGATATTACAGGATC
ACTTACGGAGAAACAGGAGGAAATAGCCCTGTCCAGGAGTTCACTGTGCCTGGGAGCAAG
TCTACAGCTACCATCAGCGGCCTTAAACCTGGAGTTGATTATACCATCACTGTGTATGCTG
TCACTGGCCGTGGAGACAGCCCCGCAAGCAGCAAGCCAATTTCCATTAATTACCGAACAG
AAATTGACAAACCATCCCAGATGCAAGTGACCGATGTTCAGGACAACAGCATTAGTGTCA
AGTGGCTGCCTTCAAGTTCCCCTGTTACTGGTTACAGAGTAACCACCACTCCCAAAAATGG
ACCAGGACCAACAAAAACTAAAACTGCAGGTCCAGATCAAACAGAAATGACTATTGAAG
GCTTGCAGCCCACAGTGGAGTATGTGGTTAGTGTCTATGCTCAGAATCCAAGCGGAGAGA
GTCAGCCTCTGGTTCAGACTGCAGTAACCACTATTCCTGCACCAACTGACCTGAAGTTCAC
TCAGGTCACACCCACAAGCCTGAGCCGCCAGTGGACACCACCCAATGTTCACTCACTGGAT
ATCGAGTGCGGGTGACCCCCAAGGAGAAGACCCGGACCCATGAAAGAAATCAACCTTGCT
CCTGACAGCTCATCCGNGGGTGTATCAGGACTTATGGGGGACTGCCCCGGCNGGCCGNTC
GAAANCGAATTNTGAAATTTCCTTCNCACTGGGNGGCGNTTCGAGCTTNCTTNTANANGGC
CCAATTCNCCTNTAGNGGGTCGTN

61_16499.edit

AGCGTGGTCGCGGCCGAGGTCNAGGA

62_16483.edit

TCGAGCGGCCGCCCGGGCAGGTCCACCACACCCAATTCCTTGCTGGTATCATGGCAGCCGC
CACGTGCCAGGATTACCGGCTACATCATCAAGTATGAGAAGCCTGGGTCTCCTCCCAGAGA
AGTGGTCCCTCGGCCCCGCCCTGGTGTCACAGAGGCTACTATTACTGGCCTGGAACCGGGA
ACCGAATATACAATTTATGTCATTGCCCTGAAGAATAATCAGAAGAGCGAGCCCCTGATTG
GAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGG
GTATGACACTGGAAATGGTATTCAGCTTCCTGGCACTTCTGGTCAGCAACCCAGTGTTGGG
CAACAAATGATCTTTGAGGAACATGGTTTTAGGCGGACCACACCGCCCACAACGGGCACC
CCCATAAGGNATAGGCCAAGACCATACCCCGCCGAATGTAGGACAAGAAGCTCTNTCTCA
ACAACCATCTCATGGGCCCCATTCCAGGACACTTCTGAGTACATCATTTCATGTCATCCTG
GTGGGCACTTGATGAANAACCCTTACAGTTCAGGGTTCCTGGAACTTCTACCAGNGCCACT
TCTGACAGGANCTTGGGCGNGACCACCCCT

*FIG. 15OO*

63_16500.edit

AGCGTGGTCGCGGCCGAGGTCCATTTTCTCCCTGACGGTCCCACTTCTCTCCAATCTTGTAG
TTCACACCATTGTCATGGCACCATCTAGATGAATCACATCTGAAATGACCACTTCCAAAGC
CTAAGCACTGGCACAACAGTTTAAAGCCTGATTCAGACATTCGTTCCCACTCATCTCCAAC
GGCATAATGGGAAACTGTGTAGGGGTCAAAGCACGAGTCATCCGTAGGTTGGTTCAAGCC
TTCGTTGACAGAGTTGCCCACGGTAACAACCTCTTCCCGAACCTTATGCCTCTGCTGGTCTT
TCAGTGCCTCCACTATGATGTTGTAGGTGGCACCTCTGGTGAGGACCTGCCCGGGCGGCCC
GCTCGA

64_16493.edit

AGCGTGGTCGCGGCCGAGGTGTGCCCCAGACCAGGAATTCGGCTTCGACGTTGGCCCTGTC
TGCTTCCTGTAAACTCCCTCCATCCCAACCTGGCTCCCTCCCACCCAACCAACTTTCCCCCC
AACCCGGAAACAGACAAGCAACCCAAACTGAACCCCCTCAAAAGCCAAAAAAATGGGAG
ACAATTTCACATGGACTTTGGAAAATATTTTTTTCCTTTGCATTCATCTCTCAAACTTAGTT
TTTATCTTTGACCAACCGAACATGACCAAAAACCAAAAGTGACCTGCCCGGGCGGCCGCTC
GA

64_16500.edit

TCGAGCGGCCGCCCGGGCAGGTCCTCACCAGAGGTGCCACCTACAACATCATAGTGGAGG
CACTGAAAGACCAGCAGAGGCATAAGGTTCGGGAAGAGGTTGTTACCGTGGGCAACTCTG
TCAACGAAGGCTTGAACCAACCTACGGATGACTCGTGCTTTGACCCCTACACAGTTTCCCA
TTATGCCGTTGGAGATGAGTGGGAACGAATGTCTGAATCAGGCTTTAAACTGTTGTGCCAG
TGCTTAGGCTTTGGAAGTGGTCATTTCAGATGTGATTCATCTAGATGGTGCCATGACAATG
GTGTGAACTACAAGATTGGAGAGAAGTGGGACCGTCAGGGAGAAAATGGACCTCGGCCG
CGACCACGCT

*FIG. 15PP*

16501.edit

TCGAGCGGCCGCCCGGGCAGGTACCGGGGTGGTCAGCGAGGAGCCATTCACACTGAACTT
CACCATCAACAACCTGCGGTATGAGGAGAACATGCAGCACCCTGGCTCCAGGAAGTTCAA
CACCACGGAGAGGGTCCTTCAGGGCCTGCTCAGGTCCCTGTTCAAGAGCACCAGTGTTGGC
CCTCTGTACTCTGGCTGCAGACTGACTTTGCTCAGACCTGAGAAACATGGGGCAGCCACTG
GAGTGGACGCCATCTGCACCCTCCGCCTTGATCCCACTGGTNCTGGACTGGACANANAGCG
GCTATACTTGGGAGCTGANCCNAACCTTTGGCGGNGACNCCNCTT

16501.2.edit

GAGGACTGGCTCAGCTCCCAGTATAGCCGCTCTCTGTCCAGTCCAGGACCAGTGGGATCAA
GGCGGAGGGTGCAGATGGCGTCCACTCCAGTGGCTGCCCCATGTTTCTCAAGTCTGAGCAA
AGNCAGTCTGCAGCCAGAGTACAGAGGGCCAACACTGGTGCTCTTGAACAGGGACCTGAG
CAGGCCCTGAAGGACCCTCTCCGTGGTGTTGAACTTCCTGGAGCCAGGGTGCTGCATGTTC
TCCTCATACCGCAGGTTGTTGATGGTGAAGTTCAGTGTGAATGGCTCCTCGCTGACCACCC

16502.1.edit

AGCGTGGTCGCGGCCGAGGTCCACCACACCCAATTCCTTGCTGGTATCATGGCAGCCGCCA
CGTGCCAGGATTACCGGCTACATCATCAAGTATGAGAAGCCTGGGTCTCCTCCCAGAGAA
GTGGTCCCTCGGCCCCGCCCTGGTGTCACAGAGGCTACTATTACTGGCCTGGAACCGGGAA
CCGAATATACAATTTATGTCATTGCCCTGAAGAATAATCAGAAGAGCGAGCCCCTGATTGG
AAGGAAAAAGACAGACGAGCTTCCCCAACTGGTAACCCTTCCACACCCCAATCTTCATGG
ACCANANANCTTGGATNGTCCTTTCACNGGTTNAAAAAACCCTTTTCGCCCCCCCACCTTG
GGGATTAACCTTGGGAAANGGGGATTTNACCNTTCC

16502.2.edit

TCGAGCGGCCGCCCGGGCAGGTCCTGTCAGAGTGGCACTGGTAGAAGTTCCAGGAACCCT
GAACTGTAAGGGTTCTTCATCAGTGCCAACAGGATGACATGAAATGATGTACTCAGAAGT
GTCCTGGAATGGGGCCCATGAGATGGTTGTCTGAGAGAGAGCTTCTTGTCCTACATTCGGC
GGGTATGGTCTTGGCCTATGCCTTATGGGGGTGGCCGTTGTGGGCGGTGTGGTCCGCCTAA
AACCATGTTCCTCAAAGATCATTTGTTGCCCAACACTGGGTTGCTGACCAGAAGTGCCAGG
AAGCTGAATACCATTTCCAGTGTCATACCCAGGGNGGGTGACCAAAGGGGGTCNTTTNGA
CCTGGNGAAAGGAACCATCCAAAANCTCTGNCCCATG

*FIG. 15QQ*

16503.1.edit

AGCGTGGNCGCGGCCGAGGTCTGAGGATGTAAACTCTTCCCAGGGGAAGGCTGAAGTGCT
GACCATGGTGCTACTGGGTCCTTCTGAGTCAGATATGTGACTGATGNGAACTGAAGTAGGT
ACTGTAGATGGTGAAGTCTGGGTGTCCCTAAATGCTGCATCTCCAGAGCCTTCCATCATTA
CCGTTTCTTCTTTTGCTATGGGATGAGACACTGTTGAGTATTCTCTAAAGTCACCACTGAAA
TCTTCCTCCAAAGGAAAACCTGTGGAAAAGCCCCTTATTTCTGCCCCATAATTTGGTTCTCC
TAATCNCTCTGAAATCACTATTTCCCTGGAANGTTTGGGAAAAANNGGGCNACCTGNCAN
TGGAAANTGGATANAAAGATCCCACCATTTTACCCAACNAGCAGAAAGTGGGAANGGTAC
CGAAAAGCTCCAAGTAANAAAAAGGAGGGAAGTAAAGGTCAAGTGGGCACCAGTTTCAA
ACAAAACTTTCCCCAAACTATANAACCCA

16503.2.edit

AAGCGGCCGCCCGGGCAGGNNCAGNAGTGCCTTCGGGACTGGGNTCACCCCCAGGTCTGC
GGCAGTTGTCACAGCGCCAGCCCCGCTGGCCTCCAAAGCATGTGCAGGAGCAAATGGCAC
CGAGATATTCCTTCTGCCACTGTTCTCCTACGTGGTATGTCTTCCCATCATCGTAACACGTT
GCCTCATGAGGGTCACACTTGAATTCTCCTTTTCCGTTCCCAAGACATGTGCAGCTCATTTG
GCTGGCTCTATAGTTTGGGGAAAGTTTGTTGAAACTGTGCCACTGACCTTTACTTCCTCCTT
CTCTACTGGAGCTTTCCGTACCTTCCACTTCTGCTGNTGGNAAAAAGGGNGGAACNTCTTA
TCAATTTCATTGGACAGTANCCCNCTTTCTNCCCAAAACATNCAAGGGAAAATATTGATTN
CNAGAGCGGATTAAGGAACAACCCNAATTATGGGGGCCAGAAATAAAGGGGGCTTTTCCA
CAGGTNTTTTCCT

16504.1.edit

TCGAGCGGCCGCCCGGGCAGGTCTGCAGGCTATTGTAAGTGTTCTGAGCACATATGAGAT
AACCTGGGCCAAGCTATGATGTTCGATACGTTAGGTGTATTAAATGCACTTTTGACTGCCA
TCTCAGTGGATGACAGCCTTCTCACTGACAGCAGAGATCTTCCTCACTGTGCCAGTGGGCA
GGAGAAAGAGCATGCTGCGACTGGACCTCGGCCGCGACCACGCT

16504.2.edit

AGCGTGGTCGCGGCCGAGGTCCAGTCGCAGCATGCTCTTTCTCCTGCCCACTGGCACAGTG
AGGAAGATCTCTGCTGTCAGTGAGAAGGCTGTCATCCACTGAGATGGCAGTCAAAAGTGC
ATTTAATACACCTAACGTATCGAACATCATAGCTTGGCCCAGGTTATCTCATATGTGCTCA
GAACACTTACAATAGCCTGCAGACCTGCCCGGGCGGCCGCTCGA

*FIG. 15RR*

16505.1.edit

CGAGCGGCCGCCCGGGCAGGTCCAGACTCCAATCCAGAGAACCACCAAGCCAGATGTCAG
AAGCTACACCATCACAGGTTTACAACCAGGCACTGACTACAAGATCTACCTGTACACCTTG
AATGACAATGCTCGGAGCTCCCCTGTGGTCATCGACGCCTCCACTGCCATTGATGCACCAT
CCAACCTGCGTTTCCTGGCCACCACACCCAATTCCTTGCTGGTATCATGGCAGCCGCCACG
TGCCAGGATTACCGGCTACATCATCAAGTATGAGAAGCCTGGGTCTCCTCCCAGAGAAGT
GGTCCCTCGGCCCCGCCCTGGTGNCACAGAAGCTACTATTACTGGCCTGGAACCGGGAACC
GAATATACAATTTATGTCATTGCCCTGAAGAATAATCANAAGAGCGAGCCCCTGATTGGA
AGG

16505.2.edit

AGCGTGGTCGCGGCCGAGGTCCTGTCAGAGTGGCACTGGTAGAAGTTCCAGGAACCCTGA
ACTGTAAGGGTTCTTCATCAGTGCCAACAGGATGACATGAAATGATGTACTCAGAAGTGTC
CTGGAATGGGGCCCATGAGATGGTTGTCTGAGAGAGAGCTTCTTGTCCTGTCTTTTTCCTTC
CAATCAGGGGCTCGCTCTTCTGATTATTCTTCAGGGCAATGACATAAATTGTATATTCGGTT
CCCGGTTCCAGGCCAGTAATAGTAGCCTCTGTGACACCAGGGCGGGGCCGAGGGACCACT
TCTCTGGGAGGAGACCCAGGCTTCTCATACTTGATGATGTANCCGGTAATCCTGGCACCGT
GGCGGCTGCCATGATACCAGCAAGGAATTGGGTGTGGTGGCCAAGAAACGCAGGTTGGAT
GGTGCATCAATGGCAGTGGAGGCGTCGATNACCACAGGGGAGCTCCGANCATTGTCATTC
AAGGTGGACAGGTAGAATCTTGTAATCAGGTGCCTGGTTTGTAAACCTG

16506.1.edit

TCGAGCGGCCGCCCGGGCAGGTTTCGTGACCGTGACCTCGAGGTGGACACCACCCTCAAG
AGCCTGAGCCAGCAGATCGAGAACATCCGGAGCCCAGAGGGCAGCCGCAAGAACCCCGC
CCGCACCTGCCGTGACCTCAAGATGTGCCACTCTGACTGGAAGAGTGGAGAGTACTGGAT
TGACCCCAACCAAGGCTGCAACCTGGATGCCATCAAAGTCTTCTGCAACATGGAGACTGGT
GAGACCTGCGTGTACCCCACTCAGCCCAGTGTGGCCCAGAAGAACTGGTACATCAGCAAG
AACCCCAAGGACAAGAAGCATGTCTGGTTCGGCGAAAGCATGACCGATGGATTCCAGTTC
GAGTATGGCGGCCAGGGCTCCGACCCTGCCGATGTGGACCTCGGCCGCGACCACGCTAAG
CCCGAATTCCAGCACACTGGCGGCCGTTACTAGTGGGATCCGAGCTTCGGTACCAAGCTTG
GCGTAATCATGGGNCATAGCTGTTTCCTGNGTGAAAATGGTATTCCGCTTCACAATTTCCC
AC

16506.2.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACGCAGGTCTCACCAGT
CTCCATGTTGCAGAAGACTTTGATGGCATCCAGGTTGCAGCCTTGGTTGGGGTCAATCCAG
TACTCTCCACTCTTCCAGTCAGAGTGGCACATCTTGAGGTCACGGCAGGTGCGGGCGGGGT
TCTTGCGGCTGCCCTCTGGGCTCCGGATGTTCTCGATCTGCTGGCTCAAGCTCTTGAAGGGT
GGTGTCCACCTCGAGGTCACGGTCACGAAACCTGCCCGGGCGGCCGCTCGA

*FIG. 15SS*

16507.1.edit

AGCGTGGTCGCGGCCGAGGTCAAGAACCCCGCCCGCACCTGCCGTGACCTCAAGATGTGC
CACTCTGACTGGAAGAGTGGAGAGTACTGGATTGACCCCAACCAAGGCTGCAACCTGGAT
GCCATCAAAGTCTTCTGCAACATGGAGACTGGTGAGACCTGCGTGTACCCCACTCAGCCCA
GTGTGGCCCAGAAGAACTGGTACATCAGCAAGAACCCCAAGGACAAGAGGCATGTCTGGT
TCGGCGAGAGCATGACCGATGGATTCCAGTTCGAGTATGGCGGCCAGGGCTCCGACCCTG
CCGATGTGGACCTGCCCGNGCCGGNCCGCTCGAAAAGCCCNAATTTCCAGNCACACTTGG
CCGGCCGTTACTACTG 16507.2.edit TCGAGCGGCCGCCCGGGCAGGTCCACATCGGCAGGGTCGGAGCCCTGGCCGCCATACTCG
AACTGGAATCCATCGGTCATGCTCTCGCCGAACCAGACATGCCTCTTGTCCTTGGGGTTCT
TGCTGATGTACCAGTTCTTCTGGGCCACACTGGGCTGAGTGGGGTACACGCAGGTCTCACC
AGTCTCCATGTTGCAGAAGACTTTGATGGCATCCAGGTTGCAGCCTTGGTTGGGGTCAATC
CAGTACTCTCCACTCTTCCAGTCAGAGTGGCACATCTTGAGGTCACGGCAGGTGCGGGCGG
GGTTCTTGACCTCGGCCGCGACCACGCT 16508.1.edit CGAGCGGCCGCCCGGGCAGGTCCCCCCCCTTTTTTTTTTTTTTTTTTTTTTTTTTTTTTTTTTT
TTTTTTTTTTTTTTTTTTTTTTTTTTTTTT 16508.2.edit AGCGTGGTCGCGGCCGAGGTCTGGCATTCCTTCGACTTCTCTCCAGCCGAGCTTCCCAGAA
CATCACATATCACTGCAAAAATAGCATTGCATACATGGATCAGGCCAGTGGAAATGTAAA
GAAGGCCCTGAAGCTGATGGGGTCAAATGAAGGTGAATTCAAGGCTGAAGGAAATAGCA
AATTCACCTACACAGTTCTGGAGGATGGTTGCACGAAACACACTGGGGAATGGAGCAAAA
CAGTCTTTGAATATCGAACACGCAAGGCTGTGAGACTACCTATTGTAGATATTGCACCCTA
TGACATTGGTGGTCCTGATCAAGAATTTGGTGTGGACGTTGGCCCTGTTTGCTTTTTATAAA
CCAAACTCTATCTGAAATCCCAACAAAAAAAATTTAACTCCATATGTGNTCCTCTTGTTCT
AATCTTGGCAACCAGTGCAAGTGACCGACAAAATTCCAGTTATTTATTTCCAAAATGTTTG
GAAACAGTATAATTTGACAAAGAAAAAAGGATACTTCTCTTTTTTTGGCTGGTCCACCAAA
TACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT

*FIG. 15TT*

16509.1.edit

AGCGTGGTCGCGGCCGAGGTCTGGGATGCTCCTGCTGTCACAGTGAGATATTACAGGATC
ACTTACGGAGAAACAGGAGGAAATAGCCCTGTCCAGGAGTTCACTGTGCCTGGGAGCAAG
TCTACAGCTACCATCAGCGGCCTTAAACCTGGAGTTGATTATACCATCACTGTGTATGCTG
TCACTGGCCGTGGAGACAGCCCCGCAAGCAGCAAGCCAATTTCCATTAATTACCGAACAG
AAATTGACAAACCATCCCAGATGCAAGTGACCGATGTTCAGGACAACAGCATTAGTGTCA
AGTGGCTGCCTTCAAGTTCCCCTGTTACTGGTTACAGAAGTAACCACCACTCCCAAAAATG
GACCAGGACCAACAAAAACTAAAACTGCAGGTCCAGATCAAACAGAAAATGGACTATTG
AAGGCTTGCAGCCCACAGTGGAAGTATGTGGNTAGGNGTCTATGCTCAGAATCCCAAGCC
GGAGAAAGTCAGCCTTCTGGTTTAGACTGCAGTAACCAACATTGATCGCCCTAAAGGACT
GGNCATTCACTTGGATGGTGGATGTCCAATTC

16509.2.edit

TCGAGCGGCCGCCCGGGCAGGTCCTTGCAGCTCTGCAGNGTCTTCTTCACCATCAGGTGCA
GGGAATAGCTCATGGATTCCATCCTCAGGGCTCGAGTAGGTCACCCTGTACCTGGAAACTT
GCCCCTGTGGGCTTTCCCAAGCAATTTTGATGGAATCGACATCCACATCAGNGAATGCCAG
TCCTTTAGGGCGATCAATGTTGGTTACTGCAGTCTGAACCAGAGGCTGACTCTCTCCGCTT
GGATTCTGAGCATAGACACTAACCACATACTCCACTGTGGGCTGCAAGCCTTCAATAGTCA
TTTCTGTTTGATCTGGACCTGCAGTTTTAAGTTTTTGGTGGTCCTGNCCCATTTTTGGGAAG
TGGGGGGTTACTCTGTAACCAGTAACAGGGGAACTTGAAGGCAGCCACTTGACACTAATG
CTGTTGTCCTGAACATCGGTCACTTGCATCTGGGGATGGTTTTGACAATTTCTGGTTCGGCA
AATTAATGGAAATTGGCTTGCTGCTTGGCGGGGCTGNCTCCACGGGCCAGTGACAGCATA
C

16510.1.edit

TCGAGCGGCCGCCCGGGCAGGTCCTTGCAGCTCTGCAGTGTCTTCTTCACCATCAGGTGCA
GGGAATAGCTCATGGATTCCATCCTCAGGGCTCGAGTAGGTCACCCTGTACCTGGAAACTT
GCCCCTGTGGGCTTTCCCAAGCAATTTTGATGGAATCGACATCCACATCAGTGAATGCCAG
TCCTTTAGGGCGATCAATGTTGGTTACTGCAGTCTGAACCAGAGGCTGACTCTCTCCGCTT
GGATTCTGAGCATAGACACTAACCACATACTCCACTGTGGGCTGCAAGCCTTCAATAGTCA
TTTCTGTTTGATCTGGACCTGCAGTTTTAAGTTTTTGTTGGNCCTGNNCCATTTTTGGGGAA
GGGGTGGTTACTCTTGTAACCAGTAACAGGGGAACTTGAAGCAGCCACTTGACACTAATG
CTGGTGGCCTGAACATCGGTCACTTGCATCTGGGATGGTTTGGTCAATTTCTGTTCGGTAAT
TAATGGGAAATTGGCTTACTGGCTTGCGGGGGCTGTCTCCACGGNCAGTGACAAGCATAC
ACAGGNGATGGGTATAATCAACTCCAGGTTTAAGGCCNCTGATGGTA

16510.2.edit

AGCGTGGTCGCGGCCGAGGTCTGGGATGCTCCTGCTGTCACAGTGAGATATTACAGGATC
ACTTACGGAGAAACAGGAGGAAATAGCCCTGTCCAGGAGTTCACTGTGCCTGGGAGCAAG
TCTACAGCTACCATCAGCGGCCTTAAACCTGGAGTTGATTATACCATCACTGTGTATGCTG
TCACTGGCCGTGGAGACAGCCCCGCAAGCAGTAAGCCAATTTCCATTAATTACCGAACAG
AAATTGACAAACCATCCCAGATGCAAGTGACCGATGTTCAGGACAACAGCATTAGTGTCA
AGTGGCTGCCTTCAAGTTCCCCTGTTACTGGTTACAGAGTAACCACCACTCCCAAAAATGG
GACCAGGACCAACAAAAAACTAAAACTGCANGGTCCAGATCAAACAGAAATGACTATTG
AAGGCTTGCAGCCCACAGTGGAGTATGTGGGTTAGTGTCTATGCTCAGAATNCCAAGCGG
AGAGAGTCAGCCTCTGGTTCAGACT

*FIG. 15UU*

16511.1.edit

TCGAGCGGCCGCCCGGGCAGGTCAGCGCTCTCAGGACGTCACCACCATGGCCTGGGCTCT
GCTCCTCCTCACCCTCCTCACTCAGGGCACAGGGTCCTGGGCCCAGTCTGCCCTGACTCAG
CCTCCCTCCGCGTCCGGGTCTCCTGGACAGTCAGTCACCATCTCCTGCACTGGAACCAGCA
GTGACGTTGGTGCTTATGAATTTGTCTCCTGGTACCAACAACACCCAGGCAAGGCCCCCAA
ACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATT
ATTACTGGAAGCTCATATGCAGGCAACAACAATTGGGTGTTCGGCGGAAGGGACCAAGCT
GACCGTNCTAAGGTCAAGCCCAAGGCTTGCCCCCCTCGGTCACTCTGTTCCCACCCTCCTCT
GAAGAAGCTTTCAAGCCAACAANGNCACACTGGGTGTGTCTCATAAGTGGACTTTCTACCC

16511.2.edit

AGCGTGGTCGCGGCCGAGGTCTGTAGCTTCTGTGGGACTTCCACTGCTCAGGCGTCAGGCT
CAGGTAGCTGCTGGCCGCGTACTTGTTGTTGCTTTGNTTGGAGGGTGTGGTGGTCTCCACT
CCCGCCTTGACGGGGCTGCTATCTGCCTTCCAGGCCACTGTCACGGCTCCCGGGTAGAAGT
CACTTATGAGACACACCAGTGTGGCCTTGTTGGCTTGAAGCTCCTCAGAGGAGGGTGGGA
ACAGAGTGACCGAGGGGGCAGCCTTGGGCTGACCTAGGACGGTCAGCTTGGTCCCTCCGC
CGAACACCCAATTGTTGTTGCCTGCATATGAGCTGCAGTAATAATCAGCCTCATCCTCAGC
CTGGAGCCCAGAGACNGTCAAGGGAGGCCCGTGTTTGCCAAGACTTGGAAGCCAGANAAG
CGATCAGGGACCCCTGAGGGCCGCTTTACNGACCTCAAAAAATCATGAATTTGGGGGGCC
TTTGCCTGGGNGTTGGTTGGTNACCAGNAAAACAAAATTTCATAAAGCACCAACGTCACT
GCTGGTTTCCAGTGCANGAANATGGTGAACTGAANTGTCC

16512.1.edit

AGCGTGGTCGCGGCCGAGGTCCAGCATCAGGAGCCCCGCCTTGCCGGCTCTGGTCATCGCC
TTTCTTTTTGTGGCCTGAAACGATGTCATCAATTCGCAGTAGCAGAACTGCCGTCTCCACTG
CTGTCTTATAAGTCTGCAGCTTCACAGCCAATGGCTCCCATATGCCCAGTTCCTTCATGTCC
ACCAAAGTACCCGTCTCACCATTTACACCCCAGGTCTCACAGTTCTCCTGGGTGTGCTTGG
CCCGAAGGGAGGTAAGTANACGGATGGTGCTGGTCCCACAGTTCTGGATCAGGGTACGAG
GAATGACCTCTAGGGCCTGGGCNACAAGCCCTGTATGGACCTGCCCGGGCGGGCCCGCTC
GA

16512.2.edit

TCGAGCGGCCGCCCGGGCAGGTCCATACAGGGCTGTTGCCCAGGCCCTAGAGGNCATTCC
TTGTACCCTGATCCAGAACTGTGGGACCAGCACCATCCGTCTACTTACCTCCCTTCGGGCC
AAGCACACCCAGGAGAACTGTGAGACCTGGGGTGTAAATGGNGAGACGGGTACTTTGGTG
GACATGAAGGAACTGGGCATATGGGAGCCATTGGCTGNGAAGCTGCANACTTATAAGACA
GCAGTGGAGACGGCAGTTCTGCTACTGCGAATTGATGACATCGTTTCAGGCCACAAAAAG
AAAGGCGATGACCANAGCCGGCAAGGCGGGGCTTCCTGATGCTGGACCTCGGCCGCCGAC
CACGCTT

*FIG. 15VV*

16514.1.edit

AGCGTGGTCGCGGCCGAGGTCCACTAGAGGTCTGTGTGCCATTGCCCAGGCAGAGTCTCTG
CGTTACAAACTCCTAGGAGGGCTTGCTGTGCGGAGGGCCTGCTATGGTGTGCTGCGGTTCA
TCATGGAGAGTGGGGCCAAAGGCTGCGAGGTTGTGGTGTCTGGGAAACTCCGAGGACAGA
GGGCTAAATCCATGAAGTTTGTGGATGGCCTGATGATCCACAGCGGAGACCCTGTTAACTA
CTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTG
ACCACGTGAACCATTTGTGNGAACCCCAAGATGAANATACTTGCCCACCACCCCCCATTC 16514.2.edit TCGAGCGGCCGCCCGGGCAGGTCTGCCAAGGAGACCCTGTTATGCTGTGGGGACTGGCTG
GGGCATGGCAGGCGGCTCTGGCTTCCCACCCTTCTGTTCTGAGATGGGGGTGGTGGGCAGT
ATCTCATCTTTGGGTTCCACAATGCTCACGTGGTCAGGCAGGGGCTTCTTAGGGCCAATCT
TACCAGTTGGGTCCCAGGGCAGCATGATCTTCACCTTGATGCCCAGCACACCCTGTCTGAG
CAACACGTGGCGCACAGCAGTGTCAACGTAGTAGTTAACAGGGTCTCCGCTGTGGATCAT
CAGGCCATCCACAAACTTCATGGATTTAGCCCTCTGTCCTCGGAGTTTCCCAAAACACCAC
AACCTCGCCAGCCTTTGGGCCCCACTTCTTCATGAATGAAACCGCAGCACACCATTANCAA
GGCCCTTCCGCACAGGNAAGCCCTTCCTAAGGAGTTTTGTAAACGCAAAAAACTCTTGCCT
GGGGCAAATGGGCACACAGACCTNTANTNGGACCTTGGNCCGCGAACCACCGCTT 16515.1.edit AGCGTGGTCGCGGCCGAGGTCTGGCCCTCCTGGCAAGGCTGGTGAAGATGGTCACCCTGG
AAAACCCGGACGACCTGGTGAGAGAGGAGTTGTTGGACCACAGGGTGCTCGTGGTTTCCC
TGGAACTCCTGGACTTCCTGGCTTCAAAGGCATTAGGGGACACAATGGTCTGGATGGATTG
AAGGGACAGCCCGGTGCTCCTGGTGTGAAGGGTGAACCTGGNGCCCCTGGTGAAAATGGA
ACTCCAGGTCAAACAGGAGCCCGNGGGCTTCCTGGNGAGAGAGGACGTGTTGGTGCCCCT
GGCCCANACCTGCCCGGGCGGCCGCTCNAAAAGCCGAAATCCAGNACACTGGCGGCCGNT
ACTANTGGAATCCGAACTTCGGTACCAAAGCTTGGCCGTAATCATGGCCATAGCTTGTTCC
CTGGGGNGGAAATTGGTATTCCGCTNCCAATTCCACACAACATACCGAACCCGGAAAGCA
TTAAAGTGTAAAAGCCCTGGGGGGGCCTAAATGANGTGAGCNTAACTCNCATTTAATTGG
CGTTGCGCTTCACTGCCCCGCTTTTCCAGTCCGGGNA 16515.2.edit TCGAGCGGCCGCCCGGGCAGGTCTGGGCCAGGGGCACCAACACGTCCTCTCTCACCAGGA
AGCCCACGGGCTCCTGTTTGACCTGGAGTTCCATTTTCACCAGGGGCACCAGGTTCACCCT
TCACACCAGGAGCACCGGGCTGTCCCTTCAATCCATCCAGACCATTGTGNCCCCTAATGCC
TTTGAAGCCAGGAAGTCCAGGAGTTCCAGGGAAACCACGAGCACCCTGTGGTCCAACAAC
TCCTCTCTCACCAGGTCGTCCGGGTTTTCCAGGGTGACCATCTTCACCAGCCTTGCCAGGA
GGGCCAGACCTCGGCCGCGACCACGCT

*FIG. 15WW*

16516.1.edit

ANCGTGGTCGCGGCCGAGGTCCTCACCAGAGGTGNCACCTACAACATCATAGTGGAGGCA
CTGAAAGACCANCAGAGGCATAAGGTTCGGGAAGAGG

16516.2.edit

TCGAGCGGCCGCCCGGGCAGGTCCATTTTCTCCCTGACGGTCCCACTTCTCTCCAATCTTGT
AGTTCACACCATTGTCATGGCACCATCTAGATGAATCACATCTGAAATGACCACTTCCAAA
GCCTAAGCACTGGCACAACAGTTTAAAGCCTGATTCAGACATTCGTTCCCACTCATCTCCA
ACGGCATAATGGGAAACTGTGTAGGGGTCAAAGCACGAGTCATCCGTAGGTTGGTTCAAG
CCTTCGTTGACAGAGTTGTCCACGGTAACAACCTCTTCCCGAACCTTATGCCTCTGCTGGTC
TTTCAGTGCCTCCACTATGATGTTGTAGGTGGCACCTCTGGTGAGGACCTCNGNCCNGAAC
AACGCTTAAGCCCGNATTCTGCAGAATAATCCCATCACACTTGGCGGCCGCTTCGANCATG
CATCNTAAAAGGGGCCCCAATTTCCCCCTTATAAGNGAANCCGTATTTNCCAATTTCACTG
GNCCCGCCGNTTTTACAAACGNCGGTGAACTGGGGAAAAACCCTGGCGGTTACCCAACTT
TAATCGCCNTTGGCAGCACAATCCCCCCTTTTCGNCCANCNTGGGCGTAAATAACCGAAAA

16517.1.edit

ANCGNGGTCGCGGCCGANGTNTTTTTTCTTNTTTTTTT

16518.1.edit

AGCGTGGTCGCGGCCGAGGTCTGAGGTTACATGCGTGGTGGTGGACGTGAGCCACGAAGA
CCCTGAGGTCAAGTTCAACTGGTACGTGGACGGCGTGGAGGTGCATAATGCCAAGACAAA
GCCGCGGGAGGAGCAGTACAACAGCACGTACCGGGNGGTCAGCGTCCTCACCGTCCTGCA
CCAGAATTGGTTGAATGGCAAGGAGTACAAGNGCAAGGTTTCCAACAAAGCCNTCCCAGC
CCCCNTCGAAAAAACCATTTCCAAAGCCAAAGGGCAGCCCCGAGAACCACAGGTGTACAC
CCTGCCCCCATCCCGGGAGGAAAAGANCAANAACCNGGTTCAGCCTTAACTTGCTTGGTC
NAANGCTTTTTATCCCAACGNACTTCCCCCNTGGAANTGGGAAAAACCAATGGGCCAANC
CGAAAAACAATTACAANAACCCC

16518.2.edit

TCGAGCGGCCGCCCGGGCAGGTGTCGGAGTCCAGCACGGGAGGCGTGGTCTTGTAGTTGT
TCTCCGGCTGCCCATTGCTCTCCCACTCCACGGCGATGTCGCTGGGATAGAAGCCTTTGAC
CAGGCAGGTCAGGCTGACCTGGTTCTTGGTCATCTCCTCCCGGGATGGGGGCAGGGTGAA
CACCTGGGGTTCTCGGGGCTTGCCCTTTGGTTTTGAANATGGTTTTCTCGATGGGGGCTGG
AAGGGCTTTGTTGNAAACCTTGCACTTGACTCCTTGCCATTCACCCAGNCCTGGNGCAGGA
CGGNGAGGACNCTNACCACACGGAACCGGGCTGGTGGACTGCTCC

*FIG. 15XX*

16519.1.edit

AGCGTGGTCGCGGACGANGTCCTGTCAGAGTGGNACTGGTAGAAGTTCCANGAACCCTGA
ACTGTAAGGGTTCTTCATCAGTGCCAACAGGATGACATGAAATGATGTACTCAGAAGNGN
CCTGGAATGGGGCCCATGANATGGTTGCC

16519.2.edit

TCGAGCGGCCGCCCGGGCAGGTCCACCACACCCAATTCCTTGCTGGTATCATGGCAGCCGC
CACGTGCCAGGATTACCGGCTACATCATCAAGTATGAGAAGCCTGGGTCTCCTCCCAGAGA
AGTGGTCCCTCGGCCCCGCCCTGGTGTCACAGAGGCTACTATTACTGGCCTGGAACCGGGA
ACCGAATATACAATTTATGTCATTGCCCTGAAGAATAATCAGAAGAGCGAGCCCCTGATTG
GAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGG
GTATGAACCTGGGAAAANGGNANTTAANCTTTCCTGGCA

16520.1.edit

AGCGTGGTCGCGGCCGAGGTCTGGGATGCTCCTGCTGTCACAGTGAGATATTACAGGATC
ACTTACGGAGAAACAGGAGGAAATAGCCCTGTCCAGGAGTTCACTGTGCCTGGGAGCAAG
TCTACAGCTACCATCAGCGGCCTTAAACCTGGAGTTGATTATACCATCACTGTGTATGCTG
TCACTGGCCGTGGAGACAGCCCCGCAAGCAGCAAGCCAATTTCCATTAATTACCGAACAG
AAATTGACAAACCATCCCAGATGCAAGTGACCGATGTTCAGGACAACAGCATTAGTGTCA
AGTGGCTGCCTTCAAGGTNCCCTGGTACTGGGTTACAGANTAACCACCACTCCCAAAAATG
GACCAGGAACCACAAAAACTTAAACTGCAGGGTCCAGATCAAAACAGAAATGACTATTGA
ANGCTTGCAGCCCACAGTGGGAGTATGNGGGTAGTGNCTATGCTTCAGAATCCAAGCGGA
AAAANGTCAAGCCTTNTGGGTTCAA

16520.2.edit

TCGAGCGGCCGCCCGGGCAGGTCCTTGCAGCTCTGCAGTGTCTTCTTCACCATCAGGTGCA
GGGAATAGCTCATGGATTCCATCCTCAGGGCTCGAGTAGGTCACCCTGTACCTGGAAACTT
GCCCCTGTGGGCTTTCCCAAGCAATTTTGATGGAATCGACATCCACATCAGTGAATGCCAG
TCCTTTAGGGCGATCAATGTTGGTTACTGCAGNCTGAACCAGAGGCTGACTCTCTCCGCTT
GGATTCTGAGCATAGACACTAACCACATACTCCACTGTGGGCTGCAANCCTTCAATAANNC
ATTTCTGTTTGATCTGGACC

16521.2.edit

TCGAGCGGCCGCCCGGGCAGGTCTGGTGGGGTCCTGGCACACGCACATGGGGGNGTTGNT
CTNATCCAGCTGCCCAGCCCCCATTGGCGAGTTTGAGAAGGTGTGCAGCAATGACAACAA
NACCTTCGACTCTTCCTGCCACTTCTTTGCCACAAAGTGCACCCTGGAGGGCACCAAGAAG
GGCCACAAGCTCCACCTGGACTACATCGGGCCTTGCAAATACATCCCCCCCTTGCCTGGACT
CTGAGCTGACCGAATTCCCCCTTGCGCATGCGGGACTGGCTCAAGAACCGTCCTGGCACCC
TTGTATGANAGGGATGAAGACACNACCC

*FIG. 15YY*

16522.1.edit

AGCGTGGTCGCGGCCGAGGTCTGTCCTACAGTCCTCAGGACTCTACTCCCTCAGCAGCGTG
GTGACCGTGCCCTCCAGCAACTTCGGCACCCAGACCTACACCTGCAACGTAGATCACAAGC
CCAGCAACACCAAGGTGGACAAGAGAGTTGAGCCCAAATCTTGTGACAAAACTCACACAT
GCCCACCGTGCCCAGCACCTGAACTCCTGGGGGGACCGTCAGTCTTCCTCTTCCCCCGCAT
CCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTC
TGGGGGGAAATTGGTATCCNGTTTACAATTCCCNCACAACATACGAGCCGGAAGCATAAA
AGNGTAAAAGCCTGGGGGNGGCCTANTGAAGTGAAGCTAAACTCACATTAATTNGCGTTG
CCGCTCACTGGCCCGCTTTTCCAGC

16522.2.edit

TCGAGCGGCCGCCCGGGCAGGTTTGGAAGGGGGATGCGGGGGAAGAGGAAGACTGACGG
TCCCCCCAGGAGTTCAGGTGCTGGGCACGGTGGGCATGTGTGAGTTTTGTCACAAGATTTG
GGCTCAACTCTCTTGTCCACCTTGGTGTTGCTGGGCTTGTGATCTACGTTGCAGGTGTAGGT
CTGGGNGCCGAAGTTGCTGGAGGGCACGGTCACCACGCTGCTGAGGGAGTAGAGTCCTGA
GGACTGTANGACAGACCTCGGCCGNGACCACGCTAAGCCGAATTCTGCAGATATCCATCA
CACTGGCGGCCGCTCCGAGCATGCATTTTAGAGG

16523.1.edit

AGCGTGGNCGCGGACGANGACAACAACCCC

16523.2.edit

TCGAGCGGCCGCCCGGGCAGGNCCACATCGGCAGGGTCGGAGCCCTGGCCGCCATACTCG
AACTGGAATCCATCGGTCATGCTCTTGCCGAACCAGACATGCCTCTTGTCCTTGGGGTTCTT
GCTGATGNACCAGTTCTTCTGGGCCACACTGGGCTGAGTGGGGTACACGCAGGTCTCACCA
GTCTCCATGTTGCAGAAGACTTTGATGGCATCCAGGTTGCAGCCTTGGTTGGGGTCAATCC
AGTACTCTCCACTCTTCCAGTCAGAGTGGCACATCTTGAGGTCACGGCAGGTGCGGGCGGG
GTTCTTGACCT

16524.1.edit

AGCGTGGTCGCGGCCGAGGTCCAGCCTGGAGATAANGGTGAAGGTGGTGCCCCCGGACTT
CCAGGTATAGCTGGACCTCGTGGTAGCCCTGGTGAGAGAGGTGAAACTGGCCCTCCAGGA
CCTGCTGGTTTCCCTGGTGCTCCTGGACAGAATGGTGAACCTGGNGGTAAAGGAGAAAGA
GGGGCTCCGGNTGANAAAGGTGAAGGAGGCCCTCCTGNATTGGCAGGGGCCCCANGACTT
AGAGGTGGAGCTGGCCCCCCTGGCCCCGAAGGAGGAAAGGGTGCTGCTGGTCCTCCTGGG
CCACCTGG

*FIG. 15ZZ*

16524.2.edit

TCGAGCGGCCGCCCGGGCAGGTCTGGGCCAGGAGGACCAATAGGACCAGTAGGACCCCTT
GGGCCATCTTTCCCTGGGACACCATCAGCACCTGGACCGCCTGGTTCACCCTTGTCACCCTT
TGGACCAGGACTTCCAAGACCTCCTCTTTCTCCAGGCATTCCTTGCAGACCAGGAGTACCA
NCAGCACCAGGTGGCCCAGGAGGACCAGCAGCACCCTTTCCTCCTTCGGGACCAGGGGGA
CCAGCTCCACCTCTAAGTCCTGGGGCCCCTGCCAATCCAGGAGGGCCTCCTTCACCTTTCTC
ACCCGGAGCCCCTCTTTCT

16526.1.edit

TCGAGCGGCCGCCCGGGCAGGTCCACCGGGATATTCGGGGGTCTGGCAGGAATGGGAGGC
ATCCAGAACGAGAAGGAGACCATGCAAAGCCTGAACGACCGCCTGGCCTCTTACCTGGAC
AGAGTGAGGAGCCTGGAGACCGACAACCGGAGGCTGGAGAGCAAAATCCGGGAGCACTT
GGAGAAGAAGGGACCCCAGGTCAGAGACTGGAGCCATTACTTCAAGATCATCGAGGACCT
GAGGGCTCANATCTTCGCAAATACTGCNGACAATGCCCG

16526.2.edit

ATGCGNGGTCGCGGCCGANGACCANCTCTGGCTCATACTTGACTCTAAAGNCNTCACCAG
NANTTACGGNCATTGCCAATCTGCAGAACGATGCGGGCATTGTCCGCANTATTTGCGAAG
ATCTGAGCCCTCAGGNCCTCGATGATCTTGAAGTAANGGCTCCAGTCTCTGACCTGGGGTC
CCTTCTTCTCCAAGTGCTCCCGGATTTTGCTCTCCAGCCTCCGGTTCTCGGTCTCCAAGNCT
TCTCACTCTGTCCAGGAAAAGAGGCCAGGCGGNCGATCAGGGCTTTTGCATGGACT

16527.1.edit

AGCGTGGTCGCGGCCGAGGTTGTACAAGCTTTTTTTTTTTTTTTTTTTTTTTTTTTTTTTTTT
TTTTTTTTTTTTTTTTTTTTTTTTTTTTTTTTTTTT

16527.2.edit

TCGAGCGGCCGCCCGGGCAGGTCTGCCAACACCAAGATTGGCCCCCGCCGCATCCACACA
GTTNGTGTGCGGGGAGGTAACAAGAAATACCGTGCCCTGAGGNTGGACGNGGGGAATTTC
TCCTGGGGCTCAGAGTGTTGTACTCGTAAAACAAGGATCATCGATGTTGTCTACAATGCAT
CTAATAACGAGCTGGTTCGTACCAAGACCCTGGTGAAGAATTGCATCGTGCTCATNGACA
GCACACCGTACCGACAGTGGGTACCGAAGTCCCACTATGCNCCT

*FIG. 15AAA*

16528.1.edit

TCGAGCGGCCGCCCGGGCAGGTCCACCACACCCAATTCCTTGCTGGTATCATGGCAGCCGC
CACGTGCCAGGATTACCGGCTACATCATCAAGTATGAGAAGCCTGGGTCTCCTCCCAGAGA
AGTGGTCCCTCGGCCCCGCCCTGGTGTCACAGAGGCTACTATTACTGGCCTGGAACCGGGA
ACCGAATATACAATTTATGTCATTGCCCTGAAG

16528.2.edit

AGCGTGNTCNCGGCCGAGGATGGGGAAGCTCGNCTGTCTTTTTCCTTCCAATCAGGGGCTN
NNTCTTCTGATTATTCTTCAGGGCAANGACATAAATTGTATATTCGGNTCCCGGTTCCAGN
CCAGTAATAGTAGCCTCTGTGACACCAGGGCGGGGCCGAGGGACCACTTCTCTGGGAGGA
GACCCAGGCTTCTCATACTTGATGATGAAGCCGGTAATCCTGGCACGTGGGCGGCTGCCAT
GATACCACCAANGAATTGGGTGTGGTGGACCTGCCCGGGCGGGCCGCTCGAAAANCCGAA
TTCNTGCAAGAATATCCATCACACTTGGGCGGGCCGNTCGAACCATGCATCNTAAAAGGG
CCCCAATTTCCCCCCTATTAGGNGAAGCCNCATTTAACAAATTCCACTTGG

16529.1.edit

TCGAGCGGCCGCCCGGGCAGGTCTCGCGGTCGCACTGGTGATGCTGGTCCTGTTGGTCCCC
CCGGCCCTCCTGGACCTCCTGGTCCCCCTGGTCCTCCCAGCGCTGGTTTCGACTTCAGCTTC
CTGCCCCAGCCACCTCAAGAGAAGGCTCACGATGGTGGCCGCTACTACCGGGCTGATGAT
GCCAATGTGGTTCGTGACCGTGACCTCGAGGTGGACACCACCCTCAAGAGCCTTGAGCCA
GCAGAATCGAAAACATTCGGAACCCAAGAAGGGCAAGCCCGCAAAGAAACCCCGCCCGC
ACCTGGCCGNGAACCTCCAAGAANGTGCCCACNTCTTGACTGGGAAAAAAAGGGAAAANT
ACTTGGAATTGGAC

16529.2.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACGCAGGTCTCACCAGT
CTCCATGTTGCAGAAGACTTTGATGGCATCCAGGTTGCAGCCTTGGTTGGGGTCAATCCAG
TACTCTCCACTCTTCCAGTCAGAAGTGGCACATCTTGAGGTCACGGCAGGGTGCGGGCGGG
GTTCTTGCGGGCTGCCCTTCTGGGCTCCCGGAATGTTCTNNGAACTTGCTGG

*FIG. 15BBB*

16530.1.edit

AGCGTGGTCGCGGCCGAGGTCCACTAGAGGTCTGTGTGCCATTGCCCAGGCAGAGTCTCTG
CGTTACAAACTCCTAGGAGGGCTTGCTGTGCGGAGGGCCTGCTATGGTGTGCTGCGGTTCA
TCATGGAGAGTGGGGCCAAAGGCTGCGAGGTTGTGGTGTCTGGGAAACTCCGAGGACAGA
GGGCTAAATCCATGAAGTTTGTGGATGGCCTGATGATCCACAGCGGAGACCCTGTTAACTA
CTACGTTGACACTTGCTTGTGCGCCACGTGTTGCTCANACANGGGTGGGCTGGGCATCAAG
GNG

16530.2.edit

TCGAGCGGCCGCCCGGGCAGGTCTGCCAAGGAGACCCTGTTATGCTGTGGGGACTGGCTG
GGGCATGGCAGGCGGCTCTGGCTTCCCACCCTTCTGTTCTGAGATGGGGGTGGTGGGCAGT
ATCTCATCTTTGGGTTCCACAATGCTCACGTGGTCAGGCAGGGGCTTCTTAGGGCCAATCT
TACCAGTTGGGTCCCAGGGCAGCATGATCTTCACCTTGATGCCCAGCACACCCTGTCTGAG
CAACACGTGGCGCACAGCAAGTGTCAACGTAAGTAAGTTAACAGGGTCTCCGCTGTGGAT
CATCAGGCCATCCACAAACTTCATGGATTTAACCCTCTGTCCTCGGAG

16531.1.edit

TCGAGCGGCCGCCCGGGCAGGTGTTTCAGAGGTTCCAAGGTCCACTGTGGAGGTCCCAGG
AGTGCTGGTGGTGGGCACAGAGGTCCGATGGGTGAAACCATTGACATAGAGACTGTTCCT
GTCCAGGGTGTAGGGGCCCAGCTCTTTGATGCCATTGGCCAGTTGGCTCAGCTCCCAGTAC
AGCCGCTCTCTGTTGAGTCCAGGGCTTTTGGGGTCAAGATGATGGATGCAGATGGCATCCA
CTCCAGTGGCTGCTCCATCCTTCTCGGACCTGAGAGAGGTCAGTCTGCAGCCAGAGTACAG
AGGGCCAACACTGGTGTTCTTTGAATA

16531.2.edit

AGCGTGGTCGCGGCCGAGGTCTGTACTGGGAGCTAAGCAAACTGACCAATGACATTGAAG
AGCTGGGCCCCTACACCCTGGACAGGAACAGTCTCTATGTCAATGGTTTCACCCATCAGAG
CTCTGTGNCCACCACCAGCACTCCTGGGACCTCCACAGTGGATTTCAGAACCTCAGGGACT
CCATCCTCCCTCTCCAGCCCCACAATTATGGCTGCTGGCCCTCTCCTGGTACCATTCACCCT
CAACTTCACCATCACCAACCTGCAGTATGGGGAGGACATGGGTCACCCTGNCTCCAGGAA
GTTCAACACCACA

16532.1.edit

TCGAGCGGCCGCCCGGACAGGTCTGGGCGGATAGCACCGGGCATATTTTGGAATGGATGA
GGTCTGGCACCCTGAGCAGTCCAGCGAGGACTTGGTCTTAGTTGAGCAATTTGGCTAGGAG
GATAGTATGCAGCACGGNTCTGAGNCTGTGGGATAGCTGCCATGAAGTAACCTGAAGGAG
GTGCTGGCTGGTANGGGTTGATTACAGGGTTGGGAACAGCTCGTACACTTGCCATTCTCTG
CATATACTGGTTAGTGAGGTGAGCCTGGCCCTCTTCTTTTG

*FIG. 15CCC*

01_16558.3.edit

AGCGTGGTCGCGGCCGAGGTGAGCCACAGGTGACCGGGGCTGAAGCTGGGGCTGCTGGNC
CTGCTGGTCCTG

02_16558.4.edit

CAGCNGCTCCNACGGGGCCTGNGGGACCAACAACACCGTTTTCACCCTTAGGCCCTTTGGC
TCCTCTTTCTCCTTTAGCACCAGGTTGACCAGCAGCNCCANCAGGACCAGCAAATCCATTG
GGGCCAGCAGGACCGACCTCACCACGTTCACCAGGGCTTCCCCGAGGACCAGCAGGACCA
GCAGGACCAGCAGCCCCAGCTTCGCCCCGGTCACCTGTGGCTCACCTCGGCCGCGACCACG
CT

03_16535.1.edit

TCGAGCGGTCGCCCGGGCAGGTCCACCGGGATAGCCGGGGGTCTGGCAGGAATGGGAGGC
ATCCAGAACGAGAAGGAGACCATGCAAAGCCTGAACGACCGCCTGGCCTCTTACCTGGAC
AGAGTGAGGAGCCTGGAGACCGANAACCGGAGGCTGGANAGCAAAATCCGGGAGCACTT
GGAGAAGAAGGGACCCCAGGTCAAGAGACTGGAGCCATTACTTCAAGATCATCGAGGGA
CCTGGAGG

04_16535.2.edit

AGCGNGGTCGCGGCCGAGGTCCAGCTCTGTCTCATACTTGACTCTAAAGTCATCAGCAGCA
AGACGGGCATTGTCAATCTGCAGAACGATGCGGGCATTGTCCGCAGTATTTGCGAAGATCT
GAGCCCTCAGGTCCTCGATGATCTTGAAGTAATGGCTCCAGTCTCTGACCTGGGGTCCCTT
CTTCTCCAAGTGCTCCCGGATTTTGCTCTCCAGCCTCCGGTTCTCGGTCTCCAGGCTCCTCA
CTCTGTCCAGGTAAGAAGGCCCAGGCGGTCGTTCAGGCTTTGCATGGTCTCCTTCTCGTTCT
GGATGCCTCCCATTCCTGCCAGACCC

05_16536.1.edit

TCGAGCGGCCGCCCGGGCAGGTCAGGAAGCACATTGGTCTTAGAGCCACTGCCTCCTGGA
TTCCACCTGTGCTGCGGACATCTCCAGGGAGTGCAGAAGGGAAGCAGGTCAAACTGCTCA
GATCAGTCAGACTGGCTGTTCTCAGTTCTCACCTGAGCAAGGTCAGTCTGCAGCCAGAGTA
CAGAGGGCCAACACTGGTGTTCTTGAACAAGGGCTTGAGCAGACCCTGCAGAACCCTCTTC
CGTGGTGTTGAACTTCCTGGAAACCAGGGTGTTGCATGTTTTTCCTCATAATGCAAGGTTG
GTGATGG

*FIG. 15DDD*

07_16537.1.edit

AGCGTGGTCGCGGCCGAGGTCCACATCGGCAGGGTCGGAGCCCTGGCCGCCATACTCGAA
CTGGAATCCATCGGTCATGCTCTCGCCGAACCAGACATGCCTCTTGTCCTTGGGGTTCTTGC
TGATGTACCAGTTCTTCTGGGCCACACTGGGCTGAGTGGGGTACACCGCAGGTCTCACCAG
TCTCCATGTTGCAGAAGACTTTGATGGCATCCAGGTTGCAGCCTTGGTTGGGGTCAATCCA
GTACTCTCCACTCTTCCAGTCAGAAGTGGGCACATCTTGAGGTCACCGGCAGGTGCCGGGC
CGGGGGTTCTTGCGGCTTGCCCTCTGGGCTCCGGATGTTCTCGATCTGCTTGGCTCAGGCTC
TTGAGGGTGGGTGTCCACCTCGAGGTCACGGTCACCGAAACCTGCCCGGGCGGCCCGCTC
GA

08_16537.2.edit

TCGAGCGGTCGCCCGGGCAGGTTTCGTGACCGTGACCTCGAGGTGGACACCACCCTCAAG
AGCCTGAGCCAGCAGATCGAGAACATCCGGAGCCCAGAGGGCAGCCGCAAGAACCCCGC
CCGCACCTGCCGTGACCTCAAGATGTGCCACTCTGACTGGAAGAGTGGAGAGTACTGGAT
TGACCCCAACCAAGGCTGCAACCTGGATGCCATCAAAGTCTTCTGCAACATGGAGACTGGT
GAGACCTGCGTGTACCCCACTCAGCCCAGTGTGGGCCCAGAAGAAACTGGTACATCAGCA
AGGAACCCCAAGGACAAGAGGCATTGTCTTGGTTCGGCGAGNAGCATGACCCGATGGATT
CCAGTTTCGAGTATTGGCGGCCAGGGCTTCCCGACCCTTGCCGATGTGGACCTCGGCCGCG
ACCACCGCT

*FIG. 15EEE*

COMPOSITIONS AND METHODS FOR DIAGNOSIS OF OVARIAN CANCER

TECHNICAL FIELD

The present invention relates generally to cancer diagnosis and monitoring. The invention is more specifically related to polypeptides comprising at least a portion of an ovarian carcinoma protein, and to polynucleotides encoding such polypeptides. Such polypeptides and polynucleotides may be used to generate compounds for the diagnosis and monitoring of cancer, such as ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

In order to improve cancer treatment and survival, it would be beneficial to identify ovarian carcinoma antigens that permit an earlier or more accurate diagnosis. In addition, further antigens are needed to facilitate the selection of a course of treatment and monitoring of patients. The present invention fulfills these needs and further provides other related advantages.

SUMMARY OF THE INVENTION

Briefly stated, this invention provides compositions and methods for the detection and monitoring of cancer, such as ovarian cancer. Polypeptides are disclosed that comprise at least an immunogenic portion of an ovarian carcinoma protein, or a variant thereof that differs in one or more substitutions, deletions, additions and/or insertions such that the ability of the variant to react with ovarian carcinoma-specific antisera is not substantially diminished. Within certain embodiments, the ovarian carcinoma protein comprises a sequence that is encoded by a polynucleotide sequence selected from the group consisting of SEQ ID NOs:1–310, and complements of such polynucleotides. Polynucleotides that encode all or a portion of an ovarian carcinoma protein are also provided. Such polypeptides, polynucleotides, and compounds that bind to the polypeptides or polynucleotides, may be used in the diagnosis and monitoring of cancer, such as ovarian cancer.

Within certain aspects, the present provides methods for determining the presence or absence of a cancer in a patient, comprising (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be ovarian cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes an ovarian carcinoma protein, wherein the ovarian carcinoma protein comprises an amino acid sequence that is encoded by a polynucleotide sequence selected from the group consisting of: (i) polynucleotides recited in any one of SEQ ID NOs:1–310; and (ii) complements of the foregoing polynucleotides; (b) detecting in the sample a level of a polynucleotide that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide that encodes a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes an ovarian carcinoma protein, wherein the ovarian carcinoma protein comprises an amino acid sequence that is encoded by a polynucleotide sequence selected from the group consisting of: (i) polynucleotides recited in any one of SEQ ID NOs:1–310; and (ii) complements of the foregoing polynucleotides; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 12h.

FIGS. 15A–EEE depict partial sequences of additional polynucleotides encoding representative secreted ovarian carcinoma antigens (SEQ ID NOs:82–310).

DETAILED DESCRIPTION OF THE INVENTION

As noted above, the present invention is generally directed to compounds and methods for the diagnosis and monitoring of cancer, such as ovarian cancer. The compounds described herein include polypeptides that comprise at least a portion (such as an immunogenic portion) of an ovarian carcinoma protein or a variant thereof. Certain ovarian carcinoma proteins have been identified using an immunoassay, and are referred to herein as ovarian carcinoma antigens. An "ovarian carcinoma antigen" is a protein that is expressed by ovarian tumor cells (preferably human cells) and that reacts detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, ovarian carcinoma antigens provided herein are generally secreted antigens. Certain nucleic acid sequences of the subject invention comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain ovarian carcinoma partial polynucleotide sequences are presented in FIGS. 4–9 as well as SEQ ID NOs:75–81. Proteins encoded by genes comprising such polynucleotide sequences (or complements thereof) are also considered ovarian carcinoma proteins.

Compounds provided herein also include binding agents such as antibodies (i.e., immune system proteins, or antigen-binding fragments thereof) that bind to a polypeptide as provided herein.

OVARIAN CARCINOMA POLYNUCLEOTIDES

Any polynucleotide that encodes an ovarian carcinoma antigen or a portion or other variant thereof as described herein is encompassed by the present invention. Preferred polynucleotides comprise at least 10 consecutive nucleotides, preferably at least 15 consecutive nucleotides, and more preferably at least 30 consecutive nucleotides, that encode a portion of an ovarian carcinoma protein. Within certain embodiments, a polynucleotide encodes an immunogenic portion of an ovarian carcinoma antigen. Polynucleotides complementary to any of the above sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions relative to a polynucleotide that encodes the native protein. For certain variants, modifications are made such that the immunogenicity of the encoded polypeptide is not substantially diminished, relative to a native ovarian carcinoma protein. For other variants, modifications may be made such that the ability of the polynucleotide to detect an ovarian carcinoma polynucleotide is not substantially diminished. The effect on the immunogenicity of the encoded polypeptide and on the ability of the polynucleotide to detect an ovarian carcinoma polynucleotide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native ovarian carcinoma antigen (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically. contemplated by the present invention.

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera of SCID mice implanted with late passage ovarian tumors. Ovarian carcinoma polynucleotides may also be identified using any of a variety of techniques designed to evaluate differential gene expression. Alternatively, polypeptides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (CDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$p) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. CDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS:1 to 71) and FIGS. 15A to 15 EEE (SEQ ID NOs:82 to 310). These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of CDNA molecules that encode immunogenic portions of secreted tumor antigens. The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

The sequences provided in FIGS. 1A–1S appear to be novel. Database searches revealed known substantially identical sequences for the sequences provided in FIGS. 15A–15 EEE.

Other nucleic acid sequences of cDNA molecules encoding portions of ovarian carcinoma proteins are provided in FIGS. 4–9 (SEQ ID NOs:75–81). These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from 10–$10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a coding sequence or a complementary sequence may also be designed as a probe or primer to detect gene expression. Probes may be labeled by a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2'O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. Other formulations include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

OVARIAN CARCINOMA POLYPEPTIDES

Within the context of the present invention, polypeptides may comprise at least a portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immune deficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera and antibodies may be prepared as described herein, and using well known techniques. An immunogenic portion of a native ovarian carcinoma protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using a detection reagent, such as $^{125}$I-labeled Protein A.

As noted above, a polypeptide may be a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with antigen-specific antisera may be enhanced or unchanged, relative to the native antigen, or may be diminished by less than 50%, and preferably less than 20%, relative to the native antigen. Such variants may generally be identified by modifying one of the above polypeptide sequences and evaluating the reactivity of the modified polypeptide with antigen-specific antibodies or antisera as described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian tumor antigen, or a variant of such an antigen. Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.*, 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

BINDING AGENTS

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules (each of which may be in solution or present on the surface of a cell or solid support) such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents are further capable of differentiating between patients with and without a cancer, such as ovarian cancer, using the representative assays provided herein. In other words, antibodies or other binding agents that bind to an ovarian carcinoma protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, ascites fluid, sera, urine and/or tumor biopsies) from patients with and without ovarian cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome with or without a peptide component, an RNA molecule or a polypeptide. In a preferred embodiment, a binding agent is an antibody or an antigen-binding fragment thereof. Such antibodies may be polyclonal or monoclonal. In addition, the antibodies may be single chain, chimeric, CDR-grafted or humanized.

Binding agents may be further linked to a reporter group, to facilitate diagnostic assays. Suitable reporter groups will be apparent to those of ordinary skill in the art, and include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. To generate antibodies, a polypeptide immunogen may be the full length ovarian carcinoma protein or an immunogenic portion thereof. If an immunogenic portion is employed, the resulting antibody should indicate the presence of ovarian cancer in substantially all (i.e., at least 80%, and preferably at least 90%) of the patients for which ovarian cancer would be indicated using an antibody raised against the full length antigen. The antibody should also indicate the absence of ovarian cancer in substantially all of those samples that would be negative when tested with an antibody raised against the full length antigen. The representative assays provided herein, such as the two-antibody sandwich assay, may generally be employed for evaluating the ability of an antibody to detect ovarian cancer.

In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

METHODS FOR DETECTING CANCER

In general, a cancer may be detected in a patient based on the presence of one or more ovarian carcinoma proteins and/or polynucleotides encoding such proteins in a biological sample obtained from the patient. In other words, ovarian carcinoma proteins may be used as markers to indicate the presence or absence of a cancer such as ovarian cancer. In addition, such proteins may be useful for the detection of other cancers. The binding agents provided herein generally permit detection of the level of ovarian carcinoma protein that binds to the agent in the biological sample. Polynucleotide primers and probes may be used to detect the level of mRNA encoding an ovarian carcinoma protein, which is also indicative of the presence or absence of a cancer.

There are a variety of assay formats known to those of ordinary skill in the art for using a binding agent to detect polypeptide markers in a sample. See, e.g, Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma antigens and portions thereof to which the binding agent binds, as described above.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g, Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of ovarian cancer is the average mean signal obtained when the immobilized antibody is incubated with samples from patients without ovarian cancer. In general, a sample generating a signal that is three standard deviations above the predetermined cut-off value is considered positive for ovarian cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for ovarian cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of ovarian cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the antigens or binding agents of the present invention. The above descriptions are intended to be exemplary only.

In another embodiment, the above polypeptides may be used as markers for the progression of cancer, such as ovarian cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

As noted above, a cancer may also, or alternatively, be detected based on the level of MRNA encoding an ovarian carcinoma protein in a biological sample. For example, at least two oligonucleotide primers may be employed in a polymerase chain reaction (PCR) based assay to amplify a portion of an ovarian carcinoma antigen cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence of an ovarian carcinoma polynucleotide. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a sample tissue and is reverse transcribed to produce cDNA molecules. PCR amplification using at least one specific primer generates a cDNA molecule, which may be separated and visualized using, for example, gel electrophoresis. Amplification may be performed on samples obtained from biological samples taken from a test patient and an individual who is not afflicted with ovarian cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

Another preferred assay is real-time PCR. This amplification technique permits the quantification of an ovarian carcinoma mRNA in a sample (see Gibson et al., *Genome Research* 6:995–1001, 1996; Heid et al., *Genome Research* 6:986–994, 1996). Real-time PCR is a technique that evaluates the level of PCR product accumulation during amplification. Briefly, MRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10–10^6$ copies of the gene of interest are generally sufficient. In addition, a standard curve is generated for the control sequence. This permits standardization of initial RNA content of a tissue sample to the amount of control for comparison purposes.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein or polynucleotide markers may be assayed within a given sample. It will be apparent that binding agents specific for different antigens provided herein may be combined within a single assay. Further, multiple primers or probes may be used concurrently. The selection of markers may be based on routine experiments to determine combinations that results in optimal sensitivity. In addition, or alternatively, assays for markers provided herein may be combined with assays for other known tumor antigens.

DIAGNOSTIC KITS

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian tumor antigen. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

SCREENS FOR IDENTIFYING SECRETED OVARIAN CARCINOMA ANTIGENS

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 μL of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.)

and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of *E. coli* and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, many antigens identified by such methods should be secreted. This permits the identification of antigens that are highly suitable for routine diagnostic tests performed on non-tumor samples, such as blood.

The following Examples are offered by way of illustration and not by way of limitation.

EXAMPLES

Example 1

Identification of Representative Ovarian Carcinoma Antigen cDNAs

This Example illustrates the identification of cDNA molecules encoding ovarian carcinoma antigens.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences are provided in FIGS. 1A–1S and SEQ ID NOs:1 to 71. These sequences appear to be novel. Three complete insert sequences are shown in FIGS. 2A–2C (SEQ ID NOs;72 to 74). Other clones having known sequences are presented in FIGS. 15A–15EEE (SEQ ID NOs:82 to 310).

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs using Microarray Technology

This Example illustrates the identification of ovarian carcinoma polynucleotides by screening a microarray of cDNAs for ovarian tumor-specific expression. Such screens were performed using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

cDNA was generated from ovarian tumor tissue and from normal ovarian tissue, and a subtracted cDNA library was prepared and arrayed on the chip. The chip was then probed with fluorescent probes generated from normal and tumor cDNA. The slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this methods are referred to herein as 3f, 6b, 8e, 8h, 12c and 12h. Sequences of these clones are shown in FIGS. 5 to 9 and SEQ ID NOs:75–81. Microarray analyses were performed as described above, and are presented in FIGS. 10 to 14.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NOs:82–310 are ovarian carcinoma antigen polynucleotides shown in FIGS. 15A–15EEE.

What is claimed is:

1. A method for determining the presence of ovarian cancer in a patient, comprising the steps of:

(a) contacting a biological sample obtained from said patient with an oligonucleotide or polynucleotide that hybridizes under moderately stringent conditions, wherein the moderately stringent conditions are defined as prewashing in a solution of 5×SSC, 0.5% SDS, 1.0 mM EDTA (pH 8.0), hybridizing at 50° C.–65° C., 5×SSC, overnight; followed by washing twice at 65° C. for 20 minutes with each of 2×, 0.5× and 0.2×SSC containing 0.1% SDS, to a polynucleotide sequence selected from the group consisting of:

(i) a polynucleotide sequence consisting of any one of SEQ ID NOs:76–78 and 80–81; and (ii) complements of the foregoing polynucleotides;

(b) detecting in the sample an amount of an expressed polynucleotide that hybridizes to the oligonucleotide or polynucleotide; and (c) comparing the amount of expressed polynucleotide that hybridizes to the oligonucleotide or polynucleotide to a predetermined cut-off value, and therefrom determining the presence of ovarian cancer in the patient.

2. The method according to claim 1, wherein the amount of expressed polynucleotide that hybridizes to the oligonucleotide or polynucleotide is determined using a polymerase chain reaction.

3. The method according to claim 1, wherein the amount of expressed polynucleotide that hybridizes to the oligonucleotide or polynucleotide is determined using a hybridization assay.

4. A method for monitoring the progression of ovarian cancer in a patient, comprising the steps of:

(a) contacting a biological sample obtained from said patient with an oligonucleotide or polynucleotide that hybridizes under moderately stringent conditions, wherein the moderately stringent conditions are defined as prewashing in a solution of 5×SSC, 0.5% SDS, 1.0 mM EDTA (pH 8.0), hybridizing at 50° C.–65° C., 5×SSC, overnight; followed by washing twice at 65° C. for 20 minutes with each of 2×, 0.5× and 0.2×SSC containing 0.1% SDS, to a polynucleotide sequence selected from the group consisting of:

(i) a polynucleotide sequence consisting of any one of SEQ ID NOs:76–78 and 80–81; and (ii) complements of the foregoing polynucleotides;

(b) detecting in the sample an amount of an expressed polynucleotide that hybridizes to the oligonucleotide or polynucleotide; and (c) repeating steps (a) and (b) using a biological sample obtained from the patient at a subsequent point in time; and (d) comparing the amount of expressed polynucleotide detected in step (c) to the amount detected in step (b) and therefrom monitoring the progression of the cancer in the patient.

5. The method according to claim 4, wherein the amount of expressed polynucleotide that hybridizes to the oligonucleotide or polynucleotide is determined using a polymerase chain reaction.

6. The method according to claim 4, wherein the amount of expressed polynucleotide that hybridizes to the oligonucleotide or polynucleotide is determined using a hybridization assay.

7. A method for determining the presence of ovarian cancer in a patient, comprising the steps of:

(a) contacting a biological sample obtained from said patient with an oligonucleotide or polynucleotide that hybridizes under moderately stringent conditions, wherein the moderately stringent conditions are defined as prewashing in a solution of 5×SSC, 0.5% SDS, 1.0 mM EDTA (pH 8.0), hybridizing at 50° C.–65° C., 5×SSC, overnight; followed by washing twice at 65° C. for 20 minutes with each of 2X, 0.5X and 0.2X SSC containing 0.1% SDS, to a polynucleotide sequence selected from the group consisting of:

(i) a polynucleotide sequence consisting of any one of SEQ ID NOs:75 and 79; and (ii) complements of the foregoing polynucleotides;

(b) detecting in the sample an amount of an expressed polynucleotide that hybridizes to the oligonucleotide or polynucleotide; and (c) comparing the amount of expressed polynucleotide that hybridizes to the oligonucleotide or polynucleotide to a predetermined cut-off value, and therefrom determining the presence of ovarian cancer in the patient.

8. The method according to claim 7, wherein the amount of expressed polynucleotide that hybridizes to the oligonucleotide or polynucleotide is determined using a polymerase chain reaction.

9. The method according to claim 7, wherein the amount of expressed polynucleotide that hybridizes to the oligonucleotide or polynucleotide is determined using a hybridization assay.

10. A method for monitoring the progression of ovarian cancer in a patient, comprising the steps of:

(a) contacting a biological sample obtained from said patient with an oligonucleotide or polynucleotide that hybridizes under moderately stringent conditions, wherein the moderately stringent conditions are defined as prewashing in a solution of 5×SSC, 0.5% SDS, 1.0 mM EDTA (pH 8.0), hybridizing at 50° C.–65° C., 5×SSC, overnight; followed by washing twice at 65° C. for 20 minutes with each of 2X, 0.5X and 0.2X SSC containing 0.1% SDS, to a polynucleotide sequence selected from the group consisting of:

(i) a polynucleotide sequence consisting of any one of SEQ ID NOs:75 and 79; and (ii) complements of the foregoing polynucleotides;

(b) detecting in the sample an amount of an expressed polynucleotide that hybridizes to the oligonucleotide or polynucleotide; and (c) repeating steps (a) and (b) using a biological sample obtained from the patient at a subsequent point in time; and (d) comparing the amount of expressed polynucleotide detected in step (c) to the amount detected in step (b) and therefrom monitoring the progression of the cancer in the patient.

11. The method according to claim 10, wherein the amount of expressed polynucleotide that hybridizes to the oligonucleotide or polynucleotide is determined using a polymerase chain reaction.

12. The method according to claim 10, wherein the amount of expressed polynucleotide that hybridizes to the oligonucleotide or polynucleotide is determined using a hybridization assay.

* * * * *

SEQUENCE LISTING

<160> NUMBER OF SEQ ID NOS: 310

<210> SEQ ID NO 1
<211> LENGTH: 461
<212> TYPE: DNA
<213> ORGANISM: Homo sapien

<400> SEQUENCE: 1
ttagagaggc acagaaggaa gaagagttaa aagcagcaaa gccgggtttt tttgttttgt 60
tttgttttgt tttgttttga gatggagtct cactctgttg cccaagctgg agtacaacgg 120
catgatctca gctcgctgca acctccgcct cccacgttca agtgattctc ctgcctcagc 180
ctcccaagta gctgggatta caggcgcccg ccaccacgct cagctaattt tttttgtatt 240
tttagtagag acagggtttc accaggttgg ccaggctgct cttgaactcc tgacctcagg 300
tgatccaccc gcctcggcct cccaaagtgc tgggattaca ggcgtgagcc accacgcccg 360
gcccccaaag ctgtttcttt tgtctttagc gtaaagctct cctgccatgc agtatctaca 420
taactgacgt gactgccagc aagctcagtc actccgtggt c 461

<210> SEQ ID NO 2
<211> LENGTH: 540
<212> TYPE: DNA
<213> ORGANISM: Homo sapien

<400> SEQUENCE: 2
taggatgtgt tggaccctct gtgtcaaaaa aaacctcaca aagaatcccc tgctcattac 60
agaagaagat gcatttaaaa tatgggttat tttcaacttt ttatctgagg acaagtatcc 120
attaattatt gtgtcagaag agattgaata cctgcttaag aagcttacag aagctatggg 180
aggaggttgg cagcaagaac aatttgaaca ttataaaatc aactttgatg acagtaaaaa 240
tggcctttct gcatgggaac ttattgagct tattggaaat ggacagttta gcaaaggcat 300
ggaccggcag actgtgtcta tggcaattaa tgaagtcttt aatgaactta tattagatgt 360
gttaaagcag ggttacatga tgaaaaaggg ccacagacgg aaaaactgga ctgaaagatg 420
gtttgtacta aaacccaaca taatttctta ctatgtgagt gaggatctga aggataagaa 480
aggagacatt ctcttggatg aaaattgctg tgtagagtcc ttgcctgaca aagatggaaa 540

<210> SEQ ID NO 3
<211> LENGTH: 461
<212> TYPE: DNA
<213> ORGANISM: Homo sapien

<400> SEQUENCE: 3
ttagagaggc acagaaggaa gaagagttaa aagcagcaaa gccgggtttt tttgttttgt 60
tttgttttgt tttgttttga gatggagtct cactctgttg cccaagctgg agtacaacgg 120
catgatctca gctcgctgca acctccgcct cccacgttca agtgattctc ctgcctcagc 180
ctcccaagta gctgggatta caggcgcccg ccaccacgct cagctaattt tttttgtatt 240
tttagtagag acagggtttc accaggttgg ccaggctgct cttgaactcc tgacctcagg 300
tgatccaccc gcctcggcct cccaaagtgc tgggattaca ggcgtgagcc accacgcccg 360
gcccccaaag ctgtttcttt tgtctttagc gtaaagctct cctgccatgc agtatctaca 420
taactgacgt gactgccagc aagctcagtc actccgtggt c 461

-continued

<210> SEQ ID NO 4
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4
tctttttctt tcgatttcct tcaatttgtc acgtttgatt ttatgaagtt gttcaagggc 60
taactgctgt gtattatagc tttctctgag ttccttcagc tgattgttaa atgaatccat 120
ttctgagagc ttagatgcag tttctttttc aagagcatct aattgttctt taagtctttg 180
gcataattct tccttttctg atgacttttt atgaagtaaa ctgatccctg aatcaggtgt 240
gttactgagc tgcatgtttt taattctttc gtttaatagc tgcttctcag ggaccagata 300
gataagctta ttttgatatt ccttaagctc ttgttgaagt tgtttgattt ccataatttc 360
caggtcacac tgtttatcca aaacttctag ctcagtcttt tgtgtttgct ttctgatttg 420
gacatcttgt agtctgcctg agatctgctg atgntttcca ttcactgctt ccagttccag 480
gtggagactt tnctttctgg agctcagcct gacaatgcct tcttgntccc t 531

<210> SEQ ID NO 5
<211> LENGTH: 531
<212> TYPE: DNA
<213> ORGANISM: Homo sapien

<400> SEQUENCE: 5
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt a 531

<210> SEQ ID NO 6
<211> LENGTH: 531
<212> TYPE: DNA
<213> ORGANISM: Homo sapien

<400> SEQUENCE: 6
aatagattta atgcagagtg tcaacttcaa ttgattgata gtggctgcct agagtgctgt 60
gttgagtagg tttctgagga tgcaccctgg cttgaagaga aagactggca ggattaacaa 120
tatctaaaat ctcacttgta ggagaaacca caggcaccag agctgccact ggtgctggca 180
ccagctccac caaggccagc gaagagccca aatgtgagag tggcggtcag gctggcacca 240
gcactgaagc caccactggt gctggcactg gcactggcac tgttattggt actggtactg 300
gcaccagtgc tggcactgcc actctcttgg gctttggctt tagcttctgc tcccgcctgg 360
atccgggctt tggcccaggg tccgatatca gcttcgtccc agttgcaggg cccggcagca 420
ttctccgagc cgagcccaat gcccattcga gctctaatct cggccctagc cttggcttca 480

-continued gctgcagcct cagctgcagc cttcaaatcc gcttccatcg cctctcggta c 531

<210> SEQ ID NO 7
<211> LENGTH: 531
<212> TYPE: DNA
<213> ORGANISM: Homo sapien

<400> SEQUENCE: 7
gccaagaaag cccgaaaggt gaagcatctg gatggggaag aggatggcag cagtgatcag 60
agtcaggctt ctggaaccac aggtggccga agggtctcaa aggccctaat ggcctcaatg 120
gcccgcaggg cttcaagggg tcccatagcc ttttgggccc gcagggcatc aaggactcgg 180
ttggctgctt gggcccggag agccttgctc tccctgagat cacctaaagc ccgtaggggc 240
aaggctcgcc gtagagctgc caagctccag tcatcccaag agcctgaagc accaccacct 300
cgggatgtgg cccttttgca agggagggca aatgatttgg tgaagtacct tttggctaaa 360
gaccagacga agattcccat caagcgctcg gacatgctga aggacatcat caaagaatac 420
actgatgtgt accccgaaat cattgaacga gcaggctatt ccttggagaa ggtatttggg 480
attcaattga aggaaattga taagaatgac cacttgtaca ttcttctcag c 531

<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8
gaggtctcac tatgttgccc aggctgttct tgaactcctg ggatcaagca atccacccat 60
gttggtctcc aaaagtgctg ggatcatagg cgtgagccac ctcacccagc caccaatttt 120
caatcaggaa gactttttcc ttcttcaaga agtgaagggt ttccagagta tagctacact 180
attgcttgcc tgagggtgac tacaaaattg cttgctaaaa ggttaggatg ggtaaagaat 240
tagattttct gaatgcaaaa ataaaatgtg aactaatgaa ctttaggtaa tacatattca 300
taaaataatt attcacatat ttcctgattt atcacagaaa taatgtatga aatgctttga 360
gtttcttgga gtaaactcca ttactcatcc caagaaacca tattataagt atcactgata 420
ataagaacaa caggaccttg tcataaattc tggataagag aaatagtctc tgggtgtttg 480
ntcttaattg ataaaattta cttgtccatc ttttagttca gaatcacaaa a 531

<210> SEQ ID NO 9
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9
aagcggaaat gagaaaggag ggaaaatcat gtggtattga gcggaaaact gctggatgac 60
agggctcagt cctgttggag aactctgggt ggtgctgtag aacagggcca ctcacagtgg 120
ggtgcacaga ccagcacggc tctgtgacct gtttgttaca ggtccatgat gaggtaaaca 180
atacactgag tataagggtt ggtttagaaa ctcttacagc aatttgacaa agtaatcttc 240
tgtgcagtga atctaagaaa aaaattgggg ctgtatttgt atgttccttt ttttcatttc 300

-continued

```
atgttctgag ttacctattt ttattgcatt ttacaaaagc atccttccat gaaggaccgg    360

aagttaaaaa caaagcaggt cctttatcac agcactgtcg tagaacacag ttcagagtta    420

tccacccaag gagccaggga gctgggctaa accaaagaat tttgcttttg gttaatcatc    480

aggtacttga gttggaattg ttttaatccc atcattacca ggctggangt g             531
```

<210> SEQ ID NO 10
<211> LENGTH: 861
<212> TYPE: DNA
<213> ORGANISM: Homo sapien

<400> SEQUENCE: 10

```
ccgcggctcc tgtccagacc ctgaccctcc ctcccaaggc tcaaccgtcc cccaacaacc     60

gccagccttg tactgatgtc ggctgcgaga gcctgtgctt aagtaagaat caggccttat    120

tggagacatt caagcaaagg ttggacaact acttttccag aacagaaagg aaactcatgc    180

atcagaaaag gtgactaata aaggtaccag aagaatatgg ctgcacaaat accagaatct    240

gatcagataa aacagtttaa ggaatttctg ggacctaca ataaacttac agagacctgc     300

tttttggact gtgttagaga cttcacaaca agagaagtaa aacctgaaga gaccacctgt    360

tcagaacatt gcttacagaa atatttaaaa atgacacaaa gaatatccat gagatttcag    420

gaatatcata ttcagcagaa tgaagccctg gcagccaaag caggactcct tggccaacca    480

cgatagagaa gtcctgatgg atgaactttt gatgaaagat tgccaacagc tgctttattg    540

gaaatgagga ctcatctgat agaatcccct gaaagcagta gccaccatgt tcaaccatct    600

gtcatgactg tttggcaaat ggaaaccgct ggagaaacaa aattgctatt taccaggaat    660

aatcacaata gaaggtctta ttgttcagtg aaataataag atgcaacatt tgttgaggcc    720

ttatgattca gcagcttggt cacttgatta gaaaaataaa ccattgtttc ttcaattgtg    780

actgttaatt ttaaagcaac ttatgtgttc gatcatgtat gagatagaaa aatttttatt    840

actcaaagta aaataaatgg a                                              861
```

<210> SEQ ID NO 11
<211> LENGTH: 541
<212> TYPE: DNA
<213> ORGANISM: Homo sapien

<400> SEQUENCE: 11

```
gaaaaaaaat ataaaacaca cttttgcgaa aacggtggcc ctaaaagagg aaaagaattt     60

caccaatata aatccaattt tatgaaaact gacaatttaa tccaagaatc acttttgtaa    120

atgaagctag caagtgatga tatgataaaa taaacgtgga ggaaataaaa acacaagact    180

tggcataaga tatatccact tttgatatta aacttgtgaa gcatattctt cgacaaattg    240

tgaaagcgtt cctgatcttg cttgttctcc atttcaaata aggaggcata tcacatccca    300

agagtaacag aaaaagaaaa aagacatttt tgcattttga gatgaaccaa agacacaaaa    360

caaaacgaac aaagtgtcat gtctaattct agcctctgaa ataaaccttg aacatctcct    420

acaaggcacc gtgatttttg taattctaac ctgaagaaat gtgatgactt ttgtggacat    480

gaaaatcaga tgagaaaact gtggtctttc caaagcctga actcccctga aaacctttgc    540

a                                                                    541
```

<210> SEQ ID NO 12
<211> LENGTH: 541
<212> TYPE: DNA

-continued

<213> ORGANISM: Homo sapien

<400> SEQUENCE: 12
ctgggatcat ttctcttgat gtcataaaag actcttcttc ttcctcttca tcctcttctt 60
catcctcttc tgtacagtgc tgccgggtac aacggctatc tttgtcttta tcctgagatg 120
aagatgatgc ttctgtttct cctaccataa ctgaagaaat ttcgctggaa gtcgtttgac 180
tggctgtttc tctgacttca ccttctttgt caaacctgag tctttttacc tcatgcccct 240
cagcttccac agcatcttca tctggatgtt tatttttcaa agggctcact gaggaaactt 300
ctgattcaga ggtcgaagag tcactgtgat ttttctcctc attttgctgc aaatttgcct 360
ctttgctgtc tgtgctctca ggcaacccat ttgttgtcat gggggctgac aaagaaacct 420
ttggtcgatt aagtggcctg ggtgtcccag gcccatttat attagacctc tcagtatagc 480
ttggtgaatt tccaggaaac ataacaccat tcattcgatt taaactattg gaattggttt 540
t 541

<210> SEQ ID NO 13
<211> LENGTH: 441
<212> TYPE: DNA
<213> ORGANISM: Homo sapien

<400> SEQUENCE: 13
gagggttggt ggtagcggct tggggaggtg ctcgctctgt cggtcttgct ctctcgcacg 60 cttccccccgg ctcccttcgt ttcccccccc cggtcgcctg cgtgccggag tgtgtgcgag 120
ggagggggag ggcgtcgggg gggtgggggg aggcgttccg gtccccaaga gacccgcgga 180
gggaggcgga ggctgtgagg gactccggga agccatggac gtcgagaggc tccaggaggc 240
gctgaaagat tttgagaaga gggggaaaaa ggaagtttgt cctgtcctgg atcagtttct 300
ttgtcatgta gccaagactg gagaaacaat gattcagtgg tcccaattta aaggctattt 360
tattttcaaa ctggagaaag tgatggatga tttcagaact tcagctcctg agccaagagg 420
tcctcccaac cctaatgtcg a 441

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G

<400> SEQUENCE: 14
aagcaggcgg ctcccgcgct cgcagggccg tgccacctgc ccgcccgccc gctcgctcgc 60
tcgcccgccg cgccgcgctg ccgaccgcca gcatgctgcc gagagtgggc tgccccgcgc 120
tgccgntgcc g 131

<210> SEQ ID NO 15
<211> LENGTH: 692
<212> TYPE: DNA
<213> ORGANISM: Homo sapien

<400> SEQUENCE: 15
atctcttgta tgccaaatat ttaatataaa tctttgaaac aagttcagat gaaataaaaa 60
tcaaagtttg caaaaacgtg aagattaact taattgtcaa atattcctca ttgccccaaa 120
tcagtatttt ttttatttct atgcaaaagt atgccttcaa actgcttaaa tgatatatga 180

-continued tatgatacac aaaccagttt tcaaatagta aagccagtca tcttgcaatt gtaagaaata 240
ggtaaaagat tataagacac cttacacaca cacacacaca cacacacgtg tgcacgccaa 300
tgacaaaaaa caatttggcc tctcctaaaa taagaacatg aagaccctta attgctgcca 360
ggagggaaca ctgtgtcacc cctccctaca atccaggtag tttcctttaa tccaatagca 420
aatctgggca tatttgagag gagtgattct gacagccacg ttgaaatcct gtggggaacc 480
attcatgtcc acccactggt gccctgaaaa aatgccaata atttttcgct cccacttctg 540
ctgctgtctc ttccacatcc tcacatagac cccagacccg ctggcccctg gctgggcatc 600
gcattgctgg tagagcaagt cataggtctc gtctttgacg tcacagaagc gatacaccaa 660
attgcctggt cggtcattgt cataaccaga ga 692

<210> SEQ ID NO 16
<211> LENGTH: 728
<212> TYPE: DNA
<213> ORGANISM: Homo sapien

<400> SEQUENCE: 16
cagacggggt ttcactatgt tggctaggct ggtcttgaac tcctgacttc aggtgatctg 60
cctgccttgg cctcccaaag tgctgggatt acaggcataa gccactgcgc ccggctgatc 120
tgatggtttc ataaggcttt tccccctttt gctcagcact tctccttcct gccgccatgt 180
gaagaaggac atgtttgctt ccccttccac cacgattgta agttgtttcc tgaggcctcc 240
ccggccatgc tgaactgtga gtcaattaaa cctctttcct ttataaatta tccagttttg 300
ggtatgtctt tattagtaga atgagaacag actaatacaa ccccttaaagg agactgacgg 360 agaggattct tcctggatcc cagcacttcc tctgaatgct actgacattc ttcttgagga 420
ctttaaactg ggagatagaa aacagattcc atggctcagc agcctgagag cagggaggga 480
gccaagctat agatgacatg ggcagcctcc cctgaggcca ggtgtggccg aacctgggca 540
gtgctgccac ccaccccacc agggccaagt cctgtccttg gagagccaag cctcaatcac 600
tgctagcctc aagtgtcccc aagccacagt ggctaggggg actcagggaa cagttcccag 660
tctgccctac ttctcttacc tttacccctc atacctccaa agtagaccat gttcatgagg 720
tccaaagg 728

<210> SEQ ID NO 17
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 17
aagcgaggaa gccactgcgg ctcctggctg aaaagcggcg ccaggctcgg gaacagaggg 60
aacgcgaaga acaggagcgg aagctgcagg ctgaaaggga caagcgaatg cgagaggagc 120
agctggcccg ggaggctgaa gcccgggctg aacgtgaggc cgaggcgcgg agacgggagg 180
agcaggaggc tcgagagaag gcgcaggctg agcaggagga gcaggagcga ctgcagaagc 240
agaaagagga agccgaagcc cggtcccggg aagaagctga gcgccagcgc caggagcggg 300
aaaagcactt tcagaaggag gaacaggaga gacaagagcg aagaaagcgg ctggaggaga 360
taatgaagag gactcggaaa tcagaagccg ccgaaaccaa gaagcaggat gcaaaggaga 420

-continued ccgcagctaa caattccggc ccagaccctt gtgaaagctg tagagactcg gccctctggg 480
cttccagaaa ggattctatt gcagaaagga aggagctngg ccccccangg a 531

<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggcat 540 cacntgagaa agagctgatt ttgtatttca ggtttgaaaa gaaataactg aacatatttt 600
ttaggcaagt cagaaagaga acatggtcac ccaaaagcaa ctgtaactca gaaattaagt 660
tactcagaaa ttaagtagct cagaaattaa gaaagaatgg tataatgaac cccatatac 720 ccttccttct ggattcacca attgttaaca tttttttcct ctcagctatc cttctaattt 780
ctctctaatt tcaatttgtt tatatttacc tctgggctca ataagggcat ctgtgcagaa 840
atttggaagc catttagaaa atcttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa t 1041

<210> SEQ ID NO 19
<211> LENGTH: 1043
<212> TYPE: DNA
<213> ORGANISM: Homo sapien

<400> SEQUENCE: 19
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggcat 540 cacctgagaa agagctgatt ttgtatttca ggtttgaaaa gaaataactg aacatatttt 600

-continued ttaggcaagt cagaaagaga acatggtcac ccaaaagcaa ctgtaactca gaaattaagt 660
tactcagaaa ttaagtagct cagaaattaa gaaagaatgg tataatgaac ccccatatac 720
ccttccttct ggattcacca attgttaaca tttttttcct ctcagctatc cttctaattt 780
ctctctaatt tcaatttgtt tatatttacc tctgggctca ataagggcat ctgtgcagaa 840
atttggaagc catttagaaa atctttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa tta 1043

<210> SEQ ID NO 20
<211> LENGTH: 448
<212> TYPE: DNA
<213> ORGANISM: Homo sapien

<400> SEQUENCE: 20
ggacgacaag gccatggcga tatcggatcc gaattcaagc ctttggaatt aaataaacct 60
ggaacaggga aggtgaaagt tggagtgaga tgtcttccat atctatacct ttgtgcacag 120
ttgaatggga actgtttggg tttagggcat cttagagttg attgatggaa aaagcagaca 180
ggaactggtg ggaggtcaag tggggaagtt ggtgaatgtg gaataactta cctttgtgct 240
ccacttaaac cagatgtgtt gcagctttcc tgacatgcaa ggatctactt taattccaca 300
ctctcattaa taaattgaat aaaagggaat gttttggcac ctgatataat ctgccaggct 360
atgtgacagt aggaaggaat ggtttcccct aacaagccca atgcactggt ctgactttat 420
aaattattta ataaaatgaa ctattatc 448

<210> SEQ ID NO 21
<211> LENGTH: 411
<212> TYPE: DNA
<213> ORGANISM: Homo sapien

<400> SEQUENCE: 21
ggcagtgaca ttcaccatca tgggaaccac cttccctttt cttcaggatt ctctgtagtg 60
gaagagagca cccagtgttg ggctgaaaac atctgaaagt agggagaaga acctaaaata 120
atcagtatct cagagggctc taaggtgcca agaagtctca ctggacattt aagtgccaac 180
aaaggcatac tttcggaatc gccaagtcaa aactttctaa cttctgtctc tctcagagac 240
aagtgagact caagagtcta ctgctttagt ggcaactaca gaaaactggt gttacccaga 300
aaaacaggag caattagaaa tggttccaat atttcaaagc tccgcaaaca ggatgtgctt 360
tcctttgccc atttagggtt tcttctcttt cctttctctt tattaaccac t 411

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22
tgcgctgaaa acaacggcct cctttactgt taaaatgcag ccacaggtgc ttagccgtgg 60
gcatctcaac caccagcctc tgtgggggc aggtgggcgt ccctgtgggc ctctgggccc 120

-continued acgtccagcc tctgtcctct gccttccgtt cttcgacagt gttcccggca tccctggtca 180
cttggtactt ggcgtgggcc tcctgtgctg ctccagcagc tcctccaggn ggtcggcccg 240
cttcaccgca gcctcatgtt gtgtccggag gctgctcacg gcctcctcct tcctcgcgag 300
ggctgtcttc accctccggn gcacctcctc cagctccagc tgctggcggg cctgcagcgt 360
ggccagctcg gccttggcct gccgcgtctc ctcctcarag gctgccagcc ggtcctcgaa 420
ctcctggcgg atcacctggg ccaggttgct gcgctcgcta gaaagctgct cgttcaccgc 480
ctgcgcatcc tccagcgccc gctccttctg ccgcacaagg ccctgcagac gcagattctc 540
gccctcggcc tccccaagct ggcccttcag ctccgagcac cgctcctgaa gcttccgctc 600
cgactgctcc agctcggaga gctcggcctc gtacttgtcc cgtaagcgct tgatgcggct 660
ctcggcagcc ttctcactct cctccttggc cagcgccatg tcggcctcca gccggtgaat 720
gaccagctca atctccttgt cccggccttt ccggatttct tccctcagct cctgttcccg 780
gttcagcagc cacgcctcct ccttcctggt gcggccggcc tcccacgcct gcctctccag 840
ctccagctgc tgcttcaggg tattcagctc catctggcgg gcctgcagcg tggcca 896

<210> SEQ ID NO 23
<211> LENGTH: 111
<212> TYPE: DNA
<213> ORGANISM: Homo sapien

<400> SEQUENCE: 23
caacttatta cttgaaatta taatatagcc tgtccgtttg ctgtttccag gctgtgatat 60
attttcctag tggtttgact ttaaaaataa ataaggttta attttctccc c 111

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 24
tgcaagtcac gggagtttat ttatttaatt tttttcccca gatggagact ctgtcgccca 60
ggctggagtg caatggtgtg atcttggctc actgcaacct ccacctcctg ggttcaagcg 120
attctcctgc cacagcctcc cgagtagctg ggattacagg tgcccgccac cacacccagc 180
taatttttat atttttagta aagacagggt ttccccatgt tggccaggct ggtcttgaac 240
ttctgacctc aggtgatcca cctgcctcgg cctcccaaag tgttgggatt acaggcgtga 300
gctacccgtg cctggccagc cactggagtt taaaggacag tcatgttggc tccagcctaa 360
ggcggcattt tcccccatca gaaagcccgc ggctcctgta cctcaaaata gggcacctgt 420
aaagtcagtc agtgaagtct ctgctctaac tggccacccg gggccattgg cntctgacac 480
agccttgcca ggangcctgc atctgcaaaa gaaaagttca cttcctttcc g 531

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25

-continued cagagaatct kagaaagatg tcgcgttttc ttttaatgaa tgagagaagc ccatttgtat 60
ccctgaatca ttgagaaaag gcggcggtgg cgacagcggc gacctaggga tcgatctgga 120
gggacttggg gagcgtgcag agacctctag ctcgagcgcg agggacctcc cgccgggatg 180
cctggggagc agatggaccc tactggaagt cagttggatt cagatttctc tcagcaagat 240
actccttgcc tgataattga agattctcag cctgaaagcc aggttctaga ggatgattct 300
ggttctcact tcagtatgct atctcgacac cttcctaatc tccagacgca caaagaaaat 360
cctgtgttgg atgttgngtc caatccttga acaaacagct ggagaagaac gaggagaccg 420
gtaatagtgg gttcaatgaa catttgaaag aaaaccaggt tgcagaccct g 471

<210> SEQ ID NO 26
<211> LENGTH: 541
<212> TYPE: DNA
<213> ORGANISM: Homo sapien

<400> SEQUENCE: 26
gactgtcctg aacaagggac ctctgaccag agagctgcag gagatgcaga gtggtggcag 60
gagtggaagc caaagaacac ccaccttcct cccttgaagg agtagagcaa ccatcagaag 120
atactgtttt attgctctgg tcaaacaagt cttcctgagt tgacaaaacc tcaggctctg 180
gtgacttctg aatctgcagt ccactttcca taagttcttg tgcagacaac tgttcttttg 240
cttccatagc agcaacagat gctttggggc taaaaggcat gtcctctgac cttgcaggtg 300
gtggattttg ctcttttaca acatgtacat ccttactggg ctgtgctgtc acagggatgt 360
ccttgctgga ctgttctgct atggggatat cttcgttgga ctgttcttca tgcttaattg 420
cagtattagc atccacatca gacagcctgg tataaccaga gttggtggtt actgattgta 480
gctgctcttt gtccacttca tatggcacaa gtattttcct caacatcctg gctctgggaa 540
g 541

<210> SEQ ID NO 27
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27
gaaatgtata tttaatcatt ctcttgaacg atcagaactc traaatcagt tttctataac 60
arcatgtaat acagtcaccg tggctccaag gtccaggaag gcagtggtta acacatgaag 120
agtgtgggaa gggggctgga aacaaagtat tcttttcctt caaagcttca ttcctcaagg 180
cctcaattca agcagtcatt gtccttgctt tcaaaagtct gtgtgtgctt catggaaggt 240
atatgtttgt tgccttaatt tgaattgtgg ccaggaaggg tctggagatc taaattcaga 300
gtaagaaaac ctgagctaga actcaggcat ttctcttaca gaacttggct tgcagggtag 360
aatgaangga aagaaactta gaagctcaac aagctgaaga taatcccatc aggcatttcc 420
cataggcctt gcaactctgt tcactgagag atgttatcct g 461

<210> SEQ ID NO 28
<211> LENGTH: 541
<212> TYPE: DNA
<213> ORGANISM: Homo sapien -continued

<400> SEQUENCE: 28

```
agtctggagt gagcaaacaa gagcaagaaa caarragaag ccaaaagcag aaggctccaa     60
tatgaacaag ataaatctat cttcaaagac atattagaag ttgggaaaat aattcatgtg    120
aactagacaa gtgtgttaag agtgataagt aaaatgcacg tggagacaag tgcatcccca    180
gatctcaggg acctcccct gcctgtcacc tggggagtga gaggacagga tagtgcatgt     240
tctttgtctc tgaattttta gttatatgtg ctgtaatgtt gctctgagga agcccctgga    300
aagtctatcc caacatatcc acatcttata ttccacaaat taagctgtag tatgtaccct    360
aagacgctgc taattgactg ccacttcgca actcaggggc ggctgcattt tagtaatggg    420
tcaaatgatt cactttttat gatgcttccc aaggtgcctt ggcttctctt cccaactgac    480
aaatgcccaa gttgagaaaa atgatcataa ttttagcata aaccgagcaa tcggcgaccc    540
c                                                                    541
```

<210> SEQ ID NO 29
<211> LENGTH: 411
<212> TYPE: DNA
<213> ORGANISM: Homo sapien

<400> SEQUENCE: 29

```
tagctgtctt cctcactctt atggcaatga ccccatatct taatggatta agataatgaa     60
agtgtatttc ttacactctg tatctatcac cagaagctga ggtgatagcc cgcttgtcat    120
tgtcatccat attctgggac tcaggcggga actttctgga atattgccag ggagcatggc    180
agaggggcac agtgcattct gggggaatgc acattggctc agcctgggta atgagtgata    240
tacattacct ctgttcacaa ctcattgccc agcaccagtc acaaggcccc accaaatacc    300
agagcccaag aaatgtagtc ctgttgatat ggttttgctg tgtcccaacc caaatctcat    360
cttgaattgt aagctcccat aattcccatg tgttgtggga gggacctggt g             411
```

<210> SEQ ID NO 30
<211> LENGTH: 511
<212> TYPE: DNA
<213> ORGANISM: Homo sapien

<400> SEQUENCE: 30

```
atcatgagga tgttaccaaa gggatggtac taaaccattt gtattcgtct gttttcacac     60
tgctttgaag atactacctg agactgggta atttataaac aaaagagatt taattgactc    120
acagttctgc atggctgaag aggcctcagg aaacttacag tcatggtgga aggcaaagga    180
ggagcaaggc atgtcttaca tgtcagtagg agagagagcg agagcaggag aacctgccac    240
ttataaacca ttcagatctc ataactccct atcatgagaa aaacatggag gaaaccaccc    300
tcatgatcca atcacctccc gccaggtccc tccctcgaca cgtggggatt ataattcagg    360
attagaggga cacagagaca aaccatatca tcattcatga gaaatccacc ctcatagtcc    420
aatcagctcc taccaggccc cacctccaac actggggatt gcaattcaac atgagatttg    480
gatggggaca cagattcaaa ccatatcata c                                   511
```

<210> SEQ ID NO 31
<211> LENGTH: 827
<212> TYPE: DNA
<213> ORGANISM: Homo sapien

<400> SEQUENCE: 31

```
catggccttt ctccttagag gccagaggtg ctgccctggc tgggagtgaa gctccaggca     60
```

-continued

```
ctaccagctt tcctgatttt cccgtttggt ccatgtgaag agctaccacg agccccagcc    120

tcacagtgtc cactcaaggg cagcttggtc ctcttgtcct gcagaggcag gctggtgtga    180

ccctgggaac ttgacccggg aacaacaggt ggcccagagt gagtgtggcc tggcccctca    240

acctagtgtc cgtcctcctc tctcctggag ccagtcttga gtttaaaggc attaagtgtt    300

agatacaagc tccttgtggc tggaaaaaca cccctctgct gataaagctc agggggcact    360

gaggaagcag aggccccttg ggggtgccct cctgaagaga gcgtcaggcc atcagctctg    420

tccctctggt gctcccacgt ctgttcctca ccctccatct ctgggagcag ctgcacctga    480

ctggccacgc gggggcagtg gaggcacagg ctcagggtgg ccgggctacc tggcacccta    540

tggcttacaa agtagagttg gcccagtttc cttccacctg aggggagcac tctgactcct    600

aacagtcttc cttgccctgc catcatctgg ggtggctggc tgtcaagaaa ggccgggcat    660

gctttctaaa cacagccaca ggaggcttgt agggcatctt ccaggtgggg aaacagtctt    720

agataagtaa ggtgacttgc ctaaggcctc ccagcaccct tgatcttgga gtctcacagc    780

agactgcatg tsaacaactg gaaccgaaaa catgcctcag tataaaa                  827


<210> SEQ ID NO 32
<211> LENGTH: 291
<212> TYPE: DNA
<213> ORGANISM: Homo sapien

<400> SEQUENCE: 32

ccagaacctc cttctctttg gagaatgggg aggcctcttg gagacacaga gggtttcacc     60

ttggatgacc tctagagaaa ttgcccaaga agcccacctt ctggtcccaa cctgcagacc    120

ccacagcagt cagttggtca ggccctgctg tagaaggtca cttggctcca ttgcctgctt    180

ccaaccaatg ggcaggagag aaggccttta tttctcgccc acccattctc ctgtaccagc    240

acctccgttt tcagtcagyg ttgtccagca acggtaccgt ttacacagtc a             291


<210> SEQ ID NO 33
<211> LENGTH: 491
<212> TYPE: DNA
<213> ORGANISM: Homo sapien

<400> SEQUENCE: 33

tgcatgtagt tttatttatg tgttttsgtc tggaaaacca agtgtcccag cagcatgact     60

gaacatcact cacttcccct acttgatcta caaggccaac gccgagagcc cagaccagga    120

ttccaaacac actgcacgag aatattgtgg atccgctgtc aggtaagtgt ccgtcactga    180

cccaracgct gttacgtggc acatgactgt acagtgccac gtaacagcac tgtacttttc    240

tcccatgaac agttacctgc catgtatcta catgattcag aacattttga acagttaatt    300

ctgacacttg aataatccca tcaaaaaccg taaaatcact ttgatgtttg taacgacaac    360

atagcatcac tttacgacag aatcatctgg aaaaacagaa caacgaatac atacatctta    420

aaaaatgctg ggtgggccca ggcacagctt cacgcctgta atcccagcac tttgggaggc    480

ttaagcgggt g                                                         491


<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
```

-continued

<223> OTHER INFORMATION: n = A,T,C or G

<400> SEQUENCE: 34

```
tggggcggaa agaagccaag gccaaggagc tggtgcggca gctgcagctg gaggccgagg     60
agcagaggaa gcagaagaag cggcagagtg tgtcgggcct gcacagatac cttcacttgc    120
tggatggaaa tgaaaattac ccgtgtcttg tggatgcaga cggtgatgtg atttccttcc    180
caccaataac caacagtgag aagacaaagg ttaagaaaac gacttctgat ttgtttttgg    240
aagtaacaag tgccaccagt ctgcagattt gcaaggatgt catggatgcc ctcattctga    300
aaatggcaag aaatgaaaaa gtacacttta gaaaataaag aggaaggatc actctcagat    360
actgaagccg atgcagtctc tggacaactt ccagatccca caacgaatcc cagtgctgga    420
aaggacgggc ccttccttct ggtggtggaa cangtcccgg tggtggatct tggaanggaa    480
cctgaangtg gtgtaccccg tccaaggccg accttggcca c                        521
```

<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

```
tcccgcgctc gcagggcncg tgccacctgc cygtccgccc gctcgctcgc tcgcccgccg     60
cgccgcgctg ccgaccgyca gcatgctgcc gagagtgggc tgccccgcgc tgccgctgcc    120
gccgccgccg ctgctgccgc tgctgccgct gctgctgctg c                        161
```

<210> SEQ ID NO 36
<211> LENGTH: 341
<212> TYPE: DNA
<213> ORGANISM: Homo sapien

<400> SEQUENCE: 36

```
ggcgggtagg catggaactg agaagaacga agaagctttc agactacgtg gggaagaatg     60
aaaaaaccaa aattatcgcc aagattcagc aaaggggaca gggagctcca gcccgagagc    120
ctattattag cagtgaggag cagaagcagc tgatgctgta ctatcacaga agacaagagg    180
agctcaagag attggaagaa aatgatgatg atgcctattt aaactcacca tgggcggata    240
acactgcttt gaaaagacat tttcatggag tgaaagacat aaagtggaga ccaagatgaa    300
gttcaccagc tgatgacact tccaaagaga ttagctcacc t                        341
```

<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37

```
tctgaaggtt aaatgtttca tctaaatagg gataatgrta aacacctata gcatagagtt     60
gtttgagatt aaatgagata atacatgtaa aattatgtgc ctggcataca gcaagattgt    120
tgttgttgtt gatgatgatg atgatgatga taatattttt ctatccccag tgcacaactg    180
cttgaaccta ttagataatc aatacatgtt tcttgaactg agatcaattt ccccatgttg    240
```

-continued tctgactgat gaagccctac attttcttct agaggagatg acatttgagc aagatcttaa 300
agaaaatcag atgccttcac ctgaccactg cttggtgatc ccatggcact ttgtacatct 360
ctccattagc tctcatctca ccagcccatc attattgtat gtgctgcctt ctgaagcttg 420
cagctggcta ccatcmggta gaataaaaat catcctttca taaaatagtg accctccttt 480
tttatttgca tttcccaaag ccaagcaccg tgggangqta g 521

<210> SEQ ID NO 38
<211> LENGTH: 461
<212> TYPE: DNA
<213> ORGANISM: Homo sapien

<400> SEQUENCE: 38
tatgaagaag ggaaaagaag ataatttgtg aaagaaatgg gtccagttac tagtctttga 60
aaagggtcag tctgtagctc ttcttaatga gaataggcag ctttcagttg ctcagggtca 120
gatttcctta gtggtgtatc taatcacagg aaacatctgt ggttccctcc agtctctttc 180
tgggggactt gggcccactt ctcatttcat ttaattagag gaaatagaac tcaaagtaca 240
atttactgtt gtttaacaat gccacaaaga catggttggg agctatttct tgatttgtgt 300
aaaatgctgt ttttgtgtgc tcataatggt tccaaaaatt gggtgctggc caaagagaga 360
tactgttaca gaagccagca agaagacctc tgttcattca cacccccggg gatatcagga 420
attgactcca gtgtgtgcaa atccagtttg gcctatcttc t 461

<210> SEQ ID NO 39
<211> LENGTH: 769
<212> TYPE: DNA
<213> ORGANISM: Homo sapien

<400> SEQUENCE: 39
tgagggactg attggtttgc tctctgctat tcaattcccc aagcccactt gttcctgcag 60
cgtcctcctt ctcattccct ttagttgtac cctctctttc atctgagacc tttccttctt 120
gatgtcgcct tttcttcttc ttgctttttc tgatgttctg ctcagcatgt tctgggtgct 180
tctcatctgc atcattcctt tcagatgctg tagcttcttc ctcctctttc tgcctccttt 240
tctttttctt ttttttgggg ggcttgctct ctgactgcag ttgaggggcc ccagggtcct 300
ggcctttgag acgagccagg aaggcctgct cctgggcctc taggcgagca agcttggcct 360
tcattgtgat cccaagacgg gcagccttgt gtgctgttcg cccctcacag gcttggagca 420
gcatctcatc agtcagaatc tttggggact tggacccctg gttgtcgtca tcactgcagc 480
tctccaagtc tttgtttggc ttctctccac ctgaagtcaa tgtagccatc ttcacaaact 540
tctgatacag caagttgggc ttgggatgat tataacgggt ggtctcctta gaaaggctcc 600
ttatctgtac tccatcctgc ccagtttcca ctaccaagtt ggccgcagtc ttgttgaaga 660
gctcattcca ccagtggttt gtgaactcct tggcagggtc atgtcctacc ccatgagtgt 720
cttgcttcag ygtcaccctg agagcctgag tgataccatt ctccttccg 769

<210> SEQ ID NO 40
<211> LENGTH: 292
<212> TYPE: DNA
<213> ORGANISM: Homo sapien

<400> SEQUENCE: 40
gacaacatga aataaatcct agaggacaaa attaaactca atagagtgta gtctagttaa 60

-continued aaactcgaaa aatgagcaag tctggtggga gtggaggaag ggctatacta taaatccaag 120
tgggcctcct gatcttaaca agccatgctc attatacaca tctctgaact ggacatacca 180
cctttacgca ggaaacaggg cttggaactt ctaagggaaa ttaacatgca ccacccacat 240
ctaacctacc tgccgggtag gtaccatccc tgcttcgctg aaatcagtgc tc 292

<210> SEQ ID NO 41
<211> LENGTH: 406
<212> TYPE: DNA
<213> ORGANISM: Homo sapien

<400> SEQUENCE: 41
ttggaattaa ataaacctgg aacagggaag gtgaaagttg gagtgagatg tcttccatat 60
ctataccttt gtgcacagtt gaatgggaac tgtttgggtt tagggcatct tagagttgat 120
tgatggaaaa agcagacagg aactggtggg aggtcaagtg gggaagttgg tgaatgtgga 180
ataacttacc tttgtgctcc acttaaacca gatgtgttgc agctttcctg acatgcaagg 240
atctacttta attccacact ctcattaata aattgaataa aagggaatgt tttggcacct 300
gatataatct gccaggctat gtgacagtag gaaggaatgg tttcccctaa caagcccaat 360
gcactggtct gactttataa attatttaat aaaatgaact attatc 406

<210> SEQ ID NO 42
<211> LENGTH: 381
<212> TYPE: DNA
<213> ORGANISM: Homo sapien

<400> SEQUENCE: 42
aaactggacc tgcaacaggg acatgaattt actgcarggt ctgagcaagc tcagcccctc 60
tacctcaggg ccccacagcc atgactacct cccccaggag cgggagggtg aagggggcct 120
gtctctgcaa gtggagccag agtggaggaa tgagctctga agacacagca cccagccttc 180
tcgcaccagc caagccttaa ctgcctgcct gaccctgaac cagaacccag ctgaactgcc 240
cctccaaggg acaggaaggc tgggggaggg agtttacaac ccaagccatt ccacccccctc 300 ccctgctggg gagaatgaca catcaagctg ctaacaattg ggggaagggg aaggaagaaa 360
actctgaaaa caaaatcttg t 381

<210> SEQ ID NO 43
<211> LENGTH: 451
<212> TYPE: DNA
<213> ORGANISM: Homo sapien

<400> SEQUENCE: 43
catgcgtttc accactgttg gccaggctgg tctcgaactc ctggcctcaa gcaatccacc 60
cgcctcagcc tccaaaagtg ctgggattac agatgtgagc catggcacca tgccaaaagg 120
ctatattcct ggctctgtgt ttccgagact gcttttaatc ccaacttctc tacatttaga 180
ttaaaaaata ttttattcat ggtcaatctg gaacataatt actgcatctt aagtttccac 240
tgatgtatat agaaggctaa aggcacaatt tttatcaaat ctagtagagt aaccaaacat 300
aaaatcatta attactttca acttaataac taattgacat tcctcaaaag agctgttttc 360
aatcctgata ggttctttat tttttcaaaa tatatttgcc atgggatgct aatttgcaat 420
aaggcgcata atgagaatac cccaaactgg a 451

<210> SEQ ID NO 44
<211> LENGTH: 521

-continued

<212> TYPE: DNA
<213> ORGANISM: Homo sapien

<400> SEQUENCE: 44

```
gttggacccc cagggactgg aaagacactt cttgcccgag ctgtggcggg agaagctgat     60
gttccttttt attatgcttc tggatccgaa tttgatgaga tgtttgtggg tgtgggagcc    120
agccgtatca gaaatctttt tagggaagca aaggcgaatg ctccttgtgt tatatttatt    180
gatgaattag attctgttgg tgggaagaga attgaatctc caatgcatcc atattcaagg    240
cagaccataa atcaacttct tgctgaaatg gatggtttta aacccaatga aggagttatc    300
ataataggag ccacaaactt cccagaggca ttagataatg ccttaatacc gtcctggtcg    360
ttttgacatg caagttacag ttccaaggcc agatgtaaaa ggtcgaacag aaattttgaa    420
atggtatctc aataaaataa agtttgatca atcccgttga tccagaaatt atagcctcga    480
ggtactggtg gcttttccgg aagcagagtt gggagaatct t                        521
```

<210> SEQ ID NO 45
<211> LENGTH: 585
<212> TYPE: DNA
<213> ORGANISM: Homo sapien

<400> SEQUENCE: 45

```
gcctacaaca tccagaaaga gtctaccctg cacctggtgc tscgtctcag aggtgggatg     60
cagatcttcg tgaagaccct gactggtaag accatcactc tcgaagtgga gccgagtgac    120
accatygaga acgtcaaagc aaagatccar gacaaggaag gcrtycctcc tgaccagcag    180
aggttgatct ttgccggaaa gcagctggaa gatggdcgca ccctgtctga ctacaacatc    240
cagaaagagt cyaccctgca cctggtgctc cgtctcagag gtgggatgca ratcttcgtg    300
aagaccctga ctggtaagac catcaccctc gaggtggagc ccagtgacac catcgagaat    360
gtcaaggcaa agatccaaga taaggaaggc atccctcctg atcagcagag gttgatcttt    420
gctgggaaac agctggaaga tggacgcacc ctgtctgact acaacatcca gaaagagtcc    480
actctgcact tggtcctgcg cttgaggggg ggtgtctaag tttccccttt taaggtttcm    540
acaaatttca ttgcactttc ctttcaataa agttgttgca ttccc                    585
```

<210> SEQ ID NO 46
<211> LENGTH: 481
<212> TYPE: DNA
<213> ORGANISM: Homo sapien

<400> SEQUENCE: 46

```
gaactgggcc ctgagcccaa gtcatgcctt gtgtccgcat ctgccgtgtc acctctgtkc     60
ctgcccctca cccctccctc ctggtcttct gagccagcac catctccaaa tagcctattc    120
cttcctgcaa atcacacaca catgcgggcc acacatacct gctgccctgg agatggggaa    180
gtaggagaga tgaatagagg cccatacatt gtacagaagg aggggcaggt gcagataaaa    240
gcagcagacc cagcggcagc tgaggtgcat ggagcacggt tggggccggc attgggctga    300
gcacctgatg ggcctcatct cgtgaatcct cgaggcagcg ccacagcaga ggagttaagt    360
ggcacctggg ccgagcagag caggagactg agggtcagag tggaggctaa gctgccctgg    420
aactcctcaa tcttgcctgc cccctagtat gaagccccct tcctgcccct acaattcctg    480
a                                                                    481
```

<210> SEQ ID NO 47

-continued

```
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47

atggatctta ctttgccacc caggttggag tgcagtgctg caatcttggc tcactgcagc     60

cttaacctcc caggctcaag ctatcctcct gccaaagcct tccacatagc tgggactaca    120

ggtacacngc caccacaccc agctaaaatt tttgtatttt ttgtagagac gggatctcgc    180

cacgttgccc aggctggtcc catcctgacc tcaagcagat ctgcccacct cagccccccca    240

acgtgctagg attacaggcg tgagccaccg cacccagcct ttgttttgct tttaatggaa    300

tcaccagttc ccctccgtgt ctcagcagca gctgtgagaa atgctttgca tctgtgacct    360

ttatgaaggg gaacttccat gctgaatgag ggtaggatta catgctcctg tttcccgggg    420

gtcaagaaag cctcagactc cagcatgata agcagggtga g                        461


<210> SEQ ID NO 48
<211> LENGTH: 571
<212> TYPE: DNA
<213> ORGANISM: Homo sapien

<400> SEQUENCE: 48

ataggggctt taaggaggga attcaggttc aatgaggtcg taaggccagg gctcttatcc     60

agtaagactg ggtccttag atgagaaaga gacacccgag gtccttctct ctgccgtgtg    120

aggatgcatc aagaaggcgg ccgtctgcaa gcgaaggaga ggccgcacca gaaaccgaca    180

ccttcatctt ggacttgcag cctctagaac tgagaaaata actgtctgtt ggttaagcca    240

cccagtttgt agtattctct tatggcttcc taagcagact aacaaacaaa cacccaaaat    300

taactgatgg cttcgctgtc ttctgtaaaa attgctatga gagaactttt cactcactgt    360

tttgcagttt ctccctcagt ccctggttct ttcttctcac ataatcccaa tttcaattta    420

tagttcatgg cccaggcaga gtcattcatc acggcatctc ctgagctaaa ccagcacctg    480

ctctgctcac ttcttgactg gctgctcatc atcagccctc ttgcagagat ttcatttcct    540

cccgtgccag gtacttcacg caccaagctc a                                  571


<210> SEQ ID NO 49
<211> LENGTH: 511
<212> TYPE: DNA
<213> ORGANISM: Homo sapien

<400> SEQUENCE: 49

ggataatgaa gttgttttat ttagcttgga caaaaaggca tattcctcta ttttcttata     60

caacaaatat ccccaaaata aagcaagcat atatatcttg aatgtgtaat aatccagtga    120

taaacaagag cagtacttta aaagaaaaaa aaatatgtat ttctgtcagg ttaaaatgag    180

aatcaaaacc atttactctg ctaactcatt attttttgct ttctttttgg ttaagagagg    240

caatgcaata cactgaaaaa ggtttttatc ttatctggca ttggaattag acatattcaa    300

accccagccc ccatttccaa actttaagac cacaaacaag taatttactt ttctgaacat    360

tggtttttttc tggaaaatgg gaattataaa atagactttg cagactctta tgagattaaa    420

taagataatg tatgaaattc tttcttcttt tttacttctt tttcctttt gagatggagt    480

ctcaccccgt cacccaggct ggagtacagt g                                  511
```

-continued

<210> SEQ ID NO 50
<211> LENGTH: 561
<212> TYPE: DNA
<213> ORGANISM: Homo sapien

<400> SEQUENCE: 50
ccactgcact ccagcctggg tgacggagtg agactctgtc tcaaaaaaac aaacaaacaa 60
acaaacaaaa aactgaaaag gaaatagagt tcctctttcc tcatatatga atatattatt 120
tcaacagatt gttgatcacc taccatatgc ttggtattgt tctaattgct ggggatacag 180
caagaggttc tgcagaactt catggagcat gaaagtaaat aaacaaagtt aatttcaagg 240
ccaggcatgg ttgctcacac ctttagtccc agcactttgg gaggctgagg caggtggatc 300
acttgggccc aggagttcaa ggctgcagtg agccaagatt gtgccactac tctccaggct 360
gggcaacaga gcaagaccct gtctcagggg gaacaaaaag ttaatttcag attttgttaa 420
gtgctgtaaa ggaagtaaat aggttgatat tcaagagagc acctgaaggc caggcgtggt 480
ggctcacgcc tgtggtctaa cgctttggga agcccgagcg ggcggatcac aaggtcagga 540
gaattttggc caggcatggt g 561

<210> SEQ ID NO 51
<211> LENGTH: 451
<212> TYPE: DNA
<213> ORGANISM: Homo sapien

<400> SEQUENCE: 51
agaatccatt tattgggttt taaactagtt acacaactga aatcagtttg gcactacttt 60
atacagggat tacgcctgtg tatgccgaca cttaaatact gtaccaggac cactgctgtg 120
cttaggtctg tattcagtca ttcagcatgt agatactaaa aatatactgt agtgttcctt 180
taaggaagac tgtacagggt gtgttgcaag atgacattca ccaatttgtg aattatttca 240
acccagaaga tacctttcac tctataaact tgtcataggc aaacatgtgg tgttagcatt 300
gagagatgca cacaaaaatg ttacataaaa gttcagacat tctaatgata agtgaactga 360
aaaaaaaaaa aaccccacat ctcaattttt gtaacaagat aaagaaaata atttaaaaac 420
acaaaaaatg gcattcagtg ggtacaaagc c 451

<210> SEQ ID NO 52
<211> LENGTH: 682
<212> TYPE: DNA
<213> ORGANISM: Homo sapien

<400> SEQUENCE: 52
caaatattta atataaatct ttgaaacaag ttcagakgaa ataaaaatca aagtttgcaa 60
aaacgtgaag attaacttaa ttgtcaaata ttcctcattg ccccaaatca gtattttttt 120
tatttctatg caaaagtatg ccttcaaact gcttaaatga tatatgatat gatacacaaa 180
ccagttttca aatagtaaag ccagtcatct tgcaattgta agaaataggt aaaagattat 240
aagacacctt acacacacac acacacacac acacacacgt gtgcaccgcc aatgacaaaa 300
aacaatttgg cctctcctaa aataagaaca tgaagaccct taattgctgc caggagggaa 360
cactgtgtca cccctcccta caatccaggt agtttccttt aatccaatag caaatctggg 420
catatttgag aggagtgatt ctgacagcca csgttgaaat cctgtgggga accattcatg 480
tccacccact ggtgccctga aaaaatgcca ataatttttc gctcccactt ctgctgctgt 540

-continued

```
ctcttccaca tcctcacata gaccccagac ccgctggccc ctggctgggc atcgcattgc    600

tggtagagca agtcataggt ctcgtctttg acgtcacaga agcgatacac caaattgcct    660

ggtcggtcat tgtcataacc ag                                             682
```

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53

```
tttgacttta gtaggggtct gaactattta ttttactttg ccmgtaatat ttaraccyta     60

tatatctttc attatgccat cttatcttct aatgbcaagg gaacagwtgc taamctggct    120

tctgcattwa tcacattaaa aatggctttc ttggaaaatc ttcttgatat gaataaagga    180

tcttttavag ccatcattta aagcmggntt ctctccaaca cgagtctgct sasgggggk    240

gagctgtgaa ctctggctga aggctttccc atacacactg caatgacmtg gtttctgacc    300

agbgtgagtt a                                                         311
```

<210> SEQ ID NO 54
<211> LENGTH: 561
<212> TYPE: DNA
<213> ORGANISM: Homo sapien

<400> SEQUENCE: 54

```
agagaagccc cataaatgca atcagtgtgg gaaggccttc agtcagagct caagcctttt     60

cctccatcat cgggttcata ctggagagaa accctatgta tgtaatgaat gcggcagagc    120

ctttggtttt aactctcatc ttactgaaca cgtaaggatt cacacaggag aaaaaaccta    180

tgtttgtaat gagtgcggca aagcctttcg tcggagttcc actcttgttc agcatcgaag    240

agttcacact ggggagaagc cctaccagtg cgttgaatgt gggaaagctt tcagccagag    300

ctcccagctc accctacatc agccgagttc acactggaga gaagccctat gactgtggtg    360

actgtgggaa ggccttcagc cggaggtcaa ccctcattca gcatcagaaa gttcacagcg    420

gagagactcg taagtgcaga aaacatggtc cagcctttgt tcatggctcc agcctcacag    480

cagatggaca gattcccact ggagagaagc acggcagaac ctttaaccat ggtgcaaatc    540

tcattctgcg ctggacagtt c                                              561
```

<210> SEQ ID NO 55
<211> LENGTH: 811
<212> TYPE: DNA
<213> ORGANISM: Homo sapien

<400> SEQUENCE: 55

```
gagacagggt ctcactttgt cacccaggct ggaatgcagt ggtgcgatct tacgtagctc     60

actgcagccc tgacctcctg gactcaaaca attctcctgc ctcagccctg caagtagctg    120

ggactgtggg tgcatgccac catgcctggc taacttttgt agtttttgta aagatggggt    180

tttgccatgt tgcacatgct ggtcttgaac tcctgagctc aaacgatctg cccacctcgg    240

cctcccagaa tgttgggatt acaggggtaa accaccacgc ctggccccat tagggtattc    300

ttagcatcca cttgctcact gagattaatc ataagagatg ataagcactg gaagaaaaaa    360

atttttacta ggctttggat attttttttcc tttttcagct ttatacagag gattggatct    420
```

-continued ttagttttcc tttaactgat aataaaacat tgaaaggaaa taagtttacc tgagattcac 480
agagataacc ggcatcactc ccttgctcaa ttccagtctt taccacatca attattttca 540
gaggtgcagg ataaaggcct ttagtctgct ttcgcacttt ttcttccact tttttgtaaa 600
cctgttgcct gacaaatgga attgacagcg tatgccatga ctattccatt tgtcaggcat 660
acgctgtcaa tttttccacc aatcccttgt ctctctttgg agagatcttc ttatcagcta 720
gtcctttggc aaaagtaatt gcaacttctt ctaggtattc tattgtccgt tccactggtg 780
gaacccctgg gaccaggact aaaacctcca g 811

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56
atctcatata tatatttctt cctgacttta tttgcttgct tctgncacgc atttaaaata 60
tcacagagac caaaatagag cggctttctg gtggaacgca tggcagtcac aggacaaaat 120
acaaaactag gggctctgt cttctcatac atcatacaat tttcaagtat ttttttatg 180 tacaaagagc tactctatct gaaaaaaaat taaaaaataa atgagacaag atagtttatg 240
catcctagga agaaagaatg ggaagaaaga acggggcagt tgggtacaga ttcctgtccc 300
ctgttcccag ggaccactac cttcctgcca ctgagttccc ccacagcctc acccatcatg 360
tcacagggca agtgccaggg taggtgggga ccagtggaga caggaaccag caacatactt 420
tggcctggaa gataaggaga aagtctcaga aacacactgg tgggaagcaa tcccacnggc 480
cgtgccccan gagcttccca cctgctgctg gctccctggg tggctttggg aacagcttgg 540
gcaggccctt ttgggtgggg nccaactggg cctttgggcc cgtgtggaaa g 591

<210> SEQ ID NO 57
<211> LENGTH: 481
<212> TYPE: DNA
<213> ORGANISM: Homo sapien

<400> SEQUENCE: 57
aaacattgag atggaatgat agggtttccc agaatcaggt ccatatttta actaaatgaa 60
aattatgatt tatagccttc tcaaatacct gccatacttg atatctcaac cagagctaat 120
tttacctctt tacaaattaa ataagcaagt aactggatcc acaatttata atacctgtca 180
attttttctg tattaaacct ctatcatagt ttaagcctat tagggtactt aatccttaca 240
aataaacagg tttaaaatca cctcaatagg caactgccct tctggttttc ttctttgact 300
aaacaatctg aatgcttaag attttccact ttgggtgcta gcagtacaca gtgttacact 360
ctgtattcca gacttcttaa attatagaaa aaggaatgta cactttttgt attctttctg 420
agcagggccg ggaggcaaca tcatctacca tggtagggac ttgtatgcat ggactacttt 480
a 481

<210> SEQ ID NO 58
<211> LENGTH: 141
<212> TYPE: DNA
<213> ORGANISM: Homo sapien -continued

<400> SEQUENCE: 58
actctgtcgc ccaggctgga gcccabtggm gcgatctcga ctccctgcaa gctmcgcctc 60
acaggwtcat gccattctcc tgcctcagca tctggagtag ctgggactac aggcgccagc 120
caccatgccc agctaatttt t 141

<210> SEQ ID NO 59
<211> LENGTH: 191
<212> TYPE: DNA
<213> ORGANISM: Homo sapien

<400> SEQUENCE: 59
accttaaaga cataggagaa tttatactgg gagagaaagc ttacaaatgt aaggtttctg 60
acaagacttg ggagtgattc acacctggaa caacatactg gacttcacac tggabagaaa 120
ccttacaagt gtaatgagtg tggcaaagcc tttggcaagc agtcaacact tattcaccat 180
caggcaattc a 191

<210> SEQ ID NO 60
<211> LENGTH: 480
<212> TYPE: DNA
<213> ORGANISM: Homo sapien

<400> SEQUENCE: 60
agtcaggatc atgatggctc agtttcccac agcgatgaat ggagggccaa atatgtgggc 60
tattacatct gaagaacgta ctaagcatga taaacagttt gataacctca aaccttcagg 120
aggttacata acaggtgatc aagcccgtac tttttttccta cagtcaggtc tgccggcccc 180
ggttttagct gaaatatggg ccttatcaga tctgaacaag gatgggaaga tggaccagca 240
agagttctct atagctatga aactcatcaa gttaaagttg cagggccaac agctgcctgt 300
agtcctccct cctatcatga aacaaccccc tatgttctct ccactaatct ctgctcgttt 360
tgggatggga agcatgccca atctgtccat tcatcagcca ttgcctccag ttgcacctat 420
agcaacaccc ttgtcttctg ctacttcagg gaccagtatt cctccctaat gatgcctgct 480

<210> SEQ ID NO 61
<211> LENGTH: 381
<212> TYPE: DNA
<213> ORGANISM: Homo sapien

<400> SEQUENCE: 61
ctttcgattt ccttcaattt gtcacgtttg attttatgaa gttgttcaag ggctaactgc 60
tgtgtattat agctttctct gagttccttc agctgattgt taaatgaatc catttctgag 120
agcttagatg cagtttcttt ttcaagagca tctaattgtt ctttaagtct ttggcataat 180
tcttcctttt ctgatgactt tctatgaagt aaactgatcc ctgaatcagg tgtgttactg 240
agctgcatgt ttttaattct ttcgtttaat agctgcttct cagggaccag atagataagc 300
ttattttgat attccttaag ctcttggtga agttgttcga tttccataat ttccaggtca 360
cactggttat cccaaacttc t 381

<210> SEQ ID NO 62
<211> LENGTH: 906
<212> TYPE: DNA
<213> ORGANISM: Homo sapien

<400> SEQUENCE: 62
gtggaggtga aacggaggca agaaaggggg ctacctcagg agcgagggac aaagggggcg 60

-continued tgaggcacct aggccgcggc accccggcga caggaagccg tcctgaaccg ggctaccggg 120
taggggaagg gcccgcgtag tcctcgcagg gccccagagc tggagtcggc tccacagccc 180
cgggccgtcg gcttctcact tcctggacct ccccggcgcc cgggcctgag gactggctcg 240
gcggagggag aagaggaaac agacttgagc agctccccgt tgtctcgcaa ctccactgcc 300
gaggaactct catttcttcc ctcgctcctt caccccccac ctcatgtaga aaggtgctga 360
agcgtccgga gggaagaaga acctgggcta ccgtcctggc cttcccmccc ccttcccggg 420
gcgctttggt gggcgtggag ttggggttgg gggggtgggt gggggttctt ttttggagtg 480
ctggggaact tttttccctt cttcaggtca ggggaaaggg aatgcccaat tcagagagac 540
atgggggcaa gaaggacggg agtggaggag cttctggaac tttgcagccg tcatcgggag 600
gcggcagctc taacagcaga gagcgtcacc gcttggtatc gaagcacaag cggcataagt 660
ccaaacactc caaagacatg ggttggtga cccccgaagc agcatccctg ggcacagtta 720
tcaaaccttt ggtggagtat gatgatatca gctctgattc cgacaccttc tccgatgaca 780
tggccttcaa actagaccga agggagaacg acgaacgtcg tggatcagat cggagcgacc 840
gcctgcacaa acatcgtcac caccagcaca ggcgttcccg ggacttacta aaagctaaac 900
agaccg 906

<210> SEQ ID NO 63
<211> LENGTH: 491
<212> TYPE: DNA
<213> ORGANISM: Homo sapien

<400> SEQUENCE: 63
gacatgtttg cctgcagggg accagagaca atgggattag ccagtgctca ctgttcttta 60
tgcttccaga gaggatgggg acagctctca ggtcagaatc caggctgaga aggccatgct 120 ggttggggc ccccggaagc acggtccgga tcctccctgg catcagcgta gacccgctgc 180
tcaggcttgg ggtaccaaac tcatgctctg tactgttttg gccccatgcg gtgagaggaa 240
aacctagaaa aagattggtc gtgctaagga atcagctgcc ccctcatcct ccgcatccaa 300
tgctggtgac aacatattcc ctctcccagg acacagactc ggtgactcca cactgggctg 360
agtggcctct ggaggctcgt ggcctaaggc agggctccgt aaggctgatc ggctgaactg 420
ggtggggtga gggtttctga cccttcgctt cccatcccat aaccgctgtc aatgagctca 480
cactgtggtc a 491

<210> SEQ ID NO 64
<211> LENGTH: 511
<212> TYPE: DNA
<213> ORGANISM: Homo sapien

<400> SEQUENCE: 64
gatggcatgg tcgttgctaa tgtgcctgct gggatggagc acttcctcct gtgagcccag 60
gggacccgcc tgtccctgga gcttggggca aggagggaag agtgatacca ggaaggtggg 120
gctgcagcca ggggccagag tcagttcagg gagtggtcct cggccctcaa agctcctccg 180
gggactgctc aggagtgatg gtgccctgga gtttgcccca acttccctgg ccaccctgga 240
aggtgcctgg ctgctccagg cctctaggct gggctgatgg gtttctccag gacacaagta 300
tcattaaagc caccctctcc tcagcttgtc aggccgcaca tgtgggacag gctgtgctca 360
caaccccctc gcctgccctg ccctccatca ggaggagcca gtggaacctt cggaaagctc 420

-continued

```
ccagcatctc agcagccctc aaaagtcgtc ctggggcaag ctctggttct cctgactgga    480

ggtcatctgg gcttggcctg ctctctctcg c                                   511


<210> SEQ ID NO 65
<211> LENGTH: 394
<212> TYPE: DNA
<213> ORGANISM: Homo sapien

<400> SEQUENCE: 65

taaaaaagtg taacaaaggt ttatttagac tttcttcatg cccccagatc caggatgtct     60

atgtaaaccg ttatcttaca aagaaagcac aatatttggt ataaactaag tcagtgactt    120

gcttaactga aatagcgtcc atccaaaagt gggtttaagg taaaactacc tgacgatatt    180

ggcggggatc ctgcagtttg gactgcttgc cgggtttgtc cagggttccg ggtctgttct    240

tggcactcat ggggacaggc atcctgctcg tctgtggggc cccgctggag cccttacgtg    300

aagctgaagg tatcgaccst agggggctct agggcagtgg gaccttcatc cggaactaac    360

aagggtcggg gagaggcctc ttgggctatg tggg                                394


<210> SEQ ID NO 66
<211> LENGTH: 359
<212> TYPE: DNA
<213> ORGANISM: Homo sapien

<400> SEQUENCE: 66

caagcgttcc tttatggatg taaattcaaa cagtcatgct gagccatccc gggctgacag     60

tcacgttwaa gacactaggt cgggcgccac agtgccaccc aaggagaaga agaatttgga    120

atttttccat gaagatgtac ggaaatctga tgttgaatat gaaaatggcc cccaaatgga    180

attccaaaag gttaccacag gggctgtaag acctagtgac cctcctaagt gggaaagagg    240

aatggagaat agtatttctg atgcatcaag aacatcagaa tataaaactg agatcataat    300

gaaggaaaat tccatatcca atatgagttt actcagagac agtagaaact attcccagg     359


<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67

taggaataac aaatgtttat tcagaaatgg ataagtaata cataatcacc cttcatctct     60

taatgcccct tcctctcctt ctgcacagga gacacagatg ggtaacatag aggcatggga    120

agtggaggag gacacaggac tagcccacca ccttctcttc ccggtctccc aagatgactg    180

cttatagagt ggaggaggca aacaggtccc ctcaatgtac cagatggtca cctatagcac    240

cagctccaga tggccacgtg gttgcagctg gactcaatga aactctgtga caaccagaag    300

atacctgctt tgggatgaga gggaggataa agccatgcag ggaggatatt taccatccct    360

accctaagca cagtgcaagc agtgagcccc cggctcccag tacctgaaaa accaaggcct    420

actgnctttt ggatgctctc ttgggccacg                                     450


<210> SEQ ID NO 68
<211> LENGTH: 511
<212> TYPE: DNA
<213> ORGANISM: Homo sapien
```

-continued

<400> SEQUENCE: 68
aagcctcctg ccctggaaat ctggagcccc ttggagctga gctggacggg gcagggaggg 60
gctgagaggc aagaccgtct ccctcctgct gcagctgctt ccccagcagc cactgctggg 120
cacagcagaa acgccagcag agaaaatggg agccgagagt ccttagccct ggagctgagg 180
ctgcctctgg gctgacccgc tggctgtacg tggccagaac tggggttggc atctggcatc 240
catttgaggc cagggtggag gaaagggagg ccaacagagg aaaacctatt cctgctgtga 300
caacacagcc cttgtcccac gcagcctaag tgcagggagc gtgatgaagt caggcagcca 360
gtcggggagg acgaggtaac tcagcagcaa tgtcaccttg tagcctatgc gctcaatggc 420
ccggaggggc agcaaccccc cgcacacgtc agccaacagc agtgcctctg caggcaccaa 480
gagagcgatg atggacttga gcgccgtgtt c 511

<210> SEQ ID NO 69
<211> LENGTH: 511
<212> TYPE: DNA
<213> ORGANISM: Homo sapien

<400> SEQUENCE: 69
gtttggcaga agacatgttt aataacattt tcatatttaa aaaatacagc aacaattctc 60
tatctgtcca ccatcttgcc ttgcccttcc tggggctgag gcagacaaag gaaaggtaat 120
gaggttaggg cccccaggcg ggctaagtgc tattggcctg ctcctgctca aagagagcca 180
tagccagctg ggcacggccc cctagcccct ccaggttgct gaggcggcag cggtggtaga 240
gttcttcact gagccgtggg ctgcagtctc gcagggagaa cttctgcacc agccctggct 300
ctacggcccg aaagaggtgg agccctgaga accggaggaa aacatccatc acctccagcc 360
cctccagggc ttcctcctct tcctggcctg ccagttcacc tgccagccgg gctcgggccg 420
ccaggtagtc agcgttgtag aagcagccct ccgcagaagc ctgccggtca aatctccccg 480
ctataggagc cccccgggag gggtcagcac c 511

<210> SEQ ID NO 70
<211> LENGTH: 511
<212> TYPE: DNA
<213> ORGANISM: Homo sapien

<400> SEQUENCE: 70
caagttgaac gtcaggcttg gcagaggtgg agtgtagatg aaaacaaagg tgtgattatg 60
aagaggatgt gagtcctttg ggtgtaggag agaaaggctg ttgagcttct atttcaagat 120
acttttacct gtgcaaaaag cacattttcc acctccttct catggcattt gtgtaaggtg 180
agtatgattc ctattccatc tgcattttag aggtgaagaa taacgtacaa gggattcagt 240
gattagcaag ggacccctca ctaagtgttg atggagttag gacagagctc agctgtttga 300
atctcagagc ccaggcagct ggagctgggt aggatcctgg agctggcact aatgtgaggt 360
gcattccctc caacccaggc tcagatccgg aacctgaccg tgctgacccc cgaaggggag 420
gcagggctga gctggcccgt tgggctccct gctcctttca caccacactc tcgctttgag 480
gtgctgggct gggactactt cacagagcag c 511

<210> SEQ ID NO 71
<211> LENGTH: 511
<212> TYPE: DNA
<213> ORGANISM: Homo sapien -continued

<400> SEQUENCE: 71
tggcctgggc aggattggga gagaggtagc tacccggatg cagtcctttg ggatgaagac 60
tatagggtat gaccccatca tttccccaga ggtctcggcc tcctttggtg ttcagcagct 120
gcccctggag gagatctggc ctctctgtga tttcatcact gtgcacactc ctctcctgcc 180
ctccacgaca ggcttgctga atgacaacac ctttgcccag tgcaagaagg gggtgcgtgt 240
ggtgaactgt gcccgtggag ggatcgtgga cgaaggcgcc ctgctccggg ccctgcagtc 300
tggccagtgt gccggggctg cactggacgt gtttacggaa gagccgccac gggaccgggc 360
cttggtggac catgagaatg tcatcagctg tccccacctg ggtgccagca ccaaggaggc 420
tcagagccgc tgtggggagg aaattgctgt tcagttcgtg gacatggtga aggggaaatc 480
tctcacgggg gttgtgaatg cccaggccct t 511

<210> SEQ ID NO 72
<211> LENGTH: 2017
<212> TYPE: DNA
<213> ORGANISM: Homo sapien

<400> SEQUENCE: 72
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt acatcctcat 540
taccaaatgg aactgccagt ctcattcagc ctttatccat tccttattct tcttcaacat 600
tgcctcatgc atcatcttac agcctgatga tgggaggatt tggtggtgct agtatccaga 660
aggcccagtc tctgattgat ttaggatcta gtagctcaac ttcctcaact gcttccctct 720
cagggaactc acctaagaca gggacctcag agtgggcagt tcctcagcct tcaagattaa 780
agtatcggca aaaatttaat agtctagaca aaggcatgag cggatacctc tcaggttttc 840
aagctagaaa tgcccttctt cagtcaaatc tctctcaaac tcagctagct actatttgga 900
ctctggctga catcgatggt gacggacagt tgaaagctga agaatttatt ctggcgatgc 960
acctcactga catggccaaa gctggacagc cactaccact gacgttgcct cccgagcttg 1020
tccctccatc tttcagaggg ggaaagcaag ttgattctgt taatggaact ctgccttcat 1080
atcagaaaac acaagaagaa gagcctcaga agaaactgcc agttactttt gaggacaaac 1140
ggaaagccaa ctatgaacga ggaaacatgg agctggagaa gcgacgccaa gtgttgatgg 1200
agcagcagca gagggaggct gaacgcaaag cccagaaaga gaaggaagag tggggagcgga 1260 aacagagaga actgcaagag caagaatgga agaagcagct ggagttggag aaacgcttgg 1320
agaaacagag agagctggag agacagcggg aggaagagag gagaaaggag atagaaagac 1380
gagaggcagc aaaacaggag cttgagagac aacgccgttt agaatgggaa agactccgtc 1440
ggcaggagct gctcagtcag aagaccaggg aacaagaaga cattgtcagg ctgagctcca 1500
gaaagaaaag tctccacctg gaactggaag cagtgaatgg aaaacatcag cagatctcag 1560

-continued gcagactaca agatgtccaa atcagaaagc aaacacaaaa gactgagcta gaagttttgg 1620
ataaacagtg tgacctggaa attatggaaa tcaaacaact tcaacaagag cttaaggaat 1680
atcaaaataa gcttatctat ctggtccctg agaagcagct attaaacgaa agaattaaaa 1740
acatgcagct cagtaacaca cctgattcag ggatcagttt acttcataaa aagtcatcag 1800
aaaaggaaga attatgccaa agacttaaag aacaattaga tgctcttgaa aaagaaactg 1860
catctaagct ctcagaaatg gattcattta acaatcagct gaaggaactc agagaaagct 1920
ataatacaca gcagttagcc cttgaacaac ttcataaaat caaacgtgac aaattgaagg 1980
aaatcgaaag aaaaagatta gagcaaaaaa aaaaaaa 2017

<210> SEQ ID NO 73
<211> LENGTH: 414
<212> TYPE: DNA
<213> ORGANISM: Homo sapien

<400> SEQUENCE: 73
atggcagtga cattcaccat catgggaacc accttccctt ttcttcagga ttctctgtag 60
tggaagagag cacccagtgt tgggctgaaa acatctgaaa gtagggagaa gaacctaaaa 120
taatcagtat ctcagagggc tctaaggtgc caagaagtct cactggacat ttaagtgcca 180
acaaaggcat actttcggaa tcgccaagtc aaaactttct aacttctgtc tctctcagag 240
acaagtgaga ctcaagagtc tactgcttta gtggcaacta cagaaaactg gtgttaccca 300
gaaaaacagg agcaattaga aatggttcca atatttcaaa gctccgcaaa caggatgtgc 360
tttcctttgc ccatttaggg tttcttctct ttcctttctc tttattaacc acta 414

<210> SEQ ID NO 74
<211> LENGTH: 1567
<212> TYPE: DNA
<213> ORGANISM: Homo sapien

<400> SEQUENCE: 74
atatctagaa gtctggagtg agcaaacaag agcaagaaac aaaaagaagc caaaagcaga 60
aggctccaat atgaacaaga taaatctatc ttcaaagaca tattagaagt tgggaaaata 120
attcatgtga actagacaag tgtgttaaga gtgataagta aaatgcacgt ggagacaagt 180
gcatccccag atctcaggga cctccccctg cctgtcacct ggggagtgag aggacaggat 240
agtgcatgtt ctttgtctct gaatttttag ttatatgtgc tgtaatgttg ctctgaggaa 300
gcccctggaa agtctatccc aacatatcca catcttatat tccacaaatt aagctgtagt 360
atgtacccta agacgctgct aattgactgc cacttcgcaa ctcaggggcg gctgcatttt 420
agtaatgggt caaatgattc actttttatg atgcttccaa aggtgccttg gcttctcttc 480
ccaactgaca aatgccaaag ttgagaaaaa tgatcataat tttagcataa acagagcagt 540
cggcgacacc gattttataa ataaactgag caccttcttt ttaaacaaac aaatgcgggt 600
ttatttctca gatgatgttc atccgtgaat ggtccaggga aggacctttc accttgacta 660
tatggcatta tgtcatcaca agctctgagg cttctccttt ccatcctgcg tggacagcta 720
agacctcagt tttcaatagc atctagagca gtgggactca gctggggtga tttcgccccc 780
catctccggg ggaatgtctg aagacaattt tgttacctca atgagggagt ggaggaggat 840
acagtgctac taccaactag tggataaagg ccagggatgc tgctcaacct cctaccatgt 900
acaggacgtc tccccattac aactacccaa tccgaagtgt caactgtgtc aggactaaga 960

-continued aaccctggtt ttgagtagaa aagggcctgg aaagagggga gccaacaaat ctgtctgctt 1020
cctcacatta gtcattggca aataagcatt ctgtctcttt ggctgctgcc tcagcacaga 1080
gagccagaac tctatcgggc accaggataa catctctcag tgaacagagt tgacaaggcc 1140
tatgggaaat gcctgatggg attatcttca gcttgttgag cttctaagtt tctttccctt 1200
cattctaccc tgcaagccaa gttctgtaag agaaatgcct gagttctagc tcaggttttc 1260
ttactctgaa tttagatctc cagacccttc ctggccacaa ttcaaattaa ggcaacaaac 1320
atataccttc catgaagcac acacagactt ttgaaagcaa ggacaatgac tgcttgaatt 1380
gaggccttga ggaatgaagc tttgaaggaa aagaatactt tgtttccagc cccttcccca 1440
cactcttcat gtgttaacca ctgccttcct ggaccttgga gccacggtga ctgtattaca 1500
tgttgttata gaaaactgat tttagagttc tgatcgttca agagaatgat taaatataca 1560
tttccta 1567

<210> SEQ ID NO 75
<211> LENGTH: 240
<212> TYPE: DNA
<213> ORGANISM: Homo sapien

<400> SEQUENCE: 75
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg gggaaaaaca ccatggtttt atccaccctg agatctttga acaacttcat 180
ctctcagcgt gcggagggag gctctggact ggatatttct acctcggccg cgaccacgct 240

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 76
tagcgyggtc gcggccgagg yctgcttytc tgtccagccc agggcctgtg gggtcagggc 60
ggtgggtgca gatggcatcc actccggtgg cttccccatc tttctctggc ctgagcaagg 120
tcagcctgca gccagagtac agagggccaa cactggtgtt cttgaacaag ggccttagca 180
ggccctgaag grccctctct gtagtgttga acttcctgga gccaggccac atgttctcct 240
cataccgcag gytagygatg gtgaagttga gggtgaaata gtattmangr agatggctgg 300
caracctgcc cgggcggccg ctcsaaatcc 330

<210> SEQ ID NO 77
<211> LENGTH: 361
<212> TYPE: DNA
<213> ORGANISM: Homo sapien

<400> SEQUENCE: 77
agcgtggtcg cggccgaggt gtccttcagg gtctgcttat gcccttgttc aagaacacca 60
gtgtcagctc tctgtactct ggttgcagac tgaccttgct caggcctgag aaggatgggg 120
cagccaccag agtggatgct gtctgcaccc atcgtcctga ccccaaaagc cctggactgg 180
acagagagcg gctgtactgg aagctgagcc agctgaccca cggcatcact gagctgggcc 240
cctacaccct ggacagggac agtctctatg tcaatggttt cacccatcgg agctctgtac 300

-continued

```
ccaccaccag caccggggtg gtcagcgagg agccattcaa cctgcccggg cggccgctcg    360

a                                                                     361


<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78

ttggggnttt mgagcggccg cccgggcagg taccggggtg gtcagcgagg agccattcac     60

actgaacttc accatcaaca acctgcggta tgaggagaac atgcagcacc ctggctccag    120

gaagttcaac accacggaga gggtccttca gggcctgctc aggtccctgt tcaagagcac    180

cagtgttggc cctctgtact ctggctgcag actgactttg ctcagacttg agaaacatgg    240

ggcagccact ggagtggacg ccatctgcac cctccgcctt gatcccactg gtcctggact    300

ggacagagag cggctatact gggagctgag ccagtcctct ggcggngacn ccnctt        356


<210> SEQ ID NO 79
<211> LENGTH: 226
<212> TYPE: DNA
<213> ORGANISM: Homo sapien

<400> SEQUENCE: 79

agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226


<210> SEQ ID NO 80
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80

tgtggtgttg aacttcctgg agncagggtg acccatgtcc tccccatact gcaggttggt     60

gatggtgaag ttgagggtga atggtaccag gagagggcca gcagccataa ttgtsgrgck    120

gsmgmssgag gmwggwgtyy cwgaggttcy rarrtccact gtggaggtcc caggagtgct    180

ggtggtgggc acagagstcy gatgggtgaa accattgaca tagagactgt tcctgtccag    240

ggtgtagggg cccagctctt yratgycatt ggycagttkg ctyagctccc agtacagccr    300

ctctckgyyg mgwccagsgc ttttggggtc aagatgatgg atgcagatgg catccactcc    360

agtggctgct ccatccttct cggacctgag agaggtcagt ctgcagccag agtacagagg    420

gccaacactg gtgttctttg aata                                           444


<210> SEQ ID NO 81
<211> LENGTH: 310
<212> TYPE: DNA
<213> ORGANISM: Homo sapien
```

-continued

<400> SEQUENCE: 81

```
tcgagcggcc gcccgggcag gtcaggaagc acattggtct tagagccact gcctcctgga     60

ttccacctgt gctgcggaca tctccaggga gtgcagaagg gaagcaggtc aaactgctca    120

gatcagtcag actggctgtt ctcagttctc acctgagcaa ggtcagtctg cagccagagt    180

acagagggcc aacactggtg ttcttgaaca agggcttgag cagaccctgc agaaccctct    240

tccgtggtgt tgaacttcct ggaaaccagg gtgttgcatg tttttcctca taatgcaagg    300

ttggtgatgg                                                          310
```

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82

```
acggtttcaa tggacacttt tattgtttac ttaatggatc atcaattttg tctcactacc     60

tacaaatgga atttcatctt gtttccatgc tgagtagtga aacagtgaca aagctaatca    120

taataaccta catcaaaaga gaactaagct aacactgctc actttctttt taacaggcaa    180

aatataaata tatgcactct anaatgcaca atggtttagt cactaaaaaa ttcaaatggg    240

atcttgaaga atgtatgcaa atccagggtg cagtgaagat gagctgagat gctgtgcaac    300

tgtttaaggg ttcctggcac tgcatctctt ggccactagc tgaatcttga catggaaggt    360

tttagctaat gccaagtgga gatgcagaaa atgctaagtt gacttagggg ctgtgcacag    420

gaactaaaag gcaggaaagt actaaatatt gctgagagca tccaccccag gaaggacttt    480

accttccagg agctccaaac tggcaccacc cccagtgctc acatggctga ctttatcctc    540

cgtgttccat ttggcacagc aagtggcagt g                                  571
```

<210> SEQ ID NO 83
<211> LENGTH: 551
<212> TYPE: DNA
<213> ORGANISM: Homo sapien

<400> SEQUENCE: 83

```
aaggctggtg ggtttttgat cctgctggag aacctccgct ttcatgtgga ggaagaaggg     60

aagggaaaag atgcttctgg gaacaaggtt aaagccgagc cagccaaaat agaagctttc    120

cgagcttcac tttccaagct aggggatgtc tatgtcaatg atgcttttgg cactgctcac    180

agagcccaca gctccatggt aggagtcaat ctgccacaga aggctggtgg gtttttgatg    240

aagaaggagc tgaactactt tgcaaaggcc ttggagagcc cagagcgacc cttcctggcc    300

atcctgggcg gagctaaagt tgcagacaag atccagctca tcaataatat gctggacaaa    360

gtcaatgaga tgattattgg tggtggaatg gcttttacct tccttaaggt gctcaacaac    420

atggagattg gcacttctct gtttgatgaa gagggagcca agattgtcaa agacctaatg    480

tccaaagctg agaagaatgg tgtgaagatt accttgcctg ttgactttgt cactgctgac    540

aagtttgatg a                                                        551
```

<210> SEQ ID NO 84
<211> LENGTH: 571
<212> TYPE: DNA
<213> ORGANISM: Homo sapien -continued

<400> SEQUENCE: 84
tttgttcctt acatttttct aaagagttac ttaaatcagt caactggtct ttgagactct 60
taagttctga ttccaactta gctaattcat tctgagaact gtggtatagg tggcgtgtct 120
cttctagctg ggacaaaagt tctttgtttt ccccctgtag agtatcacag accttctgct 180
gaagctggac ctctgtctgg gccttggact cccaaatctg cttgtcatgt tcaagcctgg 240
aaatgttaat ctttaattct tccatatgga tggacatctg tctaagttga tcctttagaa 300
cactgcaatt atcttctttg agtctaattt cttcttcttt gctttgaatc gcatcactaa 360
acttcctctc ccatttctta gcttcatcta tcaccctgtc acgatcatcc tggagggaag 420
acatgctctt agtaaaggct gcaagctggg tcacagtact gtccaagttt tcctgaagtt 480
gctgaacttc cttgtctttc ttgttcaaag taacctgaat ctctccaatt gtctcttcca 540
agtggacttt ttctctgcgc aaagcatcca g 571

<210> SEQ ID NO 85
<211> LENGTH: 561
<212> TYPE: DNA
<213> ORGANISM: Homo sapien

<400> SEQUENCE: 85
tcattgcctg tgatggcatc tggaatgtga tgagcagcca ggaagttgta gatttcattc 60
aatcaaagga ttcagcatgt ggtggaagct gtgaggcaag agaaacaaga actgtatggc 120
aagttaagaa gcacagaggc aaacaagaag gagacagaaa agcagttgca ggaagctgag 180
caagaaatgg aggaaatgaa agaaaagatg agaaagtttg ctaaatctaa acagcagaaa 240
atcctagagc tggaagaaga gaatgaccgg cttagggcag aggtgcaccc tgcaggagat 300
acagctaaag agtgtatgga aacacttctt tcttccaatg ccagcatgaa ggaagaactt 360
gaaagggtca aaatggagta tgaaaccctt tctaagaagt ttcagtcttt aatgtctgag 420
aaagactctc taagtgaaga ggttcaagat ttaaagcatc agatagaagg taatgtatct 480
aaacaagcta acctagaggc caccgagaaa catgataacc aaacgaatgt cactgaagag 540
ggaacacagt ctataccagg t 561

<210> SEQ ID NO 86
<211> LENGTH: 795
<212> TYPE: DNA
<213> ORGANISM: Homo sapien

<400> SEQUENCE: 86
aagccaataa tcaccattta ttacttaata tatgccaacc actgtacttg gcagttcaca 60
aattctcacc gttacaacaa ccccatgagg tatttattcc cattctatag atagggaaac 120
cacagctcaa gtaagttagg aaactgagcc aagtatacac agaatacgaa gtggcaaaac 180
tagaaggaaa gactgacact gctatctgct ggcctccagt gtcctggctc ttttcacacg 240
ggttcaatgt ctccagcgct gctgctgctg ctgcattacc atgccctcat tgtttttctt 300
cctctggtgt tcaactgcat ccttcaaaga atctaactca ttccagagac cacttatttc 360
tttctctctt tctgaaatta cttttaataa ttcttcatga gggggaaaag aagatgcctg 420
ttggtagttt tgttgtttaa gctgctcaat ttgggactta aacaatttgt tttcatcttg 480
tacatcctgt aacagctgtg ttttgctaga aagatcactc tccctctctt ttagcatggc 540
ttctaacctc ttcaattcat tttccttttc tttcaacaca atctcaagtt cttcaaactg 600

-continued

```
tgatgcagaa gaggcctctt tcaagttatg ttgtgctact tcctgaacat gtgcttttaa    660

agattcattt tcttcttgaa gatcctgtaa ccacttccct gtattggcta ggtctttctc    720

tttctcttcc aaaacagcct tcatggtatt catctgttcc tcttttcctt ttaataagtt    780

caggagcttc agaac                                                     795


<210> SEQ ID NO 87
<211> LENGTH: 594
<212> TYPE: DNA
<213> ORGANISM: Homo sapien

<400> SEQUENCE: 87

caagcttttt tttttttttt aaaaagtgtt agcattaatg ttttattgtc acgcagatgg     60

caactgggtt tatgtcttca tattttatat ttttgtaaat taaaaaaatt acaagtttta    120

aatagccaat ggctggttat attttcagaa aacatgatta gactaattca ttaatggtgg    180

cttcaagctt ttccttattg gctccagaaa attcacccac cttttgtccc ttcttaaaaa    240

actggaatgt tggcatgcat ttgacttcac actctgaagc aacatcctga cagtcatcca    300

catctacttc aaggaatatc acgttggaat acttttcaga gagggaatga aagaaaggct    360

tgatcatttt gcaaggccca caccacgtgg ctgagaagtc aactactaca agtttatcac    420

ctgcagcgtc caaggcttcc tgaaaagcag tcttgctctc gatctgcttc accatcttgg    480

ctgctggagt ctgacgagcg gctgtaagga ccgatggaaa tggatccaaa gcaccaaaca    540

gagcttcaag actcgctgct tggcttgaat tcggatccga tatcgccatg gcct          594


<210> SEQ ID NO 88
<211> LENGTH: 557
<212> TYPE: DNA
<213> ORGANISM: Homo sapien

<400> SEQUENCE: 88

aagtgttagc attaatgttt tattgtcacg cagatggcaa ctgggtttat gtcttcatat     60

tttatatttt tgtaaattaa aaaaattmca agttttaaat agccaatggc tggttatatt    120

ttcagaaaac atgattagac taattcatta atggtggctt caagcttttc cttattggct    180

ccagaaaatt cacccacctt ttgtcccttc ttaaaaaact ggaatgttgg catgcatttg    240

acttcacact ctgaagcaac atcctgacag tcatccacat ctacttcaag gaatatcacg    300

ttggaatact tttcagagag ggaatgaaag aaaggcttga tcattttgca aggcccacac    360

cacgtggctg agaagtcaac tactacaagt ttatcacctg cagcgtccaa ggcttcctga    420

aaagcagtct tgctctcgat ctgcttcacc atcttggctg ctggagtctg acgagcggct    480

gtaaggaccg atggaaatgg atccaaagca ccaaacagag cttcaagact cgctgcttgg    540

catgaattcg gatccga                                                   557


<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89

tacaaacttt attgaaacgc acacgcgcac acacacaaac acccctgtgg atagggaaaa     60

gcacctggcc acagggtcca ctgaaacggg gaggggatgg cagcttgtaa tgtggctttt    120
```

-continued

```
gccacaaccc ccttctgaca gggaaggcct tagattgagg ccccacctcc catggtgatg    180

gggagctcag aatggggtcc agggagaatt tggttagggg gaggtgctag ggaggcatga    240

gcagagggca ccctccgagt ggggtcccga gggctgcaga gtcttcagta ctgtccctca    300

cagcagctgt ctcaaggctg ggtccctcaa aggggcgtcc cagcgcgggg cctccctgcg    360

caaacacttg gtacccctgg ctgcgcagcg gaagccagca ggacagcagt ggcgccgatc    420

agcacaacag acgccctggc ggtagggaca gcaggcccag ccctgtcggt tgtctcggca    480

gcaggtctgg ttatcatggc agaagtgtcc ttcccacact tcacgtcctt cacacccacg    540

tganggctac nggccaggaa g                                              561
```

```
<210> SEQ ID NO 90
<211> LENGTH: 561
<212> TYPE: DNA
<213> ORGANISM: Homo sapien

<400> SEQUENCE: 90

cccgtgggtg ccatccacgg agttgttacc tgatctttgg aagcaggatc gcccgtctgc     60

actgcagtgg aagccccgtg ggcagcagtg atggccatcc ccgcatgcca cggcctctgg    120

gaaggggcag caactggaag tccctgagac ggtaaagatg caggagtggc cggcagagca    180

gtgggcatca acctggcagg ggccacccag atgcctgctc agtgttgtgg gccatttgtc    240

cagaagggga cggcagcagc tgtagctggc tcctccgggg tccaggcagc aggccacagg    300

gcagaactga ccatctgggc accgcgttcc agccaccagc cctgctgtta aggccaccca    360

gctcaccagg gtccacatgg tctgcctgcg tccgactccg cggtccttgg gccctgatgg    420

ttctacctgc tgtgagctgc ccagtgggaa gtatggctgc tgccaatgcc caacgccacc    480

tgctgctccg atcacctgca ctgctgcccc aagacactgt gtgtgacctg atccagagta    540

agtgcctctc caaggagaac g                                              561
```

```
<210> SEQ ID NO 91
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91

gaatcacctt tctggtttag ctagtacttt gtacagaaca atgaggtttc ccacagcgga     60

gtctccctgg gctctgtttg gctctcggta aggcaggcct acaccttttc ctctcctcta    120

tggagagggg aatatgcatt aaggtgaaaa gtcaccttcc aaaagtgaga aagggattcg    180

attgctgctt caggactgtg gaattatttg gaatgtttta caaatggttg ctacaaaaca    240

acaaaaaagg taattacaaa atgtgtacat cacaacatgc tttttaaaga cattatgcat    300

tgtgctcaca ttcccttaaa tgttgtttcc aaaggtgctc agcctctagc ccagctggat    360

tctccgggaa gaggcagaga cagtttggcg aaaaagacac agggaaggag ggggtggtga    420

aaggagaaag cagccttcca gttaaagatc agccctcagt taaaggtcag cttcccgcan    480

gctggcctca ngcggagtct gggtcagagg gaggagcagc agcagggtgg gactggggcg    540

t                                                                    541
```

```
<210> SEQ ID NO 92
```

-continued

<211> LENGTH: 551
<212> TYPE: DNA
<213> ORGANISM: Homo sapien

<400> SEQUENCE: 92
aaccggagcg cgagcagtag ctgggtgggc accatggctg ggatcaccac catcgaggcg 60
gtgaagcgca agatccaggt tctgcagcag caggcagatg atgcagagga gcgagctgag 120
cgcctccagc gagaagttga gggagaaagg cgggcccggg aacaggctga ggctgaggtg 180
gcctccttga accgtaggat ccagctggtt gaagaagagc tggaccgtgc tcaggagcgc 240
ctggccactg ccctgcaaaa gctggaagaa gctgaaaaag ctgctgatga gagtgagaga 300
ggtatgaagg ttattgaaaa ccgggcctta aaagatgaag aaaagatgga actccaggaa 360
atccaactca aagaagctaa gcacattgca gaagaggcag ataggaagta tgaagaggtg 420
gctcgtaagt tggtgatcat tgaaggagac ttggaacgca cagaggaacg agctgagctg 480
gcagagtccc gttgccgaga gatggatgag cagattagac tgatggacca gaacctgaag 540
tgtctgagtg c 551

<210> SEQ ID NO 93
<211> LENGTH: 531
<212> TYPE: DNA
<213> ORGANISM: Homo sapien

<400> SEQUENCE: 93
gagaacttgg cctttattgt gggcccagga gggcacaaag gtcaggaggc ccaagggagg 60
gatctggttt tctggatagc caggtcatag catgggtatc agtaggaatc cgctgtagct 120
gcacaggcct cacttgctgc agttccgggg agaacacctg cactgcatgg cgttgatgac 180
ctcgtggtac acgacagagc cattggtgca gtgcaagggc acgcgcatgg gctccgtcct 240
cgagggcagg cagcaggagc attgctcctg cacatcctcg atgtcaatgg agtacacagc 300
tttgctggca cactttccct ggcagtaatg aatgtccact tcctcttggg acttacaatc 360
tcccactttg atgtactgca ccttggctgt gatgtctttg caatcaggct cctcacatgt 420
gtcacagcag gtgcctggaa ttttcacgat tttgcctcct tcagccagac acttgtgttc 480
atcaaatggt gggcagcccg tgaccctctt ctcccagatg tactctcctc t 531

<210> SEQ ID NO 94
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 94
gcctggacct tgccggatca gtgccacaca gtgacttgct tggcaaatgg ccagaccttg 60
ctgcagagtc atcgtgtcaa ttgtgaccat ggaccccggc cttcatgtgc caacagccag 120
tctcctgttc gggtggagga gacgtgtggc tgccgctgga cctgcccttg tgtgtgcacg 180
ggcagttcca ctcggcacat cgtcaccttc gatgggcaga atttcaagct tactggtagc 240
tgctcctatg tcatctttca aaacaaggag caggacctgg aagtgctcct ccacaatggg 300
gcctgcagcc ccggggcaaa acaagcctgc atgaagtcca ttgagattaa gcatgctggc 360
gtctctgctg agctgcacag taacatggag atggcagtgg atgggagact ggtccttgcc 420
ccgtacgttg gtgaaaacat ggaagtcagc atctacggcg ctatcatgta tgaagtcagg 480

-continued tttacccatc ttggccacat cctcacatac accgccncaa aacaacgagt t 531

<210> SEQ ID NO 95
<211> LENGTH: 605
<212> TYPE: DNA
<213> ORGANISM: Homo sapien

<400> SEQUENCE: 95
agatcaacct ctgctggtca ggaggaatgc cttccttgtc ttggatcttt gctttgacgt 60
tctcgatagt rwcaactkkr ytsramskma agkgyratgr wmttksywgw rasyktmwwm 120
rsgraraytt agacayccm cctcwgagac gsagkaccar gtgcagaggt ggactctttc 180
tggatgttgt agtcagacag ggtgcgtcca tcttccagct gtttcccagc aaagatcaac 240
ctctgctgat caggagggat gccttcctta tcttggatct ttgccttgac attctcgatg 300
gtgtcactgg gctccacctc gagggtgatg gtcttaccag tcagggtctt cacgaagaty 360
tgcatcccac ctctgagacg gagcaccagg tgcagggtrg actctttctg gatgttgtag 420
tcagacaggg tgcgyccatc ttccagctgc tttccsagca aagatcaacc tctgctggtc 480
aggaggratg ccttccttgt cytggatctt tgcyttgacr ttctcratgg tgtcactcgg 540
ctccacttcg agagtgatgg tcttaccagt caggtcttc acgaagatct gcatcccacc 600
tctaa 605

<210> SEQ ID NO 96
<211> LENGTH: 531
<212> TYPE: DNA
<213> ORGANISM: Homo sapien

<400> SEQUENCE: 96
aagtcacaaa cagacaaaga ttattaccag ctgcaagcta tattagaagc tgaacgaaga 60
gacagaggtc atgattctga gatgattgga gaccttcaag ctcgaattac atctttacaa 120
gaggaggtga agcatctcaa acataatctc gaaaaagtgg aaggagaaag aaaagaggct 180
caagacatgc ttaatcactc agaaaaggaa aagaataatt tagagataga tttaaactac 240
aaacttaaat cattacaaca acggttagaa caagaggtaa atgaacacaa agtaaccaaa 300
gctcgtttaa ctgacaaaca tcaatctatt gaagaggcaa agtctgtggc aatgtgtgag 360
atggaaaaaa agctgaaaga agaaagagaa gctcgagaga aggctgaaaa tcgggttgtt 420
cagattgaga aacagtgttc catgctagac gttgatctga agcaatctca gcagaaacta 480
gaacatttga ctggaaataa agaaaggatg gaggatgaag ttaagaatct a 531

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97
cgcctccacc atgtccatca gggtgaccca gaagtcctac aaggtgtcca cctctggccc 60
ccgggccttc agcagccgct cctacacgag tgggcccggt tcccgcatca gctcctcgag 120
cttctcccga gtgggcagca gcaactttcg cggtggcctg ggcggcggct atggtggggc 180
cagcggcatg ggaggcatca ccgcagttac ggtcaaccag agcctgctga gcccccttgt 240

-continued

```
cctggaggtg gaccccaaca tccaggccgt gcgcacccag gagaaggagc agatcaagac    300

cctcaacaac aagtttgcct ccttcataga caaggtacgg ttcctggagc agcagaacaa    360

gatgctggag accaagtgga gcctcctgca gcagcagaag acggctcgaa gcaacatgga    420

caacatgttc gagagctaca tcaacarcct taggcggcag ctggagactc tgggccagga    480

gaagctgaag ctggaggcgg agcttggcaa catgcagggg ctggtggagg acttcaagaa    540

caagtatgag gatgagatca ataagcgtac agagatggag aacgaatttg tcctcatcaa    600

gaaggatgtg gatgaagctt acatgaacaa ggtagagctg gagtctcgcc tggaagggct    660

gaccgacgag atcaacttcc tcaggcagct gtatgaagag gagatccggg agctgcagtc    720

ccagatctcg gacacatctg tggtgctgtc catggacaac agccgctccc tggacatgga    780

cagcatcatt gctgaggtca aggcacagta cgaggatatt gccaaccgca gccgggctga    840

ggctgagagc atgtaccagg tcaagtatga ggagctgcag agcctggctg ggaagcacgg    900

ggatgacctg cggcgcacaa agactgagat ctctgagatg aacccggaac atcagcccgg    960

ctncaggctg agattgaggg cctcaaaggc caganggctt ncctggangn ccgccat      1017
```

<210> SEQ ID NO 98
<211> LENGTH: 561
<212> TYPE: DNA
<213> ORGANISM: Homo sapien

<400> SEQUENCE: 98

```
cccggagcca gccaacgagc ggaaaatggc agacaatttt tcgctccatg atgcgttatc     60

tgggtctgga aacccaaacc ctcaaggatg gcctggcgca tgggggaacc agcctgctgg    120

ggcagggggc tacccagggg cttcctatcc tggggcctac cccgggcagg cacccccagg    180

ggcttatcct ggacaggcac ctccaggcgc ctaccctgga gcacctggag cttatcccgg    240

agcacctgca cctggagtct acccagggcc acccagcggc cctggggcct acccatcttc    300

tggacagcca agtgccaccg gagcctaccc tgccactggc ccctatggcg cccctgctgg    360

gccactgatt gtgccttata acctgccttt gcctggggga gtggtgcctc gcatgctgat    420

aacaattctg ggcacggtga agcccaatgc aaacagaatt gctttagatt tccaaagagg    480

gaatgatgtt gccttccact ttaacccacg cttcaatgag aacaacagga gagtcattgg    540

ttgcaataca aagctggata a                                              561
```

<210> SEQ ID NO 99
<211> LENGTH: 636
<212> TYPE: DNA
<213> ORGANISM: Homo sapien

<400> SEQUENCE: 99

```
gggaatgcaa caactttatt gaaaggaaag tgcaatgaaa tttgttgaaa ccttaaaagg     60

ggaaacttag acaccccccc tcragcgmag kaccargtgc araggtggac tctttctgga    120

tgttgtagtc agacagggtr cgwccatctt ccagctgttt yccrgcaaag atcaacctct    180

gctgatcagg aggratgcct tccttatctt ggatctttgc cttgacattc tcgatggtgt    240

cactgggctc cacctcgagg gtgatggtct taccagtcag ggtcttcacg aagatytgca    300

tcccacctct gagacggagc accaggtgca gggtrgactc tttctggatg ttgtagtcag    360

acagggtgcg yccatcttcc agctgctttc csagcaaaga tcaacctctg ctggtcagga    420

ggratgcctt ccttgtcytg gatctttgcy ttgacrttct caatggtgtc actcggctcc    480

acttcgagag tgatggtctt accagtcagg gtcttcacga agatctgcat cccacctcta    540
```

-continued agacggagca ccaggtgcag ggtggactct ttctggatgg ttgtagtcag acagggtgcg 600
tccatcttcc agctgtttcc cagcaaagat caacct 636

<210> SEQ ID NO 100
<211> LENGTH: 697
<212> TYPE: DNA
<213> ORGANISM: Homo sapien

<400> SEQUENCE: 100
aggttgatct ttgctgggaa acagctggaa gatggacgca ccctgtctga ctacaaccat 60
ccagaaagag tccaccctgc acctggtgct ccgtcttaga ggtgggatgc agatcttcgt 120
gaagaccctg actggtaaga ccatcactct cgaagtggag ccgagtgaca ccattgagaa 180
ygtcaargca aagatccarg acaaggaagg catycctcct gaccagcaga ggttgatctt 240
tgctsggaaa gcagctggaa gatggrcgca ccctgtctga ctacaacatc cagaaagagt 300
cyaccctgca cctggtgctc cgtctcagag gtgggatgca ratcttcgtg aagaccctga 360
ctggtaagac catcaccctc gaggtggagc ccagtgacac catcgagaat gtcaaggcaa 420
agatccaaga taaggaaggc atccctcctg atcagcagag gttgatcttt gctgggaaac 480
agctggaaga tggacgcacc ctgtctgact acaacatcca gaaagagtcc acctytgcac 540
ytggtmctbc gtctyagagg kgggrtgcaa atctwmgtkw agacactcac tkkyaagryy 600
atcamcmwtg akktcgakys castkwcact wtcrakaamg tyrwwgcawa gatccmagac 660
aaggaaggca ttcctcctga ccagcagagg ttgatct 697

<210> SEQ ID NO 101
<211> LENGTH: 451
<212> TYPE: DNA
<213> ORGANISM: Homo sapien

<400> SEQUENCE: 101
atggagtctc actctgtcga ccaggctgga gcgctgtggt gcgatatcgg ctcactgcag 60
tctccacttc ctgggttcaa gcgatcctcc tgcctcagcc tcccgagtag ctgggactac 120
aggcaggcgt caccataatt tttgtatttt tagtagagac atggtttcgc catgttggct 180
gggctggtct cgaactcctg acctcaagtg atctgtcctg gcctcccaaa gtgttgggat 240
tacaggcgaa agccaacgct cccggccagg gaacaacttt agaatgaagg aaatatgcaa 300
aagaacatca catcaaggat caattaatta ccatctatta attactatat gtgggtaatt 360
atgactattt cccaagcatt ctacgttgac tgcttgagaa gatgtttgtc ctgcatggtg 420
gagagtggag aagggccagg attcttaggt t 451

<210> SEQ ID NO 102
<211> LENGTH: 571
<212> TYPE: DNA
<213> ORGANISM: Homo sapien

<400> SEQUENCE: 102
agcgcggtct tccggcgcga gaaagctgaa ggtgatgtgg ccgccctcaa ccgacgcatc 60
cagctcgttg aggaggagtt ggacagggct caggaacgac tggccacggc cctgcagaag 120
ctggaggagg cagaaaaagc tgcagatgag agtgagagag gaatgaaggt gatagaaaac 180
cgggccatga aggatgagga gaagatggag attcaggaga tgcagctcaa agaggccaag 240
cacattgcgg aagaggctga ccgcaaatac gaggaggtag ctcgtaagct ggtcatcctg 300

-continued gagggtgagc tggagagggc agaggagcgt gcggaggtgt ctgaactaaa atgtggtgac 360
ctggaagaag aactcaagaa tgttactaac aatctgaaat ctctggaggc tgcatctgaa 420
aagtattctg aaaaggagga caaatatgaa gaagaaatta aacttctgtc tgacaaactg 480
aaagaggctg agacccgtgc tgaatttgca gagagaacgg ttgcaaaact ggaaaagaca 540
attgatgacc tggaagagaa acttgcccag c 571

<210> SEQ ID NO 103
<211> LENGTH: 451
<212> TYPE: DNA
<213> ORGANISM: Homo sapien

<400> SEQUENCE: 103
gtgcacaggt cccatttatt gtagaaaata ataataatta cagtgatgaa tagctcttct 60
taaattacaa aacagaaacc acaaagaagg aagaggaaaa accccaggac ttccaagggt 120
gaagctgtcc cctcctccct gccaccctcc caggctcatt agtgtccttg gaaggggcag 180
aggactcaga ggggatcagt ctccaggggc cctgggctga agcgggtgag gcagagagtc 240
ctgaggccac agagctgggc aacctgagcc gcctctctgg ccccctcccc caccactgcc 300
caaacctgtt tacagcacct tcgcccctcc cctctaaacc cgtccatcca ctctgcactt 360
cccaggcagg tgggtgggcc aggcctcagc catactcctg ggcgcgggtt tcggtgagca 420
aggcacagtc ccagaggtga tatcaaggcc t 451

<210> SEQ ID NO 104
<211> LENGTH: 441
<212> TYPE: DNA
<213> ORGANISM: Homo sapien

<400> SEQUENCE: 104
gcaaggaact ggtctgctca cacttgctgg cttgcgcatc aggactggct ttatctcctg 60
actcacggtg caaaggtgca ctctgcgaac gttaagtccg tccccagcgc ttggaatcct 120
acggccccca cagccggatc ccctcagcct tccaggtcct caactcccgt ggacgctgaa 180
caatggcctc catggggcta caggtaatgg gcatcgcgct ggccgtcctg ggctggctgg 240
ccgtcatgct gtgctgcgcg ctgcccatgt ggcgcgtgac ggccttcatc ggcagcaaca 300
ttgtcacctc gcagaccatc tgggagggcc tatggatgaa ctgcgtggtg cagagcaccg 360
gccagatgca gtgcaaggtg tacgactcgc tgctggcact gccgcaggac ctgcaggcgg 420
cccgcgccct cgtcatcatc a 441

<210> SEQ ID NO 105
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105
tgcaaaaggg acacaggggt tcaaaaataa aaatttctct tccccctccc caaacctgta 60
ccccagctcc ccgaccacaa ccccccttcct cccccgggga aagcaagaag gagcaggtgt 120
ggcatctgca gctgggaaga gagaggccgg ggaggtgccg agctcggtgc tggtctcttt 180
ccaaatataa atacntgtgt cagaactgga aaatcctcca gcacccacca cccaagcact 240
ctccgttttc tgccggtgtt tggagagggg cgggggggcag gggcgccagg caccggctgg 300

-continued ctgcggtcta ctgcatccgc tgggtgtgca ccccgcgagc ctcctgctgc tcattgtaga 360
agagatgaca ctcggggtcc ccccggatgg tgggggctcc ctggatcagc ttcccggtgt 420
tggggttcac acaccagcac tccccacgct gcccgttcag agacatcttg cactgtttga 480
ggttgtacag gccatgcttg tcacagttg 509

<210> SEQ ID NO 106
<211> LENGTH: 571
<212> TYPE: DNA
<213> ORGANISM: Homo sapien

<400> SEQUENCE: 106
gggttggagg gactggttct ttatttcaaa aagacacttg tcaatattca gtatcaaaac 60
agttgcacta ttgatttctc tttctcccaa tcggccccaa agagaccaca taaaaggaga 120
gtacatttta agccaataag ctgcaggatg tacacctaac agacctccta gaaaccttac 180
cagaaaatgg ggactgggta gggaaggaaa cttaaaagat caacaaactg ccagcccacg 240
gactgcagag gctgtcacag ccagatgggg tggccagggt gccacaaacc caaagcaaag 300
tttcaaaata atataaaatt taaaaagttt tgtacataag ctattcaaga tttctccagc 360
actgactgat acaaagcaca attgagatgg cacttctaga gacagcagct tcaaacccag 420
aaaagggtga tgagatgagt ttcacatggc taaatcagtg gcaaaaacac agtcttcttt 480
ctttctttct ttcaaggagg caggaaagca attaagtggt cacctcaaca taagggggac 540
atgatccatt ctgtaagcag ttgtgaaggg g 571

<210> SEQ ID NO 107
<211> LENGTH: 555
<212> TYPE: DNA
<213> ORGANISM: Homo sapien

<400> SEQUENCE: 107
caggaaccgg agcgcgagca gtagctgggt gggcaccatg gctgggatca ccaccatcga 60
ggcggtgaag cgcaagatcc aggttctgca gcagcaggca gatgatgcag aggagcgagc 120
tgagcgcctc cagcgagaag ttgagggaga aaggcgggcc cgggaacagg ctgaggctga 180
ggtggcctcc ttgaaccgta ggatccagct ggttgaagaa gagctggacc gtgctcagga 240
gcgcctggcc actgccctgc aaaagctgga agaagctgaa aaagctgctg atgagagtga 300
gagaggtatg aaggttattg aaaaccgggc cttaaaagat gaagaaaaga tggaactcca 360
ggaaatccaa ctcaaagaag ctaagcacat tgcagaagag gcagatagga agtatgaaga 420
ggtggctcgt aagttggtga tcattgaagg agacttggaa cgcacagagg aacgagctga 480
gctggcagag tcccgttgcc gagagatgga tgagcagatt agactgatgg accagaacct 540
gaagtgtctg agtgc 555

<210> SEQ ID NO 108
<211> LENGTH: 541
<212> TYPE: DNA
<213> ORGANISM: Homo sapien

<400> SEQUENCE: 108
atctacgtca tcaatcaggc tggagacacc atgttcaatc gagctaagct gctcaatatt 60
ggctttcaag aggccttgaa ggactatgat tacaactgct ttgtgttcag tgatgtggac 120
ctcattccga tggacgaccg taatgcctac aggtgttttt cgcagccacg gcacatttct 180

-continued

```
gttgcaatgg acaagttcgg gtttagcctg ccatatgttc agtattttgg aggtgtctct    240

gctctcagta aacaacagtt tcttgccatc aatggattcc ctaataatta ttggggttgg    300

ggaggagaag atgacgacat ttttaacaga ttagttcata aaggcatgtc tatatcacgt    360

ccaaatgctg tagtagggag gtgtcgaatg atccggcatt caagagacaa gaaaaatgag    420

cccaatcctc agaggtttga ccggatcgca catacaaagg aaacgatgcg cttcgatggt    480

ttgaactcac ttacctacaa ggtgttggat gtcagagata cccgttatat acccaaatca    540

c                                                                    541
```

```
<210> SEQ ID NO 109
<211> LENGTH: 411
<212> TYPE: DNA
<213> ORGANISM: Homo sapien

<400> SEQUENCE: 109

ctagacctct aattaaaagg cacaatcatg ctggagaatg aacagtctga ccccgagggc     60

cacagcgaat tttagggaag gaggcaaaga ggtgagaagg gaaaggaaag aaggaaggaa    120

ggagaacaat aagaactgga gacgttgggt gggtcaggga gtgtggtgga ggctcggaga    180

gatggtaaac aaacctgact gctatgagtt ttcaacccca tagtctaggg ccatgagggc    240

gtcagttctt ggtggctgag ggtccttcca cccagcccac ctgggggagt ggagtgggga    300

gttctgccag gtaagcagat gttgtctccc aagttcctga cccagatgtc tggcaggata    360

acgctgacct gttccctcaa caagggacct gaaagtaatt ttgctcttta c            411
```

```
<210> SEQ ID NO 110
<211> LENGTH: 451
<212> TYPE: DNA
<213> ORGANISM: Homo sapien

<400> SEQUENCE: 110

ccgaattcaa gcgtcaacga tccytccctt accatcaaat caattggcca ccaatggtac     60

tgaacctacg agtacaccga ctacgggcgg actaatcttc aactcctaca tacttccccc    120

attattccta gaaccaggcg acctgcgact ccttgacgtt gacaatcgag tagtactccc    180

gattgaagcc cccattcgta taataattac atcacaagac gtcttgcact catgagctgt    240

ccccacatta ggcttaaaaa cagatgcaat tcccggacgt ctaagccaaa ccactttcac    300

cgctacacga ccgggggtat actacggtca atgctctgaa atctgtggag caaaccacag    360

tttcatgccc atcgtcctag aattaattcc cctaaaaatc tttgaaatag ggcccgtatt    420

taccctatag caccccctct acccccctcta g                                 451
```

```
<210> SEQ ID NO 111
<211> LENGTH: 541
<212> TYPE: DNA
<213> ORGANISM: Homo sapien

<400> SEQUENCE: 111

gctcttcaca cttttattgt taattctctt cacatggcag atacagagct gtcgtcttga     60

agaccaccac tgaccaggaa atgccacttt tacaaaatca tccccccttt tcatgattgg    120

aacagttttc ctgaccgtct gggagcgttg aagggtgacc agcacatttg cacatgcaaa    180

aaaggagtga ccccaaggcc tcaaccacac ttcccagagc tcaccatggg ctgcaggtga    240

cttgccaggt ttggggttcg tgagctttcc ttgctgctgc ggtggggagg ccctcaagaa    300

ctgagaggcc ggggtatgct tcatgagtgt taacatttac gggacaaaag cgcatcatta    360
```

-continued ggataaggaa cagccacagc acttcatgct tgtgagggtt agctgtagga gcgggtgaaa 420
ggattccagt ttatgaaaat ttaaagcaaa caacggtttt tagctgggtg ggaaacagga 480
aaactgtgat gtcggccaat gaccaccatt tttctgccca tgtgaaggtc cccatgaaac 540
c 541

<210> SEQ ID NO 112
<211> LENGTH: 521
<212> TYPE: DNA
<213> ORGANISM: Homo sapien

<400> SEQUENCE: 112
caagcgcttg gcgtttggac ccagttcagt gaggttcttg ggttttgtgc ctttggggat 60
tttggtttga cccaggggtc agccttagga aggtcttcag gaggaggccg agttcccctt 120
cagtaccacc cctctctccc cactttccct ctcccggcaa catctctggg aatcaacagc 180
atattgacac gttggagccg agcctgaaca tgcccctcgg ccccagcaca tggaaaaccc 240
ccttccttgc ctaaggtgtc tgagtttctg gctcttgagg catttccaga cttgaaattc 300
tcatcagtcc attgctcttg agtctttgca gagaacctca gatcaggtgc acctgggaga 360
aagactttgt ccccacttac agatctatct cctcccttgg gaagggcagg gaatggggac 420
ggtgtatgga ggggaaggga tctcctgcgc ccttcattgc cacacttggt gggaccatga 480
acatctttag tgtctgagct tctcaaatta ctgcaatagg a 521

<210> SEQ ID NO 113
<211> LENGTH: 568
<212> TYPE: DNA
<213> ORGANISM: Homo sapien

<400> SEQUENCE: 113
agcgtcaaat cagaatggaa aagactcaaa accatcatca acaccaagat caaaaggaca 60
agratccttc aagaaacagg aaaaaactcc taaaacacca aaaggaccta gttctgtaga 120
agacattaaa gcaaaaatgc aagcaagtat agaaaaaggt ggttctcttc ccaaagtgga 180
agccaaattc atcaattatg tgaagaattg cttccggatg actgaccaag aggctattca 240
agatctctgg cagtggagga agtctcttta agaaaatagt ttaaacaatt tgttaaaaaa 300
ttttccgtct tatttcattt ctgtaacagt tgatatctgg ctgtcctttt tataatgcag 360
agtgagaact ttccctaccg tgtttgataa atgttgtcca ggttctattg ccaagaatgt 420
gttgtccaaa atgcctgttt agtttttaaa gatggaactc caccctttgc ttggttttaa 480
gtatgtatgg aatgttatga taggacatag tagtagcggt ggtcagacat ggaaatggtg 540
ggsmgacaaa aatatacatg tgaaataa 568

<210> SEQ ID NO 114
<211> LENGTH: 483
<212> TYPE: DNA
<213> ORGANISM: Homo sapien

<400> SEQUENCE: 114
tccgaattcc aagcgaatta tggacaaacg attcctttta gaggattact tttttcaatt 60
tcggttttag taatctaggc tttgcctgta aagaatacaa cgatggattt taaatactgt 120
ttgtggaatg tgtttaaagg attgattcta gaacctttgt atatttgata gtatttctaa 180
ctttcatttc tttactgttt gcagttaatg ttcatgttct gctatgcaat cgtttatatg 240

-continued

```
cacgtttctt taattttttt agattttcct ggatgtatag tttaaacaac aaaaagtcta    300

tttaaaactg tagcagtagt ttacagttct agcaaagagg aaagttgtgg ggttaaactt    360

tgtattttct ttcttataga ggcttctaaa aaggtatttt tatatgttct ttttaacaaa    420

tattgtgtac aacctttaaa acatcaatgt ttggatcaaa acaagaccca gcttattttc    480

tgc                                                                  483
```

<210> SEQ ID NO 115
<211> LENGTH: 521
<212> TYPE: DNA
<213> ORGANISM: Homo sapien

<400> SEQUENCE: 115

```
tgtggtggcg cgggctgagg tggaggccca ggactctgac cctgcccctg ccttcagcaa     60

ggcccccggc agcgccggcc actacgaact gccgtgggtt gaaaaaatata ggccagtaaa    120

gctgaatgaa attgtcggga atgaagacac cgtgagcagg ctagaggtct ttgcaaggga    180

aggaaatgtg cccaacatca tcattgcggg ccctccagga accggcaaga ccacaagcat    240

tctgtgcttg gcccgggccc tgctgggccc agcactcaaa gatgccatgt tggaactcaa    300

tgcttcaaat gacaggggca ttgacgttgt gaggaataaa attaaaatgt ttgctcaaca    360

aaaagtcact cttcccaaag gccgacataa gatcatcatt ctggatgaag cagacagcat    420

gaccgacgga gcccagcaag ccttgaggag aaccatggaa atctactcta aaaccactcg    480

ttcgcccttg cttgtaatgc ttcggataag atcatcgagc c                        521
```

<210> SEQ ID NO 116
<211> LENGTH: 501
<212> TYPE: DNA
<213> ORGANISM: Homo sapien

<400> SEQUENCE: 116

```
ctttgcaaag cttttatttc atgtctgcgg catggaatcc acctgcacat ggcatcttag     60

ctgtgaagga gaaagcagtg cacgagaagg aatgagtggg cggaaccaac ggcctccaca    120

agctgccttc cagcagcctg ccaaggccat ggcagagaga gactgcaaac aaacacaagc    180

aaacagagtc tcttcacagc tggagtctga aagctcatag tggcatgtgt gaatctgaca    240

aaattaaaag tgtgcatagt ccattacatg cataaaacac taataataat cctgtttaca    300

cgtgactgca gcaggcaggt ccagctccac cactgccctc ctgccacatc acatcaagtg    360

ccatggttta gagggttttt catatgtaat tcttttattc tgtaaaaggt aacaaaatat    420

acagaacaaa actttccctt tttaaaacta atgttacaaa tctgtattat cacttggata    480

taaatagtat ataagctgat c                                              501
```

<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117

```
caagggatat atgttgaggg tacrgrgtga cactgaacag atcacaaagc acgagaaaca     60

ttagttctct ccctccccag cgtctccttc gtctccctgg ttttccgatg tccacagagt    120

gagattgtcc ctaagtaact gcatgatcag agtgctgkct ttataagact cttcattcag    180
```

-continued cgtatccaat tcagcaattg cttcatcaaa tgccgttttt gccaggctac aggccttttc 240
aggagagttt agaatctcat agtaaaagac tgagaaattt agtgccagac caagacgaat 300
tgggtgtgta ggctgcattn ctttcttact aatttcaaat gcttcctggt aagcctgctg 360
ggagttcgac acaagtggtt tgtttgttgc tccagatgcc acttcagaaa gatacctaaa 420
ataatctcct ttcattttca aagtagaaca c 451

<210> SEQ ID NO 118
<211> LENGTH: 501
<212> TYPE: DNA
<213> ORGANISM: Homo sapien

<400> SEQUENCE: 118
tccggagccg gggtagtcgc cgccgccgcc gccggtgcag ccactgcagg caccgctgcc 60
gccgcctgag tagtgggctt aggaaggaag aggtcatctc gctcggagct tcgctcggaa 120
gggtctttgt tccctgcagc cctcccacgg gaatgacaat ggataaaagt gagctggtac 180
agaaagccaa actcgctgag caggctgagc gatatgatga tatggctgca gccatgaagg 240
cagtcacaga acaggggcat gaactctcca acgaagagag aaatctgctc tctgttgcct 300
acaagaatgt ggtaaggccg cccgccgctc ttcctggcgt gtcatctcca gcattgagca 360
gaaaacagag aggaatgaga agaagcagca gatgggcaaa gagtaccgtg agaagataga 420
ggcagaactg caggacatct gcaatgatgt tctggagctt gttggacaaa tatcttattc 480
caatgctaca caacccagaa a 501

<210> SEQ ID NO 119
<211> LENGTH: 391
<212> TYPE: DNA
<213> ORGANISM: Homo sapien

<400> SEQUENCE: 119
aaaaagcagc argttcaaca caaaatagaa atctcaaatg taggatagaa caaaaccaag 60
tgtgtgaggg gggaagcaac agcaaaagga agaaatgaga tgttgcaaaa aagatggagg 120
agggttcccc tctcctctgg ggactgactc aaacactgat gtggcagtat acaccattcc 180
agagtcaggg gtgttcattc ttttttggga gtaagaaaag gtggggatta agaagacgtt 240
tctggaggct tagggaccaa ggctggtctc tttccccct cccaacccc ttgatccctt 300 tctctgatca ggggaaagga gctcgaatga gggaggtaga gttggaaagg gaaaggattc 360
cacttgacag aatgggacag actccttccc a 391

<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120
tggcaatagc acagccatcc aggagctctt cargcgcatc tcggagcagt tcactgccat 60
gttccgccgg aaggccttcc tccactggta cacaggcgag ggcatggacg agatggagtt 120
caccgaggct gagagcaaca tgaacgacct cgtctctgag tatcaagcag taccaggatg 180
ccaccgcaga agaggaggag gatttcggtg aggaggccga agaggaggcc taaggcagag 240

-continued

```
cccccatcac ctcaggcttc tcagttccct tagccgtctt actcaactgc ccctttcctc    300

tccctcagaa tttgtgtttg ctgcctctat cttgtttttt gttttttctt ctgggggggt    360

ctagaacagt gcctggcaca tagtaggcgc tcaataaata cttggttgnt gaatgtctcc    420

t                                                                    421


<210> SEQ ID NO 121
<211> LENGTH: 206
<212> TYPE: DNA
<213> ORGANISM: Homo sapien

<400> SEQUENCE: 121

agctggcgct agggctcggt tgtgaaatac agcgtrgtca gcccttgcgc tcagtgtaga     60

aacccacgcc tgtaaggtcg gtcttcgtcc atctgctttt ttctgaaata cactaagagc    120

agccacaaaa ctgtaacctc aaggaaacca taaagcttgg agtgccttaa tttttaacca    180

gtttccaata aaacggttta ctacct                                         206


<210> SEQ ID NO 122
<211> LENGTH: 131
<212> TYPE: DNA
<213> ORGANISM: Homo sapien

<400> SEQUENCE: 122

ggagatgaag atgaggaagc tgagtcagct acgggcargc gggcagctga agatgatgag     60

gatgacgatg tcgataccaa gaagcagaag accgacgagg atgactagac agcaaaaaag    120

gaaaagttaa a                                                         131


<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G

<400> SEQUENCE: 123

gatgaaaatt aaatacttaa attaatcaaa aggcactacg ataccaccta aaacctactg     60

cctcagtggc agtakgctaa kgaagatcaa gctacagsac atyatctaat atgaatgtta    120

gcaattacat akcargaagc atgtttgctt tccagaagac tatggnacaa tggtcattwg    180

ggcccaagag gatatttggc cnggaaagga tcaagataga tnaangtaaa g             231


<210> SEQ ID NO 124
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124

gagtagcaac gcaaagcgct tggtattgag tctgtgggsg acttcggttc cggtctctgc     60

agcagccgtg atcgcttagt ggagtgctta gggtagttgg ccaggatgcc gaatatcaaa    120

atcttcagca ggcagctccc accaggactt atctcasaaa attgctgacc gcctgggcct    180

ggagctaggc aaggtggtga ctaagaaatt cagcaaccag gagacctgtg tggaaattgg    240

tgaaagtgta ccgtggagag gatgtctaca ttgttcagag tggntgtggc gaaatcaatg    300
```

-continued

```
acaatttaat ggagcttttg atcatgatta atgcctgcaa gattgcttca gccagccggg    360

ttactgcagt catcccatgc ttcccttatg ccccggcagg ataagaaaga tnagagccgg    420

gccgccaatc tcagccaagc ttggtgcaaa tatgctatct gtagcagtgc agatcatatt    480

atcaccatgg acctacatgc ttctcaaatt canggctttt t                        521


<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125

atgcaaaagg ggacacaggg ggttcaaaaa taaaaatttc tcttccccct ccccaaacct     60

gtaccccagc tccccgacca caaccccctt cctcccccgg ggaaagcaag aaggagcagg    120

tgtggcatct gcagctggga agagagaggc cggggaggtg ccgagctcgg tgctggtctc    180

tttccaaata taaatacgtg tgtcagaact ggaaaatcct ccagcaccca ccacccaagc    240

actctccgtt ttctgccggt gtttggagag gggcggnggg caggggcgcc aggcaccggc    300

tggctgcggt ctactgcatc cgctgggtgt gcaccccgcg a                        341


<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126

aggttggaga aggtcatgca ggtgcagatt gtccaggskc agccacaggg tcaagcccaa     60

caggcccaga gtggcactgg acagaccatg caggtgatgc agcagatcat cactaacaca    120

ggagagatcc agcagatccc ggtgcagctg aatgccggcc agctgcagta tatccgctta    180

gcccagcctg tatcaggcac tcaagttgtg cagggacaga tccagacact tgccaccaat    240

gctcaacaga ttacacagac agaggtccag caaggacagc agcagttcaa gccagttcac    300

aagatggaca gcagctctac cagatccagc aagtcaccat gcctgcgggc cangacctcg    360

ccagcccatg ttcatccagt caagccaacc agcccttcna cgggcaggcc ccccaggtga    420

ccggcgactg aagggcctga gctggcaagg ccaangacac ccaacacaat ttttgccata    480

cagcccccag gcaatgggca cagcctttct tcccagagga c                        521


<210> SEQ ID NO 127
<211> LENGTH: 351
<212> TYPE: DNA
<213> ORGANISM: Homo sapien

<400> SEQUENCE: 127

tgagatttat tgcatttcat gcagcttgaa gtccatgcaa aggrgactag cacagttttt     60

aatgcattta aaaaataaaa gggaggtggg cagcaaacac acaaagtcct agtttcctgg    120

gtccctggga gaaaagagtg tggcaatgaa tccacccact ctccacaggg aataaatctg    180

tctcttaaat gcaaagaatg tttccatggc ctctggatgc aaatacacag agctctgggg    240
```

-continued

```
tcagagcaag ggatggggag aggaccacga gtgaaaaagc agctacacac attcacctaa    300

ttccatctga gggcaagaac aacgtggcaa gtcttggggg tagcagctgt t             351


<210> SEQ ID NO 128
<211> LENGTH: 521
<212> TYPE: DNA
<213> ORGANISM: Homo sapien

<400> SEQUENCE: 128

tccagacatg ctcctgtcct aggcggggag caggaaccag acctgctatg ggaagcagaa     60

agagttaagg gaaggtttcc tttcattcct gttccttctc ttttgctttt gaacagtttt    120

taaatatact aatagctaag tcatttgcca gccaggtccc ggtgaacagt agagaacaag    180

gagcttgcta agaattaatt ttgctgtttt tcaccccatt caaacagagc tgccctgttc    240

cctgatggag ttccattcct gccagggcac ggctgagtaa cacgaagcca ttcaagaaag    300

gcgggtgtga aatcactgcc accccatgga cagacccctc actcttcctt cttagccgca    360

gcgctactta ataaatatat ttatactttg aaattatgat aaccgatttt tcccatgcgg    420

catcctaagg gcacttgcca gctcttatcc ggacagtcaa gcactgttgt tggacaacag    480

ataaaggaaa agaaaaagaa gaaaacaacc gcaacttctg t                        521


<210> SEQ ID NO 129
<211> LENGTH: 521
<212> TYPE: DNA
<213> ORGANISM: Homo sapien

<400> SEQUENCE: 129

tgagacggac cactggcctg gtcccccctc atktgctgtc gtaggacctg acatgaaacg     60

cagatctagt ggcagagagg aagatgatga ggaacttctg agacgtcggc agcttcaaga    120

agagcaatta atgaagctta actcaggcct gggacagttg atcttgaaag aagagatgga    180

gaaagagagc cgggaaaggt catctctgtt agccagtcgc tacgattctc ccatcaactc    240

agcttcacat attccatcat ctaaaactgc atctctccct ggctatggaa gaaatgggct    300

tcaccggcct gtttctaccg acttcgctca gtataacagc tatggggatg tcagcggggg    360

agtgcgagat taccagacac ttccagatgg ccacatgcct gcaatgagaa tggaccgagg    420

agtgtctatg cccaacatgt tggaaccaaa gatatttcca tatgaaatgc tcatggtgac    480

caacagaggg ccgaaaccaa atctcagaga ggtggacaga a                        521


<210> SEQ ID NO 130
<211> LENGTH: 270
<212> TYPE: DNA
<213> ORGANISM: Homo sapien

<400> SEQUENCE: 130

tcactttatt tttcttgtat aaaaacccta tgttgtagcc acagctggag cctgagtccg     60

ctgcacggag actctggtgt gggtcttgac gaggtggtca gtgaactcct gatagggaga    120

cttggtgaat acagtctcct tccagaggtc gggggtcagg tagctgtagg tcttagaaat    180

ggcatcaaag gtggccttgg cgaagttgcc cagggtggca gtgcagcccc gggctgaggt    240

gtagcagtca tcgataccag ccatcatgag                                     270


<210> SEQ ID NO 131
<211> LENGTH: 341
<212> TYPE: DNA
<213> ORGANISM: Homo sapien
```

-continued

<400> SEQUENCE: 131
ctggaatata gacccgtgat cgacaaaact ttgaacgagg ctgactgtgc caccgtcccg 60
ccagccattc gctcctactg atgagacaag atgtggtgat gacagaatca gcttttgtaa 120
ttatgtataa tagctcatgc atgtgtccat gtcataactg tcttcatacg cttctgcact 180
ctggggaaga aggagtacat tgaagggaga ttggcaccta gtggctggga gcttgccagg 240
aacccagtgg ccagggagcg tggcacttac ctttgtccct tgcttcattc ttgtgagatg 300
ataaaactgg gcacagctct taaataaaat ataaatgaac a 341

<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132
tgaatgggga ggagctgacc caggaaatgg agcttgngga gaccaggcct gcaggggatg 60
gaaccttcca gaagtgggca tctgtggtgg tgcctcttgg gaaggagcag aagtacacat 120
gccatgtgga acatgagggg ctgcctgagc ccctcaccct gagatggggc aaggaggagc 180
ctccttcatc caccaagact aacacagtaa tcattgctgt tccggttgtc cttggagctg 240
tggtcatcct tggagctgtg atggcttttg tgatgaagag gaggagaaac acaggtggaa 300
aaggagggga ctatgctctg gctccaggct cccagagctc tgatatgtct ctcccagatt 360
gtaaagtgtg aagacagctg cctggtgtgg acttggtgac agacaatgtc ttcacacatc 420
tcctgtgaca tccagagacc tcagttctct ttagtcaagt gtctgatgtt ccctgtgagt 480
ctgcgggctc aaagtgaaga actgtggagc ccagtccacc cctgcacacc aggaccctat 540
ccctgcactg ccctgtgttc ccttccacag ccaaccttgc tgctccagcc aaacattggt 600
ggacatctgc agcctgtcag ctccatgcta ccctgacctt caactcctca cttccacact 660
gagaataata atttgaatgt gggtggctgg agagatggct cagcgctgac tgctcttcca 720
aaggtcctga gttcaaatcc cagcaaccac atggtggctc acaaccatct gtaatgggat 780
ctaataccct cttctgcagt gtctgaagac asctacagtg tacttacata taataataaa 840
taag 844

<210> SEQ ID NO 133
<211> LENGTH: 601
<212> TYPE: DNA
<213> ORGANISM: Homo sapien

<400> SEQUENCE: 133
ggccgggcgc gcgcgccccc gccacacgca cgccgggcgt gccagtttat aaagggagag 60
agcaagcagc gagtcttgaa gctctgtttg gtgctttgga tccatttcca tcggtcctta 120
cagccgctcg tcagactcca gcagccaaga tggtgaagca gatcgagagc aagactgctt 180
ttcaggaagc cttggacgct gcaggtgata aacttgtagt agttgacttc tcagccacgt 240
ggtgtgggcc ttgcaaaatg atcaagcctt tctttcattc cctctctgaa aagtattcca 300
acgtgatatt ccttgaagta gatgtggatg actgtcagga tgttgcttca gagtgtgaag 360
tcaaatgcat gccaacattc cagtttttta agaagggaca aaaggtgggt gaattttctg 420

-continued

```
gagccaataa ggaaaagctt gaagccacca ttaatgaatt agtctaatca tgttttctga    480

aaatataacc agccattggc tatttaaaac ttgtaatttt tttaatttac aaaaatataa    540

aatatgaaga cataaacccm gttgccatct gcgtgacaat aaaacattaa tgctaacact    600

t                                                                    601
```

```
<210> SEQ ID NO 134
<211> LENGTH: 421
<212> TYPE: DNA
<213> ORGANISM: Homo sapien

<400> SEQUENCE: 134

tcacataaga aatttaagca agttacrcta tcttaaaaaa cacaacgaat gcattttaat     60

agagaaaccc ttccctccct ccacctccct cccccaccct cctcatgaat taagaatcta    120

agagaagaag taaccataaa accaagtttt gtggaatcca tcatccagag tgcttacatg    180

gtgattaggt taatattgcc ttcttacaaa atttctattt taaaaaaaat tataaccttg    240

attgcttatt acaaaaaaat tcagtacaaa agttcaatat attgaaaaat gcttttcccc    300

tccctcacag caccgtttta tatatagcag agaataatga agagattgct agtctagatg    360

gggcaatctt caaattacac caagacgcac agtggtttat ttaccctccc cttctcataa    420

g                                                                    421
```

```
<210> SEQ ID NO 135
<211> LENGTH: 511
<212> TYPE: DNA
<213> ORGANISM: Homo sapien

<400> SEQUENCE: 135

ggaaaggatt caagaattag aggacttgct tgctrragaa aaagacaact ctcgtcgcat     60

gctgacagac aaagagagag agatggcgga aataagggat caaatgcagc aacagctgaa    120

tgactatgaa cagcttcttg atgtaaagtt agccctggac atggaaatca gtgcttacag    180

gaaactctta gaaggcgaag aagagaggtt gaagctgtct ccaagccctt cttcccgtgt    240

gacagtatcc cgagcatcct caagtcgtag tgtaccgtac aactagagga aagcggaaga    300

gggttgatgt ggaagaatca gaggcgaagt agtagtgtta gcatctctca ttccgcctca    360

accactggaa atgtttgcat cgaagaaatt gatgttgatg ggaaatttat cccgcttgaa    420

gaacacttct gaacaggatc aaccaatggg aaggcttggg agatgatcag aaaaattgga    480

gacacatcag tcagttataa atatacctca a                                   511
```

```
<210> SEQ ID NO 136
<211> LENGTH: 341
<212> TYPE: DNA
<213> ORGANISM: Homo sapien

<400> SEQUENCE: 136

catgggtttc accaggttgg ccaggctgct cttgaactsc tgacctcagg tgatccaccc     60

gcctcggcct cccaaagtgc tgggattaca ggcgtgagcc accacgcccg gcccccaaag    120

ctgtttcttt tgtctttagc gtaaagctct cctgccatgc agtatctaca taactgacgt    180

gactgccagc aagctcagtc actccgtggt ctttttctct ttccagttct tctctctctc    240

ttcaagttct gcctcagtga aagctgcagg tccccagtta agtgatcagg tgagggttct    300

ttgaacctgg ttctatcagt cgaattaatc cttcatgatg g                        341
```

-continued

<210> SEQ ID NO 137
<211> LENGTH: 551
<212> TYPE: DNA
<213> ORGANISM: Homo sapien

<400> SEQUENCE: 137
gatgtgttgg accctctgtg tcaaaaaaaa cctcacaaag aatcccctgc tcattacaga 60
agaagatgca tttaaaatat gggttatttt caacttttta tctgaggaca agtatccatt 120
aattattgtg tcagaagaga ttgaatacct gcttaagaag cttacagaag ctatgggagg 180
aggttggcag caagaacaat ttgaacatta taaaatcaac tttgatgaca gtaaaaatgg 240
cctttctgca tgggaactta ttgagcttat tggaaatgga cagtttagca aaggcatgga 300
ccggcagact gtgtctatgg caattaatga agtctttaat gaacttatat tagatgtgtt 360
aaagcagggt tacatgatga aaaagggcca cagacggaaa aactggactg aaagatggtt 420
tgtactaaaa cccaacataa tttcttacta tgtgagtgag gatctgaagg ataagaaagg 480
agacattctc ttggatgaaa attgctgtgt agaagtcctt gcctgacaaa agatggaaag 540
aaatgccttt t 551

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138
gactggttct ttatttcaaa aagacacttg tcaatattca gtrtcaaaac agttgcacta 60
ttgatttctc tttctcccaa tcggccccaa agagaccaca taaaaggaga gtacatttta 120
agccaataag ctgcaggatg tacacctaac agacctccta gaaaccttac cagaaaatgg 180
ggactgggta gggaaggaaa cttaaaagat caacaaactg ccagcccacg gactgcagag 240
gctgtcacag ccagatgggg tggccagggt gccacaaacc caaagcaaag tttcaaaata 300
atataaaatt taaaaagttt tgtacataag ctattcaaga tttctccagc actgactgat 360
acaaagcaca attgagatgg cacttctaga gacagcagct tcaaacccag aaaagggtga 420
tgagatgaag tttcacatgg ctaaatcagt ggcaaaaaca cagtcttctt tctttctttc 480
tttcaaggan gcaggaaagc aattaagtgg tcaccttaac ataaggggga c 531

<210> SEQ ID NO 139
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139
tgggtgggca ccatggctgg gatcaccacc atcgaggcgg tgaagcgcaa gatccaggtt 60
ctgcagcagc aggcagatga tgcagaggag cgagctgagc gcctccagcg agaagttgag 120
ggagaaaggc gggcccggga acaggctgag gctgaggtgg cctccttgaa ccgtaggatc 180
cagctggttg aagaagagct ggaccgtgct caggagcgcc tggccactgc cctgcaaaag 240
ctggaagaag ctgaaaaagc tgctgatgag agtgagagag gtatgaaggt tattgaaaac 300

-continued

```
cgggccttaa aagatgaaga aaagatggaa ctccaggaaa tccaactcaa agaagctaag    360

cacattgcag aagaggcaga taggaagtat gaagaggtgg ctcgtaagtt ggtgatcatt    420

gaaggagact tggaaccgca cagaaggaac gagcttgagc ttggcaaaag tcccgttgcc    480

cagagatggg atgaaccaga ttagactgat ggaccanaac c                        521
```

```
<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140

aggggcngcg ggtgcgtggg ccactgggtg accgacttag cctggccaga ctctcagcac     60

ctggaagcgc cccgagagtg acagcgtgag gctgggaggg aggacttggc ttgagcttgt    120

taaactctgc tctgagcctc cttgtcgcct gcatttagat ggctcccgca aagaagggtg    180

gcgagaagaa aaagggccgt tctgccatca acgaagtggt aacccgagaa tacaccatca    240

acattcacaa gcgcatccat ggagtgggct tcaagaagcg tgcacctcgg gcactcaaag    300

agattcggaa atttgccatg aaggagatgg gaactccaga tgtgcgcatt gacaccaggc    360

tcaacaaagc tgtctgggcc aaaggaataa ggaatgtgcc ataccgaatc cggtgtgcgg    420

ctgtccagaa aacgtaatga ggatgaagat tcaccaaata agctatatac tttggttacc    480

tatgtacctg ttaccacttt caaaaatcta cagacagtca atgtggatga gaactaatcg    540

ctgatcgtca gatcaaataa agttataaaa t                                   571
```

```
<210> SEQ ID NO 141
<211> LENGTH: 531
<212> TYPE: DNA
<213> ORGANISM: Homo sapien

<400> SEQUENCE: 141

tcgggagcca cacttggccc tcttcctctc caaagsgcca gaacctcctt ctctttggag     60

aatggggagg cctcttggag acacagaggg tttcaccttg gatgacctct agagaaattg    120

cccaagaagc ccaccttctg gtcccaacct gcagacccca cagcagtcag ttggtcaggc    180

cctgctgtag aaggtcactt ggctccattg cctgcttcca accaatgggc aggagagaag    240

gcctttattt ctcgcccacc cattcctcct gtaccagcac ctccgttttc agtcagtgtt    300

gtccagcaac ggtaccgttt acacagtcac ctcagacaca ccatttcacc tcccttgcca    360

agctgttagc cttagagtga ttgcagtgaa cactgtttac acaccgtgaa tccattccca    420

tcagtccatt ccagttggca ccagcctgaa ccatttggta cctggtgtta actggagtcc    480

tgtttacaag gtggagtcgg ggcttgctga cttctcttca tttgagggca c             531
```

```
<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142

acctagacag aaggtgggtg agggaggact ggtaggaggc tgaggcaatt ccttggtagt     60
```

-continued ttgtcctgaa accctactgg agaagtcagc atgaggcacc tactgagaga agtgcccaga 120
aactgctgac tgcatctgtt aagagttaac agtaaagagg tagaagtgtg tttctgaatc 180
agagtggaag cgtctcaagg gtcccacagt ggaggtccct gagctacctc ccttccgtga 240
gtgggaagag tgaagcccat gaagaactga gatgaagcaa ggatggggtt cctgggctcc 300
aggcaagggc tgtgctctct gcagcaggga gccccacgag tcagaagaaa agaactaatc 360
atttgttgca agaaaccttg cccggatact agcggaaaac tggaggcggn ggtgggggca 420
caggaaagtg gaagtgattt gatggagagc agagaagcct atgcacagtg gccgagtcca 480
cttgtaaagt g 491

<210> SEQ ID NO 143
<211> LENGTH: 515
<212> TYPE: DNA
<213> ORGANISM: Homo sapien

<400> SEQUENCE: 143
ttcaagcaat tgtaacaagt atatgtagat tagagtgagc aaaatcatat acaattttca 60
tttccagttg ctattttcca aattgttctg taatgtcgtt aaaattactt aaaaattaac 120
aaagccaaaa attatattta tgacaagaaa gccatcccta cattaatctt acttttccac 180
tcaccggccc atctccttcc tctttttcct aactatgcca ttaaaactgt tctactgggc 240
cgggcgtgtg gctcatgcct gtaatcccag cattttggga ggccaaggca ggcggatcat 300
gaggtcaaga gattgagacc atcctggcca acatggtgaa accccgcctc gactaagaat 360
acaaaaatta gctgggcatg gtggcgcatg cctgtagtct cagctactcg ggaggctgag 420
gcagaagaat cgcttgaacc cgggaggcag aggatgcagt gagccccgat cgcgccactg 480
cactctagcc tgggcgacag actgagactc tgctc 515

<210> SEQ ID NO 144
<211> LENGTH: 340
<212> TYPE: DNA
<213> ORGANISM: Homo sapien

<400> SEQUENCE: 144
tgtgccagtc tacaggccta tcagcagcga ctccttcagc aacagatggg gtcccctgtt 60
cagcccaacc ccatgagccc ccagcagcat atgctcccaa atcaggccca gtccccacac 120
ctacaaggcc agcagatccc taattctctc tccaatcaag tgcgctctcc ccagcctgtc 180
ccttctccac ggccacagtc ccagcccccc cactccagtc cttccccaag gatgcagcct 240
cagccttctc cacaccacgt ttccccacag acaagttccc cacatcctgg actggtagtt 300
gcccaggcca accccatgga acaagggcat tttgccagcc 340

<210> SEQ ID NO 145
<211> LENGTH: 630
<212> TYPE: DNA
<213> ORGANISM: Homo sapien

<400> SEQUENCE: 145
tgtaaaaact tgtttttaat tttgtataaa ataaaggtgg tccatgccca cgggggctgt 60
aggaaatcca agcagaccag ctggggtggg gggatgtagc ctacctcggg ggactgtctg 120
tcctcaaaac gggctgagaa ggcccgtcag gggcccaggt cccacagaga ggcctgggat 180
actcccccaa cccgaggggc agactgggca gtggggagcc cccatcgtgc cccagaggtg 240

-continued

```
gccacaggct gaaggagggg cctgaggcac cgcagcctgc aacccccagg gctgcagtcc    300

actaactttt tacagaataa aaggaacatg gggatgggga aaaaagcacc aggtcaggca    360

gggcccgagg gccccagatc ccaggagggc caggactcag gatgccagca ccaccctagc    420

agctcccaca gctcctggca caggaggccg ccacggattg gcacaggccg ctgctggcca    480

tcacgccaca tttggagaac ttgtcccgac agaggtcagc tcggaggagc tcctcgtggg    540

cacacactgt acgaacacag atctccttgt taatgacgta cacacggcgg aggctgcggg    600

gacagggcac gggaggtctc agccccactt                                     630
```

<210> SEQ ID NO 146
<211> LENGTH: 521
<212> TYPE: DNA
<213> ORGANISM: Homo sapien

<400> SEQUENCE: 146

```
atggctgctg gatttaggtg gtaatagggg ctgtgggcca taaatctgaa gccttgagaa     60

ccttgggtct ggagagccat gaagagggaa ggaaaagagg gcaagtcctg aacctaacca    120

atgacctgat ggattgctcg accaagacac agaagtgaag tctgtgtctg tgcacttccc    180

acagactgga gtttttggtg ctgaatagag ccagttgcta aaaaattggg ggtttggtga    240

agaaatctga ttgttgtgtg tattcaatgt gtgattttaa aaataaacag caacaacaat    300

aaaaaccctg actggctgtt ttttccctgt attctttaca actatttttt gaccctctga    360

aaattattat acttcaccta aatggaagac tgctgtgttt gtggaaattt tgtaattttt    420

taatttattt tattctctct ccttttttatt ttgcctgcag aatccgttga gagactaata    480

aggcttaata tttaattgat ttgtttaata tgtatataaa t                        521
```

<210> SEQ ID NO 147
<211> LENGTH: 562
<212> TYPE: DNA
<213> ORGANISM: Homo sapien

<400> SEQUENCE: 147

```
ggcatgcgag cgcactcggc ggacgcaagg gcggcgggga gcacacggag cactgcaggc     60

gccgggttgg gacagcgtct tcgctgctgc tggatagtcg tgttttcggg gatcgaggat    120

actcaccaga aaccgaaaat gccgaaacca atcaatgtcc gagttaccac catggatgca    180

gagctggagt ttgcaatcca gccaaataca actggaaaac agctttttga tcaggtggta    240

aagactatcg gcctccggga agtgtggtac tttggcctcc actatgtgga taataaagga    300

tttcctacct ggctgaagct ggataagaag gtgtctgccc aggaggtcag gaaggagaat    360

cccctccagt tcaagttccg ggccaaagtt ctaccctgaa gatgtggctg aggagctcat    420

ccaggacatc acccagaaac ttttcttcct tcaagtgaag gaaggaatcc ttagcgatga    480

gatctactgc ccccccttgar actgccgtgc tcttggggtc ctacgcttgt gcatgccaag    540

tttggggact accaccaaga ag                                             562
```

<210> SEQ ID NO 148
<211> LENGTH: 820
<212> TYPE: DNA
<213> ORGANISM: Homo sapien

<400> SEQUENCE: 148

```
gaaggagtcg ggatactcag cattgatgca ccccaatttc aaagcggcat tcttcggcag     60

gtctctggga caatctctag ggtcactacc tggaaactcg ttagggtaca actgaatgct    120
```

-continued

```
gaaaggaaag aacacctgca gaaccggaca gaaattcacc ccggcgatca gctgattgat    180

ctcggtcgac cagaagtcat ggctaaagat gacgaggacg ttgtcaattc cctgggcttt    240

tcgaagtgag tccagcagca gtctgaggta ttcgggccgg ttatgcacct ggaccaccag    300

caccagctcc cggggggccc aggtgccagc cttatctaca ttcctcaggg tctgatcaaa    360

gttcagctgg tacaccaggg accggtaccg cagcgtcagg ttgtccgctc gggctggggg    420

accgccggga ccagggaagc cgccgacacg ttggagaccc tgcggatgcc cacagccaca    480

gaggggtggt ccccaccgcg gccgccggca ccccgcgcgg gttcggcgtc cagcaacggt    540

ggggcgaggg cctcgttctt cctttgtcgc ccattgctgc tccagaggac gaagccgcag    600

gcggccacca cgagcgtcag gattagcacc ttccgtttgt agatgcggaa cctcatggtc    660

tccagggccg ggagcgcagc tacagctcga gcgtcggcgc cgccgctagg agccgcggct    720

cggcttcgtc tccgtcctct ccattcagca ccacgggtcc cggaaaaagc tcagccscgg    780

tcccaaccgc accctagctt cgttacctgc gcctcgcttg                          820
```

<210> SEQ ID NO 149
<211> LENGTH: 501
<212> TYPE: DNA
<213> ORGANISM: Homo sapien

<400> SEQUENCE: 149

```
cagattttta tttgcagtcg tcactggggc cgtttcttgc tgcttatttg tctgctagcc     60

tgctcttcca gctgcatggc caggcgcaag gccttgatga catctcgcag ggctgagaaa    120

tgcttggctt gctgggccag agcagattcc gctttgttca caaaggtctc caggtcatag    180

tctggctgct cggtcatctc agagagctca agccagtctg gtccttgctg tatgatctcc    240

ttgagctctt ccatagcctt ctcctccagc tccctgatct gagtcatggc ttcgttaaag    300

ctggacatct gggaagacag ttcctcctct tccttggata aattgcctgg aatcagcgcc    360

ccgttagagc aggcttccat ctcttctgtt tccatttgaa tcaactgctc tccactgggc    420

ccactgtggg ggctcagctc cttgaccctg ctgcatatct taagggtgtt taaaggatat    480

tcacaggagc ttatgcctgg t                                              501
```

<210> SEQ ID NO 150
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 150

```
ctcctcttgg tacatgaacc caagttgaaa gtggacttaa caaagtatct ggagaaccaa     60

gcattctgct ttgactttgc atttgatgaa acagcttcga atgaagttgt ctacaggttc    120

acagcaaggc cactggtaca gacaatcttt gaaggtggaa aagcaacttg ttttgcatat    180

ggccagacag gaagtggcaa gacacatact atgggcggag acctctctgg gaaagcccag    240

aatgcatcca aagggatcta tgccatggcc ttccgggacg tcttcttctg aagaatcaac    300

cctgctaccg gaagttgggc ctggaagtct atgtgacatt cttcgagatc tacaatggga    360

agctgtttga cctgctcaac aagaaggcca agcttgcgcg tgctggaaga cggcaagcaa    420

caggtgcaag tggtgggggc ttgcaggaac atctggntaa ctctgcttga tgatggcant    480
```

-continued

```
caagatgatc gacatgggca gcgcctgcag a                                  511


<210> SEQ ID NO 151
<211> LENGTH: 566
<212> TYPE: DNA
<213> ORGANISM: Homo sapien

<400> SEQUENCE: 151

tcccgaattc aagcgacaaa ttggawagtg aaatggaaga tgcctatcat gaacatcagg     60

caaatctttt gcgccaagat ctgatgagac gacaggaaga attaagacgc atggaagaac    120

ttcacaatca agaaatgcag aaacgtaaag aaatgcaatt gaggcaagag gaggaacgac    180

gtagaagaga ggaagagatg atgattcgtc aacgtgagat ggaagaacaa atgaggcgcc    240

aaagagagga aagttacagc cgaatgggct acatggatcc acgggaaaga gacatgcgaa    300

tgggtggcgg aggagcaatg aacatgggag atccctatgg ttcaggaggc cagaaatttc    360

cacctctagg aggtggtggt ggcataggtt atgaagctaa tcctggcgtt ccaccagcaa    420

ccatgagtgg ttccatgatg ggaagtgaca tgcgtactga gcgctttggg cagggaggtg    480

cggggcctgt gggtggacag ggtcctagag gaatggggcc tggaactcca gcaggatatg    540

gtagagggag agaagagtac gaaggc                                         566


<210> SEQ ID NO 152
<211> LENGTH: 518
<212> TYPE: DNA
<213> ORGANISM: Homo sapien

<400> SEQUENCE: 152

ttcgtgaaga ccctgactgg taagaccatc actctcgaag tggagcccga gtgacaccat     60

tgagaatgtc aaggcaaaga tccaagacaa ggaaggcatc cctcctgacc agcakaggtt    120

gatctttgct gggaaacagc tggaagatgg acgcaccctg tctgactaca acatccagaa    180

agagtccacc ctgcacctgg tgctccgtct cagaggtggg atgcaaatct tcgtgaagac    240

cctgactggt aagaccatca ccctcgaggt ggagcccagt gacaccatcg agaatgtcaa    300

ggcaaagatc caagataagg aaggcatccc tcctgatcag cagaggttga tctttgctgg    360

gaaacagctg gaagatggac gcaccctgtc tgactacaac atccagaaag agtccactct    420

gcacttggtc ctgcgcttga ggggggtgt ctaagtttcc ccttttaagg tttcaacaaa    480

tttcattgca ctttcctttc aataaagttg ttgcattc                            518


<210> SEQ ID NO 153
<211> LENGTH: 542
<212> TYPE: DNA
<213> ORGANISM: Homo sapien

<400> SEQUENCE: 153

gcgcgggtgc gtgggccact gggtgaccga cttagcctgg ccagactctc agcacctgga     60

agcgccccga gagtgacagc gtgaggctgg gagggaggac ttggcttgag cttgttaaac    120

tctgctctga gcctccttgt cgcctgcatt tagatggctc ccgcaaagaa gggtggcgag    180

aagaaaaagg gccgttctgc catcaacgaa gtggtaaccc gagaatacac catcaacatt    240

cacaagcgca tccatggagt gggcttcaag aagcgtgcac ctcgggcact caaagagatt    300

cggaaatttg ccatgaagga gatgggaact ccagatgtgc gcattgacac caggctcaac    360

aaagctgtct gggccaaagg aataaggaat gtgccatacc gaatccgtgt gcggctgtcc    420

agaaaacgta atgaggatga agattcacca aataagctat atactttggt tacctatgta    480
```

-continued cctgttacca ctttcaaaaa tctacagaca gtcaatgtgg atgagaacta atcgctgatc 540
gt 542

<210> SEQ ID NO 154
<211> LENGTH: 411
<212> TYPE: DNA
<213> ORGANISM: Homo sapien

<400> SEQUENCE: 154
aattctttat ttaaatcaac aaactcatct tcctcaagcc ccagaccatg gtaggcagcc 60
ctccctctcc atcccctcac cccacccctt agccacagtg aagggaatgg aaaatgagaa 120
gccacgaggg cccctgccag ggaaggctgc cccagatgtg tggtgagcac agtcagtgca 180
gctgtggctg gggcagcagc tgccacaggc tcctccctat aaattaagtt cctgcagcca 240
cagctgtggg agaagcatac ttgtagaagc aaggccagtc cagcatcaga aggcagaggc 300
agcatcagtg actcccagcc atggaatgaa cggaggacac agagctcaga gacagaacag 360 gccagggggga agaaggagag acagaatagg ccagggcatg gcggtgaggg a 411

<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155
tgatgaatct gggtgggctg gcagtagccc gagatgatgg gctcttctct ggggatccca 60
actggttccc taagaaatcc aaggagaatc ctcggaactt ctcggataac cagctgcaag 120
agggcaagaa cgtgatcggg ttacagatgg gcaccaaccg cggggcgtct cangcaggca 180
tgactggcta cgggatgcca cgccagatcc tctgatccca ccccaggcct tgcccctgcc 240
ctcccacgaa tggttaatat atatgtagat atatatttta gcagtgacat tcccagagag 300
ccccagagct ctcaagctcc tttctgtcag ggtggggggt tcaagcctgt cctgtcacct 360
ctgaagtgcc tgctggcatc ctctccccca tgcttactaa tacattccct tccccatagc 420
c 421

<210> SEQ ID NO 156
<211> LENGTH: 670
<212> TYPE: DNA
<213> ORGANISM: Homo sapien

<400> SEQUENCE: 156
agcggagctc cctcccctgg tggctacaac ccacacacgc caggctcagg catcgagcag 60
aactccagcg actgggtaac cactgacatt caggtgaagg tgcgggacac ctacctggat 120
acacaggtgg tgggacagac aggtgtcatc cgcagtgtca cggggggcat gtgctctgtg 180
tacctgaagg acagtgagaa ggttgtcagc atttccagtg agcacctgga gcctatcacc 240
cccaccaaga acaacaaggt gaaagtgatc ctgggcgagg atcgggaagc cacgggcgtc 300
ctactgagca ttgatggtga ggatggcatt gtccgtatgg accttgatga gcagctcaag 360
atcctcaacc tccgcttcct ggggaagctc ctggaagcct gaagcaggca gggccggtgg 420
acttcgtcgg atgaagagtg atcctccttc cttccctggc ccttggctgt gacacaagat 480

-continued

```
cctcctgcag ggctaggcgg attgttctgg atttcctttt gtttttcctt ttaggtttcc    540

atcttttccc tccctggtgc tcattggaat ctgagtagag tctgggggag ggtccccacc    600

ttcctgtacc tcctccccac agcttgcttt tgttgtaccg tctttcaata aaaagaagct    660

gtttggtcta                                                            670


<210> SEQ ID NO 157
<211> LENGTH: 421
<212> TYPE: DNA
<213> ORGANISM: Homo sapien

<400> SEQUENCE: 157

ggttcacagc actgctgctt gtgtgttgcc ggccaggaat tccaggctca caaggctatc     60

ttagcagctc gttctccggt ttttagtgcc atgtttgaac atgaaatgga ggagagcaaa    120

aagaatcgag ttgaaatcaa tgatgtggag cctgaagttt ttaaggaaat gatgtgcttc    180

atttacacgg ggaaggctcc aaacctcgac aaaatggctg atgatttgct ggcagctgct    240

gacaagtatg ccctggagcg cttaaaggtc atgtgtgagg atgccctctg cagtaacctg    300

tccgtggaga acgctgcaga aattctcatc ctggccgacc tccacagtgc agatcagttg    360

aaaactcagg cagtggattt catcaactat catgcttcgg atgtcttgga gacctcttgg    420

g                                                                     421


<210> SEQ ID NO 158
<211> LENGTH: 321
<212> TYPE: DNA
<213> ORGANISM: Homo sapien

<400> SEQUENCE: 158

tcgtagccat ttttctgctt ctttggagaa tgacgccaca ctgactgctc attgtcgttg     60

gttccatgcc aattggtgaa atagaacctc atccggtagt ggagccggag ggacatcttg    120

tcatcaacgg tgatggtgcg atttggagca taccagagct tggtgttctc gccatacagg    180

gcaaagaggt tgtgacaaag aggagagata cggcatgcct gtgcagccct gatgcacagt    240

tcctctgctg tgtactctcc actgcccagc cggaggggct ccctgtccga cagatagaag    300

atcacttcca cccctggctt g                                              321


<210> SEQ ID NO 159
<211> LENGTH: 596
<212> TYPE: DNA
<213> ORGANISM: Homo sapien

<400> SEQUENCE: 159

tggcacactg ctcttaagaa actatgawga tctgagattt ttttgtgtat gtttttgact     60

cttttgagtg gtaatcatat gtgtctttat agatgtacat acctccttgc acaaatggag    120

gggaattcat tttcatcact gggagtgtcc ttagtgtata aaaaccatgc tggtatatgg    180

cttcaagttg taaaaatgaa agtgacttta aaagaaaata ggggatggtc caggatctcc    240

actgataaga ctgtttttaa gtaacttaag gacctttggg tctacaagta tatgtgaaaa    300

aaatgagact tactgggtga ggaaattcat tgtttaaaga tggtcgtgtg tgtgtgtgtg    360

tgtgtgtgtg ttgtgttgtg ttttgttttt taagggaggg aatttattat ttaccgttgc    420

ttgaaattac tgkgtaaata tatgtytgat aatgatttgc tytttgvcma ctaaaattag    480

gvctgtataa gtwctaratg cmtccctggg kgttgatytt ccmagatatt gatgatamcc    540

cttaaaattg taaccygcct ttttcccttt gctytcmatt aaagtctatt cmaaag        596
```

-continued

<210> SEQ ID NO 160
<211> LENGTH: 515
<212> TYPE: DNA
<213> ORGANISM: Homo sapien

<400> SEQUENCE: 160
gggggtaggc tctttattag acggttattg ctgtactaca gggtcagagt gcagtgtaag 60
cagtgtcaga ggcccgcgtt cagcccaaga atgtggattt tctctcccta ttgatcacag 120
tgggtgggtt tcttcagaaa agccccagag gcagggacca gtgagctcca aggttagaag 180
tggaactgga aggcttcagt cacatgctgc ttccacgctt ccaggctggg cagcaaggag 240
gagatgccca tgacgtgcca ggtctcccca tctgacacca gtgaagtctg gtaggacagc 300
agccgcacgc ctgcctctgc caggaggcca atcatggtag gcagcattgc agggtcagag 360
gtctgagtcc ggaataggag caggggcagg tccctgcgga gaggcacttc tggcctgaag 420
acagctccat tgagcccctg cagtacaggy gtagtgcctt ggaccaagcc cacagcctgg 480
taaggggcgc ctgccagggc cacggccagg aggca 515

<210> SEQ ID NO 161
<211> LENGTH: 936
<212> TYPE: DNA
<213> ORGANISM: Homo sapien

<400> SEQUENCE: 161
taatttctta gtcgtttgga atccttaagc atgcaaaagc tttgaacaga agggttcaca 60
aaggaaccag ggttgtctta tggcatccag ttaagccaga gctgggaatg cctctgggtc 120
atccacatca ggagcagaag cacttgactt gtcggtcctg ctgccacggt ttgggcgccc 180
accacgccca cgtccacctc gtcctcccct gccgccacgt cctgggcggc caaggtctcc 240
aaaattgatc tccagctgag acgttatatc atttgctggc ttccggaaat gatggtccat 300
aaccgaatct tcagcatgag cctcttcact ctttgattta tgaagaacaa atcccttctt 360
ccactgccca tcagcacctt catttggttt tcggatatta aattctactt ttgcccggtc 420
cttattttga atagccttcc actcatccaa agtcatctct tttggaccct cctcttttac 480
ctcttcaact tcattctcct tattttcagt gtctgccact ggatgatgtt cttcaccttc 540
aggtgtttcc tcagtcacat ttgattgatc caagtcagtt aattcgtctt tgacagttcc 600
ccagttgtga gatccgctac ctccacgttt gtcctcgtgc ttcaggccag atctatcact 660
tccactatgc ctatcaaatt cacgtttgcc acgagaatca aatccatctc ctcggcccat 720
tccacgtcca cggccccctc gacctcttcc aagaccacca cgacctcgaa taggtcggtc 780
aataatcggt ctatcaactg aaaattcgcc tccttcaccc ttttcttcaa gtggcttttc 840
gaatcttcgt tcacgaggtg gtcgcctttc tggtcttcta tcaattattt tcccttcacc 900
ctgaagttgt tgatcaggtc ttcttccaac tcgtgc 936

<210> SEQ ID NO 162
<211> LENGTH: 950
<212> TYPE: DNA
<213> ORGANISM: Homo sapien

<400> SEQUENCE: 162
aagcggatgg acctgagtca gccgaatcct agccccttcc cttgggcctg ctgtggtgct 60
cgacatcagt gacagacgga agcagcagac catcaaggct acgggaggcc cggggcgctt 120

-continued gcgaagatga agtttggctg cctctccttc cggcagcctt atgctggctt tgtcttaaat 180
ggaatcaaga ctgtggagac gcgctggcgt cctctgctga gcagccagcg gaactgtacc 240
atcgccgtcc acattgctca cagggactgg gaaggcgatg cctgtcggga gctgctggtg 300
gagagactcg ggatgactcc tgctcagatt caggccttgc tcaggaaagg ggaaaagttt 360
ggtcgaggag tgatagcggg actcgttgac attggggaaa ctttgcaatg ccccgaagac 420
ttaactcccg atgaggttgt ggaactagaa aatcaagctg cactgaccaa cctgaagcag 480
aagtacctga ctgtgatttc aaaccccagg tggttactgg agcccatacc taggaaagga 540
ggcaaggatg tattccaggt agacatccca gagcacctga tccctttggg gcatgaagtg 600
tgacaagtgt gggctcctga aaggaatgtt ccrgagaaac cagctaaatc atggcacctt 660
caatttgcca tcgtgacgca gacctgtata aattaggtta aagatgaatt tccactgctt 720
tggagagtcc cacccactaa gcactgtgca tgtaaacagg ttcctttgct cagatgaagg 780
aagtaggggg tggggctttc cttgtgtgat gcctccttag gcacacaggc aatgtctcaa 840
gtactttgac cttagggtag aaggcaaagc tgccagtaaa tgtctcagca ttgctgctaa 900
ttttggtcct gctagtttct ggattgtaca aataaatgtg ttgtagatga 950

<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtgt 180
acacctgtgg ttctcggggc tgccctttgg ctttggagat ggttttctcg atgggggctg 240
ggagggcttt gttggagacc ttgcacttgt actccttgcc attcaaccag tcctggtgca 300
ngacggtgag gacgctnacc acacggtacg ngctggtgta ctgctcctcc cgcggctttg 360
tcttggcatt atgcacctcc acgccgtcca cgtaccaatt gaacttgacc tcagggtctt 420
cgtggctcac gtccaccacc acgcatgtaa cctcaaanct cggncgcgan cacgc 475

<210> SEQ ID NO 164
<211> LENGTH: 476
<212> TYPE: DNA
<213> ORGANISM: Homo sapien

<400> SEQUENCE: 164
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgtgtggtc agcgtcctca ccgtcctgca 180
ccaggactgg ctgaatggca aggagtacaa gtgcaaggtc tccaacaaag ccctcccagc 240
ccccatcgag aaaaccatct ccaaagccaa agggcagccc cgagaaccac aggtgtacac 300
cctgccccca tcccgggagg agatgaccaa gaaccaggtc agcctgacct gcctggtcaa 360
aggcttctat cccagcgaca tcgcccgtgg agtgggagag caatgggcag ccggagaaca 420
actacaagac cacgcctccc gtgctggact ccgacacctg ccgggcggcc gctcga 476

-continued

<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165
agcgtggttn cggccgaggt cccaaccaag gctgcancct ggatgccatc aaagtcttct 60
gcaacatgga gactggtgag acctgcgtgt accccactca gcccagtgtg gcccagaaga 120
actggtacat cagcaagaac cccaaggaca agaggcatgt ctggttcggc gagagcatga 180
ccgatggatt ccagttcgag tatggcggcc agggctccga ccctgccgat gtggacctgc 240
ccgggcggnc gctcga 256

<210> SEQ ID NO 166
<211> LENGTH: 332
<212> TYPE: DNA
<213> ORGANISM: Homo sapien

<400> SEQUENCE: 166
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgg gcggccgctc ga 332

<210> SEQ ID NO 167
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167
tcgagcggtc gcccgggcag gtccacatcg gcagggtcgg agccctggcc gccatactcg 60
aactggaatc catcggncat gctctcgccg aaccagacat gcctcttgnc cttggggttc 120
ttgctgatgt accagntctt ctgggccaca ctgggctgag tggggtacac gcaggtctca 180
ccantctcca tgttgcanaa gactttgatg gcatccaggt tgcagccttg gttggggtca 240
atccagtact ctccactctt ccagacagag tggcacatct tgaggtcacg gcaggtgcgg 300
gcggggttct tgacctcggt cgcgaccacg ct 332

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168

-continued tcgagcggcc gcccgggcag gtcctcctca gagcggtagc tgttcttatt gccccggcag 60
cctccataga tnaagttatt gcangagttc ctctccacgt caaagtacca gcgtgggaag 120
gatgcacggc aaggcccagt gactgcgttg gcggtgcagt attcttcata gttgaacata 180
tcgctggagt ggacttcaga atcctgcctt ctgggagcac ttgggacaga ggaatccgct 240
gcattcctgc tggtggacct cggccgcgac cacgct 276

<210> SEQ ID NO 169
<211> LENGTH: 276
<212> TYPE: DNA
<213> ORGANISM: Homo sapien

<400> SEQUENCE: 169
agcgtggtcg cggccgaggt ccaccagcag gaatgcagcg gattcctctg tcccaagtgc 60
tcccagaagg caggattctg aagaccactc cagcgatatg ttcaactatg aagaatactg 120
caccgccaac gcagtcactg ggccttgccg tgcatccttc ccacgctggt actttgacgt 180
ggagaggaac tcctgcaata acttcatcta tggaggctgc cggggcaata agaacagcta 240
ccgctctgag gaggacctgc ccgggcggcc gctcga 276

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagccagaa tggcacatct tgaggtcacg gcangtgcgg 300
gcggggttct tgacctcggc cgcgaccacg ct 332

<210> SEQ ID NO 171
<211> LENGTH: 333
<212> TYPE: DNA
<213> ORGANISM: Homo sapien

<400> SEQUENCE: 171
agcgtggtcg cggccgaggt caagaaaccc cgcccgcacc tgccgtgacc tcaagatgtg 60
ccactctggc tggaagagtg gagagtactg gattgacccc aaccaaggct gcaacctgga 120
tgccatcaaa gtcttctgca acatggagac tggtgagacc tgcgtgtacc ccactcagcc 180
cagtgtggcc cagaagaact ggtacatcag caagaacccc aaggacaaga ggcatgtctg 240
gctcggcgag agcatgaccg atggattcca gttcgagtat ggcggccagg gctccgaccc 300
tgccgatgtg gacctgcccg ggcggccgct cga 333

<210> SEQ ID NO 172
<211> LENGTH: 527
<212> TYPE: DNA
<213> ORGANISM: Homo sapien
<220> FEATURE:
<221> NAME/KEY: misc_feature -continued
<222> LOCATION: (1)...(527)
<223> OTHER INFORMATION: n = A,T,C or G

<400> SEQUENCE: 172
agcgtggtcg cggccgaggt cctgtcagag tggcactggt agaagntcca ggaaccctga 60
actgtaaggg ttcttcatca gtgccaacag gatgacatga aatgatgtac tcagaagtgt 120
cctgnaatgg ggcccatgan atggttgnct gagagagagc ttcttgtcct acattcggcg 180
ggtatggtct tggcctatgc cttatggggg tggccgttgn gggcggtgng gtccgcctaa 240
aaccatgttc ctcaaagatc atttgttgcc caacactggg ttgctgacca naagtgccag 300
gaagctgaat accatttcca gtgtcatacc cagggtgggt gacgaaaggg gtcttttgaa 360
ctgtggaagg aacatccaag atctctgntc catgaagatt ggggtgtgga agggttacca 420
gttggggaag ctcgctgtct tttccttcc aatcangggc tcgctcttct gaatattctt 480
cagggcaatg acataaattg tatattcggt tcccggttcc aggccag 527

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgangaacat ggntttaggc ggaccacacc ggccacaacg 480
ggcaccccca taaggcatag gccaagaaca tacccgncga atgtaggaca agaagctctn 540
tctcanacaa ncatctcatg ggccccattc cangacactt ctgagtacat canttcatgg 600
catcctggtg gcactgataa aaacccttac agtta 635

<210> SEQ ID NO 174
<211> LENGTH: 572
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174
agcgtggtcg cgggcgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300

-continued

```
gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcanggg ctcgctcttc tgattattct    480

tcagggcaat gacataaatt gtatattcgg ntcccgggtn cagccaataa taataaccct    540

ctgtgacacc anggcggggc cgaagganca ct                                  572
```

<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175

```
agcgtggtcg cggccgaggt cctcaccaga ggtaccacct acaacatcat agtggaggca     60

ctgaaagacc agcagaggca taaggttcgg gaagaggttg ttaccgtggg caactctgtc    120

aacgaaggct tgaaccaacc tacggatgac tcgtgctttg acccctacac agtttcccat    180

tatgccgttg gagatgagtg ggaacgaatg tctgaatcag gctttaaact gttgtgccag    240

tgcttangct ttggaagtgg tcatttcaga tgtgattcat ctagatggtg ccatgacaat    300

ggtgtgaact acaagattgg agagaagtgg gaccgtcagg gagaaaatgg acctgcccgg    360

gcggccgctc ga                                                        372
```

<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176

```
tcgagcggcc gcccgggcag gtccattttc tccctgacgg tcccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ntgacagagt tgcccacggt aacaacctct tcccgaacct tatgcctctg    300

ctggtctttc agtgcctcca ctatgatgtt gtaggtggta cctctggtga ggacctcggc    360

cgcgaccacg ct                                                        372
```

<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177

```
agcgtggccg cggccgaggt ccattggctg gaacggcatc aacttggaag ccagtgatcg     60

tctcagcctt ggttctccag ctaatggtga tggnggtctc agtagcatct gtcacacgag    120

cccttcttgg tgggctgaca ttctccagag tggtgacaac accctgagct ggtctgcttg    180
```

-continued

```
tcaaagtgtc cttaagagca tagacactca cttcatattt ggcgnccacc ataagtcctg    240

atacaaccac ggaatgacct gtcaggaac                                      269


<210> SEQ ID NO 178
<211> LENGTH: 529
<212> TYPE: DNA
<213> ORGANISM: Homo sapien

<400> SEQUENCE: 178

tcgagcggcc gcccgggcag gtcctcagac cgggttctga gtacacagtc agtgtggttg     60

ccttgcacga tgatatggag agccagcccc tgattggaac ccagtccaca gctattcctg    120

caccaactga cctgaagttc actcaggtca cacccacaag cctgagcgcc cagtggacac    180

cacccaatgt tcagctcact ggatatcgag tgcgggtgac ccccaaggag aagaccggac    240

caatgaaaga aatcaacctt gctcctgaca gctcatccgt ggttgtatca ggacttatgg    300

cggccaccaa atatgaagtg agtgtctatg ctcttaagga cactttgaca agcagaccag    360

ctcagggtgt tgtcaccact ctggagaatg tcagcccacc aagaagggct cgtgtgacag    420

atgctactga gaccaccatc accattagct ggagaaccaa gactgagacg atcactggct    480

tccaagttga tgccgttcca gccaatggac ctcggccgcg accacgctt                529


<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179

agcgtggtcg cggccgaggt ctggccgaac tgccagtgta cagggaagat gtacatgtta     60

tagntcttct cgaagtcccg ggccagcagc tccacggggt ggtctcctgc ctccaggcgc    120

ttctcattct catggatctt cttcacccgc agcttctgct tctcagtcag aaggttgttg    180

tcctcatccc tctcatacag ggtgaccagg acgttcttga gccagtcccg catgcgcagg    240

gggaattcgg tcagctcaga gtccaggcaa ggggggatgt atttgcaagg cccgatgtag    300

tccaagtgga gcttgtggcc cttcttggtg ccctccaagg tgcactttgt ggcaaagaag    360

tggcaggaag agtcgaaggt cttgttgtca ttgctgcaca ccttctcaaa ctcgccaatg    420

ggggctgggc agacctgccc gggcggccgc tcga                                454


<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180

tcgagcggcc gcccgggcag gtctgcccag cccccattgg cgagtttgag aaggngtgca     60

gcaatgacaa caagaccttc gactcttcct gccacttctt tgccacaaag tgcaccctgg    120

agggcaccaa gaagggccac aagctccacc tggactacat cgggccttgc aaatacatcc    180

ccccttgcct ggactctgag ctgaccgaat tccccctgcg catgcgggac tggctcaaga    240
```

-continued

```
acgtcctggt caccctgtat gagagggatg aggacaacaa ccttctgact gagaagcana    300

agctgcgggt gaagaanatc catgagaatg anaagcgcct gnaggcanga gaccaccccg    360

tggagctgct ggcccgggac ttcgagaaga actataacat gtacatcttc cctgtacact    420

ggcagttcgg ccagacctcg gccgcgacca cgct                                454
```

<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181

```
agcgtggntg cggacgacgc ccacaaagcc attgtatgta gttttanttc agctgcaaan     60

aataccncca gcatccacct tactaaccag catatgcaga ca                       102
```

<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182

```
tcgagcggtc gcccgggcag gtctgggcgg atagcaccgg gcatattttg gaatggatga     60

ggtctggcac cctgagcagc ccagcgagga cttggtctta gttgagcaat ttggctagga    120

ggatagtatg cagcacggtt ctgagtctgt gggatagctg ccatgaagna acctgaagga    180

ggcgctggct ggtangggtt gattacaggg ctgggaacag ctcgtacact tgccattctc    240

tgcatatact ggntagtgag gcgagcctgg cgctcttctt tgcgctgagc taaagctaca    300

tacaatggct ttgnggacct cggccgcgac cacgctt                             337
```

<210> SEQ ID NO 183
<211> LENGTH: 374
<212> TYPE: DNA
<213> ORGANISM: Homo sapien

<400> SEQUENCE: 183

```
tcgagcggcc gcccgggcag gtccattttc tccctgacgg tcccacttct ctccaatctt     60

gtagttcaca ccattgtcat gacaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagaag ttgcccacgg taacaacctc ttcccgaacc ttatgcctct    300

gctggtcttt caagtgcctc cactatgatg ttgtaggtgg cacctctggt gaggacctcg    360

gccgcgacca cgct                                                      374
```

<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G -continued

<400> SEQUENCE: 184
agcgtggttt gcggccgagg tcctcaccan aggtgccacc tacaacatca tagtggaggc 60
actgaaagac cagcagaggc ataaggttcg ggaagaggtt gttaccgtgg gcaactctgt 120
caacgaaggc ttgaaccaac ctacggatga ctcgtgcttt gacccctaca cagnttccca 180
ttatgccgtt ggagatgagt gggaacgaat gtctgaatca ggctttaaac tgttgtgcca 240
gtgcttangc tttggaagtg gtcatttcag atgtgattca tctanatggt gtcatgacaa 300
tggtgngaac tacaagattg gagagaagtg gnaccgtcag ggganaaaat ggacctgccc 360
gggcggcncg ctcga 375

<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185
agcgtggtcg cggccgaggt ctggcttnct gctcangtga ttatcctgaa ccatccaggc 60
caaataagcg ccggctatgc ccctgnattg gattgccaca cggctcacat tgcatgcaag 120
tttgctgagc tgaaggaaaa gattgatc 148

<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186
tcgagcggcc gcccgggcag gtccaattga aacaaacagt tctgagaccg ttcttccacc 60
actgattaag agtggggngg cgggtattag ggataatatt catttagcct tctgagcttt 120
ctgggcagac ttggtgacct tgccagctcc agcagccttc tggtccactg ctttgatgac 180
acccaccgca actgtctgtc tcatatcacg aacagcaaag cgacccaaag gtggatagtc 240
tgagaagctc tcaacacaca tgggcttgcc aggaaccata tcaacaatgg gcagcatcac 300
cagacttcaa gaatttaagg gccatcttcc agctttttac cagaacggcg atcaatcttt 360
tccttcagct cagcaaactt gcatgcaatg tgagccg 397

<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187
tcgagcggcc gcccgggcag gtccagaggg ctgtgctgaa gtttgctgct gccactggag 60
ccactccaat tgctggccgc ttcactcctg gaaccttcac taaccagatc caggcagcct 120
tccgggagcc acggcttctt gtggntactg accccagggc tgaccaccag cctctcacgg 180

-continued

```
aggcatctta tgttaaccta cctaccattg cgctgtgtaa cacagattct cctctgcgct    240

atgtggacat tgccatccca tgcaacaaca agggagctca ctcagngggg tttgatgtgg    300

tggatgctgg ctcgggaagt tctgcgcatg cgtggcacca tttcccgtga acacccatgg    360

gangncatgc ctgatctgga cttctacaga gatcctgaag agattgaaaa agaagaacag    420

gctgnttgct ganaaagcaa gtgaccaagg angaaatttc angggtgaaa nggactgctc    480

ccgctcctga attcactgct actcaacctg angntgcaga ctggtcttga aggngnacan    540

gggccctctg ggcctattta agcancttcg gtcgcgaaca cgnt                     584
```

```
<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188

agcgtgngtc gcggccgagg tgctgaatag gcacagaggg cacctgtaca ccttcagacc     60

agtctgcaac ctcaggctga gtagcagtga actcaggagc gggagcagtc cattcaccct    120

gaaattcctc cttggncact gccttctcag cagcagcctg ctcttctttt tcaatctctt    180

caggatctct gtagaagtac agatcaggca tgacctccca tgggtgttca cgggaaatgg    240

tgccacgcat gcgcagaact tcccgagcca gcatccacca catcaaaccc actgagtgag    300

ctcccttgtt gttgcatggg atgggcaatg tccacatagc gcagaggaga atctgtgtta    360

cacagcgcaa tggtaggtag gttaacataa gatgcctccg cgagaagctg gtggtcagcc    420

ctggggtcaa gtaaccacaa gaagccgtgg ctcccggaag gctgcctgga tctggttagt    480

gaaggntcca ggagtgaagc ggccaacaat tggagtggct tcagtggcaa gcagcaaact    540

tcagcacaag ccctctggac ctgcccggcg gccgctcga                           579
```

```
<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189

tcgagcggcc gcccgggcag gtccattttc tccctgacgg ncccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgcccacggt aacaacctcn tccccgaacc ttatgcctct    300

gctgggcttt cagngcctcc actatgatgn tgtagggggg cacctctggn gangacctcg    360

gccgcgacca cgct                                                      374
```

```
<210> SEQ ID NO 190
<211> LENGTH: 373
<212> TYPE: DNA
<213> ORGANISM: Homo sapien
<220> FEATURE:
<221> NAME/KEY: misc_feature
```

-continued

<222> LOCATION: (1)...(373)
<223> OTHER INFORMATION: n = A,T,C or G

<400> SEQUENCE: 190
agcgtggtcg cggccgaggt cctcaccaga ggtgccacct acaacatcat agtggaggca 60
ctgaaagacc agcagaggca taaggctcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg gtcatttcag atgtgattca tctagatggt gccatgacaa 300
tggngngaac tacaagattg gagagaagtg gnaccgncag ggagaaaatg gacctgcccg 360
ggcggccgct cga 373

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggntg caaccttggt tggggtcaat 240
ccagtactct ccactcttcc agccagagtg gcacatcttg aggtcacggc aggtgcggnc 300
gggggntttt gcggctgccc tctggncttc ggntgtnctc natctgctgg ctca 354

<210> SEQ ID NO 192
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192
tcgagcggcc gcccgggcag gtctcgcggt cgcactggtg atgctggtcc tgttggtccc 60
cccggccctc ctggacctcc tggccccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagncgca agaaccccgc ccgcacctgc 300
cgtgacctca agatgtgcca ctctgactgg aagagtggag agtactggat tgaccccaac 360
caagctgcaa cctggatgcc atcaaagtct tctgcaacat ggagactggt gagacctgcg 420
tgtaccccac tcagcccagt gtggcccaaa agaactggta catcagcaag aaccccaagg 480
acaagaagca tgtctggttc ggcgagaaca tgaccgatgg attccagttc gagtatggcg 540
ggcagggctc cgaccctgcc gatggggacc ttggccgcga acacgct 587

<210> SEQ ID NO 193
<211> LENGTH: 98
<212> TYPE: DNA

-continued

<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193
agcgtggnng cggccgaggt ataaatatcc agnccatatc ctccctccac acgctganag 60
atgaagctgt ncaaagatct cagggtggan aaaaccat 98

<210> SEQ ID NO 194
<211> LENGTH: 240
<212> TYPE: DNA
<213> ORGANISM: Homo sapien

<400> SEQUENCE: 194
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg ggggaaaaca ccatggtttt atccaccctg agatctttga acaacttcat 180
ctctcagcgt gcggagggag gctctggact ggatatttct acctcggccg cgaccacgct 240

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195
cgagcgggcg accgggcagg tncagactcc aatccanana accatcaagc cagatgtcag 60
aagctacacc atcacaggtt tacaaccagg cactgactac aaganctacc tgcacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggta catcatcnag tatganaagc ctgggcctcc tcccagagaa 300
gnggtccctc ggccccgccc tgntgtccca naggntacta ttactgngcc ngcaaccggc 360
aaccgatatc nattttgnca ttggccttca acaataatta 400

<210> SEQ ID NO 196
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 196
agcgtggttc gcggccgang tcctgtcaga gtggcactgg tagaagttcc aggaaccctg 60
aactgtaagg gttcttcatc agngccaaca ggatgacatg aaatgatgta ctcagaagtg 120
tcctggaatg ggcccatga gatggttgtc tgagagagag cttcttgncc tgtctttttc 180
cttccaatca ggggctcgct cttctgatta ttcttcaggg caatgacata aattgtatat 240
tcgggtcccg gntccaggcc agtaatagta ncctctgtga caccagggcg gngccgaggg 300
accacttctc tgggaggaga cccaggcttc tcatacttga tgatgtaacc ggtaatcctg 360
gcacgtggcg gctgccatga taccagcaag gaattggggt gtggtggcca ggaaacgcag 420

-continued gttggatggn gcatcaatgg cagtggaggc cgtcgatgac cacaggggga gctccgacat 480
tgtcattcaa ggtg 494

<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197
agcgtggncg cggccgaggt gcagcgcggg ctgtgccacc ttctgctctc tgcccaacga 60
taaggagggt ncctgccccc aggagaacat taactntccc cagctcggcc tctgccgg 118

<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198
tcgagcggcc gcccgggcag gtttttttg ctgaaagtgg ntactttatt ggntgggaaa 60
gggagaagct gtggtcagcc caagagggaa tacagagncc cgaaaaaggg gagggcaggt 120
gggctggaac cagacgcagg gccaggcaga aactttctct cctcactgct cagcctggtg 180
gtggctggag ctcanaaatt gggagtgaca caggacacct tcccacagcc attgcggcgg 240
catttcatct ggccaggaca ctggctgtcc acctggcact ggtcccgaca gaagcccgag 300
ctggggaaag ttaatgttca cctgggggca ggaaccctcc ttatcattgn gcagagagca 360
gaaggtggca cagcccgcgc tgcacctcgg ccgcgaccac gct 403

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199
tcgagcggcc gcccgggcag gtccaccata agtcctgata caaccacgga tgagctgtca 60
ggagcaaggt tgatttcttt cattggtccg gncttctcct tgggggncac ccgcactcga 120
tatccagtga gctgaacatt gggtggcgtc cactgggcgc tcaggct 167

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200
tcgagcggtt cgcccgggca ggtccaccac acccaattcc ttgctggtat catggcagcc 60

-continued

```
gccacgtgcc aggattaccg gctacatcat caagtatgag aagcctgggt ctcctcccag    120

agaagcggtc cctcggcccc gccctggtgt cacagaggct actattactg gcctggaacc    180

gggaaccgaa tatacaattt atgtcattgn cctgaagaat aatcannaan agcganccccc    240

tgattggaag ga                                                        252


<210> SEQ ID NO 201
<211> LENGTH: 91
<212> TYPE: DNA
<213> ORGANISM: Homo sapien

<400> SEQUENCE: 201

agcgtggtcg cggccgaggt tgtacaagct tttttttttt tttttttttt tttttttttt     60

tttttttttt tttttttttt tttttttttt t                                    91


<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202

tcgagcggnc gcccgggcag gtctgccaac accaagattg gcccccgccg catccacaca     60

gtccgtgtgc ggggaggtaa caagaaatac cgtgccctga ggttggacgt ggggaatttc    120

tcctggggct cagagtgttg tactcgtaaa acaaggatca tcgatgttgt ctacaatgca    180

tctaataacg agctggttcg taccaagacc ctggtgaaga attgcatcgt gctcatcgac    240

agcacaccgt accgacagtg gtacgagtcc cactatgcgc tgcccctggg ccgcaagaag    300

ggagccaagc tgactcctga ggaagaagag attttaaaca aaaaacgatc taanaaaaaa    360

aaaacaat                                                             368


<210> SEQ ID NO 203
<211> LENGTH: 340
<212> TYPE: DNA
<213> ORGANISM: Homo sapien

<400> SEQUENCE: 203

agcgtggtcg cggccgaggt gaaatggtat tcagcttcct ggcacttctg gtcagcaacc     60

cagtgttggg caacaaatga tctttgagga acatggtttt aggcggacca caccgcccac    120

aacggccacc cccataaggc ataggccaag accatacccg ccgaatgtag gacaagaagc    180

tctctctcag acaaccatct catgggcccc attccaggac acttctgagt acatcatttc    240

atgtcatcct gttggcactg atgaagaacc cttacagttc agggttcctg gaacttctac    300

cagtgccact ctgacaggac ctgcccgggc ggccgctcga                          340


<210> SEQ ID NO 204
<211> LENGTH: 341
<212> TYPE: DNA
<213> ORGANISM: Homo sapien

<400> SEQUENCE: 204

tcgagcggcc gcccgggcag gtcctgtcag agtggcactg gtagaagttc caggaaccct     60

gaactgtaag ggttcttcat cagtgccaac aggatgacat gaaatgatgt actcagaagt    120

gtcctggaat ggggcccatg agatggttgt ctgagagaga gcttcttgtc ctacattcgg    180
```

-continued

```
cgggtatggt cttggcctat gccttatggg ggtggccgtt gtgggcggtg tggtccgcct    240

aaaaccatgt tcctcaaaga tcatttgttg cccaacactg ggttgctgac cagaagtgcc    300

aggaagctga ataccatttc acctcggccg cgaccacgct a                        341


<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205

tcgagcggcc gcccgggcag gtctcccttc ttgcggccca ggggcagcgc atagtgggac     60

tcgtaccact gtcggtacgg tgtgctgtcg atgagcacga tgcaattctt caccagggtc    120

ttggtacgaa ccagctcgtt attagatgca ttgtagacaa catcgatgat ccttgtttta    180

cgagtacaac actctgagcc ccaggagaaa ttccccacgt ccaacctcag ggcacggtat    240

ttcttgttac ctccccgcac acggactgtg tggatgcggc gggggccaag ctgactcctg    300

aggaagaaga gattttaaac aaaaaacgat ctaaaaaaat tcagaagaaa tatgatgaaa    360

ggaaaaagaa tgccaaaatc agcagtctcc tggaggagca gttccagcag ggcaagcttc    420

ttgcgtgcat cgcttcaagg ccgggacagt gtgaccgagc agatggctat gtgctagagg    480

gcaaagaagt ggagttctat cttaagaaaa tcagggccca gaatggtgng tcttcaacta    540

atccaaaggg gagtttcaga ccagtgcaat cagcaaaaac attgatactg ntggccaaat    600

ttattggtgc agggcttgca cantangann ggctgggtct tggggcttgg attggnacaa    660

gctttggcag ccttttcttt ggttttgcca aaaacctttt gntgaagang anacctnggg    720

cggacccctt aaccgattcc acnccnggng gcgttctang gncccncttg               770


<210> SEQ ID NO 206
<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206

agcgtggtcg cggccgaggt ctgctgcttc agcgaagggt ttctggcata accaatgata     60

aggctgccaa agactgttcc aataccagca ccagaaccag ccactcctac tgttgcagca    120

cctgcaccaa taaatttggc agcagtatca atgtctctgc tgattgcact ggtctgaaac    180

tccctttgga ttagctgaga cacaccattc tgggccctga ttttcctaag atagaactcc    240

aactctttgc cctctagcac atagccatct gctcggtcac actgtcccgg ccttgaagcg    300

atgcacgcaa gaagcttgcc ctgctggaac tgctcctcca ggagactgct gattttggca    360

ttcttttttcc tttcatcata tttcttctga atttttttag atcgtttttt gtttaaaatc    420

tcttcttcct caggagtcag cttggccccc gccgcatcca cacagtccgt gtgcggggag    480

gtaacaagaa ataccgtgcc ctgaggttgg acgtggggaa tttctcctgg ggctcagagt    540

ggtgtactcg taaaacaagg atcatcgatg gtgnctacaa tgcatctaat aacgagctgg    600

gtcggaccca aagaacctgg ngaanaaatg gatcgnctca tcgacaggac accgtacccg    660
```

-continued

```
acaggggnac gantcccact atgcgcttgc ccctgggccg caanaaagga aaactgcccg    720

ggcggccntc gaaagcccaa ttntggaaaa aatccatcac actgggnggc cngtcgagca    780

tgcatntana ggggcccatt cccccctnann                                    810
```

<210> SEQ ID NO 207
<211> LENGTH: 257
<212> TYPE: DNA
<213> ORGANISM: Homo sapien

<400> SEQUENCE: 207

```
tcgagcggcc gcccgggcag gtccccaacc aaggctgcaa cctggatgcc atcaaagtct     60

tctgcaacat ggagactggt gagacctgcg tgtaccccac tcagcccagt gtggcccaga    120

agaactggta catcagcaag aaccccaagg acaagaggca tgtctggttc ggcgagagca    180

tgaccgatgg attccagttc gagtatggcg gccagggctc cgaccctgcc gatgtggacc    240

tcggccgcga ccacgct                                                   257
```

<210> SEQ ID NO 208
<211> LENGTH: 257
<212> TYPE: DNA
<213> ORGANISM: Homo sapien

<400> SEQUENCE: 208

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggacctg    240

cccgggcggc cgctcga                                                   257
```

<210> SEQ ID NO 209
<211> LENGTH: 747
<212> TYPE: DNA
<213> ORGANISM: Homo sapien
<220> FEATURE:
<221> NAME/KEY: misc_feature
<222> LOCATION: (1)...(747)
<223> OTHER INFORMATION: n = A,T,C or G

<400> SEQUENCE: 209

```
tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agaccccttt cgtcacccac    360

cctgggtatg acactggaaa tggtattcag cttcctggca cttctggtca gcaacccagt    420

gttgggcaac aaatgatctt tgaggaacat ggntttaggc ggaccacacc gcccacaacg    480

gccaccccca taaggcatag gccaagacca tacccgccga atgtaggaca agaagctntn    540

tntcanacac catntnatgg gccccattcc aggacacttc tgagtacatc atttatgnca    600

tctgtggcac ttgatgaaaa cccttacagt tcagggttct ggaactttta ccaggcctnt    660

tacaggactn ggccggacnc cttaagccna ttncaccctg ggcgttcta nggtcccact    720

cgnncactgg ngaaaatggc tactgtn                                        747
```

-continued

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgngaaac tccnaggaca 180
ngagggctaa attccatgaa gtttgtggat ggcctgatga tccacaatcg gagaccctgt 240
taactactac cgtctnaccn cctgctgtnc ncccccnttt ctgctnaana catngggntn 300
ntncttgncc ntccttgggt ngaanatnna atngcctncc cnttcntanc nctactngnt 360
ccananttgg cctttaaana atccnccttg ccttnnncac tgttcanntn tttnntcgta 420
aaccctatna nttnnattan atnntnnnnn nctcaccccc ctcntcattn anccnatang 480
ctnnnaantc cttnanncct cccncccnnt ncnctcntac tnantncttc tnncccatta 540
cnnagctctt tcntttaana taatgnngcc nngctctnca tntctacnat ntgnnnaatn 600
cccccncccc cnancgnntt tttgacctnn naacctcctt tcctcttccc tncnnaaatt 660
ncnnanttcc ncnttccnnc ntttcggntn ntcccatnct ttccannnct tcantctanc 720
ncnctncaac ttattttcct ntcatccctt nttctttaca nnccccctnn tctactcnnc 780
nnttncatta natttgaaac tnccacnnct anttncctcn ctctacnntt ttattttncg 840
ntcnctctac ntaatanttt aatnanttnt cn 872

<210> SEQ ID NO 211
<211> LENGTH: 517
<212> TYPE: DNA
<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacaa gcagtgtcaa cgtagtaagt taacagggtc tccgctgtgg 300
atcatcaggc catccacaaa cttcatggat ttagccctct gtcctcggag tttcccagac 360
accacaacct cgcagccttt ggccccactc tccatgatga accgcagcac accatagcag 420
gccctccgca caagcaagcc ctcctaagaa tttgtaacgc ananactctg ctggcaatgg 480
cacacaaacc tctagtggac ctcggncgcg accacgc 517

<210> SEQ ID NO 212
<211> LENGTH: 695
<212> TYPE: DNA
<213> ORGANISM: Homo sapien
<220> FEATURE:

-continued

<221> NAME/KEY: misc_feature
<222> LOCATION: (1)...(695)
<223> OTHER INFORMATION: n = A,T,C or G

<400> SEQUENCE: 212
tcgagcggcc gcccgggcag gtctggtcca ggatagcctg cgagtcctcc tactgctact 60
ccagacttga catcatatga atcatactgg ggagaatagt tctgaggacc agtagggcat 120
gattcacaga ttccaggggg gccaggagaa ccaggggacc ctggttgtcc tggaatacca 180
gggtcaccat ttctcccagg aataccagga gggcctggat ctcccttggg gccttgaggt 240
ccttgaccat taggagggcg agtaggagca gttggaggct gtgggcaaac tgcacaacat 300
tctccaaatg gaatttctgg gttggggcag tctaattctt gatccgtcac atattatgtc 360
atcgcagaga acggatcctg agtcacagac acatatttgg catggttctg gcttccagac 420
atctctatcc gncataggac tgaccaagat gggaacatcc tccttcaaca agcttnctgt 480
tgtgccaaaa ataatagtgg gatgaagcag accgagaagt anccagctcc cctttttgca 540
caaagcntca tcatgtctaa atatcagaca tgagacttct ttgggcaaaa aaggagaaaa 600
agaaaaagca gttcaaagta nccnccatca agttggttcc ttgcccnttc agcacccggg 660
ccccgttata aaacacctng ggccggaccc ccctt 695

<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213
agcgtggtcg cggccgaggt gttttatgac gggcccggtg ctgaagggca gggaacaact 60
tgatggtgct actttgaact gcttttcttt tctccttttt gcacaaagag tctcatgtct 120
gatatttaga catgatgagc tttgtgcaaa aggggagctg gctacttctc gctctgcttc 180
atcccactat tattttggca caacaggaag ctgttgaagg aggatgttcc catcttggtc 240
agtcctatgc ggatagagat gtctggaagc cagaaccatg ccaaatatgt gtctgtgact 300
caggatccgt tctctgcgat gacataatat gtgacgatca agaattagac tgccccaacc 360
cagaaattcc atttggagaa tgttgtgcag tttgcccaca gcctccaact gctcctactc 420
gccctcctaa tggtcaagga cctcaaggcc ccaagggaga tccaggccct cctggtattc 480
ctgggagaaa tggtgaccct ggtattccag gacaaccagg gtcccctggt tctcctggcc 540
cccctggaat cnggngaatc atgccctact ggtcctcaaa ctattctccc anatgattca 600
tatgatgtca agtctgggat agcnagtang ganggactcg caggctattc tggaccanac 660
ctgccggggg ggcgttcgaa agcccgaatc tgcanannta cnttcacact ggcggccgtc 720
gagctgcttt aaaagggcca ttccnccttt agngnggggg antacaatta ctnggcggcg 780
ttttanancg cgngnctggg aaat 804

<210> SEQ ID NO 214
<211> LENGTH: 594
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G -continued

<400> SEQUENCE: 214
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagagtg gcacatcttg aggtcacggc aggtgcgggc 300
ggggttcttg cggctgccct ctgggctccg gatgttctcg atctgctggc tcaggctctt 360
gagggtggtg tccacctcga ggtcacggtc acgaaccaca ttggcatcat cagcccggta 420
gtagcggcca ccatcgtgag ccttctcttg angtggctgg ggcaggaact gaagtcgaaa 480
ccagcgctgg gaggaccagg gggaccaana ggtccaggaa gggcccgggg gggaccaaca 540
ggaccagcat caccaagtgc gacccgcgag aacctgcccg gccgnccgct cgaa 594

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215
tcgagcgnnc gcccgggcag gtctcgcggt cgcactggtg atgctggtcc tgttggtccc 60
cccggccctc ctggacctcc tggtccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagccgca agaaccccgc ccgcacctgc 300
cgtgacctca agatgtgcca ctctgactgg aagagtggag agtactggat tgaccccaac 360
caaggctgca acctggatgc catcaaagtc ttctgcaaca tggagactgg tgagacctgc 420
gtgtacccca ctcagcccag tgtggcccag aagaactggt acatcagcaa gaaccccaag 480
gacaagaggc atgtctggtt cggcgagagc atgaccgatg gattccagtt cgagtatggc 540
ggccagggct cccaccctgc cgatgtggac ctccggccgc gaccaccctt 590

<210> SEQ ID NO 216
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216
tngagcggcc gcccgggcag gntgnnaacg ctggtcctgc tggtcctcct ggcaaggctg 60
gtgaagatgg tcaccctgga aaacccggac gacctggtga gagaggagtt gttggaccac 120
agggtgctcg tggtttccct ggaactcctg gacttcctgg cttcaaaggc attaggggac 180
acaatggtct ggatggattg aagggacagc ccggtgctcc tggtgtgaag ggtgaacctg 240
gtgcccctgg tgaaaatgga actccaggtc aaacaggagc ccgtgggctt cctggtgaga 300
gaggaccgtg ttggtgcccc tggcccanac ctcggccgcg accacgctaa gcccgaattt 360

-continued ccagcacact ggnggccgtt actantggat ccgagctcgg taccaagctt ggcgtaatca 420
tggtcatagc tgtttcctgn gtgaaattgt tatccgctca caatttcaca cancatacga 480
agccggaaag cataaagtgt aaagccttgg ggtgctaatg agtgagctaa ctcncattaa 540
attgcgttgc gctcactgcc cgcttttcca nnngggaaac cntggcntng ccngcttgcn 600
ttaantgaaa tccgccnacc cccggggaaa agncggtttg cngtattggg gcnctttttc 660
cctttcctcg gnttacttga nttantgggc tttggncgnt tcgggttgng gcgancnggt 720
tcaacntcac nccaaaggng gnaanacggt tttcccanaa tccgggggnt ancccaangn 780
aaaacatnng ncnaangggc t 801

<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217
agcgtggttn gcggccgagg tctgggccag gggcaccaac acgtcctctc tcaccaggaa 60
gcccacgggc tcctgtttga cctggagttc cattttcacc aggggcacca ggttcaccct 120
tcacaccagg agcaccgggc tgtcccttca atccatncag accattgtgn cccctaatgc 180
ctttgaagcc aggaagtcca ggagttccag ggaaaccacc gagcaccctg tggtccaaca 240
actcctctct caccaggtcg tccgggtttt ccagggtgac catcttcacc agccttgcca 300
ggaggaccag caggaccagc gttaccaacc tgcccgggcg gccgctcga 349

<210> SEQ ID NO 218
<211> LENGTH: 372
<212> TYPE: DNA
<213> ORGANISM: Homo sapien

<400> SEQUENCE: 218
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300
ctggtctttc agtgcctcca ctatgatgtt gtaggtggca cctctggtga ggacctcggc 360
cgcgaccacg ct 372

<210> SEQ ID NO 219
<211> LENGTH: 374
<212> TYPE: DNA
<213> ORGANISM: Homo sapien

<400> SEQUENCE: 219
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaag atgtgattca tctagatggt gccatgacaa 300

-continued

```
tggtgtgaac tacaagattg gagagaagtg ggaccgtcag ggagaaaatg gacctgcccg    360

ggccggccgc tcga                                                      374
```

<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220

```
tcgagcgnnc gcccgggcag gtccagtagt gccttcggga ctgggttcac ccccaggtct     60

gcggcagttg tcacagcgcc agccccgctg gcctccaaag catgtgcagg agcaaatggc    120

accgagatat tccttctgcc actgttctcc tacgtggtat gtcttcccat catcgtaaca    180

cgttgcctca tgagggtcac acttgaattc tccttttccg ttcccaagac atgtgcagct    240

catttggctg gctctatagt ttggggaaag tttgttgaaa ctgtgccact gacctttact    300

tcctccttct ctactggagc tttcgtacct tccacttctg ctgttggtaa aatggtggat    360

cttctatcaa tttcattgac agtacccact tctcccaaac atccagggaa atagtgattt    420

cagagcgatt aggagaacca aattatgggg cagaaataag gggcttttcc acaggttttc    480

ctttggagga agatttcagt ggtgacttta aaagaatact caacagtgtc ttcatcccca    540

tagcaaaaga agaaacngta aatgatggaa ngcttctgga gatgccnnca tttaagggac    600

ncccagaact tcaccatcta caggacctac ttcagtttac annaagncac atantctgac    660

tcanaaagga cccaagtagc nccatggnca gcactttnag cctttcccct ggggaaaann    720

ttacnttctt aaancctngg ccnngacccc cttaagncca aattntggaa aanttccntn    780

cnnctggggg gcngttcnac atgcntttna agggcccaat tnccccnt                 828
```

<210> SEQ ID NO 221
<211> LENGTH: 476
<212> TYPE: DNA
<213> ORGANISM: Homo sapien

<400> SEQUENCE: 221

```
tcgagcggcc gcccgggcag gtgtcggagt ccagcacggg aggcgtggtc ttgtagttgt     60

tctccggctg cccattgctc tcccactcca cggcgatgtc gctgggatag aagcctttga    120

ccaggcaggt caggctgacc tggttcttgg tcatctcctc ccgggatggg ggcagggtgt    180

acacctgtgg ttctcggggc tgccctttgg ctttggagat ggttttctcg atgggggctg    240

ggagggcttt gttggagacc ttgcacttgt actccttgcc attcagccag tcctggtgca    300

ggacggtgag gacgctgacc acacggtacg tgctgttgta ctgctcctcc cgcggctttg    360

tcttggcatt atgcacctcc acgccgtcca cgtaccagtt gaacttgacc tcagggtctt    420

cgtggctcac gtccaccacc acgcatgtaa cctcagacct cggccgcgac cacgct        476
```

<210> SEQ ID NO 222
<211> LENGTH: 477
<212> TYPE: DNA
<213> ORGANISM: Homo sapien

<400> SEQUENCE: 222

```
agcgtggtcg cggccgaggt ctgaggttac atgcgtggtg gtggacgtga gccacgaaga     60
```

-continued

```
ccctgaggtc aagttcaact ggtacgtgga cggcgtggag gtgcataatg ccaagacaaa    120

gccgcgggag gagcagtaca acagcacgta ccgtgtggtc agcgtcctca ccgtcctgca    180

ccaggactgg ctgaatggca aggagtacaa gtgcaaggtc tccaacaaag ccctcccagc    240

ccccatcgag aaaaccatct ccaaagccaa agggcaagcc ccgagaacca caggtgtaca    300

ccctgccccc atcccgggag gagatgacca agaaccaggt cagcctgacc tgcctggtca    360

aaggcttcta tcccagcgac atcgccgtgg agtgggagag caatgggcag ccggagaaca    420

actacaagac cacgcctccc gtgctggact ccgacacctg cccgggcggc cgctcga       477
```

<210> SEQ ID NO 223
<211> LENGTH: 361
<212> TYPE: DNA
<213> ORGANISM: Homo sapien

<400> SEQUENCE: 223

```
tcgagcggcc gcccgggcag gttgaatggc tcctcgctga ccaccccggt gctggtggtg     60

ggtacagagc tccgatgggt gaaaccattg acatagagac tgtccctgtc cagggtgtag    120

gggcccagct cagtgatgcc gtgggtcagc tggctcagct tccagtacag ccgctctctg    180

tccagtccag ggcttttggg gtcaggacga tgggtgcaga cagcatccac tctggtggct    240

gccccatcct tctcaggcct gagcaaggtc agtctgcaac cagagtacag agagctgaca    300

ctggtgttct tgaacaaggg cataagcaga ccctgaagga cacctcggcc gcgaccacgc    360

t                                                                    361
```

<210> SEQ ID NO 224
<211> LENGTH: 361
<212> TYPE: DNA
<213> ORGANISM: Homo sapien

<400> SEQUENCE: 224

```
agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                    361
```

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300
```

-continued gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcagggg ctcgctcttc tgattattct 480
tcagggcaat gacataaatt gtatattcgg tcccggttcc aggccagtaa tagtagcctc 540
tgtgacacca gggcggggcc gagggaccct tctnttggaa gagaccagct tctcatactt 600
gatgatgagn ccggtaatcc tggcacgtgg nggttgcatg atnccaccaa ggaaatnggn 660
gggggnggac ctgcccggcg gccgttcnaa agcccaattc cacacacttg gnggccgtac 720
tatggatccc actcngtcca acttggngga atatggcata actttt 766

<210> SEQ ID NO 226
<211> LENGTH: 364
<212> TYPE: DNA
<213> ORGANISM: Homo sapien

<400> SEQUENCE: 226
tcgagcggcc gcccgggcag gtccttgacc ttttcagcaa gtgggaaggt gtaatccgtc 60
tccacagaca aggccaggac tcgtttgtac ccgttgatga tagaatgggg tactgatgca 120
acagttgggt agccaatctg cagacagaca ctggcaacat tgcggacacc ctccaggaag 180
cgagaatgca gagtttcctc tgtgatatca agcacttcag ggttgtagat gctgccattg 240
tcgaacacct gctggatgac cagcccaaag gagaaggggg agatgttgag catgttcagc 300
agcgtggctt cgctggctcc cactttgtct ccagtcttga tcagacctcg gccgcgacca 360
cgct 364

<210> SEQ ID NO 227
<211> LENGTH: 275
<212> TYPE: DNA
<213> ORGANISM: Homo sapien

<400> SEQUENCE: 227
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct ggggggaccg tcagtcttcc tcttcccccg 240
catccccctt ccaaacctgc ccgggcggcc gctcg 275

<210> SEQ ID NO 228
<211> LENGTH: 275
<212> TYPE: DNA
<213> ORGANISM: Homo sapien

<400> SEQUENCE: 228
cgagcggccg cccgggcagg tttggaaggg ggatgcgggg gaagaggaag actgacggtc 60
cccccaggag ttcaggtgct gggcacggtg ggcatgtgtg agttttgtca caagatttgg 120
gctcaactct cttgtccacc ttggtgttgc tgggcttgtg atctacgttg caggtgtagg 180
tctgggtgcc gaagttgctg gagggcacgg tcaccacgct gctgagggag tagagtcctg 240
aggactgtag gacagacctc ggccgcgacc acgct 275

<210> SEQ ID NO 229
<211> LENGTH: 40
<212> TYPE: DNA

-continued

<213> ORGANISM: Homo sapien
<220> FEATURE:
<221> NAME/KEY: misc_feature
<222> LOCATION: (1)...(40)
<223> OTHER INFORMATION: n = A,T,C or G

<400> SEQUENCE: 229
nggnnggtcc ggncngncag gaccactcnt cttcgaaata 40

<210> SEQ ID NO 230
<211> LENGTH: 208
<212> TYPE: DNA
<213> ORGANISM: Homo sapien

<400> SEQUENCE: 230
agcgtggtcg cggccgaggt cctcacttgc ctcctgcaaa gcaccgatag ctgcgctctg 60
gaagcgcaga tctgttttaa agtcctgagc aatttctcgc accagacgct ggaagggaag 120
tttgcgaatc agaagttcag tggacttctg ataacgtcta atttcacgga gcgccacagt 180
accaggacct gcccgggcgg ccgctcga 208

<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231
tcgagcggcc gcccgggcag gtcctggtac tgnggcgctc cgtgaaatta gacgttatca 60
gaagtccact gaacttctga ttcgcaaact tcccttccag cgtctggtgc gagaaattgc 120
tcaggacttt aaaacagatc tgcgcttcca gagcgcagct atcggtgctt tgcaggaggc 180
aagtgaggac ctcggccgcg accacgct 208

<210> SEQ ID NO 232
<211> LENGTH: 332
<212> TYPE: DNA
<213> ORGANISM: Homo sapien

<400> SEQUENCE: 232
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 233
<211> LENGTH: 415
<212> TYPE: DNA
<213> ORGANISM: Homo sapien
<220> FEATURE:
<221> NAME/KEY: misc_feature
<222> LOCATION: (1)...(415)
<223> OTHER INFORMATION: n = A,T,C or G

<400> SEQUENCE: 233
gtgggnttga acccntttna nctccgcttg gtaccgagct cggatccact agtaacggcc 60

-continued

```
gccagtgtgc tggaattcgg cttagcgtgg tcgcggccga ggtcaagaac cccgcccgca    120

cctgccgtga cctcaagatg tgccactctg actggaagag tggagagtac tggattgacc    180

ccaaccaagg ctgcaacctg gatgccatca aagtcttctg caacatggag actggtgaga    240

cctgcgtgta ccccactcag cccagtgtgg cccagaagaa ctggtacatc agcaagaacc    300

ccaaggacaa gaggcatgtc tggttcggcg agagcatgac cgatggattc cagttcgagt    360

atggcggcca gggctccgac cctgccgatg tggacctgcc cgggcggccg ctcga         415


<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234

agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagag taaccaccac tcccaaaaat    360

ggaccaggac caacaaaaac taaaactgca ggtccagatc aaacagaaat gactattgaa    420

ggcttgcagc ccacagtgga gtatgtggtt aagtgtctat gctcagaatc caagcggaga    480

gaagtcagcc tctggttcag actgnaagta accaacattg atcgcctaaa ggactggcat    540

tcactgatgn ggatgccgat tccatcaaaa ttgnttggga aaacccacag gggcaagttt    600

ncangtcnag gnggacctac tcgagccctg aggatggaat ccttgactnt tccttnncct    660

gatggggaaa aaaaaccttn aaaacttgaa ggacctgccc gggcggccgt ncaaaaccca    720

attccacccc cttgggggcg ttctatgggn cccactcgga ccaaacttgg ggtaan        776


<210> SEQ ID NO 235
<211> LENGTH: 805
<212> TYPE: DNA
<213> ORGANISM: Homo sapien
<220> FEATURE:
<221> NAME/KEY: misc_feature
<222> LOCATION: (1)...(805)
<223> OTHER INFORMATION: n = A,T,C or G

<400> SEQUENCE: 235

tcgagcggcc gcccgggcag gtccttgcag ctctgcagtg tcttcttcac catcaggtgc     60

agggaatagc tcatggattc catcctcagg gctcgagtag gtcaccctgt acctggaaac    120

ttgcccctgt gggctttccc aagcaatttt gatggaatcg gcatccacat cagtgaatgc    180

cagtccttta gggcgatcaa tgttggttac tgcagtctga accagaggct gactctctcc    240

gcttggattc tgagcataga cactaaccac atactccact gtgggctgca agccttcaat    300

agtcatttct gtttgatctg gacctgcagt tttagttttt gttggtcctg gtccattttt    360

gggagtggtg gttactctgt aaccagtaac aggggaactt gaaggcagcc acttgacact    420

aatgctgttg tcctgaacat cggtcacttg catctgggat ggtttgtcaa tttctgttcg    480
```

-continued gtaattaatg gaaattggct tgctgcttgc ggggcttgtc tccacggcca gtgacagcat 540
acacagtgat ggtataatca actccaggtt taagccgctg atggtagctg aaactttgct 600
ccaggcacaa gtgaactcct gacagggcta tttcctnctg ttctccgtaa gtgatcctgt 660
aatatctcac tgggacagca ggangcattc caaaacttcg ggcgngaccc cctaagccga 720
attntgcaat atncatcaca ctggcgggcg ctcgancatt cattaaaagg cccaatcncc 780
cctataggga gtntantaca attng 805

<210> SEQ ID NO 236
<211> LENGTH: 262
<212> TYPE: DNA
<213> ORGANISM: Homo sapien

<400> SEQUENCE: 236
tcgagcggcc gcccgggcag gtcacttttg gtttttggtc atgttcggtt ggtcaaagat 60
aaaaactaag tttgagagat gaatgcaaag gaaaaaaata ttttccaaag tccatgtgaa 120
attgtctccc attttttgg cttttgaggg ggttcagttt gggttgcttg tctgtttccg 180
ggttgggggg aaagttggtt gggtgggagg gagccaggtt gggatggagg gagtttacag 240
gaagcagaca gggccaacgt cg 262

<210> SEQ ID NO 237
<211> LENGTH: 372
<212> TYPE: DNA
<213> ORGANISM: Homo sapien

<400> SEQUENCE: 237
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 238
<211> LENGTH: 372
<212> TYPE: DNA
<213> ORGANISM: Homo sapien

<400> SEQUENCE: 238
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300
ctggtctttc agtgcctcca ctatgatgtt gtaggtggca cctctggtga ggacctcggc 360
cgcgaccacg ct 372

<210> SEQ ID NO 239
<211> LENGTH: 720
<212> TYPE: DNA
<213> ORGANISM: Homo sapien -continued
<220> FEATURE:
<221> NAME/KEY: misc_feature
<222> LOCATION: (1)...(720)
<223> OTHER INFORMATION: n = A,T,C or G

<400> SEQUENCE: 239
tcgagcggcc gcccgggcag gtccaccata agtcctgata caaccacgga tgagctgtca 60
ggagcaaggt tgatttcttt cattggtccg gtcttctcct tgggggtcac ccgcactcga 120
tatccagtga gctgaacatt gggtggtgtc cactgggcgc tcaggcttgt gggtgtgacc 180
tgagtgaact tcaggtcagt tggtgcagga atagtggtta ctgcagtctg aaccagaggc 240
tgactctctc cgcttggatt ctgagcatag acactaacca catactccac tgtgggctgc 300
aagccttcaa tagtcatttc tgtttgatct ggacctgcag ttttagtttt tgttggtcct 360
ggtccatttt tgggagtggt ggttactctg taaccagtaa caggggaact tgaaggcagc 420
cacttgacac taatgctgtt gtcctgaaca tcggtcactt gcatctggga tggtttgnca 480
atttctgttc ggtaattaat ggaaattggc ttgctgcttg cggggctgtc tccacggcca 540
gtgacagcat acacagngat ggnatnatca actccaagtt taaggccctg atggtaactt 600
taaacttgct cccagccagn gaacttccgg acagggtatt tcttctggtt ttccgaaagn 660
gancctggaa tnntctcctt gganc agaag gancntccaa aacttgggcc ggaacccctt 720

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300
gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcagggg ctcgctcttc tgattattct 480
tcagggcaat gacataaatt gtatattcgg ttcccggttc caggccagta atagtagcct 540
cttgtgacac caggcggggc ccanggacca cttctctggg angagaccca gcttctcata 600
cttgatgatg taacccggta atcctgcacg tggcggctgn catgatacca ncaaggaatt 660
gggtgnggng gacctgcccg gcggccctcn a 691

<210> SEQ ID NO 241
<211> LENGTH: 808
<212> TYPE: DNA
<213> ORGANISM: Homo sapien
<220> FEATURE:
<221> NAME/KEY: misc_feature
<222> LOCATION: (1)...(808)
<223> OTHER INFORMATION: n = A,T,C or G

<400> SEQUENCE: 241

-continued

```
agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagag taaccaccac tcccaaaaat    360

ggaccaggac caacaaaaac taaaactgca ggtccagatc aaacagaaat gactattgaa    420

ggcttgcagc ccacagtgga gtatgtggtt agtgtctatg ctcagaatcc aagcggagag    480

agtcagcctc tggttcagac tgcagtaacc actattcctg caccaactga cctgaagttc    540

actcaggtca cacccacaag cctgagccgc cagtggacac cacccaatgt tcactcactg    600

gatatcgagt gcgggtgacc cccaaggaga agacccggac ccatgaaaga aatcaacctt    660

gctcctgaca gctcatccgn gggtgtatca ggacttatgg gggactgccc cggcnggccg    720

ntcgaaancg aattntgaaa tttccttcnc actgggnggc gnttcgagct tncttntana    780

nggcccaatt cncctntagn gggtcgtn                                       808
```

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242

```
agcgtggtcg cggccgaggt cnagga                                          26
```

<210> SEQ ID NO 243
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 243

```
tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agacccctt cgtcacccac     360

cctgggtatg acactggaaa tggtattcag cttcctggca cttctggtca gcaacccagt    420

gttgggcaac aaatgatctt tgaggaacat ggttttaggc ggaccacacc gcccacaacg    480

ggcaccccca taaggnatag gccaagacca taccccgccg aatgtaggac aagaagctct    540

ntctcaacaa ccatctcatg ggccccattc caggacactt ctgagtacat catttcatgt    600

catcctggtg ggcacttgat gaanaaccct tacagttcag ggttcctgga acttctacca    660

gngccacttc tgacagganc ttgggcgnga ccaccct                             697
```

-continued

<210> SEQ ID NO 244
<211> LENGTH: 373
<212> TYPE: DNA
<213> ORGANISM: Homo sapien

<400> SEQUENCE: 244
agcgtggtcg cggccgaggt ccattttctc cctgacggtc ccacttctct ccaatcttgt 60
agttcacacc attgtcatgg caccatctag atgaatcaca tctgaaatga ccacttccaa 120
agcctaagca ctggcacaac agtttaaagc ctgattcaga cattcgttcc cactcatctc 180
caacggcata atgggaaact gtgtaggggt caaagcacga gtcatccgta ggttggttca 240
agccttcgtt gacagagttg cccacggtaa caacctcttc ccgaacctta tgcctctgct 300
ggtctttcag tgcctccact atgatgttgt aggtggcacc tctggtgagg acctgcccgg 360
gcggcccgct cga 373

<210> SEQ ID NO 245
<211> LENGTH: 307
<212> TYPE: DNA
<213> ORGANISM: Homo sapien

<400> SEQUENCE: 245
agcgtggtcg cggccgaggt gtgccccaga ccaggaattc ggcttcgacg ttggccctgt 60
ctgcttcctg taaactccct ccatcccaac ctggctccct cccacccaac caactttccc 120
cccaacccgg aaacagacaa gcaacccaaa ctgaaccccc tcaaaagcca aaaaaatggg 180
agacaatttc acatggactt tggaaaatat ttttttcctt tgcattcatc tctcaaactt 240
agtttttatc tttgaccaac cgaacatgac caaaaaccaa aagtgacctg cccgggcggc 300
cgctcga 307

<210> SEQ ID NO 246
<211> LENGTH: 372
<212> TYPE: DNA
<213> ORGANISM: Homo sapien

<400> SEQUENCE: 246
tcgagcggcc gcccgggcag gtcctcacca gaggtgccac ctacaacatc atagtggagg 60
cactgaaaga ccagcagagg cataaggttc gggaagaggt tgttaccgtg ggcaactctg 120
tcaacgaagg cttgaaccaa cctacggatg actcgtgctt tgacccctac acagtttccc 180
attatgccgt tggagatgag tgggaacgaa tgtctgaatc aggctttaaa ctgttgtgcc 240
agtgcttagg ctttggaagt ggtcatttca gatgtgattc atctagatgg tgccatgaca 300
atggtgtgaa ctacaagatt ggagagaagt gggaccgtca gggagaaaat ggacctcggc 360
cgcgaccacg ct 372

<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 247
tcgagcggcc gcccgggcag gtaccggggt ggtcagcgag gagccattca cactgaactt 60
caccatcaac aacctgcggt atgaggagaa catgcagcac cctggctcca ggaagttcaa 120

-continued

```
caccacggag agggtccttc agggcctgct caggtccctg ttcaagagca ccagtgttgg    180

ccctctgtac tctggctgca gactgacttt gctcagacct gagaaacatg gggcagccac    240

tggagtggac gccatctgca ccctccgcct tgatcccact ggtnctggac tggacanana    300

gcggctatac ttgggagctg anccnaacct ttggcggnga cnccnctt                 348
```

<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248

```
gaggactggc tcagctccca gtatagccgc tctctgtcca gtccaggacc agtgggatca     60

aggcggaggg tgcagatggc gtccactcca gtggctgccc catgtttctc aagtctgagc    120

aaagncagtc tgcagccaga gtacagaggg ccaacactgg tgctcttgaa cagggacctg    180

agcaggccct gaaggaccct ctccgtggtg ttgaacttcc tggagccagg gtgctgcatg    240

ttctcctcat accgcaggtt gttgatggtg aagttcagtg tgaatggctc ctcgctgacc    300

accc                                                                 304
```

<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249

```
agcgtggtcg cggccgaggt ccaccacacc caattccttg ctggtatcat ggcagccgcc     60

acgtgccagg attaccggct acatcatcaa gtatgagaag cctgggtctc ctcccagaga    120

agtggtccct cggccccgcc ctggtgtcac agaggctact attactggcc tggaaccggg    180

aaccgaatat acaatttatg tcattgccct gaagaataat cagaagagcg agcccctgat    240

tggaaggaaa aagacagacg agcttcccca actggtaacc cttccacacc ccaatcttca    300

tggaccanan ancttggatn gtcctttcac nggttnaaaa aaccctttc gcccccccac    360

cttggggatt aaccttggga aangggggatt tnaccnttcc                         400
```

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250

```
tcgagcggcc gcccgggcag gtcctgtcag agtggcactg gtagaagttc caggaaccct     60

gaactgtaag ggttcttcat cagtgccaac aggatgacat gaaatgatgt actcagaagt    120

gtcctggaat ggggcccatg agatggttgt ctgagagaga gcttcttgtc ctacattcgg    180

cgggtatggt cttggcctat gccttatggg ggtggccgtt gtgggcggtg tggtccgcct    240

aaaaccatgt tcctcaaaga tcatttgttg cccaacactg ggttgctgac cagaagtgcc    300
```

-continued

```
aggaagctga ataccatttc cagtgtcata cccagggngg gtgaccaaag ggggtcnttt    360

ngacctggng aaaggaacca tccaaaanct ctgncccatg                          400
```

```
<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251

agcgtggncg cggccgaggt ctgaggatgt aaactcttcc caggggaagg ctgaagtgct     60

gaccatggtg ctactgggtc cttctgagtc agatatgtga ctgatgngaa ctgaagtagg    120

tactgtagat ggtgaagtct gggtgtccct aaatgctgca tctccagagc cttccatcat    180

taccgtttct tcttttgcta tgggatgaga cactgttgag tattctctaa agtcaccact    240

gaaatcttcc tccaaaggaa aacctgtgga aaagcccctt atttctgccc cataatttgg    300

ttctcctaat cnctctgaaa tcactatttc cctggaangt ttgggaaaaa nngggcnacc    360

tgncantgga aantggatan aaagatccca ccattttacc caacnagcag aaagtgggaa    420

nggtaccgaa aagctccaag taanaaaaag gagggaagta aaggtcaagt gggcaccagt    480

ttcaaacaaa actttcccca aactatanaa ccca                                514
```

```
<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252

aagcggccgc ccgggcaggn ncagnagtgc cttcgggact gggntcaccc ccaggtctgc     60

ggcagttgtc acagcgccag ccccgctggc ctccaaagca tgtgcaggag caaatggcac    120

cgagatattc cttctgccac tgttctccta cgtggtatgt cttcccatca tcgtaacacg    180

ttgcctcatg agggtcacac ttgaattctc cttttccgtt cccaagacat gtgcagctca    240

tttggctggc tctatagttt ggggaaagtt tgttgaaact gtgccactga cctttacttc    300

ctccttctct actggagctt tccgtacctt ccacttctgc tgntggnaaa aagggnggaa    360

cntcttatca atttcattgg acagtanccc nctttctncc caaaacatnc aagggaaaat    420

attgattncn agagcggatt aaggaacaac ccnaattatg ggggccagaa ataaaggggg    480

cttttccaca ggtntttttcc t                                              501
```

```
<210> SEQ ID NO 253
<211> LENGTH: 226
<212> TYPE: DNA
<213> ORGANISM: Homo sapien

<400> SEQUENCE: 253

tcgagcggcc gcccgggcag gtctgcaggc tattgtaagt gttctgagca catatgagat     60

aacctgggcc aagctatgat gttcgatacg ttaggtgtat taaatgcact tttgactgcc    120

atctcagtgg atgacagcct tctcactgac agcagagatc ttcctcactg tgccagtggg    180
```

-continued caggagaaag agcatgctgc gactggacct cggccgcgac cacgct 226

<210> SEQ ID NO 254
<211> LENGTH: 226
<212> TYPE: DNA
<213> ORGANISM: Homo sapien

<400> SEQUENCE: 254
agcgtggtcg cggccgaggt ccagtcgcag catgctcttt ctcctgccca ctggcacagt 60
gaggaagatc tctgctgtca gtgagaaggc tgtcatccac tgagatggca gtcaaaagtg 120
catttaatac acctaacgta tcgaacatca tagcttggcc caggttatct catatgtgct 180
cagaacactt acaatagcct gcagacctgc ccgggcggcc gctcga 226

<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255
cgagcggccg cccgggcagg tccagactcc aatccagaga accaccaagc cagatgtcag 60
aagctacacc atcacaggtt tacaaccagg cactgactac aagatctacc tgtacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggct acatcatcaa gtatgagaag cctgggtctc ctcccagaga 300
agtggtccct cggccccgcc ctggtgncac agaagctact attactggcc tggaaccggg 360
aaccgaatat acaatttatg tcattgccct gaagaataat canaagagcg agcccctgat 420
tggaagg 427

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct gtctttttcc 180
ttccaatcag ggctcgctc ttctgattat tcttcagggc aatgacataa attgtatatt 240
cggttcccgg ttccaggcca gtaatagtag cctctgtgac accagggcgg ggccgaggga 300
ccacttctct gggaggagac ccaggcttct catacttgat gatgtanccg gtaatcctgg 360
caccgtggcg gctgccatga taccagcaag gaattgggtg tggtggccaa gaaacgcagg 420
ttggatggtg catcaatggc agtggaggcg tcgatnacca caggggagct ccgancattg 480
tcattcaagg tggacaggta gaatcttgta atcaggtgcc tggtttgtaa acctg 535

<210> SEQ ID NO 257
<211> LENGTH: 544

-continued

<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257
tcgagcggcc gcccgggcag gtttcgtgac cgtgacctcg aggtggacac caccctcaag 60
agcctgagcc agcagatcga gaacatccgg agcccagagg gcagccgcaa gaaccccgcc 120
cgcacctgcc gtgacctcaa gatgtgccac tctgactgga agagtggaga gtactggatt 180
gaccccaacc aaggctgcaa cctggatgcc atcaaagtct tctgcaacat ggagactggt 240
gagacctgcg tgtaccccac tcagcccagt gtggcccaga agaactggta catcagcaag 300
aaccccaagg acaagaagca tgtctggttc ggcgaaagca tgaccgatgg attccagttc 360
gagtatggcg gccagggctc cgaccctgcc gatgtggacc tcggccgcga ccacgctaag 420
cccgaattcc agcacactgg cggccgttac tagtgggatc cgagcttcgg taccaagctt 480
ggcgtaatca tgggncatag ctgtttcctg ngtgaaaatg gtattccgct tcacaatttc 540
ccac 544

<210> SEQ ID NO 258
<211> LENGTH: 418
<212> TYPE: DNA
<213> ORGANISM: Homo sapien

<400> SEQUENCE: 258
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagagtg gcacatcttg aggtcacggc aggtgcgggc 300
ggggttcttg cggctgccct ctgggctccg gatgttctcg atctgctggc tcaagctctt 360
gaagggtggt gtccacctcg aggtcacggt cacgaaacct gcccgggcgg ccgctcga 418

<210> SEQ ID NO 259
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 259
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgn gccggnccgc tcgaaaagcc cnaatttcca gncacacttg 360
gccggccgtt actactg 377

<210> SEQ ID NO 260

-continued

<211> LENGTH: 332
<212> TYPE: DNA
<213> ORGANISM: Homo sapien

<400> SEQUENCE: 260
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 261
<211> LENGTH: 94
<212> TYPE: DNA
<213> ORGANISM: Homo sapien

<400> SEQUENCE: 261
cgagcggccg cccgggcagg tcccccccct tttttttttt tttttttttt tttttttttt 60
tttttttttt tttttttttt tttttttttt tttt 94

<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262
agcgtggtcg cggccgaggt ctggcattcc ttcgacttct ctccagccga gcttcccaga 60
acatcacata tcactgcaaa aatagcattg catacatgga tcaggccagt ggaaatgtaa 120
agaaggccct gaagctgatg gggtcaaatg aaggtgaatt caaggctgaa ggaaatagca 180
aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgctttttat 360
aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480
gtttggaaac agtataattt gacaaagaaa aaaggatact tctcttttttt tggctggtcc 540 accaaataca attcaaaagg ctttttggtt ttattttttt anccaattcc aatttcaaaa 600
tgtctcaatg gngcttataa taaaataaac tttcaccctt nttttntgat 650

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120

-continued

```
tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagaa gtaaccacca ctcccaaaaa    360

tggaccagga ccaacaaaaa ctaaaactgc aggtccagat caaacagaaa atggactatt    420

gaaggcttgc agcccacagt ggaagtatgt ggntaggngt ctatgctcag aatcccaagc    480

cggagaaagt cagccttctg gtttagactg cagtaaccaa cattgatcgc cctaaaggac    540

tggncattca cttggatggt ggatgtccaa ttc                                 573
```

```
<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 264

tcgagcggcc gcccgggcag gtccttgcag ctctgcagng tcttcttcac catcaggtgc     60

agggaatagc tcatggattc catcctcagg gctcgagtag gtcaccctgt acctggaaac    120

ttgcccctgt gggctttccc aagcaatttt gatggaatcg acatccacat cagngaatgc    180

cagtccttta gggcgatcaa tgttggttac tgcagtctga accagaggct gactctctcc    240

gcttggattc tgagcataga cactaaccac atactccact gtgggctgca agccttcaat    300

agtcatttct gtttgatctg gacctgcagt tttaagtttt tggtggtcct gncccatttt    360

tgggaagtgg ggggttactc tgtaaccagt aacaggggaa cttgaaggca gccacttgac    420

actaatgctg ttgtcctgaa catcggtcac ttgcatctgg ggatggtttt gacaatttct    480

ggttcggcaa attaatggaa attggcttgc tgcttggcgg ggctgnctcc acgggccagt    540

gacagcatac                                                           550
```

```
<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 265

tcgagcggcc gcccgggcag gtccttgcag ctctgcagtg tcttcttcac catcaggtgc     60

agggaatagc tcatggattc catcctcagg gctcgagtag gtcaccctgt acctggaaac    120

ttgcccctgt gggctttccc aagcaatttt gatggaatcg acatccacat cagtgaatgc    180

cagtccttta gggcgatcaa tgttggttac tgcagtctga accagaggct gactctctcc    240

gcttggattc tgagcataga cactaaccac atactccact gtgggctgca agccttcaat    300

agtcatttct gtttgatctg gacctgcagt tttaagtttt tgttggncct gnnccatttt    360

tggggaaggg gtggttactc ttgtaaccag taacagggga acttgaagca gccacttgac    420

actaatgctg gtggcctgaa catcggtcac ttgcatctgg gatggtttgg tcaatttctg    480

ttcggtaatt aatgggaaat tggcttactg gcttgcgggg gctgtctcca cggncagtga    540
```

-continued caagcataca caggngatgg gtataatcaa ctccaggttt aaggccnctg atggta 596

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agtaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
gggaccagga ccaacaaaaa actaaaactg canggtccag atcaaacaga aatgactatt 420
gaaggcttgc agcccacagt ggagtatgtg ggttagtgtc tatgctcaga atnccaagcg 480
gagagagtca gcctctggtt cagact 506

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267
tcgagcggcc gcccgggcag gtcagcgctc tcaggacgtc accaccatgg cctgggctct 60
gctcctcctc accctcctca ctcagggcac agggtcctgg gcccagtctg ccctgactca 120
gcctccctcc gcgtccgggt ctcctggaca gtcagtcacc atctcctgca ctggaaccag 180
cagtgacgtt ggtgcttatg aatttgtctc ctggtaccaa caacacccag gcaaggcccc 240
caaactcatg atttctgagg tcactaagcg gccctcaggg gtccctgatc gcttctctgg 300
ctccaagtct ggcaacacgg cctccctgac cgtctctggg ctccangctg aggatgangc 360
tgattattac tggaagctca tatgcaggca acaacaattg ggtgttcggc ggaagggacc 420
aagctgaccg tnctaaggtc aagcccaagg cttgcccccc tcggtcactc tgttcccacc 480
ctcctctgaa gaagctttca agccaacaan gncacactgg gtgtgtctca taagtggact 540
ttctaccc 548

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 268
agcgtggtcg cggccgaggt ctgtagcttc tgtgggactt ccactgctca ggcgtcaggc 60
tcaggtagct gctggccgcg tacttgttgt tgctttgntt ggagggtgtg gtggtctcca 120

-continued

```
ctcccgcctt gacggggctg ctatctgcct tccaggccac tgtcacggct cccgggtaga    180

agtcacttat gagacacacc agtgtggcct tgttggcttg aagctcctca gaggagggtg    240

ggaacagagt gaccgagggg gcagccttgg gctgacctag gacggtcagc ttggtccctc    300

cgccgaacac ccaattgttg ttgcctgcat atgagctgca gtaataatca gcctcatcct    360

cagcctggag cccagagacn gtcaagggag gcccgtgttt gccaagactt ggaagccaga    420

naagcgatca gggacccctg agggccgctt tacngacctc aaaaaatcat gaatttgggg    480

ggcctttgcc tgggngttgg ttggtnacca gnaaaacaaa atttcataaa gcaccaacgt    540

cactgctggt ttccagtgca ngaanatggt gaactgaant gtcc                     584
```

```
<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

agcgtggtcg cggccgaggt ccagcatcag gagccccgcc ttgccggctc tggtcatcgc     60

ctttcttttt gtggcctgaa acgatgtcat caattcgcag tagcagaact gccgtctcca    120

ctgctgtctt ataagtctgc agcttcacag ccaatggctc ccatatgccc agttccttca    180

tgtccaccaa agtacccgtc tcaccattta caccccaggt ctcacagttc tcctgggtgt    240

gcttggcccg aagggaggta agtanacgga tggtgctggt cccacagttc tggatcaggg    300

tacgaggaat gacctctagg gcctgggcna caagccctgt atggacctgc ccgggcgggc    360

ccgctcga                                                             368
```

```
<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

tcgagcggcc gcccgggcag gtccatacag ggctgttgcc caggccctag aggncattcc     60

ttgtaccctg atccagaact gtgggaccag caccatccgt ctacttacct cccttcgggc    120

caagcacacc caggagaact gtgagacctg ggtgtaaat ggngagacgg gtactttggt    180

ggacatgaag gaactgggca tatgggagcc attggctgng aagctgcana cttataagac    240

agcagtggag acggcagttc tgctactgcg aattgatgac atcgtttcag gccacaaaaa    300

gaaaggcgat gaccanagcc ggcaaggcgg ggcttcctga tgctggacct cggccgccga    360

ccacgctt                                                             368
```

```
<210> SEQ ID NO 271
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G
```

```
<400> SEQUENCE: 271

agcgtggtcg cggccgaggt ccactagagg tctgtgtgcc attgcccagg cagagtctct    60

gcgttacaaa ctcctaggag ggcttgctgt gcggagggcc tgctatggtg tgctgcggtt   120

catcatggag agtggggcca aaggctgcga ggttgtggtg tctgggaaac tccgaggaca   180

gagggctaaa tccatgaagt ttgtggatgg cctgatgatc cacagcggag accctgttaa   240

ctactacgtt gacactgctg tgcgccacgt gttgctcana cagggtgtgc tgggcatcaa   300

ggtgaagatc atgctgccct gggacccanc tggcaaaaat ggcccttaaa aaccccttgc   360

cntgaccacg tgaaccattt gtgngaaccc caagatgaan atacttgccc accacccccc   420

attc                                                                424

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272

tcgagcggcc gcccgggcag gtctgccaag gagaccctgt tatgctgtgg ggactggctg    60

gggcatggca gcggctctg gcttcccacc cttctgttct gagatggggg tggtgggcag   120

tatctcatct ttgggttcca caatgctcac gtggtcaggc aggggcttct tagggccaat   180

cttaccagtt gggtcccagg gcagcatgat cttcaccttg atgcccagca caccctgtct   240

gagcaacacg tggcgcacag cagtgtcaac gtagtagtta acagggtctc cgctgtggat   300

catcaggcca tccacaaact tcatggattt agccctctgt cctcggagtt tcccaaaaca   360

ccacaacctc gccagccttt gggccccact tcttcatgaa tgaaaccgca gcacaccatt   420

ancaaggccc ttccgcacag gnaagccctt cctaaggagt tttgtaaacg caaaaaactc   480

ttgcctgggg caaatgggca cacagacctn tantnggacc ttggnccgcg aaccaccgct   540

t                                                                   541

<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 273

agcgtggtcg cggccgaggt ctggccctcc tggcaaggct ggtgaagatg gtcaccctgg    60

aaaacccgga cgacctggtg agagaggagt tgttggacca cagggtgctc gtggtttccc   120

tggaactcct ggacttcctg gcttcaaagg cattagggga cacaatggtc tggatggatt   180

gaagggacag cccggtgctc ctggtgtgaa gggtgaacct ggngcccctg gtgaaaatgg   240

aactccaggt caaacaggag cccgngggct tcctggngag agaggacgtg ttggtgcccc   300

tggcccanac ctgcccgggc ggccgctcna aaagccgaaa tccagnacac tggcggccgn   360

tactantgga atccgaactt cggtaccaaa gcttggccgt aatcatggcc atagcttgtt   420

ccctggggng gaaattggta ttccgctncc aattccacac aacataccga acccggaaag   480

cattaaagtg taaaagccct gggggggcct aaatgangtg agcntaactc ncatttaatt   540
```

-continued ggcgttgcgc ttcactgccc cgcttttcca gtccgggna 579

<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274
tcgagcggcc gcccgggcag gtctgggcca ggggcaccaa cacgtcctct ctcaccagga 60
agcccacggg ctcctgtttg acctggagtt ccattttcac caggggcacc aggttcaccc 120
ttcacaccag gagcaccggg ctgtcccttc aatccatcca gaccattgtg ncccctaatg 180
cctttgaagc caggaagtcc aggagttcca gggaaaccac gagcaccctg tggtccaaca 240
actcctctct caccaggtcg tccgggtttt ccagggtgac catcttcacc agccttgcca 300
ggagggccag acctcggccg cgaccacgct 330

<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275
ancgtggtcg cggccgaggt cctcaccaga ggtgncacct acaacatcat agtggaggca 60
ctgaaagacc ancagaggca taaggttcgg gaagagg 97

<210> SEQ ID NO 276
<211> LENGTH: 610
<212> TYPE: DNA
<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgtccacggt aacaacctct tcccgaacct tatgcctctg 300
ctggtctttc agtgcctcca ctatgatgtt gtaggtggca cctctggtga ggacctcngn 360
ccngaacaac gcttaagccc gnattctgca gaataatccc atcacacttg gcggccgctt 420
cgancatgca tcntaaaagg ggccccaatt tcccccttat aagngaancc gtatttncca 480
atttcactgg ncccgccgnt tttacaaacg ncggtgaact ggggaaaaac cctggcggtt 540
acccaacttt aatcgccntt ggcagcacaa tccccccttt tcgnccancn tgggcgtaaa 600
taaccgaaaa 610

<210> SEQ ID NO 277

-continued

<211> LENGTH: 38
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277
ancgnggtcg cggccgangt nttttttctt ntttttt 38

<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgggnggtc agcgtcctca ccgtcctgca 180
ccagaattgg ttgaatggca aggagtacaa gngcaaggtt tccaacaaag ccntcccagc 240
ccccntcgaa aaaaccattt ccaaagccaa agggcagccc cgagaaccac aggtgtacac 300 cctgcccccca tcccgggagg aaaagancaa naaccnggtt cagccttaac ttgcttggtc 360
naangctttt tatcccaacg nacttccccc ntggaantgg gaaaaaccaa tgggccaanc 420
cgaaaaacaa ttacaanaac ccc 443

<210> SEQ ID NO 279
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 279
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtga 180
acacctgggg ttctcggggc ttgccctttg gttttgaana tggttttctc gatgggggct 240
ggaagggctt tgttgnaaac cttgcacttg actccttgcc attcacccag ncctggngca 300
ggacggngag gacnctnacc acacggaacc gggctggtgg actgctcc 348

<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

<400> SEQUENCE: 280
agcgtggtcg cggacgangt cctgtcagag tggnactggt agaagttcca ngaaccctga 60
actgtaaggg ttcttcatca gtgccaacag gatgacatga aatgatgtac tcagaagngn 120

-continued

```
cctggaatgg ggcccatgan atggttgcc                                    149


<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agaccccttt cggcaccccc    360

cctgggtatg aacctgggaa aanggnantt aanctttcct ggca                     404


<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282

agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaaggtn ccctggtact gggttacaga ntaaccacca ctcccaaaaa    360

tggaccagga accacaaaaa cttaaactgc agggtccaga tcaaaacaga aatgactatt    420

gaangcttgc agcccacagt gggagtatgn gggtagtgnc tatgcttcag aatccaagcg    480

gaaaaangtc aagccttntg ggttcaa                                        507


<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283

tcgagcggcc gcccgggcag gtccttgcag ctctgcagtg tcttcttcac catcaggtgc     60

agggaatagc tcatggattc catcctcagg gctcgagtag gtcaccctgt acctggaaac    120

ttgcccctgt gggctttccc aagcaatttt gatggaatcg acatccacat cagtgaatgc    180

cagtccttta gggcgatcaa tgttggttac tgcagnctga accagaggct gactctctcc    240
```

-continued gcttggattc tgagcataga cactaaccac atactccact gtgggctgca anccttcaat 300
aanncatttc tgtttgatct ggacc 325

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284
tcgagcggcc gcccgggcag gtctggtggg gtcctggcac acgcacatgg gggngttgnt 60
ctnatccagc tgcccagccc ccattggcga gtttgagaag gtgtgcagca atgacaacaa 120
naccttcgac tcttcctgcc acttctttgc cacaaagtgc accctggagg gcaccaagaa 180
gggccacaag ctccacctgg actacatcgg gccttgcaaa tacatccccc cttgcctgga 240
ctctgagctg accgaattcc cccttgcgca tgcgggactg gctcaagaac cgtcctggca 300
cccttgtatg anagggatga agacacnacc c 331

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct ggggggaccg tcagtcttcc tcttcccccg 240 catcccccttt ccaaacctgc ccgggcggcc gctcgaaagc cgaattccag cacactggcg 300
gccggtacta gtgganccna acttggnanc caacctggng gaantaatgg gcataanctg 360
tttctggggg gaaattggta tccngtttac aattcccnca caacatacga gccggaagca 420
taaaagngta aaagcctggg ggnggcctan tgaagtgaag ctaaactcac attaattngc 480
gttgccgctc actggcccgc ttttccagc 509

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286
tcgagcggcc gcccgggcag gtttggaagg gggatgcggg ggaagaggaa gactgacggt 60
ccccccagga gttcaggtgc tgggcacggt gggcatgtgt gagttttgtc acaagatttg 120
ggctcaactc tcttgtccac cttggtgttg ctgggcttgt gatctacgtt gcaggtgtag 180
gtctgggngc cgaagttgct ggagggcacg gtcaccacgc tgctgaggga gtagagtcct 240
gaggactgta ngacagacct cggccgngac cacgctaagc cgaattctgc agatatccat 300

-continued cacactggcg gccgctccga gcatgcattt tagagg 336

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287
agcgtggncg cggacganga caacaacccc 30

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 289
agcgtggtcg cggccgaggt ccagcctgga gataanggtg aaggtggtgc ccccggactt 60
ccaggtatag ctggacctcg tggtagccct ggtgagagag gtgaaactgg ccctccagga 120
cctgctggtt tccctggtgc tcctggacag aatggtgaac ctggnggtaa aggagaaaga 180
ggggctccgg ntganaaagg tgaaggaggc cctcctgnat tggcaggggc cccangactt 240
agaggtggag ctggcccccc tggccccgaa ggaggaaagg gtgctgctgg tcctcctggg 300
ccacctgg 308

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 290
tcgagcggcc gcccgggcag gtctgggcca ggaggaccaa taggaccagt aggacccctt 60

-continued

```
gggccatctt tccctgggac accatcagca cctggaccgc ctggttcacc cttgtcaccc    120

tttggaccag gacttccaag acctcctctt tctccaggca ttccttgcag accaggagta    180

ccancagcac caggtggccc aggaggacca gcagcaccct ttcctccttc gggaccaggg    240

ggaccagctc cacctctaag tcctggggcc cctgccaatc caggagggcc tccttcacct    300

ttctcacccg gagcccctct ttct                                           324


<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291

tcgagcggcc gcccgggcag gtccaccggg atattcgggg gtctggcagg aatgggaggc     60

atccagaacg agaaggagac catgcaaagc ctgaacgacc gcctggcctc ttacctggac    120

agagtgagga gcctggagac cgacaaccgg aggctggaga gcaaaatccg ggagcacttg    180

gagaagaagg gaccccaggt cagagactgg agccattact tcaagatcat cgaggacctg    240

agggctcana tcttcgcaaa tactgcngac aatgcccg                            278


<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292

atgcgnggtc gcggccgang accanctctg gctcatactt gactctaaag ncntcaccag     60

nanttacggn cattgccaat ctgcagaacg atgcgggcat tgtccgcant atttgcgaag    120

atctgagccc tcaggncctc gatgatcttg aagtaanggc tccagtctct gacctggggt    180

cccttcttct ccaagtgctc ccggattttg ctctccagcc tccggttctc ggtctccaag    240

ncttctcact ctgtccagga aaagaggcca ggcggncgat cagggctttt gcatggact     299


<210> SEQ ID NO 293
<211> LENGTH: 101
<212> TYPE: DNA
<213> ORGANISM: Homo sapien

<400> SEQUENCE: 293

agcgtggtcg cggccgaggt tgtacaagct tttttttttt tttttttttt tttttttttt     60

tttttttttt tttttttttt tttttttttt tttttttttt t                        101


<210> SEQ ID NO 294
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 294

tcgagcggcc gcccgggcag gtctgccaac accaagattg gcccccgccg catccacaca     60
```

-continued

```
gttngtgtgc ggggaggtaa caagaaatac cgtgccctga ggntggacgn ggggaatttc    120

tcctggggct cagagtgttg tactcgtaaa acaaggatca tcgatgttgt ctacaatgca    180

tctaataacg agctggttcg taccaagacc ctggtgaaga attgcatcgt gctcatngac    240

agcacaccgt accgacagtg ggtaccgaag tcccactatg cncct                    285


<210> SEQ ID NO 295
<211> LENGTH: 216
<212> TYPE: DNA
<213> ORGANISM: Homo sapien

<400> SEQUENCE: 295

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaag                              216


<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296

agcgtgntcn cggccgagga tggggaagct cgnctgtctt tttccttcca atcaggggct     60

nnntcttctg attattcttc agggcaanga cataaattgt atattcggnt cccggttcca    120

gnccagtaat agtagcctct gtgacaccag ggcggggccg agggaccact tctctgggag    180

gagacccagg cttctcatac ttgatgatga agccggtaat cctggcacgt gggcggctgc    240

catgatacca ccaangaatt gggtgtggtg gacctgcccg ggcgggccgc tcgaaaancc    300

gaattcntgc aagaatatcc atcacacttg ggcgggccgn tcgaaccatg catcntaaaa    360

gggccccaat ttccccccta ttaggngaag ccncatttaa caaattccac ttgg          414


<210> SEQ ID NO 297
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 297

tcgagcggcc gcccgggcag gtctcgcggt cgcactggtg atgctggtcc tgttggtccc     60

cccggccctc ctggacctcc tggtccccct ggtcctccca gcgctggttt cgacttcagc    120

ttcctgcccc agccacctca agagaaggct cacgatggtg gccgctacta ccgggctgat    180

gatgccaatg tggttcgtga ccgtgacctc gaggtggaca ccaccctcaa gagccttgag    240

ccagcagaat cgaaaacatt cggaacccaa gaagggcaag cccgcaaaga aacccccgccc   300

gcacctggcc gngaacctcc aagaangtgc ccacntcttg actgggaaaa aaagggaaaa    360

ntacttggaa ttggac                                                    376


<210> SEQ ID NO 298
```

-continued

<211> LENGTH: 357
<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagaagt ggcacatctt gaggtcacgg cagggtgcgg 300
gcggggttct tgcgggctgc ccttctgggc tcccggaatg ttctnngaac ttgctgg 357

<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgggaaac tccgaggaca 180
gagggctaaa tccatgaagt ttgtggatgg cctgatgatc cacagcggag accctgttaa 240
ctactacgtt gacacttgct tgtgcgccac gtgttgctca nacangggtg ggctgggcat 300 caaggng 307

<210> SEQ ID NO 300
<211> LENGTH: 351
<212> TYPE: DNA
<213> ORGANISM: Homo sapien

<400> SEQUENCE: 300
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacag caagtgtcaa cgtaagtaag ttaacagggt ctccgctgtg 300
gatcatcagg ccatccacaa acttcatgga tttaaccctc tgtcctcgga g 351

<210> SEQ ID NO 301
<211> LENGTH: 330
<212> TYPE: DNA
<213> ORGANISM: Homo sapien

<400> SEQUENCE: 301
tcgagcggcc gcccgggcag gtgtttcaga ggttccaagg tccactgtgg aggtcccagg 60
agtgctggtg gtgggcacag aggtccgatg ggtgaaacca ttgacataga gactgttcct 120
gtccagggtg taggggccca gctctttgat gccattggcc agttggctca gctcccagta 180

-continued

```
cagccgctct ctgttgagtc cagggctttt ggggtcaaga tgatggatgc agatggcatc    240

cactccagtg gctgctccat ccttctcgga cctgagagag gtcagtctgc agccagagta    300

cagagggcca acactggtgt tctttgaata                                     330
```

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302

```
agcgtggtcg cggccgaggt ctgtactggg agctaagcaa actgaccaat gacattgaag     60

agctgggccc ctacaccctg gacaggaaca gtctctatgt caatggtttc acccatcaga    120

gctctgtgnc caccaccagc actcctggga cctccacagt ggatttcaga acctcaggga    180

ctccatcctc cctctccagc cccacaatta tggctgctgg ccctctcctg gtaccattca    240

ccctcaactt caccatcacc aacctgcagt atggggagga catgggtcac cctgnctcca    300

ggaagttcaa caccaca                                                   317
```

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303

```
tcgagcggcc gcccggacag gtctgggcgg atagcaccgg gcatattttg gaatggatga     60

ggtctggcac cctgagcagt ccagcgagga cttggtctta gttgagcaat ttggctagga    120

ggatagtatg cagcacggnt ctgagnctgt gggatagctg ccatgaagta acctgaagga    180

ggtgctggct ggtangggtt gattacaggg ttgggaacag ctcgtacact tgccattctc    240

tgcatatact ggttagtgag gtgagcctgg ccctcttctt ttg                      283
```

<210> SEQ ID NO 304
<211> LENGTH: 72
<212> TYPE: DNA
<213> ORGANISM: Homo sapien
<220> FEATURE:
<221> NAME/KEY: misc_feature
<222> LOCATION: (1)...(72)
<223> OTHER INFORMATION: n = A,T,C or G

<400> SEQUENCE: 304

```
agcgtggtcg cggccgaggt gagccacagg tgaccggggc tgaagctggg gctgctggnc     60

ctgctggtcc tg                                                         72
```

<210> SEQ ID NO 305
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G -continued

<400> SEQUENCE: 305
cagcngctcc nacggggcct gngggaccaa caacaccgtt ttcaccctta ggccctttgg 60
ctcctctttc tcctttagca ccaggttgac cagcagcncc ancaggacca gcaaatccat 120
tggggccagc aggaccgacc tcaccacgtt caccagggct tccccgagga ccagcaggac 180
cagcaggacc agcagcccca gcttcgcccc ggtcacctgt ggctcacctc ggccgcgacc 240
acgct 245

<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306
tcgagcggtc gcccgggcag gtccaccggg atagccgggg gtctggcagg aatgggaggc 60
atccagaacg agaaggagac catgcaaagc ctgaacgacc gcctggcctc ttacctggac 120
agagtgagga gcctggagac cganaaccgg aggctggana gcaaaatccg ggagcacttg 180
gagaagaagg gaccccaggt caagagactg gagccattac ttcaagatca tcgagggacc 240
tggagg 246

<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307
agcgnggtcg cggccgaggt ccagctctgt ctcatacttg actctaaagt catcagcagc 60
aagacgggca ttgtcaatct gcagaacgat gcgggcattg tccgcagtat ttgcgaagat 120
ctgagccctc aggtcctcga tgatcttgaa gtaatggctc cagtctctga cctggggtcc 180
cttcttctcc aagtgctccc ggattttgct ctccagcctc cggttctcgg tctccaggct 240
cctcactctg tccaggtaag aaggcccagg cggtcgttca ggctttgcat ggtctccttc 300
tcgttctgga tgcctcccat tcctgccaga ccc 333

<210> SEQ ID NO 308
<211> LENGTH: 310
<212> TYPE: DNA
<213> ORGANISM: Homo sapien

<400> SEQUENCE: 308
tcgagcggcc gcccgggcag gtcaggaagc acattggtct tagagccact gcctcctgga 60
ttccacctgt gctgcggaca tctccaggga gtgcagaagg gaagcaggtc aaactgctca 120
gatcagtcag actggctgtt ctcagttctc acctgagcaa ggtcagtctg cagccagagt 180
acagagggcc aacactggtg ttcttgaaca agggcttgag cagaccctgc agaaccctct 240
tccgtggtgt tgaacttcct ggaaaccagg gtgttgcatg tttttcctca taatgcaagg 300
ttggtgatgg 310

-continued

<210> SEQ ID NO 309
<211> LENGTH: 429
<212> TYPE: DNA
<213> ORGANISM: Homo sapien

<400> SEQUENCE: 309
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacaccg caggtctcac 180
cagtctccat gttgcagaag actttgatgg catccaggtt gcagccttgg ttggggtcaa 240
tccagtactc tccactcttc cagtcagaag tgggcacatc ttgaggtcac cggcaggtgc 300
cgggccgggg gttcttgcgg cttgccctct gggctccgga tgttctcgat ctgcttggct 360
caggctcttg agggtgggtg tccacctcga ggtcacggtc accgaaacct gcccgggcgg 420
cccgctcga 429

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310
tcgagcggtc gcccgggcag gtttcgtgac cgtgacctcg aggtggacac caccctcaag 60
agcctgagcc agcagatcga gaacatccgg agcccagagg gcagccgcaa gaaccccgcc 120
cgcacctgcc gtgacctcaa gatgtgccac tctgactgga agagtggaga gtactggatt 180
gaccccaacc aaggctgcaa cctggatgcc atcaaagtct tctgcaacat ggagactggt 240
gagacctgcg tgtaccccac tcagcccagt gtgggcccag aagaaactgg tacatcagca 300
aggaacccca aggacaagag gcattgtctt ggttcggcga gnagcatgac ccgatggatt 360
ccagtttcga gtattggcgg ccagggcttc ccgacccttg ccgatgtgga cctcggccgc 420
gaccaccgct 430